(12) United States Patent
Jarosch et al.

(10) Patent No.: US 9,976,145 B2
(45) Date of Patent: May 22, 2018

(54) NUCLEIC ACID MOLECULE HAVING BINDING AFFINITY TO A TARGET MOLECULE AND A METHOD FOR GENERATING THE SAME

(75) Inventors: Florian Jarosch, Berlin (DE); Sven Klussmann, Berlin (DE); Simone Sell, Berlin (DE); Werner Purschke, Berlin (DE); Christian Maasch, Berlin (DE); Axel Vater, Berlin (DE); Kai Hohlig, Berlin (DE)

(73) Assignee: NOXXON Pharma AG, Berlin (DE)

( * ) Notice: Subject to any disclaimer, the term of this patent is extended or adjusted under 35 U.S.C. 154(b) by 778 days.

(21) Appl. No.: 13/978,804

(22) PCT Filed: Jan. 10, 2012

(86) PCT No.: PCT/EP2012/000089
§ 371 (c)(1),
(2), (4) Date: Jan. 25, 2014

(87) PCT Pub. No.: WO2012/095303
PCT Pub. Date: Jul. 19, 2012

(65) Prior Publication Data
US 2014/0350088 A1 Nov. 27, 2014

(30) Foreign Application Priority Data

Jan. 10, 2011 (EP) ..................... 11000117
Apr. 21, 2011 (WO) ................. PCT/EP2011/002068
Oct. 21, 2011 (EP) ..................... 11008467

(51) Int. Cl.
| | |
|---|---|
| *C12N 15/115* | (2010.01) |
| *C12N 15/11* | (2006.01) |
| *G01N 33/53* | (2006.01) |
| *C12N 15/10* | (2006.01) |

(52) U.S. Cl.
CPC .......... *C12N 15/115* (2013.01); *C12N 15/102* (2013.01); *C12N 15/111* (2013.01); *G01N 33/5308* (2013.01); *C12N 2310/16* (2013.01); *C12N 2310/32* (2013.01); *C12N 2320/13* (2013.01); *C12N 2330/31* (2013.01); *G01N 2400/10* (2013.01); *G01N 2500/04* (2013.01)

(58) Field of Classification Search
None
See application file for complete search history.

(56) References Cited

U.S. PATENT DOCUMENTS

| | | |
|---|---|---|
| 8,394,946 B2 | 3/2013 | Todd et al. |
| 2007/0009907 A1 | 1/2007 | Burmeister et al. |
| 2007/0031840 A1 | 2/2007 | Klussmann et al. |
| 2007/0231810 A1 | 10/2007 | Todd et al. |
| 2009/0075342 A1 | 3/2009 | Cload et al. |
| 2011/0143338 A1 | 6/2011 | Todd et al. |
| 2012/0101267 A1 | 4/2012 | Todd et al. |

(Continued)

FOREIGN PATENT DOCUMENTS

WO   02100442   12/2002

OTHER PUBLICATIONS

Eulberg et al., "Spiegelmers: Biostable Aptamers," ChemBioChem 2003, 4:979-983.*
Katilius et al., "Exploring . . .microarrays," NAR 35, 7626-7635, 2007.
Esposito et al., "A Mini . . .sites," Nucleos Nucleot Nucl Acids 26, 1145-1149, 2007.
Huang et al., "Profiling . . . siRNAs," NAR 37, 7560-7569, 2009.
Prakash et al., "Positional . . . cells," J Med Chem 48, 4247-4253, 2005.

(Continued)

*Primary Examiner* — Kaijiang Zhang
(74) *Attorney, Agent, or Firm* — MDIP LLC

(57) ABSTRACT

The present invention is related to a method for generating a nucleic acid molecule capable of binding to a target molecule comprising the following steps: a) providing a reference nucleic acid molecule, wherein the reference nucleic acid molecule is capable of binding to the target molecule and wherein the reference nucleic acid molecule comprises a sequence of nucleotides, wherein the sequence of nucleotides comprises n nucleotides; b) preparing a first level derivative of the reference nucleic acid molecule, wherein the first level derivative of the reference nucleic acid molecule differs from the reference nucleic acid molecule at one nucleotide position, wherein the first level derivative is prepared by replacing the ribonucleotide at the one nucleotide position by a 2'-deoxyribonucleotide in case the reference nucleic acid has a ribonucleotide at the nucleotide position and wherein the first level derivative is prepared by replacing the 2'-deoxyribonucleotide at the one nucleotide position by a ribonucleotide in case the reference nucleic acid has a 2'-deoxyribonucleotide at the nucleotide position and wherein the nucleotide position at which the replacement is made is the modified nucleotide position; and c) repeating step b) for each nucleotide position of the reference nucleic acid molecule, thus preparing a group of first level derivatives of the reference nucleic acid molecule, wherein the group of first level derivatives of the reference nucleic acid molecule consists of n first level derivatives, wherein each of the first level derivatives of the reference nucleic acid molecule differs from the reference nucleic acid molecule by a single nucleotide replacement and wherein each of the first level derivatives of the reference nucleic acid molecule has a single modified nucleotide position which is different from the single modified nucleotide of all of the single modified nucleotide positions of the other first level derivatives of the group of first level derivatives of the reference nucleic acid molecule.

6 Claims, 52 Drawing Sheets

(56) References Cited

U.S. PATENT DOCUMENTS

2013/0123480 A1  5/2013  Todd et al.
2013/0165501 A1  6/2013  Purschke et al.

OTHER PUBLICATIONS

Bernal-Mendez et al., "Conformational . . . study," JBC 276, 35320-35327, 2001.
Eaton et al., "Post . . . aptamers," Bioorg Med Chem 5, 1087-1096, 1997.
Zimmerman et al., "Molecular . . . aptamer," RNA 6, 659-667, 2000.
Ui-Tei et al., "Functional . . . effects," NAR 36, 2136-2151, 2008.
Hoheisel et al., "Sequence . . . stabilities," NAR 24, 430-432, 1996.

* cited by examiner

| name | sequence: 5'-3' | pull-down ranking | competitive pull-down assay (K_D) |
|---|---|---|---|
| L-S1P-215-F9-002 | GCGUGAAUAGCCGUUGAAACGCCUUUAGAGAAGCACUAGCACGC | | 31.5 |
| L-S1P-215-F9-002-D01 | dGCGUGAAUAGCCGUUGAAACGCCUUUAGAGAAGCACUAGCACGC | < F9-002 | |
| L-S1P-215-F9-002-D02 | GdCGUGAAUAGCCGUUGAAACGCCUUUAGAGAAGCACUAGCACGC | > F9-002 | |
| L-S1P-215-F9-002-D03 | GCdGUGAAUAGCCGUUGAAACGCCUUUAGAGAAGCACUAGCACGC | > F9-002 | |
| L-S1P-215-F9-002-D04 | GCGdTGAAUAGCCGUUGAAACGCCUUUAGAGAAGCACUAGCACGC | > F9-002 | |
| L-S1P-215-F9-002-D05 | GCGUdGAAUAGCCGUUGAAACGCCUUUAGAGAAGCACUAGCACGC | > F9-002 | |
| L-S1P-215-F9-002-D06 | GCGUGdAAUAGCCGUUGAAACGCCUUUAGAGAAGCACUAGCACGC | = F9-002 | |
| L-S1P-215-F9-002-D07 | GCGUGAdAUAGCCGUUGAAACGCCUUUAGAGAAGCACUAGCACGC | > F9-002 | |
| L-S1P-215-F9-002-D08 | GCGUGAAdTAGCCGUUGAAACGCCUUUAGAGAAGCACUAGCACGC | > F9-002 | |
| L-S1P-215-F9-002-D09 | GCGUGAAUdAGCCGUUGAAACGCCUUUAGAGAAGCACUAGCACGC | > F9-002 | |
| L-S1P-215-F9-002-D10 | GCGUGAAUAdGCCGUUGAAACGCCUUUAGAGAAGCACUAGCACGC | > F9-002 | |
| L-S1P-215-F9-002-D11 | GCGUGAAUAGdCCGUUGAAACGCCUUUAGAGAAGCACUAGCACGC | < F9-002 | |
| L-S1P-215-F9-002-D12 | GCGUGAAUAGCdCGUUGAAACGCCUUUAGAGAAGCACUAGCACGC | = F9-002 | |
| L-S1P-215-F9-002-D13 | GCGUGAAUAGCCdGUUGAAACGCCUUUAGAGAAGCACUAGCACGC | = F9-002 | |
| L-S1P-215-F9-002-D14 | GCGUGAAUAGCCGdTUGAAACGCCUUUAGAGAAGCACUAGCACGC | > F9-002 | |
| L-S1P-215-F9-002-D15 | GCGUGAAUAGCCGUdTGAAACGCCUUUAGAGAAGCACUAGCACGC | = F9-002 | |
| L-S1P-215-F9-002-D16 | GCGUGAAUAGCCGUUdGAAACGCCUUUAGAGAAGCACUAGCACGC | = F9-002 | |
| L-S1P-215-F9-002-D17 | GCGUGAAUAGCCGUUGdAAACGCCUUUAGAGAAGCACUAGCACGC | > F9-002 | |
| L-S1P-215-F9-002-D18 | GCGUGAAUAGCCGUUGAdAACGCCUUUAGAGAAGCACUAGCACGC | > F9-002 | |
| L-S1P-215-F9-002-D19 | GCGUGAAUAGCCGUUGAAdACGCCUUUAGAGAAGCACUAGCACGC | < F9-002 | 16nM |
| L-S1P-215-F9-002-D20 | GCGUGAAUAGCCGUUGAAAdCGCCUUUAGAGAAGCACUAGCACGC | > F9-002 | |

> weaker binding, = equal binding and < stronger binding compared to Spiegelmer L-S1P-215-F9-002 (=F9-002) as determined by competitive pull-down ranking assay; A, C, G, U = ribonucleotides; dA, dC, dG, dT = 2'-deoxyribonucleotide

Fig. 1A

| name | sequence: 5'-3' | pull-down ranking | competitive pull-down assay (K_D) |
|---|---|---|---|
| L-S1P-215-F9-002 | GCGUGAAUAGCCGUUGAAACGCCUUUAGAGAAGCACUAGCACGC | | 31.5 |
| L-S1P-215-F9-002-D21 | GCGUGAAUAGCCGUUGAAACdGCCUUUAGAGAAGCACUAGCACGC | < F9-002 | 11.3 |
| L-S1P-215-F9-002-D22 | GCGUGAAUAGCCGUUGAAACGdCCUUUAGAGAAGCACUAGCACGC | < F9-002 | 30nM |
| L-S1P-215-F9-002-D23 | GCGUGAAUAGCCGUUGAAACGCdCUUUAGAGAAGCACUAGCACGC | > F9-002 | |
| L-S1P-215-F9-002-D24 | GCGUGAAUAGCCGUUGAAACGCCdTUUAGAGAAGCACUAGCACGC | > F9-002 | |
| L-S1P-215-F9-002-D25 | GCGUGAAUAGCCGUUGAAACGCCUdTUAGAGAAGCACUAGCACGC | > F9-002 | |
| L-S1P-215-F9-002-D26 | GCGUGAAUAGCCGUUGAAACGCCUUdTAGAGAAGCACUAGCACGC | > F9-002 | |
| L-S1P-215-F9-002-D27 | GCGUGAAUAGCCGUUGAAACGCCUUUdAGAGAAGCACUAGCACGC | > F9-002 | |
| L-S1P-215-F9-002-D28 | GCGUGAAUAGCCGUUGAAACGCCUUUAdGAGAAGCACUAGCACGC | > F9-002 | |
| L-S1P-215-F9-002-D29 | GCGUGAAUAGCCGUUGAAACGCCUUUAGdAGAAGCACUAGCACGC | > F9-002 | |
| L-S1P-215-F9-002-D30 | GCGUGAAUAGCCGUUGAAACGCCUUUAGAdGAAGCACUAGCACGC | > F9-002 | |
| L-S1P-215-F9-002-D31 | GCGUGAAUAGCCGUUGAAACGCCUUUAGAGdAAGCACUAGCACGC | > F9-002 | |
| L-S1P-215-F9-002-D32 | GCGUGAAUAGCCGUUGAAACGCCUUUAGAGAdAGCACUAGCACGC | < F9-002 | |
| L-S1P-215-F9-002-D33 | GCGUGAAUAGCCGUUGAAACGCCUUUAGAGAAdGCACUAGCACGC | > F9-002 | |
| L-S1P-215-F9-002-D34 | GCGUGAAUAGCCGUUGAAACGCCUUUAGAGAAGdCACUAGCACGC | > F9-002 | |
| L-S1P-215-F9-002-D35 | GCGUGAAUAGCCGUUGAAACGCCUUUAGAGAAGCdACUAGCACGC | > F9-002 | |
| L-S1P-215-F9-002-D36 | GCGUGAAUAGCCGUUGAAACGCCUUUAGAGAAGCAdCUAGCACGC | > F9-002 | |
| L-S1P-215-F9-002-D37 | GCGUGAAUAGCCGUUGAAACGCCUUUAGAGAAGCACdTAGCACGC | > F9-002 | |
| L-S1P-215-F9-002-D38 | GCGUGAAUAGCCGUUGAAACGCCUUUAGAGAAGCACUdAGCACGC | > F9-002 | |
| L-S1P-215-F9-002-D39 | GCGUGAAUAGCCGUUGAAACGCCUUUAGAGAAGCACUAdGCACGC | = F9-002 | |
| L-S1P-215-F9-002-D40 | GCGUGAAUAGCCGUUGAAACGCCUUUAGAGAAGCACUAGdCACGC | = F9-002 | |

> weaker binding, = equal binding and < stronger binding compared to Spiegelmer L-S1P-215-F9-002 (=F9-002) as determined by competitive pull-down ranking assay; A, C, G, U = ribonucleotides; dA, dC, dG, dT = 2'-deoxyribonucleotide

Fig. 1B

| name | sequence: 5'-3' | pull-down ranking | competitive pull-down assay ($K_D$) |
|---|---|---|---|
| L-S1P-215-F9-002 | GCGUGAAUAGCCGUUGAAACGCCUUUAGAGAAGCACUAGCACGC | | 31.5 |
| L-S1P-215-F9-002-D41 | GCGUGAAUAGCCGUUGAAACGCCUUUAGAGAAGCACUAGCdACGC | = F9-002 | |
| L-S1P-215-F9-002-D42 | GCGUGAAUAGCCGUUGAAACGCCUUUAGAGAAGCACUAGCAdCCGC | = F9-002 | |
| L-S1P-215-F9-002-D43 | GCGUGAAUAGCCGUUGAAACGCCUUUAGAGAAGCACUAGCACdGC | = F9-002 | |
| L-S1P-215-F9-002-D44 | GCGUGAAUAGCCGUUGAAACGCCUUUAGAGAAGCACUAGCACGdC | n.d. | 35nM |
| L-S1P-215-F9-002-D21-22 | GCGUGAAUAGCCGUUGAAACdGdCCUUUAGAGAAGCACUAGCACGC | = D21 | |
| L-S1P-215-F9-002-D21-19 | GCGUGAAUAGCCGUUGAAdAdACdGCCUUUAGAGAAGCACUAGCACGC | < D21 | 6nM |
| L-S1P-215-F9-002-D21-19-22 | GCGUGAAUAGCCGUUGAAdAdACdGCCUUUAGAGAAGCACUAGCACGC | = D21-D19 | |
| L-S1P-215-F9-002-D01-19-21-32 | dGCGUGAAUAGCCGUUGAAdAdACdGCCUUUAGAGAGAdAGCACUAGCACGC | < D21-D19 | 5nM |
| L-S1P-215-F9-002-D01-11-19-21-32 | dGCGUGAAUAGdCCGUUGAAdAdACdGCCUUUAGAGAdAGCACUAGCACGC | < D21-D19 | 5nM |

> weaker binding, = equal binding and < stronger binding compared to Spiegelmer L-S1P-215-F9-002 (=F9-002), Spiegelmer L-S1P-215-F9-002-D21 (= D21) or Spiegelmer L-S1P-215-F9-002-D21-19 (= D21-D19) as determined by competitive pull-down ranking assay;

A, C, G, U = ribonucleotides; dA, dC, dG, dT = 2'-deoxyribonucleotide

| Name | Sequence: 5'-3' | x-fold improved affinity* |
|---|---|---|
| 226-F2-001 | CCGUGCUGUCGGAGACUACUCGUCGAGUAGAAAUAGGUCCCCUCCCACGG | 1.0 |
| 226-F2-001-D01 | <u>dC</u>CGUGCUGUCGGAGACUACUCGUCGAGUAGAAAUAGGUCCCCUCCCACGG | 0.71 |
| 226-F2-001-D02 | Cd<u>C</u>GUGCUGUCGGAGACUACUCGUCGAGUAGAAAUAGGUCCCCUCCCACGG | 0.81 |
| 226-F2-001-D03 | CCG<u>dG</u>UGCUGUCGGAGACUACUCGUCGAGUAGAAAUAGGUCCCCUCCCACGG | 3.1 |
| 226-F2-001-D04 | CCGUG<u>dT</u>GCUGUCGGAGACUACUCGUCGAGUAGAAAUAGGUCCCCUCCCACGG | 0.99 |
| 226-F2-001-D05 | CCGU<u>dG</u>CUGUCGGAGACUACUCGUCGAGUAGAAAUAGGUCCCCUCCCACGG | 2.4 |
| 226-F2-001-D06 | CCGUGC<u>dC</u>UGUCGGAGACUACUCGUCGAGUAGAAAUAGGUCCCCUCCCACGG | n.b. |
| 226-F2-001-D07 | CCGUGC<u>dT</u>GUCGGAGACUACUCGUCGAGUAGAAAUAGGUCCCCUCCCACGG | n.b. |
| 226-F2-001-D08 | CCGUGCU<u>dG</u>UCGGAGACUACUCGUCGAGUAGAAAUAGGUCCCCUCCCACGG | 3.5 |
| 226-F2-001-D09 | CCGUGCUG<u>dT</u>CGGAGACUACUCGUCGAGUAGAAAUAGGUCCCCUCCCACGG | 2.6 |
| 226-F2-001-D10 | CCGUGCUGU<u>dC</u>GGAGACUACUCGUCGAGUAGAAAUAGGUCCCCUCCCACGG | 0.65 |

* as determined by Biacore measurement;
A, C, G, U = ribonucleotides; dA, dC, dG, dT = 2'-deoxyribonucleotide; n.b.: no binding

Fig. 5A

| Name | Sequence: 5'-3' | x-fold improved affinity* |
|---|---|---|
| 226-F2-001-D11 | CCGUGCUGUCdGGAGACUACUCGUCGAGUAGAAAUAGGUCCCUCCCACGG | 0.52 |
| 226-F2-001-D12 | CCGUGCUGUCGdGAGACUACUCGUCGAGUAGAAAUAGGUCCCUCCCACGG | 0.32 |
| 226-F2-001-D13 | CCGUGCUGUCGGdAGACUACUCGUCGAGUAGAAAUAGGUCCCUCCCACGG | 0.58 |
| 226-F2-001-D14 | CCGUGCUGUCGGAGdACUACUCGUCGAGUAGAAAUAGGUCCCUCCCACGG | 2.4 |
| 226-F2-001-D15 | CCGUGCUGUCGGAGAdCUACUCGUCGAGUAGAAAUAGGUCCCUCCCACGG | 0.53 |
| 226-F2-001-D16 | CCGUGCUGUCGGAGACdTACUCGUCGAGUAGAAAUAGGUCCCUCCCACGG | 1.3 |
| 226-F2-001-D17 | CCGUGCUGUCGGAGACUdACUCGUCGAGUAGAAAUAGGUCCCUCCCACGG | n.b. |
| 226-F2-001-D18 | CCGUGCUGUCGGAGACUAdCUCGUCGAGUAGAAAUAGGUCCCUCCCACGG | 0.78 |
| 226-F2-001-D19 | CCGUGCUGUCGGAGACUACdTCGUCGAGUAGAAAUAGGUCCCUCCCACGG | 6.3 |
| 226-F2-001-D20 | CCGUGCUGUCGGAGACUACUdCGUCGAGUAGAAAUAGGUCCCUCCCACGG | 0.74 |

* as determined by Biacore measurement;
A, C, G, U = ribonucleotides; dA, dC, dG, dT = 2'-deoxyribonucleotide; n.b.: no binding

Fig. 5B

| Name | Sequence: 5'-3' | x-fold improved affinity* |
|---|---|---|
| 226-F2-001-D21 | CCGUGCUGUCGGAGACUACUdCGUCGAGUAGAAAUAGGUCCCCUCCCACGG | 0.90 |
| 226-F2-001-D22 | CCGUGCUGUCGGAGACUACUCdGUCGAGUAGAAAUAGGUCCCCUCCCACGG | 1.2 |
| 226-F2-001-D23 | CCGUGCUGUCGGAGACUACUCGdTCGAGUAGAAAUAGGUCCCCUCCCACGG | 3.4 |
| 226-F2-001-D24 | CCGUGCUGUCGGAGACUACUCGUdCGAGUAGAAAUAGGUCCCCUCCCACGG | 1.3 |
| 226-F2-001-D25 | CCGUGCUGUCGGAGACUACUCGUCdGAGUAGAAAUAGGUCCCCUCCCACGG | 1.2 |
| 226-F2-001-D26 | CCGUGCUGUCGGAGACUACUCGUCGdAGUAGAAAUAGGUCCCCUCCCACGG | 4.3 |
| 226-F2-001-D27 | CCGUGCUGUCGGAGACUACUCGUCGAdGUAGAAAUAGGUCCCCUCCCACGG | 1.0 |
| 226-F2-001-D28 | CCGUGCUGUCGGAGACUACUCGUCGAGdTAGAAAUAGGUCCCCUCCCACGG | 2.4 |
| 226-F2-001-D29 | CCGUGCUGUCGGAGACUACUCGUCGAGUdAGAAAUAGGUCCCCUCCCACGG | 0.72 |
| 226-F2-001-D30 | CCGUGCUGUCGGAGACUACUCGUCGAGUAdGAAAUAGGUCCCCUCCCACGG | 1.2 |

* as determined by Biacore measurement;
A, C, G, U = ribonucleotides; dA, dC, dG, dT = 2'-deoxyribonucleotide; n.b.: no binding

Fig. 5C

| Name | Sequence: 5'-3' | x-fold improved affinity* |
|---|---|---|
| 226-F2-001-D31 | CCGUGCUGUCGGAGACUACUCGUCGAGUAGdAAAUAGGUCCCCUCCCACGG | 0.18 |
| 226-F2-001-D32 | CCGUGCUGUCGGAGACUACUCGUCGAGUAGAdAAUAGGUCCCCUCCCACGG | 0.46 |
| 226-F2-001-D33 | CCGUGCUGUCGGAGACUACUCGUCGAGUAGAAdAUAGGUCCCCUCCCACGG | 1.7 |
| 226-F2-001-D34 | CCGUGCUGUCGGAGACUACUCGUCGAGUAGAAAdTAGGUCCCCUCCCACGG | 3.3 |
| 226-F2-001-D35 | CCGUGCUGUCGGAGACUACUCGUCGAGUAGAAAUdAGGUCCCCUCCCACGG | 0.27 |
| 226-F2-001-D36 | CCGUGCUGUCGGAGACUACUCGUCGAGUAGAAAUAdGGUCCCCUCCCACGG | 0.62 |
| 226-F2-001-D37 | CCGUGCUGUCGGAGACUACUCGUCGAGUAGAAAUAGdGUCCCCUCCCACGG | 3.1 |
| 226-F2-001-D38 | CCGUGCUGUCGGAGACUACUCGUCGAGUAGAAAUAGGdTCCCCUCCCACGG | n.b. |
| 226-F2-001-D39 | CCGUGCUGUCGGAGACUACUCGUCGAGUAGAAAUAGGUdCCCCUCCCACGG | 1.4 |
| 226-F2-001-D40 | CCGUGCUGUCGGAGACUACUCGUCGAGUAGAAAUAGGUCdCCCUCCCACGG | 0.78 |

* as determined by Biacore measurement;
A, C, G, U = ribonucleotides; dA, dC, dG, dT = 2'-deoxyribonucleotide; n.b.: no binding

Fig. 5D

| Name | Sequence: 5'-3' | x-fold improved affinity* |
|---|---|---|
| 226-F2-001-D41 | CCGUGCUGUCGGAGACUACUCGUCGAGUAGAAAUAGGUCCCdCCUCCCACGG | 5.0 |
| 226-F2-001-D42 | CCGUGCUGUCGGAGACUACUCGUCGAGUAGAAAUAGGUCCCCdCUCCCACGG | 3.8 |
| 226-F2-001-D43 | CCGUGCUGUCGGAGACUACUCGUCGAGUAGAAAUAGGUCCCCdTCCCACGG | 0.59 |
| 226-F2-001-D44 | CCGUGCUGUCGGAGACUACUCGUCGAGUAGAAAUAGGUCCCCUdCCCACGG | 4.8 |
| 226-F2-001-D45 | CCGUGCUGUCGGAGACUACUCGUCGAGUAGAAAUAGGUCCCCUCdCCACGG | 3.6 |
| 226-F2-001-D46 | CCGUGCUGUCGGAGACUACUCGUCGAGUAGAAAUAGGUCCCCUCCdCACGG | 3.1 |
| 226-F2-001-D47 | CCGUGCUGUCGGAGACUACUCGUCGAGUAGAAAUAGGUCCCCUCCCdACGG | 3.9 |
| 226-F2-001-D48 | CCGUGCUGUCGGAGACUACUCGUCGAGUAGAAAUAGGUCCCCUCCCAdCGG | 3.4 |
| 226-F2-001-D49 | CCGUGCUGUCGGAGACUACUCGUCGAGUAGAAAUAGGUCCCCUCCCACdGG | 3.0 |
| 226-F2-001-D50 | CCGUGCUGUCGGAGACUACUCGUCGAGUAGAAAUAGGUCCCCUCCCACGdG | 2.4 |

* as determined by Biacore measurement;
A, C, G, U = ribonucleotides; dA, dC, dG, dT = 2'-deoxyribonucleotide; n.b.: no binding

Fig. 5E

| Name | Sequence: 5'-3' | x-fold improved affinity* | K$_D$ (human CGRP)* |
|---|---|---|---|
| 226-F2-001 | CCGUGCUGUCGGAGACUACUCGUCGAGUAGAAAUAGGUCCCCUCCCACGG | 1.0 | 2.6 nM |
| 226-F2-001-D41 | CCGUGCUGUCGGAGACUACUCGUCGAGUAGAAAUAGGUCCdCCUCCCACGG | 4.7 | 0.55 nM |
| 226-F2-001-D44 | CCGUGCUGUCGGAGACUACUCGUCGAGUAGAAAUAGGUCCCCUCdCCACGG | 5.0 | 0.52 nM |
| 226-F2-001-D41/D44 | CCGUGCUGUCGGAGACUACUCGUCGAGUAGAAAUAGGUCCdCCUCdCCACGG | 13.0 | 0.20 nM |

* as determined by Biacore measurement;
A, C, G, U = ribonucleotides; dC = 2'-deoxyribonucleotide;

Fig. 7

Derivatives of NOX-D19001: Single ribonucleotide-to-deoxyribonucleotide substitutions

| Name | Sequence: 5'-3' | x- fold improved affinity* |
|---|---|---|
| NOX-D19001 | GCCUGAUGUGGUUGAAGGGUUGUUGGGUGUCGACGCACAGGC | 1.0 |
| NOX-D19001-D01 | dGCCUGAUGUGGUUGAAGGGUUGUUGGGUGUCGACGCACAGGC | 1.2 |
| NOX-D19001-D02 | GdCCUGAUGUGGUUGAAGGGUUGUUGGGUGUCGACGCACAGGC | 1.1 |
| NOX-D19001-D03 | GCdCUGAUGUGGUUGAAGGGUUGUUGGGUGUCGACGCACAGGC | 1.0 |
| NOX-D19001-D04 | GCCdUGAUGUGGUUGAAGGGUUGUUGGGUGUCGACGCACAGGC | 0.6 |
| NOX-D19001-D05 | GCCUdGAUGUGGUUGAAGGGUUGUUGGGUGUCGACGCACAGGC | 0.8 |
| NOX-D19001-D06 | GCCUGdAUGUGGUUGAAGGGUUGUUGGGUGUCGACGCACAGGC | 0.1 |
| NOX-D19001-D07 | GCCUGAdUGUGGUUGAAGGGUUGUUGGGUGUCGACGCACAGGC | 0.2 |
| NOX-D19001-D08 | GCCUGAUdGUGGUUGAAGGGUUGUUGGGUGUCGACGCACAGGC | 0.7 |
| NOX-D19001-D09 | GCCUGAUGdUGGUUGAAGGGUUGUUGGGUGUCGACGCACAGGC | 2.0 |
| NOX-D19001-D10 | GCCUGAUGUdGGUUGAAGGGUUGUUGGGUGUCGACGCACAGGC | 0.5 |

A, C, G, U = ribonucleotides; dA, dC, dG, dU = 2'-deoxyribonucleotides

*as determined by Biacore measurement

Fig. 11A

Derivatives of NOX-D19001: Single ribonucleotide-to-deoxyribonucleotide substitutions

| Name | Sequence: 5'-3' | x- fold improved affinity* |
|---|---|---|
| NOX-D19001-D11 | GCCUGAUGUGGdGGUGUGAAGGGUUGGGGUGUGACGCACAGGC | 0.8 |
| NOX-D19001-D12 | GCCUGAUGUGGGdUGUGAAGGGUUGGGGUGUGACGCACAGGC | 0.7 |
| NOX-D19001-D13 | GCCUGAUGUGGGUdGUGAAGGGUUGGGGUGUGACGCACAGGC | 0.2 |
| NOX-D19001-D14 | GCCUGAUGUGGGUGdGGAAGGGUUGGGGUGUGACGCACAGGC | 0.8 |
| NOX-D19001-D15 | GCCUGAUGUGGGUGGdUAAGGGUUGGGGUGUGACGCACAGGC | 0.7 |
| NOX-D19001-D16 | GCCUGAUGUGGGUGGUdGAAGGGUUGGGGUGUGACGCACAGGC | 1.3 |
| NOX-D19001-D17 | GCCUGAUGUGGGUGGUGdAAGGGUUGGGGUGUGACGCACAGGC | 1.5 |
| NOX-D19001-D18 | GCCUGAUGUGGGUGGUGAdAGGGUUGGGGUGUGACGCACAGGC | 0.8 |
| NOX-D19001-D19 | GCCUGAUGUGGGUGGUGAAdGGGUUGGGGUGUGACGCACAGGC | 0.8 |
| NOX-D19001-D20 | GCCUGAUGUGGGUGGUGAAGdGGUUGGGGUGUGACGCACAGGC | 0.7 |

A, C, G, U = ribonucleotides; dA, dC, dG, dU = 2'-deoxyribonucleotides

*as determined by Biacore measurement

Fig. 11B

Derivatives of NOX-D19001: Single ribonucleotide-to-deoxyribonucleotide substitutions

| Name | Sequence: 5'-3' | x-fold improved affinity* |
|---|---|---|
| NOX-D19001-D21 | GCCUGAUGUGGUGGUGAAGGdGGUUGGGGUGUCGACGCACAGGC | 0.7 |
| NOX-D19001-D22 | GCCUGAUGUGGUGGUGAAGGGdUUGGGGUGUCGACGCACAGGC | 1.1 |
| NOX-D19001-D23 | GCCUGAUGUGGUGGUGAAGGGUdUGGGGUGUCGACGCACAGGC | 1.0 |
| NOX-D19001-D24 | GCCUGAUGUGGUGGUGAAGGGUUdGGGGUGUCGACGCACAGGC | 0.1 |
| NOX-D19001-D25 | GCCUGAUGUGGUGGUGAAGGGUUGdUGGGUGUCGACGCACAGGC | 1.2 |
| NOX-D19001-D26 | GCCUGAUGUGGUGGUGAAGGGUUGUdUGGGUGUCGACGCACAGGC | 1.0 |
| NOX-D19001-D27 | GCCUGAUGUGGUGGUGAAGGGUUGUUdGGGGUGUCGACGCACAGGC | 0.7 |
| NOX-D19001-D28 | GCCUGAUGUGGUGGUGAAGGGUUGUUGdGGGUGUCGACGCACAGGC | 0.6 |
| NOX-D19001-D29 | GCCUGAUGUGGUGGUGAAGGGUUGUUGGdGGUGUCGACGCACAGGC | 1.2 |
| NOX-D19001-D30 | GCCUGAUGUGGUGGUGAAGGGUUGUUGGGdUGUCGACGCACAGGC | 1.8 |

A, C, G, U = ribonucleotides; dA, dC, dG, dU = 2'-deoxyribonucleotides

*as determined by Biacore measurement

Fig. 11C

Derivatives of NOX-D19001: Single ribonucleotide-to-deoxyribonucleotide substitutions

| Name | Sequence: 5'-3' | x- fold improved affinity* |
|---|---|---|
| NOX-D19001-D31 | GCCUGAUGUGGUGGUGAAGGGUUGUUGGGUdGUCGACGCACAGGC | 0.7 |
| NOX-D19001-D32 | GCCUGAUGUGGUGGUGAAGGGUUGUUGGGUGUdUCGACGCACAGGC | 1.5 |
| NOX-D19001-D33 | GCCUGAUGUGGUGGUGAAGGGUUGUUGGGUGUdCGACGCACAGGC | 0.1 |
| NOX-D19001-D34 | GCCUGAUGUGGUGGUGAAGGGUUGUUGGGUGUCdGACGCACAGGC | 0.1 |
| NOX-D19001-D35 | GCCUGAUGUGGUGGUGAAGGGUUGUUGGGUGUCGdACGCACAGGC | 1.1 |
| NOX-D19001-D36 | GCCUGAUGUGGUGGUGAAGGGUUGUUGGGUGUCGAdCGCACAGGC | 0.9 |
| NOX-D19001-D37 | GCCUGAUGUGGUGGUGAAGGGUUGUUGGGUGUCGACdGCACAGGC | 1.3 |
| NOX-D19001-D38 | GCCUGAUGUGGUGGUGAAGGGUUGUUGGGUGUCGACGdCACAGGC | 0.9 |

A, C, G, U = ribonucleotides; dA, dC, dG, dU = 2'-deoxyribonucleotides

*as determined by Biacore measurement

Fig. 11D

Derivatives of NOX-D19001: Single ribonucleotide-to-deoxyribonucleotide substitutions

| Name | Sequence: 5'-3' | x-fold improved affinity* |
|---|---|---|
| NOX-D19001-D39 | GCCUGAUGUGGUGAAGGGUUGGGUGUCGACGCdACAGGC | 1.0 |
| NOX-D19001-D40 | GCCUGAUGUGGUGAAGGGUUGGGUGUCGACGCAdCAGGC | 1.6 |
| NOX-D19001-D41 | GCCUGAUGUGGUGAAGGGUUGGGUGUCGACGCACdAGGC | 0.8 |
| NOX-D19001-D42 | GCCUGAUGUGGUGAAGGGUUGGGUGUCGACGCACAdGGC | 1.1 |
| NOX-D19001-D43 | GCCUGAUGUGGUGAAGGGUUGGGUGUCGACGCACAGdGC | 1.1 |
| NOX-D19001-D44 | GCCUGAUGUGGUGAAGGGUUGGGUGUCGACGCACAGGdC | 1.1 |

A, C, G, U = ribonucleotides; dA, dC, dG, dU = 2'-deoxyribonucleotides

*as determined by Biacore measurement

Fig. 11 E

Derivatives of NOX-D19001: Multiple ribonucleotide-to-deoxyribonucleotide substitutions

| Name | Sequence: 5'-3' | K_D (nM) * | x-fold improved* |
|---|---|---|---|
| 2 RNA-to-DNA substitutions: | | | |
| NOX-D19001-D09-30 | GCCUGAUGdUGGUGGUGGUGAAGGGUUGUUGGGdUGUCGACGCACAGGC | 0.461 | 3.1 |
| NOX-D19001-D09-32 | GCCUGAUGdUGGUGGUGGUGAAGGGUUGUUGGGdUGUCGACGCACAGGC | 0.566 | 2.5 |
| NOX-D19001-D09-40 | GCCUGAUGdUGGUGGUGGUGAAGGGUUGUUGGGdUGUCGACGCAdCAGGC | 0.570 | 2.5 |
| NOX-D19001-D30-32 | GCCUGAUGUGGUGGUGGUGAAGGGUUGUUGGGdUGdUCGACGCACAGGC | 0.855 | 1.7 |
| NOX-D19001-D30-40 | GCCUGAUGUGGUGGUGGUGAAGGGUUGUUGGGdUGUCGACGCAdCAGGC | 0.624 | 2.3 |
| NOX-D19001-D32-40 | GCCUGAUGUGGUGGUGGUGAAGGGUUGUUGGGUUGdUCGACGCAdCAGGC | 0.652 | 2.2 |
| 3 RNA-to-DNA substitutions: | | | |
| NOX-D19001-D09-30-32 | GCCUGAUGdUGGUGGUGGUGAAGGGUUGUUGGGdUGdUCGACGCACAGGC | 0.526 | 2.7 |
| NOX-D19001-D09-30-40 | GCCUGAUGdUGGUGGUGGUGAAGGGUUGUUGGGdUGUCGACGCAdCAGGC | 0.400 | 3.6 |
| NOX-D19001-D09-32-40 | GCCUGAUGdUGGUGGUGGUGAAGGGUUGUUGGGUUGdUCGACGCAdCAGGC | 0.448 | 3.2 |
| NOX-D19001-D30-32-40 | GCCUGAUGUGGUGGUGGUGAAGGGUUGUUGGGdUGdUCGACGCAdCAGGC | 0.880 | 1.6 |
| 4 RNA-to-DNA substitutions: | | | |
| NOX-D19001-D09-30-32-40 | GCCUGAUGdUGGUGGUGGUGAAGGGUUGUUGGGdUGdUCGACGCAdCAGGC | 0.385 | 3.7 |
| 5 RNA-to-DNA substitutions: | | | |
| NOX-D19001-D09-16-30-32-40 | GCCUGAUGdUGGUGGUGdGAAGGGUUGUUGGGdUGdUCGACGCAdCAGGC | 0.351 | 4.1 |
| NOX-D19001-D09-17-30-32-40 | GCCUGAUGdUGGUGGUGGdUAAGGGUUGUUGGGdUGdUCGACGCAdCAGGC | 0.308 | 4.6 |
| 6 RNA-to-DNA substitutions: | | | |
| NOX-D19001-D09-16-17-30-32-40 (= NOX-D19001-6xDNA) | GCCUGAUGdUGGUGGUGdGdAAGGGUUGUUGGGdUGdUCGACGCAdCAGGC | 0.344 | 4.2 |

A, C, G, U = ribonucleotides; dA, dC, dG, dU = 2'-deoxyribonucleotides

* as determined by Biacore measurement

Fig. 14

Derivatives of NOX-D19001: Multiple ribonucleotide-to-deoxyribonucleotide substitutions

| Name | Sequence: 5'-3' | KD (nM)* | x-fold improved* |
|---|---|---|---|
| 2 RNA-to-DNA substitutions: | | | |
| NOX-D19001-D07-30 | GCCUGAdUGUGGUGGUGAAGGGUUGUUGGGdUGUCGACGCACAGGC | 6.52 | 0.2 |
| 3 RNA-to-DNA substitutions: | | | |
| NOX-D19001-D07-30-40 | GCCUGAdUGUGGUGGUGAAGGGUUGUUGGGdUGUCGACGCAdCAGGC | 4.95 | 0.3 |
| 4 RNA-to-DNA substitutions: | | | |
| NOX-D19001-D07-30-32-40 | GCCUGAdUGUGGUGGUGAAGGGUUGUUGGGdUGdUCGACGCAdCAGGC | 4.66 | 0.3 |
| 5 RNA-to-DNA substitutions: | | | |
| NOX-D19001-D07-16-30-32-40 | GCCUGAdUGUGGUGGUdGAAGGGUUGUUGGGdUGdUCGACGCAdCAGGC | 4.19 | 0.3 |
| NOX-D19001-D07-17-30-32-40 | GCCUGAdUGUGGUGGUGdAAGGGUUGUUGGGdUGdUCGACGCAdCAGGC | 4.03 | 0.4 |
| 6 RNA-to-DNA substitutions: | | | |
| NOX-D19001-D07-16-17-30-32-40 | GCCUGAdUGUGGUGGUdGdAAGGGUUGUUGGGdUGdUCGACGCAdCAGGC | 3.91 | 0.4 |

A, C, G, U = ribonucleotides; dA, dC, dG, dU = 2'-deoxyribonucleotides

*as determined by Biacore measurement

Fig. 17

| Name | Sequence: 5'-3' | x-fold improved affinity* |
|---|---|---|
| NOX-G11stabi2 | CAGACGUGUGUGGGUAGAUGCACCUGCGAUUCGCUAAAAAGUGCCACACGUCUG | 1.0 |
| NOX-G11-D01 | <u>dC</u>AGACGUGUGUGGGUAGAUGCACCUGCGAUUCGCUAAAAAGUGCCACACGUCUG | 1.3 |
| NOX-G11-D02 | C<u>dA</u>GACGUGUGUGGGUAGAUGCACCUGCGAUUCGCUAAAAAGUGCCACACGUCUG | 1.1 |
| NOX-G11-D03 | CA<u>dG</u>ACGUGUGUGGGUAGAUGCACCUGCGAUUCGCUAAAAAGUGCCACACGUCUG | 1.2 |
| NOX-G11-D04 | CAG<u>dA</u>CGUGUGUGGGUAGAUGCACCUGCGAUUCGCUAAAAAGUGCCACACGUCUG | 1.2 |
| NOX-G11-D05 | CAGA<u>dC</u>GUGUGUGGGUAGAUGCACCUGCGAUUCGCUAAAAAGUGCCACACGUCUG | 3.7 |
| NOX-G11-D06 | CAGACGUGUGUGGGUAGAUGCACCUGCGAUUCGCUAAAAAGUGCCACACGUCUG | 1.1 |
| NOX-G11-D07 | CAGACG<u>dT</u>GUGUGGGUAGAUGCACCUGCGAUUCGCUAAAAAGUGCCACACGUCUG | 5.5 |
| NOX-G11-D08 | CAGACGU<u>dG</u>UGUGGGUAGAUGCACCUGCGAUUCGCUAAAAAGUGCCACACGUCUG | 1.8 |
| NOX-G11-D09 | CAGACGUG<u>dT</u>GUGGGUAGAUGCACCUGCGAUUCGCUAAAAAGUGCCACACGUCUG | 1.3 |
| NOX-G11-D10 | CAGACGUGU<u>dG</u>UGGGUAGAUGCACCUGCGAUUCGCUAAAAAGUGCCACACGUCUG | 1.1 |
| NOX-G11-D11 | CAGACGUGUG<u>dT</u>GGGUAGAUGCACCUGCGAUUCGCUAAAAAGUGCCACACGUCUG | 1.0 |

*as determined by Biacore measurement

A, C, G, U = ribonucleotides; dA, dC, dG, dT = 2' deoxyribonucleotides

Fig. 18A

| Name | Sequence: 5'-3' | x-fold improved affinity* |
|---|---|---|
| NOX-G11-D12 | CAGACGUGUGUGGUAGAUGdGGGUAGAUGCACCUGCGAUUCGCUAAAAAGUGCCACGUCUG | 1.6 |
| NOX-G11-D13 | CAGACGUGUGUGGUAGAUGGdGGUAGAUGCACCUGCGAUUCGCUAAAAAGUGCCACGUCUG | 1.3 |
| NOX-G11-D14 | CAGACGUGUGUGGUAGAUGGGdGUAGAUGCACCUGCGAUUCGCUAAAAAGUGCCACGUCUG | 1.3 |
| NOX-G11-D15 | CAGACGUGUGUGGUAGAUGGGGdTAGAUGCACCUGCGAUUCGCUAAAAAGUGCCACGUCUG | 3.1 |
| NOX-G11-D16 | CAGACGUGUGUGGUAGAUGGGGUdAGAUGCACCUGCGAUUCGCUAAAAAGUGCCACGUCUG | 3.9 |
| NOX-G11-D17 | CAGACGUGUGUGGUAGAUGGGGUAdGAUGCACCUGCGAUUCGCUAAAAAGUGCCACGUCUG | 1.0 |
| NOX-G11-D18 | CAGACGUGUGUGGUAGAUGGGGUAGdAUGCACCUGCGAUUCGCUAAAAAGUGCCACGUCUG | 1.2 |
| NOX-G11-D19 | CAGACGUGUGUGGUAGAUGGGGUAGAdTGCACCUGCGAUUCGCUAAAAAGUGCCACGUCUG | 4.3 |
| NOX-G11-D20 | CAGACGUGUGUGGUAGAUGGGGUAGAUdGCACCUGCGAUUCGCUAAAAAGUGCCACGUCUG | 2.3 |
| NOX-G11-D21 | CAGACGUGUGUGGUAGAUGGGGUAGAUGdCACCUGCGAUUCGCUAAAAAGUGCCACGUCUG | 6.0 |
| NOX-G11-D22 | CAGACGUGUGUGGUAGAUGGGGUAGAUGCdACCUGCGAUUCGCUAAAAAGUGCCACGUCUG | 4.6 |
| NOX-G11-D23 | CAGACGUGUGUGGUAGAUGGGGUAGAUGCAdCCUGCGAUUCGCUAAAAAGUGCCACGUCUG | 2.4 |

*as determined by Biacore measurement

A, C, G, U = ribonucleotides; dA, dC, dG, dT = 2'deoxyribonucleotides

Fig. 18B

| Name | Sequence: 5'-3' | x-fold improved affinity* |
|---|---|---|
| NOX-G11-D24 | CAGACGUGUGGGUAGAUGCCACdCUGCGAUUCGCUAAAAAGUGCCACACGUCUG | 3.0 |
| NOX-G11-D25 | CAGACGUGUGGGUAGAUGCCACCdTGCGAUUCGCUAAAAAGUGCCACACGUCUG | 2.5 |
| NOX-G11-D26 | CAGACGUGUGGGUAGAUGCCACCUdGCGAUUCGCUAAAAAGUGCCACACGUCUG | 3.1 |
| NOX-G11-D27 | CAGACGUGUGGGUAGAUGCCACCUGdCGAUUCGCUAAAAAGUGCCACACGUCUG | 2.7 |
| NOX-G11-D28 | CAGACGUGUGGGUAGAUGCCACCUGCdGAUUCGCUAAAAAGUGCCACACGUCUG | 1.3 |
| NOX-G11-D29 | CAGACGUGUGGGUAGAUGCCACCUGCGdAUUCGCUAAAAAGUGCCACACGUCUG | 1.4 |
| NOX-G11-D30 | CAGACGUGUGGGUAGAUGCCACCUGCGAdTUCGCUAAAAAGUGCCACACGUCUG | 1.4 |
| NOX-G11-D31 | CAGACGUGUGGGUAGAUGCCACCUGCGAUdTCGCUAAAAAGUGCCACACGUCUG | 1.0 |
| NOX-G11-D32 | CAGACGUGUGGGUAGAUGCCACCUGCGAUUdCGCUAAAAAGUGCCACACGUCUG | 1.1 |
| NOX-G11-D33 | CAGACGUGUGGGUAGAUGCCACCUGCGAUUCdGCUAAAAAGUGCCACACGUCUG | 1.0 |
| NOX-G11-D34 | CAGACGUGUGGGUAGAUGCCACCUGCGAUUCGdCUAAAAAGUGCCACACGUCUG | 1.0 |
| NOX-G11-D35 | CAGACGUGUGGGUAGAUGCCACCUGCGAUUCGCdTAAAAAGUGCCACACGUCUG | 1.0 |

*as determined by Biacore measurement

A, C, G, U = ribonucleotides; dA, dC, dG, dT = 2'deoxyribonucleotides

Fig. 18C

| Name | Sequence: 5'-3' | x-fold improved affinity* |
|---|---|---|
| NOX-G11-D36 | CAGACGUGUGUGGGUAGAUGCACCUGCGAUUCGCUAdAAAAGUGCCACACGUCUG | 1.2 |
| NOX-G11-D37 | CAGACGUGUGUGGGUAGAUGCACCUGCGAUUCGCUAdAAAAGUGCCACACGUCUG | 0.9 |
| NOX-G11-D38 | CAGACGUGUGUGGGUAGAUGCACCUGCGAUUCGCUAAdAAAGUGCCACACGUCUG | 1.3 |
| NOX-G11-D39 | CAGACGUGUGUGGGUAGAUGCACCUGCGAUUCGCUAAAdAAGUGCCACACGUCUG | 1.0 |
| NOX-G11-D40 | CAGACGUGUGUGGGUAGAUGCACCUGCGAUUCGCUAAAAdAGUGCCACACGUCUG | 1.0 |
| NOX-G11-D41 | CAGACGUGUGUGGGUAGAUGCACCUGCGAUUCGCUAAAAAdGUGCCACACGUCUG | 0.9 |
| NOX-G11-D42 | CAGACGUGUGUGGGUAGAUGCACCUGCGAUUCGCUAAAAAGdTGCCACACGUCUG | 0.9 |
| NOX-G11-D43 | CAGACGUGUGUGGGUAGAUGCACCUGCGAUUCGCUAAAAAGUdGCCACACGUCUG | 1.0 |
| NOX-G11-D44 | CAGACGUGUGUGGGUAGAUGCACCUGCGAUUCGCUAAAAAGUGdCCACACGUCUG | 1.3 |
| NOX-G11-D45 | CAGACGUGUGUGGGUAGAUGCACCUGCGAUUCGCUAAAAAGUGCdCACACGUCUG | 1.0 |
| NOX-G11-D46 | CAGACGUGUGUGGGUAGAUGCACCUGCGAUUCGCUAAAAAGUGCCdACACGUCUG | 2.8 |
| NOX-G11-D47 | CAGACGUGUGUGGGUAGAUGCACCUGCGAUUCGCUAAAAAGUGCCAdCACGUCUG | n.b. |

*as determined by Biacore measurement

A, C, G, U = ribonucleotides; dA, dC, dG, dT = 2'deoxyribonucleotides n.b.: no binding

Fig. 18D

| Name | Sequence: 5'-3' | x-fold improved affinity* |
|---|---|---|
| NOX-G11-D48 | CAGACGUGUGGGUAGAUGCACCUGCGAUUCGCUAAAAAGUGCCACdACGUCUG | 2.0 |
| NOX-G11-D49 | CAGACGUGUGGGUAGAUGCACCUGCGAUUCGCUAAAAAGUGCCACAdCGUCUG | n.b. |
| NOX-G11-D50 | CAGACGUGUGGGUAGAUGCACCUGCGAUUCGCUAAAAAGUGCCACACdGUCUG | 1.0 |
| NOX-G11-D51 | CAGACGUGUGGGUAGAUGCACCUGCGAUUCGCUAAAAAGUGCCACACGdTCUG | 0.9 |
| NOX-G11-D52 | CAGACGUGUGGGUAGAUGCACCUGCGAUUCGCUAAAAAGUGCCACACGUdCUG | 1.0 |
| NOX-G11-D53 | CAGACGUGUGGGUAGAUGCACCUGCGAUUCGCUAAAAAGUGCCACACGUCdTG | 1.1 |
| NOX-G11-D54 | CAGACGUGUGGGUAGAUGCACCUGCGAUUCGCUAAAAAGUGCCACACGUCUdG | 0.9 |

*as determined by Biacore measurement

A, C, G, U = ribonucleotides; dA, dC, dG, dT = 2'deoxyribonucleotides

Fig. 18E

| Name | Sequence: 5'-3' | x-fold improved affinity* |
|---|---|---|
| 259-H6-002 | ACTCGAGAGGAAAGGTTGGTAAAGGTTCGGTTGGATTCACTCGAGT | 1 |
| 259-H6-002-R01 | rACTCGAGAGGAAAGGTTGGTAAAGGTTCGGTTGGATTCACTCGAGT | 0.91 |
| 259-H6-002-R02 | ArCTCGAGAGGAAAGGTTGGTAAAGGTTCGGTTGGATTCACTCGAGT | 0.83 |
| 259-H6-002-R03 | ACrUGAGAGGAAAGGTTGGTAAAGGTTCGGTTGGATTCACTCGAGT | 0.65 |
| 259-H6-002-R04 | ACTrCGAGAGGAAAGGTTGGTAAAGGTTCGGTTGGATTCACTCGAGT | 1.0 |
| 259-H6-002-R05 | ACTCrGAGAGGAAAGGTTGGTAAAGGTTCGGTTGGATTCACTCGAGT | 0.58 |
| 259-H6-002-R06 | ACTCGrAGAGGAAAGGTTGGTAAAGGTTCGGTTGGATTCACTCGAGT | 0.96 |
| 259-H6-002-R07 | ACTCGArGAGGAAAGGTTGGTAAAGGTTCGGTTGGATTCACTCGAGT | 0.73 |
| 259-H6-002-R08 | ACTCGAGrAGGAAAGGTTGGTAAAGGTTCGGTTGGATTCACTCGAGT | 1.5 |
| 259-H6-002-R09 | ACTCGAGArGGAAAGGTTGGTAAAGGTTCGGTTGGATTCACTCGAGT | 2.0 (biphasic) |
| 259-H6-002-R10 | ACTCGAGAGrGAAAGGTTGGTAAAGGTTCGGTTGGATTCACTCGAGT | 0.44 |
| 259-H6-002-R11 | ACTCGAGAGGrAAAGGTTGGTAAAGGTTCGGTTGGATTCACTCGAGT | 0.01 |

A, C, G, T = 2'-deoxyribonucleotide; rA, rC, rG, rU = ribonucleotide

*: as determined by Biacore measurements

Fig. 21A

| Name | Sequence: 5'-3' | x-fold improved affinity* |
|---|---|---|
| 259-H6-002-R12 | ACTCGAGAGGAGAAGGAArAAGGTTGGTAAAGGTTCGGTTGGATTCACTCGAGT | 0.49 |
| 259-H6-002-R13 | ACTCGAGAGGAGAAGGAArAAGGTTGGTAAAGGTTCGGTTGGATTCACTCGAGT | 5.8 |
| 259-H6-002-R14 | ACTCGAGAGGAGAAGGAAArGGTTGGTAAAGGTTCGGTTGGATTCACTCGAGT | n.b. |
| 259-H6-002-R15 | ACTCGAGAGGAGAAGGAAAGrGTTGGTAAAGGTTCGGTTGGATTCACTCGAGT | 0.78 |
| 259-H6-002-R16 | ACTCGAGAGGAGAAGGAAAGGrUTGGTAAAGGTTCGGTTGGATTCACTCGAGT | 0.31 |
| 259-H6-002-R17 | ACTCGAGAGGAGAAGGAAAGGTrUGGTAAAGGTTCGGTTGGATTCACTCGAGT | n.b. |
| 259-H6-002-R18 | ACTCGAGAGGAGAAGGAAAGGTTrGGTAAAGGTTCGGTTGGATTCACTCGAGT | n.b. |
| 259-H6-002-R19 | ACTCGAGAGGAGAAGGAAAGGTTGrGTAAAGGTTCGGTTGGATTCACTCGAGT | 0.25 |
| 259-H6-002-R20 | ACTCGAGAGGAGAAGGAAAGGTTGGrUAAAGGTTCGGTTGGATTCACTCGAGT | 0.04 |
| 259-H6-002-R21 | ACTCGAGAGGAGAAGGAAAGGTTGGTrAAAGGTTCGGTTGGATTCACTCGAGT | 0.75 |
| 259-H6-002-R22 | ACTCGAGAGGAGAAGGAAAGGTTGGTArAAGGTTCGGTTGGATTCACTCGAGT | 2.05 |
| 259-H6-002-R23 | ACTCGAGAGGAGAAGGAAAGGTTGGTAArAGGTTCGGTTGGATTCACTCGAGT | 0.002 |

A, C, G, T = 2'-deoxyribonucleotide; rA, rG, rU = ribonucleotide

*: as determined by Biacore measurements n.b.: no binding

Fig. 21B

| Name | Sequence: 5'-3' | x-fold improved affinity* |
|---|---|---|
| 259-H6-002-R24 | ACTCGAGAGGAAAAGGTTGGTAAArGGTTCGGTTGGATTCACTCGAGT | 2.9 |
| 259-H6-002-R25 | ACTCGAGAGGAAAAGGTTGGTAAAgrGTTCGGTTGGATTCACTCGAGT | 0.83 |
| 259-H6-002-R26 | ACTCGAGAGGAAAAGGTTGGTAAAGGrUTCGGTTGGATTCACTCGAGT | n.b. |
| 259-H6-002-R27 | ACTCGAGAGGAAAAGGTTGGTAAAGGTrUCGGTTGGATTCACTCGAGT | n.b. |
| 259-H6-002-R28 | ACTCGAGAGGAAAAGGTTGGTAAAGGTTrCGGTTGGATTCACTCGAGT | 0.28 |
| 259-H6-002-R29 | ACTCGAGAGGAAAAGGTTGGTAAAGGTTCrGGTTGGATTCACTCGAGT | n.b. |
| 259-H6-002-R30 | ACTCGAGAGGAAAAGGTTGGTAAAGGTTCrGGTTGGATTCACTCGAGT | 2.7 |
| 259-H6-002-R31 | ACTCGAGAGGAAAAGGTTGGTAAAGGTTCGrUTGGATTCACTCGAGT | 2.0 |
| 259-H6-002-R32 | ACTCGAGAGGAAAAGGTTGGTAAAGGTTCGGTrUGGATTCACTCGAGT | n.b. |
| 259-H6-002-R33 | ACTCGAGAGGAAAAGGTTGGTAAAGGTTCGGTTrGGATTCACTCGAGT | n.b. |
| 259-H6-002-R34 | ACTCGAGAGGAAAAGGTTGGTAAAGGTTCGGTTGrGATTCACTCGAGT | n.b. |
| 259-H6-002-R35 | ACTCGAGAGGAAAAGGTTGGTAAAGGTTCGGTTGGrATTCACTCGAGT | 0.27 |

A, C, G, T = 2'-deoxyribonucleotide; rA, rC, rG, rU = ribonucleotide

*: as determined by Biacore measurements n.b.: no binding

Fig. 21C

| Name | Sequence: 5'-3' | x-fold improved affinity* |
|---|---|---|
| 259-H6-002-R36 | ACTCGAGAGGAAAGGTTGGTAAAGGTTCGGTTGGArUTCACTCGAGT | 2.1 |
| 259-H6-002-R37 | ACTCGAGAGGAAAGGTTGGTAAAGGTTCGGTTGGATrUCACTCGAGT | 0.55 |
| 259-H6-002-R38 | ACTCGAGAGGAAAGGTTGGTAAAGGTTCGGTTGGATTrCACTCGAGT | 1.6 |
| 259-H6-002-R39 | ACTCGAGAGGAAAGGTTGGTAAAGGTTCGGTTGGATTCrACTCGAGT | 1.3 |
| 259-H6-002-R40 | ACTCGAGAGGAAAGGTTGGTAAAGGTTCGGTTGGATTCArCTCGAGT | 0.75 |
| 259-H6-002-R41 | ACTCGAGAGGAAAGGTTGGTAAAGGTTCGGTTGGATTCACrUCGAGT | 0.90 |
| 259-H6-002-R42 | ACTCGAGAGGAAAGGTTGGTAAAGGTTCGGTTGGATTCACTrCGAGT | 0.71 |
| 259-H6-002-R43 | ACTCGAGAGGAAAGGTTGGTAAAGGTTCGGTTGGATTCACTCrGAGT | 0.92 |
| 259-H6-002-R44 | ACTCGAGAGGAAAGGTTGGTAAAGGTTCGGTTGGATTCACTCGrAGT | 1.1 |
| 259-H6-002-R45 | ACTCGAGAGGAAAGGTTGGTAAAGGTTCGGTTGGATTCACTCGArGT | 2.4 (biphasic) |
| 259-H6-002-R46 | ACTCGAGAGGAAAGGTTGGTAAAGGTTCGGTTGGATTCACTCGAGrU | 1.1 |

A, C, G, T = 2'-deoxyribonucleotide; rA, rC, rG, rU = ribonucleotide

*: as determined by Biacore measurements

Fig. 21D

| Name | Sequence: 5'-3' | $K_D$ (SPM) [nM] |
|---|---|---|
| 259-H6-002 | ACTCGAGAGGAAAGGTTGGTAAAGGTTCGGTTGGATTCACTCGAGT | 10.9 |
| 259-H6-002-R13 | ACTCGAGAGGAAAGGTTGGTAAArAAGGTTCGGTTGGATTCACTCGAGT | 1.77 |
| 259-H6-002-R24 | ACTCGAGAGGAAAGGTTGGTAAArGGTTCGGTTGGATTCACTCGAGT | 3.80 |
| 259-H6-002-R36 | ACTCGAGAGGAAAGGTTGGTAAAGGTTCGGTTGGArUTCACTCGAGT | 5.10 |
| 259-H6-002-R13_R24 | ACTCGAGAGGAAArAAGGTTGGTAAArGGTTCGGTTGGATTCACTCGAGT | 0.78 |
| 259-H6-002-R13_R36 | ACTCGAGAGGAAArAAGGTTGGTAAAGGTTCGGTTGGArUTCACTCGAGT | 0.97 |
| 259-H6-002-R13_R24_R36 | ACTCGAGAGGAAArAAGGTTGGTAAArGGTTCGGTTGGArUTCACTCGAGT | 0.43 |
| 259-H6-002-R13_R24_R30_R36 | ACTCGAGAGGAAArAAGGTTGGTAAArGGTTCGrGTTGGArUTCACTCGAGT | 0.33 |

A, C, G, T = 2'-deoxyribonucleotide; rA, rG, rU = ribonucleotide

Fig. 21E

| Name | Sequence: 5'-3' | Comp (SPM) |
|---|---|---|
| 257-E1-001 | GCAGTGGGGAAATGGGAGGGCTAGGTGGAAGGAATCTGAGCTACTGC | |
| 257-E1-R1-001 | rGCAGTGGGGAAATGGGAGGGCTAGGTGGAAGGAATCTGAGCTACTGC | < |
| 257-E1-R2-001 | GrCAGTGGGGAAATGGGAGGGCTAGGTGGAAGGAATCTGAGCTACTGC | < |
| 257-E1-R3-001 | GCrAGTGGGGAAATGGGAGGGCTAGGTGGAAGGAATCTGAGCTACTGC | < |
| 257-E1-R4-001 | GCArGTGGGGAAATGGGAGGGCTAGGTGGAAGGAATCTGAGCTACTGC | < |
| 257-E1-R5-001 | GCAGrUGGGGAAATGGGAGGGCTAGGTGGAAGGAATCTGAGCTACTGC | < |
| 257-E1-R6-001 | GCAGTrGGGGAAATGGGAGGGCTAGGTGGAAGGAATCTGAGCTACTGC | < |
| 257-E1-R7-001 | GCAGTGrGGGAAATGGGAGGGCTAGGTGGAAGGAATCTGAGCTACTGC | < |
| 257-E1-R8-001 | GCAGTGGrGGAAATGGGAGGGCTAGGTGGAAGGAATCTGAGCTACTGC | < |
| 257-E1-R9-001 | GCAGTGGGrGAAATGGGAGGGCTAGGTGGAAGGAATCTGAGCTACTGC | + |
| 257-E1-R10-001 | GCAGTGGGGrAAATGGGAGGGCTAGGTGGAAGGAATCTGAGCTACTGC | < |
| 257-E1-R11-001 | GCAGTGGGGArAATGGGAGGGCTAGGTGGAAGGAATCTGAGCTACTGC | < |
| 257-E1-R12-001 | GCAGTGGGGAArATGGGAGGGCTAGGTGGAAGGAATCTGAGCTACTGC | < |
| 257-E1-R13-001 | GCAGTGGGGAAArUGGGAGGGCTAGGTGGAAGGAATCTGAGCTACTGC | < |

A, C, G, T = 2'-desoxyribonucleotides; rA, rC, rG, rU = ribonucleotides

Comp(SPM): Molecules were tested as Spiegelmers in pull-down competition binding assay vs. 257-E1-001 as reference
+: better binding affinity than reference    <: weaker binding affinity than reference

Fig. 27A

| Name | Sequence: 5'-3' | Comp (SPM) |
|---|---|---|
| 257-E1-R14-001 | GCAGTGGGAAAT<u>rG</u>GAGGGCTAGGTGGAAGGAATCTGAGCTACTGC | < |
| 257-E1-R15-001 | GCAGTGGGAAAT<u>GrG</u>AGGGCTAGGTGGAAGGAATCTGAGCTACTGC | ++ |
| 257-E1-R16-001 | GCAGTGGGAAATGG<u>rGrG</u>GGGCTAGGTGGAAGGAATCTGAGCTACTGC | < |
| 257-E1-R17-001 | GCAGTGGGAAATGG<u>rA</u>GGGCTAGGTGGAAGGAATCTGAGCTACTGC | < |
| 257-E1-R18-001 | GCAGTGGGAAATGGGA<u>rG</u>GGCTAGGTGGAAGGAATCTGAGCTACTGC | + |
| 257-E1-R19-001 | GCAGTGGGAAATGGGAG<u>rGrG</u>CTAGGTGGAAGGAATCTGAGCTACTGC | + |
| 257-E1-R20-001 | GCAGTGGGAAATGGGAGGG<u>rG</u>CTAGGTGGAAGGAATCTGAGCTACTGC | < |
| 257-E1-R21-001 | GCAGTGGGAAATGGGAGGG<u>rC</u>TAGGTGGAAGGAATCTGAGCTACTGC | < |
| 257-E1-R22-001 | GCAGTGGGAAATGGGAGGGC<u>rU</u>AGGTGGAAGGAATCTGAGCTACTGC | < |
| 257-E1-R23-001 | GCAGTGGGAAATGGGAGGGCT<u>rA</u>GGTGGAAGGAATCTGAGCTACTGC | < |
| 257-E1-R24-001 | GCAGTGGGAAATGGGAGGGCTA<u>rG</u>GTGGAAGGAATCTGAGCTACTGC | < |
| 257-E1-R25-001 | GCAGTGGGAAATGGGAGGGCTAG<u>rG</u>TGGAAGGAATCTGAGCTACTGC | < |
| 257-E1-R26-001 | GCAGTGGGAAATGGGAGGGCTAGG<u>rU</u>GGAAGGAATCTGAGCTACTGC | = |
| 257-E1-R27-001 | GCAGTGGGAAATGGGAGGGCTAGGT<u>rG</u>GAAGGAATCTGAGCTACTGC | < |

A, C, G, T = 2'-desoxyribonucleotides; rA, rC, rG, rU = ribonucleotides

Comp(SPM): Molecules were tested as Spiegelmers in pull-down competition binding assay vs. 257-E1-001 as reference
=: similar binding affinity as reference +: better binding affinity than reference ++: much better binding affinity than reference <: weaker binding affinity than reference

Fig. 27B

| Name | Sequence: 5'-3' | Comp (SPM) |
|---|---|---|
| 257-E1-R28-001 | GCAGTGGGGAAATGGGAGGGCTAGGTGrGAAGGAATCTGAGCTACTGC | < |
| 257-E1-R29-001 | GCAGTGGGGAAATGGGAGGGCTAGGTGGrAAGGAATCTGAGCTACTGC | ++ |
| 257-E1-R30-001 | GCAGTGGGGAAATGGGAGGGCTAGGTGGArAGGAATCTGAGCTACTGC | ++ |
| 257-E1-R31-001 | GCAGTGGGGAAATGGGAGGGCTAGGTGGAArGGAATCTGAGCTACTGC | < |
| 257-E1-R32-001 | GCAGTGGGGAAATGGGAGGGCTAGGTGGAAGrGAATCTGAGCTACTGC | < |
| 257-E1-R33-001 | GCAGTGGGGAAATGGGAGGGCTAGGTGGAAGGrAATCTGAGCTACTGC | < |
| 257-E1-R34-001 | GCAGTGGGGAAATGGGAGGGCTAGGTGGAAGGArATCTGAGCTACTGC | < |
| 257-E1-R35-001 | GCAGTGGGGAAATGGGAGGGCTAGGTGGAAGGAArTCTGAGCTACTGC | < |
| 257-E1-R36-001 | GCAGTGGGGAAATGGGAGGGCTAGGTGGAAGGAATrCTGAGCTACTGC | < |
| 257-E1-R37-001 | GCAGTGGGGAAATGGGAGGGCTAGGTGGAAGGAATCrUGAGCTACTGC | < |
| 257-E1-R38-001 | GCAGTGGGGAAATGGGAGGGCTAGGTGGAAGGAATCTrGAGCTACTGC | < |
| 257-E1-R39-001 | GCAGTGGGGAAATGGGAGGGCTAGGTGGAAGGAATCTGrAGCTACTGC | < |
| 257-E1-R40-001 | GCAGTGGGGAAATGGGAGGGCTAGGTGGAAGGAATCTGArGCTACTGC | < |
| 257-E1-R41-001 | GCAGTGGGGAAATGGGAGGGCTAGGTGGAAGGAATCTGAGrCTACTGC | < |

A, C, G, T = 2'-desoxyribonucleotides; rA, rC, rG, rU = ribonucleotides

Comp(SPM): Molecules were tested as Spiegelmers in pull-down competition binding assay vs. 257-E1-001 as reference
++: much better binding affinity than reference <: weaker binding affinity than reference

Fig. 27C

| Name | Sequence: 5'-3' | Comp (SPM) |
|---|---|---|
| 257-E1-R42-001 | GCAGTGGGGAAATGGGAGGGCTAGGTGGAAGGAATCTGAGCrUACTGC | < |
| 257-E1-R43-001 | GCAGTGGGGAAATGGGAGGGCTAGGTGGAAGGAATCTGAGCTrACTGC | < |
| 257-E1-R44-001 | GCAGTGGGGAAATGGGAGGGCTAGGTGGAAGGAATCTGAGCTArCTGC | < |
| 257-E1-R45-001 | GCAGTGGGGAAATGGGAGGGCTAGGTGGAAGGAATCTGAGCTACrUGC | < |
| 257-E1-R46-001 | GCAGTGGGGAAATGGGAGGGCTAGGTGGAAGGAATCTGAGCTACTrGC | = |
| 257-E1-R47-001 | GCAGTGGGGAAATGGGAGGGCTAGGTGGAAGGAATCTGAGCTACTGrC | < |

A, C, G, T = 2'-desoxyribonucleotides; rA, rC, rG, rU = ribonucleotides

Comp(SPM): Molecules were tested as Spiegelmers in pull-down competition binding assay vs. 257-E1-001 as reference
=: similar binding affinity as reference   <: weaker binding affinity than reference

Fig. 27D

| Name | Sequence: 5'-3' | Comp (SPM) Improvement factor of affinity |
|---|---|---|
| 257-E1-R15/29-001 | GCAGTGGGGAAATGrGGAGGGCTAGGTGGrAAGGAATCTGAGCTACTGC | 10 |
| 257-E1-R29/30-001 | GCAGTGGGGAAATGGGAGGGCTAGGTGGrGrArAGGAATCTGAGCTACTGC | 3.8 |
| 257-E1-R15/29/30-001 | GCAGTGGGGAAATGrGGAGGGCTAGGTGGrGrArAGGAATCTGAGCTACTGC | 9.4 |
| 257-E1-R18/29/30-001 | GCAGTGGGGAAATGGGArGGGCTAGGTGGrGrArAGGAATCTGAGCTACTGC | 5.3 |
| 257-E1-R15/18/29/30-001 | GCAGTGGGGAAATGrGGArGGGCTAGGTGGrGrArAGGAATCTGAGCTACTGC | 9.4 |
| 257-E1-6xR-001 (=257-E1-R9/15/18/19/29/30-001) | GCAGTGGrGrGAAATGrGGArGrGGCTAGGTGGrGrArAGGAATCTGAGCTACTGC | 29 |

A, C, G, T = 2'-desoxyribonucleotides; rA, rC, rG, rU = ribonucleotides

Comp(SPM): Molecules were tested as Spiegelmers in pull-down competition binding assays vs. 257-E1-001 as reference; the listed factors represent the degree of improvement normalized to the reference molecule 257-E1-001

Fig. 27E

| Name | Sequence: 5'-3' | Comp (SPM) Improvement factor of affinity |
|---|---|---|
| 257-E1-6xR-001 | GCAGTGGGrGAAATGrGGArGrGGCTAGGTGGrArAGGAATCTGAGCTACTGC | 1 |
| 257-E1-7xR-021 | GCGCGGGrGAAArTGrGGArGrGGCTAGGTGGrArAGGAATCTGAGCCGCGC | < |
| 257-E1-7xR-022 | GCGCGGGrGAAATGrGGArGrGGCrTAGGTGGrArAGGAATCTGAGCCGCGC | < |
| 257-E1-7xR-023 | GCGCGGGrGAAATGrGGArGrGGCTAGGrTGGrArAGGAATCTGAGCCGCGC | 1.5 |
| 257-E1-7xR-024 | GCGCGGGrGAAATGrGGArGrGGCTAGGTGGrArAGGAArTCTGAGCCGCGC | < |
| 257-E1-7xR-025 | GCGCGGGrGAAATGrGGArGrGGCTAGGTGGrArAGGAATCrTGAGCCGCGC | < |

A, C, G, T = 2'-desoxyribonucleotides; rA, rC, rG, rT = ribonucleotides

Comp(SPM): Molecules were tested as Spiegelmers in pull-down competition binding assay vs. 257-E1-6xR-001 as reference; the listed factors represent the degree of improvement normalized to the reference molecule 257-E1-6xR-001

<: weaker binding affinity than reference molecule 257-E1-6xR-001

Fig. 27F

NUCLEIC ACID MOLECULE HAVING BINDING AFFINITY TO A TARGET MOLECULE AND A METHOD FOR GENERATING THE SAME

The present invention relates to a method for generating a nucleic acid molecule capable of binding to a target molecule, a nucleic acid molecule obtainable by the method, the use of the nucleic acid molecule, a nucleic acid molecule capable of binding to a target molecule wherein the nucleic acid molecule has an increased binding affinity or the same binding affinity to the target molecule compared to a reference nucleic acid molecule. Furthermore, the present invention relates to the use of the nucleic acid molecule having an increased or the same binding affinity in a method of treatment and/or diagnosis of a disease.

Besides the use of comparatively small organic molecules the development of novel therapeutic concepts resorts increasingly to monoclonal antibodies, peptides and functional nucleic acid molecules, i.e. such nucleic acid molecules that bind specifically to a target structure or target molecule. Representatives of these functional nucleic acid molecules are the so called aptamers that have already been developed against a multitude of different biomolecules. Thereby, starting from a D-nucleic acid library, one or more D-nucleic acid molecules, the so called aptamers, that are characterized by a particularly high affinity towards their target structure or target molecule, are isolated in several steps by in vitro selection. Methods for the preparation of such aptamers are described, for example, in European patent EP 0 533 838.

The first aptamers were discovered by use of combinatorial RNA or DNA oligonucleotide libraries. RNA aptamers as well as DNA aptamers are D-nucleic acid molecules and are quickly degraded in a biological system such as the human or animal body by nucleases what makes them useless for therapeutic applications. Hence, the stabilization of an aptamer is the essential step in the development process of an aptamer drug candidate. Stabilization can be achieved by a) protecting the 5'- and 3'-end of the aptamer by addition of capping moieties at both the 5'- and 3'-ends of the aptamer,
b) incorporating modifications to the ribose or the deoxyribose backbone, or
c) incorporating phosphate backbone components.

By adding capping moieties at the 5'-end of aptamers the serum and in vivo stability of aptamers can be improved, in particular with regard to 5'-->3' nucleases and 5'-->3' exonucleases present in the body fluids of the human and animal body. This kind of modification can be introduced as modified phosphoramidites in the conventional solid-phase synthesis or by post-synthesis coupling. Often a 5'-amino modifier containing a 5'-amino group is used, whereby the 5'-amino group can serve as a nucleophile for subsequent derivatization. The most common 5'-modification is polyethylene glycol. Other modifications are selected from the group of cholesterol, fatty acids, polycations and proteins. In addition to conferring stabilization of the 5'-end of the aptamers, such modification can be used for altering the pharmacokinetic profile and/or biodistribution of the aptamer.

Adding capping moieties at the 3'-end of aptamers confers to aptamers protection against 3'-->5' exonucleases present in serum of man and animals. Nucleotide and non-nucleotide 3'-caps are known. The most commonly used 3'-cap is inverted thymidine (3'-idT).

Chemical modification at the 2' position of the ribose or deoxyribose backbone of aptamers are a prerequisite for the use of aptamers in vivo. These 2'-modifications are typically selected from the group of 2'-F, 2'-O-methyl, 2'-amino. Techniques are available in the art to introduce said 2'-F, 2'-O-methyl, 2'-amino modifications into the aptamer sequence within the SELEX process (to some extent) or in a so called post-SELEX optimization process, wherein the individual aptamer sequence is optimized by the stepwise substitution of the natural nucleotides by 2'-F, 2'-O-methyl or 2'-amino nucleotides.

Phosphate backbone modifications introduce sulfur(s) in place of non-briding phosphodiester oxygens(s) thereby conferring nuclease resistance to aptamers. A preferred form of such sulfur modified backbone are phosphorothioates. Phosphorothioates can be enzymatically incorporated into aptamers with the SELEX process or by solid-phase synthesis. Phosphorodithioate aptamers have to be produced by solid-phase synthesis.

Apart from aptamers the so-called spiegelmers constitute a further form of functional nucleic acids. Like aptamers, spiegelmers bind specifically to a target molecule or target structure. Spiegelmers are identified by a process that uses a D-nucleic acid library for in vitro selection against the enantiomeric form of the target molecule or target structure, and thereupon the thus identified D-nucleic acids binding to the enantiomeric form of the target molecule or target structure are prepared as corresponding L-nucleic acids. As a result of the principle of chiral reciprocity these L-nucleic acids which are referred to as spiegelmers are able to bind to the true or actual target molecule and not to the enantiomeric form thereof used for the selection process. Preferably such true or actual target molecule or target structure is the target molecule or target structure as present in a biological system such as a human or animal body. Methods for the preparation of such spiegelmers are described, for example, in international patent application WO 98/08856.

As spiegelmers are L-nucleic acid molecules, typically L-oligonucleotides, assembled from L-nucleotides they cannot be degraded by natural enzymes. Apart from the target specificity, this characteristic qualifies them for use in the most different areas, such as, e.g., analysis of biological samples, diagnosis and therapy.

In contrast to aptamers that have to be stabilized, prior to their use, against degradation by nucleases as outlined above, there is no need for stabilizing spiegelmers prior to their use such as in functional assays, in cell-based assays, in in vivo experiments and/or in in vivo applications for therapy or diagnosis. The in vivo applicability of spiegelmers was proven in man and various animal species. For spiegelmers NOX-E36 and NOX-A12 clinical trials were initiated in 2009.

Because no chemical modification for the purpose of stabilization is needed for spiegelmers, spiegelmers, in terms of nucleotide building blocks, solely consist of ribonucleotides or 2'-deoxyribonucleotides, more precisely of L-ribonucleotides or L-2'-deoxyribonucleotides. An advantage of spiegelmers in drug development arising therefrom is the absence of the time-consuming, costly and—to date regarded as—risky process of substituting non-modified nucleotides, i.e. L-ribonucleotides and L-2'-deoxyribonucleotides, by modified nucleotides such as 2'-F-ribonucleotides, 2'-O-methylribonucleotides and 2'-aminoribonucleotides. A further advantage of spiegelmers solely consisting of L-ribonucleotides or L-2'-deoxyribonucleotides in drug development is the absence of potential toxic effects or intolerance of such chemically modified nucleotides and/or the degradation products thereof.

Thus, the in vivo potency of spiegelmers solely consisting of L-ribonucleotides or L-2'-deoxyribonucleotides typically only depends on their affinity to the target molecule and, as result thereof, on their effects on the function of the target molecule or target structure and their pharmacokinetic behaviour in the human or animal body.

The problem underlying the present invention is to provide a method for generating a nucleic acid molecule capable of binding to a target molecule starting from a reference nucleic acid molecule which is binding to a target molecule. Preferably the target molecule to which the nucleic acid molecule is capable of binding is the target molecule to which the reference nucleic acid molecule is binding.

A further problem underlying the present invention is to provide a method for generating a nucleic acid molecule capable of binding to a target molecule starting from a reference nucleic acid molecule which is binding to a target molecule, whereby the nucleic acid molecule capable of binding to a target molecule has the same or an improved binding characteristic compared to the reference nucleic acid molecule, whereby preferably the binding characteristic is the binding affinity to the target molecule.

A still further problem underlying the present invention is to provide a nucleic acid molecule and more specifically a functional nucleic acid molecule such as an aptamer or a spiegelmer having an improved binding affinity to its target molecule or the same binding affinity compared to a reference nucleic acid molecule.

These and other problems underlying the present invention are solved by the subject matter of the attached independent claims. Preferred embodiments may be taken from the dependent claims.

More specifically, the problem underlying the present invention is solved in a first aspect which is also the first embodiment of the first aspect, by a method for generating a nucleic acid molecule capable of binding to a target molecule comprising the following steps:

a) providing a reference nucleic acid molecule, wherein the reference nucleic acid molecule is capable of binding to the target molecule and wherein the reference nucleic acid molecule comprises a sequence of nucleotides, wherein the sequence of nucleotides comprises n nucleotides;

b) preparing a first level derivative of the reference nucleic acid molecule, wherein the first level derivative of the reference nucleic acid molecule differs from the reference nucleic acid molecule at one nucleotide position, wherein the first level derivative is prepared by replacing the ribonucleotide at the one nucleotide position by a 2'-deoxyribonucleotide in case the reference nucleic acid has a ribonucleotide at the nucleotide position and wherein the first level derivative is prepared by replacing the 2'-deoxyribonucleotide at the one nucleotide position by a ribonucleotide in case the reference nucleic acid has a 2'-deoxyribonucleotide at the nucleotide position and wherein the nucleotide position at which the replacement is made is the modified nucleotide position; and c) repeating step b) for each nucleotide position of the reference nucleic acid molecule, thus preparing a group of first level derivatives of the reference nucleic acid molecule, wherein the group of first level derivatives of the reference nucleic acid molecule consists of n first level derivatives, wherein each of the first level derivatives of the reference nucleic acid molecule differs from the reference nucleic acid molecule by a single nucleotide replacement and wherein each of the first level derivatives of the reference nucleic acid molecule has a single modified nucleotide position which is different from the single modified nucleotide of all of the single modified nucleotide positions of the other first level derivatives of the group of first level derivatives of the reference nucleic acid molecule.

In a second embodiment of the first aspect which is also an embodiment of the first embodiment of the first aspect, the method comprises step d) and optionally step e):

d) determining the binding characteristic to the target molecule for each of the n first level derivatives of the reference nucleic acid; and optionally e) identifying the/those first level derivative(s) of the reference nucleic acid molecule the binding characteristic of which exceed a predetermined threshold value.

In a third embodiment of the first aspect which is also an embodiment of the second embodiment of the first aspect, the binding characteristic is the binding affinity of the first level derivative(s) of the reference nucleic acid molecule to the target molecule.

In a fourth embodiment of the first aspect which is also an embodiment of the second and the third embodiment of the first aspect, the binding affinity is expressed as the $K_D$ value.

In a fifth embodiment of the first aspect which is also an embodiment of the second, the third and the fourth embodiment of the first aspect, the predetermined threshold value is Y with Y being the quotient of (binding affinity of the reference nucleic acid molecule)/(binding affinity of the first level derivative) and wherein Y>1, more preferably Y≥2 and most preferably Y≥5 or Y≥10.

In a sixth embodiment of the first aspect which is also an embodiment of the second, the third, the fourth and the fifth embodiment of the first aspect, the predetermined threshold value is X with X being the quotient of ($K_D$ value of the reference nucleic acid molecule)/($K_D$ value of the first level derivative) and wherein X>1, more preferably X≥2 and most preferably ≥5 or X≥10.

In a seventh embodiment of the first aspect which is also an embodiment of the first, the second, the third, the fourth, the fifth and the sixth embodiment of the first aspect, if in step b) the first level derivative is prepared by replacing the ribonucleotide at the one nucleotide position by a 2'-deoxyribonucleotide and (a) if the ribonucleotide is adenosine-5'-phosphate, the 2'-deoxyribonucleotide is 2'-deoxyadenosine-5-phosphate;

(b) if the ribonucleotide is guanosine-5'-phosphate, the 2'-deoxyribonucleotide is 2'-deoxyguanosine-5'-phosphate;

(c) if the ribonucleotide is cytidine-5'-phosphate, the 2'-deoxyribonucleotide is 2'-deoxycytidine-5'phosphate; and (d) if the ribonucleotide is uridine-5'-phosphate, the 2'-deoxyribonucleotide is 2'-deoxyuridine-5'-phosphate or thymidine-5-phosphate;

and if in step b) the first level derivative is prepared by replacing the 2'-deoxyribonucleotide at the one nucleotide position by a ribonucleotide and (a) if the 2'-deoxyribonucleotide is 2'-deoxyadenosine-5'-phosphate, the ribonucleotide is adenosine-5'-phosphate;

(b) if the 2'-deoxyribonucleotide is 2'-deoxyguanosine-5'phosphate, the ribonucleotide is guanosine-5'-phosphate;

(c) if the 2'-deoxyribonucleotide is 2'-deoxycytidine-5'phosphate, the ribonucleotide is cytidine-5'-phosphate; and (d) if the 2'-deoxyribonucleotide is thymidine-5'-phosphate, the ribonucleotide is uridine-5'-phosphate or 5-methyl-uridine-5'-phosphate.

In an eighth embodiment of the first aspect which is also an embodiment of the first, the second, the third, the fourth, the fifth, the sixth and the seventh embodiment of the first aspect, if in step b) the first level derivative is prepared by replacing the ribonucleotide at the one nucleotide position by a 2'-deoxyribonucleotide and
  (a) if the ribonucleotide is adenosine-5'-phosphate, the 2'-deoxyribonucleotide is 2'-deoxyadenosine-5'-phosphate;
  (b) if the ribonucleotide is guanosine-5'-phosphate, the 2'-deoxyribonucleotide is 2'-deoxyguanosine-5'-phosphate;
  (c) if the ribonucleotide is cytidine-5'-phosphate, the 2'-deoxyribonucleotide is 2'-deoxycytidine-5'-phosphate; and
  (d) if the ribonucleotide is uridine-5'-phosphate, the 2'-deoxyribonucleotide is 2'-deoxyuridine-5'-phosphate;
and
if in step b) the first level derivative is prepared by replacing the 2'-deoxyribonucleotide at the one nucleotide position by a ribonucleotide and
  (a) if the 2'-deoxyribonucleotide is 2'-deoxyadenosine-5'-phosphate, the ribonucleotide is adenosine-5'-phosphate;
  (b) if the 2'-deoxyribonucleotide is 2'-deoxyguanosine-5'-phosphate, the ribonucleotide is guanosine-5'-phosphate;
  (c) if the 2'-deoxyribonucleotide is 2'-deoxycytidine-5'-phosphate, the ribonucleotide is cytidine-5'-phosphate; and
  (d) if the 2'-deoxyribonucleotide is thymidine-5'-phosphate, the ribonucleotide is 5-methyl-uridine-5'phosphate.

In a ninth embodiment of the first aspect which is also an embodiment of the first, the second, the third, the fourth, the fifth and the sixth embodiment of the first aspect, the reference nucleic acid is a ribonucleic acid molecule and wherein in step b) the first level derivative is prepared by replacing the ribonucleotide at the one nucleotide position by a 2'-deoxyribonucleotide and wherein if
  (a) the ribonucleotide is adenosine-5'-phosphate, the 2'-deoxyribonucleotide is 2'-deoxyadenosine-5'-phosphate;
  (b) the ribonucleotide is guanosine 5'-phosphate, the 2'-deoxyribonucleotide is 2'-deoxyguanosine-5'-phosphate;
  (c) the ribonucleotide is cytidine-5'-phosphate, the 2'-deoxyribonucleotide is 2'-deoxycytidine-5'-phosphate;
  (d) the ribonucleotide is uridine-5'-phosphate, the 2'-deoxyribonucleotide is 2'-deoxy uridine-5'-phosphate or thymidine-5'phosphate.

In a tenth embodiment of the first aspect which is also an embodiment of the first, the second, the third, the fourth, the fifth, the sixth, the seventh, the eighth and the ninth embodiment of the first aspect, the reference nucleic acid is a 2'-deoxyribonucleic acid molecule and wherein in step b) the first level derivative is prepared by replacing the 2'-deoxyribonucleotide at the one nucleotide position by a ribonucleotide and wherein if
  (a) if the 2'-deoxyribonucleotide is 2'-deoxyadenosine-5'-phosphate, the ribonucleotide is adenosine-5'-phosphate;
  (b) if the 2'-deoxyribonucleotide is 2'-deoxyguanosine-5'-phosphate, the ribonucleotide is guanosine-5'-phosphate;
  (c) if the 2'-deoxyribonucleotide is 2'-deoxycytidine-5'-phosphate, the ribonucleotide is cytidine-5'-phosphate; and
  (d) if the 2'-deoxyribonucleotide is thymidine-5'phosphate, the ribonucleotide is uridine-5'-phosphate or 5-methyl-uridine 5'-phosphate.

In an eleventh embodiment of the first aspect which is also an embodiment of the tenth embodiment of the first aspect, if the 2'-deoxyribonucleotide is thymidine-5'-phosphate, the ribonucleotide is 5-methyl-uridine-5'-phosphate.

In a twelfth embodiment of the first aspect which is also an embodiment of the first, the second, the third, the fourth, the fifth, the sixth, the seventh, the eighth, the ninth, the tenth and the eleventh embodiment of the first aspect, the method is a method for generating a nucleic acid molecule capable of binding to the target molecule, wherein the binding affinity of the nucleic acid molecule is increased or the same as the binding affinity of the reference nucleic acid molecule to the target molecule.

In a thirteenth embodiment of the first aspect which is also an embodiment of the second, the third, the fourth, the fifth, the sixth, the seventh, the eighth, the ninth, the tenth, the eleventh and the twelfth embodiment of the first aspect, the first level derivative the binding characteristic of which exceeds the predetermined threshold value, is a or the nucleic acid molecule capable of binding to a or the target molecule.

In a fourteenth embodiment of the first aspect which is also an embodiment of the second, the third, the fourth, the fifth, the sixth, the seventh, the eighth, the ninth, the tenth, the eleventh, the twelfth and the thirteenth embodiment of the first aspect, a second level derivative of the reference nucleic acid molecule is prepared, wherein the second level derivative differs from the reference nucleic acid molecule at at least a first nucleotide position and a second nucleotide position, wherein the first nucleotide position is the modified nucleotide position of a first first level derivative of the reference nucleic acid molecule from the group of derivatives of the reference nucleic acid molecule consisting of n derivatives and wherein the first level derivative is one the binding characteristic of which exceeds the predetermined threshold value, and wherein the nucleotide of the first nucleotide position is identical to the nucleotide at the modified position of the first level derivative of the reference nucleic acid molecule, and wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule.

In a fifteenth embodiment of the first aspect which is also an embodiment of the fourteenth embodiment of the first aspect, the first first level derivative and the second first level derivative is any combination of two first level derivatives, wherein the binding characteristic of each of the two first level derivatives exceeds the predetermined threshold.

In a sixteenth embodiment of the first aspect which is also an embodiment of the fourteenth and the fifteenth embodiment of the first aspect, the first first level derivative and the second level derivative are the two first level derivatives which have a binding characteristic superior to the rest of the first level derivatives of the group of first level derivatives of the reference nucleic acid molecule consisting of n nucleotides.

In a seventeenth embodiment of the first aspect which is also an embodiment of the fourteenth, the fifteenth and the sixteenth embodiment of the first aspect, the second level derivative of the reference nucleic acid molecule is capable of binding to the target molecule.

In an eighteenth embodiment of the first aspect which is also an embodiment of the fifteenth, the sixteenth and the seventeenth embodiment of the first aspect, the method comprises:

determining the binding characteristic of the second level derivative of the reference nucleic acid molecule to the target molecule; and optionally identifying the/those second level derivative(s) of the reference nucleic acid molecule the binding characteristic of which exceed a predetermined threshold value.

In a nineteenth embodiment of the first aspect which is also an embodiment of the eighteenth embodiment of the first aspect, the binding characteristic is the binding affinity of the second level derivative(s) of the reference nucleic acid molecule to the target molecule.

In a twentieth embodiment of the first aspect which is also an embodiment of the eighteenth and the nineteenth embodiment of the first aspect, the binding affinity is expressed as the $K_D$ value.

In a twenty-first embodiment of the first aspect which is also an embodiment of the eighteenth, the nineteenth and the twentieth embodiment of the first aspect, the predetermined threshold value is Y with Y being the quotient of (binding affinity of the reference nucleic acid molecule)/(binding affinity of the second level derivative) and wherein Y>1, more preferably Y≥2 and most preferably Y≥5 or Y≥10 or Y≥20.

In a twenty-second embodiment of the first aspect which is also an embodiment of the eighteenth, the nineteenth, the twentieth and the twenty-first embodiment of the first aspect, the predetermined threshold value is X with X being the quotient of (KD value of the reference nucleic acid molecule)/(KD value of the second level derivative) and wherein X>1, more preferably X≥2 and most preferably X≥5 or X≥10 or X≥20.

In a twenty-third embodiment of the first aspect which is also an embodiment of the fourteenth, the fifteenth, the sixteenth, the seventeenth, the eighteenth, the nineteenth, the twentieth, the twenty-first and the twenty-second embodiment of the first aspect, the second level derivative the binding characteristic of which exceeds the predetermined threshold value, is a or the nucleic acid molecule capable of binding to a or the target molecule.

In a twenty-fourth embodiment of the first aspect which is also an embodiment of the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second and the twenty-third embodiment of the first aspect, a third level derivative of the reference nucleic acid molecule is prepared, wherein the third level derivative differs from the reference nucleic acid molecule at at least a first nucleotide position, a second nucleotide position and a third nucleotide position, wherein the first nucleotide position is the modified nucleotide position of a first first level derivative of the reference nucleic acid molecule from the group of derivatives of the reference nucleic acid molecule consisting of n derivatives and wherein the first level derivative is one the binding characteristic of which exceeds the predetermined threshold value, and wherein the nucleotide of the first nucleotide position is identical to the nucleotide at the modified position of the first first level derivative of the reference nucleic acid molecule, wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule, wherein the third nucleotide position is the modified nucleotide position of a third first level derivative of the reference nucleic acid molecule from the group of derivatives of the reference nucleic acid molecule consisting of n derivatives and wherein the third first level derivative is one the binding characteristic of which exceeds the predetermined threshold value and wherein the nucleotide of the third nucleotide position is identical to the nucleotide at the modified position of the third first level derivative of the reference nucleic acid molecule.

In a twenty-fifth embodiment of the first aspect which is also an embodiment of the twenty-fourth embodiment of the first aspect, the first first level derivative, the second first level derivative and the third first level derivative is any combination of three first level derivatives, wherein the binding characteristic of each of the three first level derivatives exceeds the predetermined threshold.

In a twenty-sixth embodiment of the first aspect which is also an embodiment of the twenty-fourth and the twenty-fifth embodiment of the first aspect, the first first level derivative, the second first level derivative and the third first level derivative are the three first level derivatives which have a binding characteristic superior to the rest of the first level derivatives of the group of first level derivatives of the reference nucleic acid molecule consisting of n nucleotides.

In a twenty-seventh embodiment of the first aspect which is also an embodiment of the twenty-fourth, the twenty-fifth and the twenty-sixth embodiment of the first aspect, the third level derivative of the reference nucleic acid molecule is capable of binding to the target molecule.

In a twenty-eighth embodiment of the first aspect which is also an embodiment of the twenty-fifth, the twenty-sixth and the twenty-seventh embodiment of the first aspect, the method comprises:

determining the binding characteristic of the third level derivative of the reference nucleic acid molecule to the target molecule; and optionally identifying the/those third level derivative(s) of the reference nucleic acid molecule the binding characteristic of which exceed a predetermined threshold value.

In a twenty-ninth embodiment of the first aspect which is also an embodiment of the twenty-eighth embodiment of the first aspect, the binding characteristic is the binding affinity of the third level derivative(s) of the reference nucleic acid molecule to the target molecule.

In a thirtieth embodiment of the first aspect which is also an embodiment of the twenty-eighth and the twenty-ninth embodiment of the first aspect, the binding affinity is expressed as the $K_D$ value.

In a thirty-first embodiment of the first aspect which is also an embodiment of the twenty-eighth, the twenty-ninth and the thirtieth embodiment of the first aspect, the predetermined threshold value is Y with Y being the quotient of (binding affinity of the reference nucleic acid molecule)/(binding affinity of the third level derivative) and wherein Y>1, more preferably Y≥2 and most preferably Y≥5 or Y≥10 or Y≥20.

In a thirty-second embodiment of the first aspect which is also an embodiment of the twenty-eighth, the twenty-ninth, the thirtieth and the thirty-first embodiment of the first aspect, the predetermined threshold value is X with X being the quotient of (KD value of the reference nucleic acid molecule)/(KD value of the third level derivative) and wherein X>1, more preferably X≥2 and most preferably X≥5 or X≥10 or X≥20.

In a thirty-third embodiment of the first aspect which is also an embodiment of the twenty-fourth, the twenty-fifth, the twenty-sixth, the twenty-seventh, the twenty-eighth, the twenty-ninth, the thirtieth, the thirty-first and the thirty-second embodiment of the first aspect, the third level derivative the binding characteristic of which exceeds the predetermined threshold value, is a or the nucleic acid molecule capable of binding to a or the target molecule.

In a thirty-fourth embodiment of the first aspect which is also an embodiment of the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second and the thirty-third embodiment of the first aspect, a fourth level derivative of the reference nucleic acid molecule is prepared, wherein the fourth level derivative differs from the reference nucleic acid molecule at at least a first nucleotide position, a second nucleotide position, a third nucleotide position and a fourth nucleotide position, wherein the first nucleotide position is the modified nucleotide position of a first first level derivative of the reference nucleic acid molecule from the group of derivatives of the reference nucleic acid molecule consisting of n derivatives and wherein the first level derivative is one the binding characteristic of which exceeds the predetermined threshold value, and wherein the nucleotide of the first nucleotide position is identical to the nucleotide at the modified position of the first first level derivative of the reference nucleic acid molecule, wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule, wherein the third nucleotide position is the modified nucleotide position of a third first level derivative of the reference nucleic acid molecule from the group of derivatives of the reference nucleic acid molecule consisting of n derivatives and wherein the third first level derivative is one the binding characteristic of which exceeds the predetermined threshold value and wherein the nucleotide of the third nucleotide position is identical to the nucleotide at the modified position of the third level derivative of the reference nucleic acid molecule, and wherein the fourth nucleotide position is the modified nucleotide position of a fourth first level derivative of the reference nucleic acid molecule from the group of derivatives of the reference nucleic acid molecule consisting of n derivatives and wherein the fourth first level derivative is one the binding characteristic of which exceeds the predetermined threshold value and wherein the nucleotide of the fourth nucleotide position is identical to the nucleotide at the modified position of the fourth first level derivative of the reference nucleic acid molecule.

In a thirty-fifth embodiment of the first aspect which is also an embodiment of the thirty-fourth embodiment of the first aspect, the first first level derivative, the second first level derivative, the third first level derivative and the fourth first level derivative is any combination of four first level derivatives, wherein the binding characteristic of each of the four first level derivatives exceeds the predetermined threshold.

In a thirty-sixth embodiment of the first aspect which is also an embodiment of the thirty-fourth and thirty-fifth embodiment of the first aspect, wherein the first first level derivative, the second first level derivative, the third first level derivative and the fourth first level derivative are the four first level derivatives which have a binding characteristic superior to the rest of the first level derivatives of the group of first level derivatives of the reference nucleic acid molecule consisting of n nucleotides.

In a thirty-seventh embodiment of the first aspect which is also an embodiment of the thirty-fourth, the thirty-fifth and the thirty-sixth embodiment of the first aspect, the fourth level derivative of the reference nucleic acid molecule is capable of binding to the target molecule.

In a thirty-eighth embodiment of the first aspect which is also an embodiment of the thirty-fifth, the thirty-sixth and the thirty-seventh embodiment of the first aspect, the method comprises:
  determining the binding characteristic of the fourth level derivative of the reference nucleic acid molecule to the target molecule; and optionally
  identifying the/those fourth level derivative(s) of the reference nucleic acid molecule the binding characteristic of which exceed a predetermined threshold value.

In a thirty-ninth embodiment of the first aspect which is also an embodiment of the thirty-eighth embodiment of the first aspect, the binding characteristic is the binding affinity of the fourth level derivative(s) of the reference nucleic acid molecule to the target molecule.

In a fortieth embodiment of the first aspect which is also an embodiment of the thirty-eighth and the thirty-ninth embodiment of the first aspect, the binding affinity is expressed as the $K_D$ value.

In a forty-first embodiment of the first aspect which is also an embodiment of the thirty-eighth, the thirty-ninth and the fortieth embodiment of the first aspect, the predetermined threshold value is Y with Y being the quotient of (binding affinity of the reference nucleic acid molecule)/(binding affinity of the fourth level derivative) and wherein Y>1, more preferably Y≥2 and most preferably Y≥5 or Y≥10 or Y≥20.

In a forty-second embodiment of the first aspect which is also an embodiment of the thirty-eighth, the thirty-ninth, the fortieth and the forty-first embodiment of the first aspect, the predetermined threshold value is X with X being the quotient of (KD value of the reference nucleic acid molecule)/(KD value of the first level derivative) and wherein X>1, more preferably X≥2 and most preferably X≥5 or X≥10 or X≥20.

In a forty-third embodiment of the first aspect which is also an embodiment of the thirty-fourth, the thirty-fifth, the thirty-sixth, the thirty-seventh, the thirty-eighth, the thirty-ninth, the fortieth, the forty-first and the forty-second embodiment of the first aspect, the fourth level derivative the binding characteristic of which exceeds the predetermined threshold value, is a or the nucleic acid molecule capable of binding to a or the target molecule.

In a forty-fourth embodiment of the first aspect which is also an embodiment of the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second and the forty-third embodiment of the first aspect, a fifth level derivative of the reference nucleic acid molecule is prepared, wherein the fifth level derivative differs from the reference nucleic acid molecule at at least a first nucleotide position, a second nucleotide position, a third nucleotide position, a fourth nucleotide position and a fifth nucleotide position, wherein the first nucleotide position is the modified nucleotide position of a first first level derivative of the reference nucleic acid molecule from the group of derivatives of the reference nucleic acid molecule consisting of n derivatives and wherein the first level derivative is one the binding characteristic of which exceeds the predetermined threshold value, and wherein the nucleotide of the first nucleotide position is identical to the nucleotide at the modified position of the first first level derivative of the reference nucleic acid molecule, wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule, wherein the third nucleotide position is the modified nucleotide position of a third first level derivative of the reference nucleic acid molecule from the group of derivatives of the reference nucleic acid molecule consisting of n derivatives and wherein the third first level derivative is one the binding characteristic of which exceeds the predetermined threshold value and wherein the nucleotide of the third nucleotide position is identical to the nucleotide at the modified position of the third level derivative of the reference nucleic acid molecule, wherein the fourth nucleotide position is the modified nucleotide position of a fourth first level derivative of the reference nucleic acid molecule from the group of derivatives of the reference nucleic acid molecule consisting of n derivatives and wherein the fourth first level derivative is one the binding characteristic of which exceeds the predetermined threshold value and wherein the nucleotide of the fourth nucleotide position is identical to the nucleotide at the modified position of the fourth first level derivative of the reference nucleic acid molecule, and wherein the fifth nucleotide position is the modified nucleotide position of a fifth first level derivative of the reference nucleic acid molecule from the group of derivatives of the reference nucleic acid molecule consisting of n derivatives and wherein the fifth first level derivative is one the binding characteristic of which exceeds the predetermined threshold value and wherein the nucleotide of the fifth nucleotide position is identical to the nucleotide at the modified position of the fifth first level derivative of the reference nucleic acid molecule.

In a forty-fifth embodiment of the first aspect which is also an embodiment of the forty-fourth embodiment of the first aspect, the first first level derivative, the second first level derivative, the third first level derivative, the fourth first level derivative and the fifth first level derivative is any combination of five first level derivatives, wherein the binding characteristic of each of the five first level derivatives exceeds the predetermined threshold.

In a forty-sixth embodiment of the first aspect which is also an embodiment of the forty-fourth and the forty-fifth embodiment of the first aspect, the first first level derivative, the second first level derivative, the third first level derivative, the fourth first level derivative and the fifth first level derivative are the five first level derivatives which have a binding characteristic superior to the rest of the first level derivatives of the group of first level derivatives of the reference nucleic acid molecule consisting of n nucleotides.

In a forty-seventh embodiment of the first aspect which is also an embodiment of the forty-fourth, the forty-fifth and the forty-sixth embodiment of the first aspect, the fifth level derivative of the reference nucleic acid molecule is capable of binding to the target molecule.

In a forty-eighth embodiment of the first aspect which is also an embodiment of the forty-fifth, the forty-sixth and the forty-seventh embodiment of the first aspect, the method comprises:
    determining the binding characteristic of the fifth level derivative of the reference nucleic acid molecule to the target molecule; and optionally
    identifying the/those fifth level derivative(s) of the reference nucleic acid molecule the binding characteristic of which exceed a predetermined threshold value.

In a forty-ninth embodiment of the first aspect which is also an embodiment of the forty-eighth embodiment of the first aspect, the binding characteristic is the binding affinity of the fifth level derivative(s) of the reference nucleic acid molecule to the target molecule.

In a fiftieth embodiment of the first aspect which is also an embodiment of the forty-eighth and the forty-ninth embodiment of the first aspect, the binding affinity is expressed as the $K_D$ value.

In a fifty-first embodiment of the first aspect which is also an embodiment of the forty-eighth, the forty-ninth and the fiftieth embodiment of the first aspect, the predetermined threshold value is Y with Y being the quotient of (binding affinity of the reference nucleic acid molecule)/(binding affinity of the fifth level derivative) and wherein Y>1, more preferably Y≥2 and most preferably Y≥5 or Y≥10 or Y≥20.

In a fifty-second embodiment of the first aspect which is also an embodiment of the forty-eighth, the forty-ninth, the fiftieth and the fifty-first embodiment of the first aspect, the predetermined threshold value is X with X being the quotient of (KD value of the reference nucleic acid molecule)/(KD value of the fifth level derivative) and wherein X>1, more preferably X≥2 and most preferably X≥5 or X≥10 or X≥20.

In a fifty-third embodiment of the first aspect which is also an embodiment of the forty-fourth, the forty-fifth, the forty-sixth, the forty-seventh, the forty-eighth, the forty-ninth, the fiftieth, the fifty-first and the fifty-second embodiment of the first aspect, the fifth level derivative the binding characteristic of which exceeds the predetermined threshold value, is a or the nucleic acid molecule capable of binding to a or the target molecule.

In a fifty-fourth embodiment of the first aspect which is also an embodiment of the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth, the fifty-first, the fifty-second and the fifty-third embodiment of the first aspect, a sixth level derivative of the reference nucleic acid molecule is prepared, wherein the sixth level derivative differs from the reference nucleic acid molecule at at least a first nucleotide position, a second nucleotide position, a third nucleotide position, a fourth nucleotide position, a fifth nucleotide position and a sixth nucleotide position, wherein the first nucleotide position is the modified nucleotide position of a first first level derivative of the reference nucleic acid molecule from the group of derivatives of the reference nucleic acid molecule consisting of n derivatives and wherein the first level derivative is one the binding characteristic of which exceeds the predetermined threshold value, and wherein the nucleotide of the first nucleotide position is identical to the nucleotide at the modified position of the first first level derivative of the reference nucleic acid molecule, wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule, wherein the third nucleotide position is the modified nucleotide position of a third first level derivative of the reference nucleic acid molecule from the group of derivatives of the reference nucleic acid molecule consisting of n derivatives and wherein the third first level derivative is one the binding characteristic of which exceeds the predetermined threshold value and wherein the nucleotide of the third nucleotide position is identical to the nucleotide at the modified position of the third level derivative of the reference nucleic acid molecule, wherein the fourth nucleotide position is the modified nucleotide position of a fourth first level derivative of the reference nucleic acid molecule from the group of derivatives of the reference nucleic acid molecule consisting of n derivatives and wherein the fourth first level derivative is one the binding characteristic of which exceeds the predetermined threshold value and wherein the nucleotide of the fourth nucleotide position is identical to the nucleotide at the modified position of the fourth first level derivative of the reference nucleic acid molecule, wherein the fifth nucleotide position is the modified nucleotide position of a fifth first level derivative of the reference nucleic acid molecule from the group of derivatives of the reference nucleic acid molecule consisting of n derivatives and wherein the fifth first level derivative is one the binding characteristic of which exceeds the predetermined threshold value and wherein the nucleotide of the fifth nucleotide position is identical to the nucleotide at the modified position of the fifth first level derivative of the reference nucleic acid molecule, and wherein the sixth nucleotide position is the modified nucleotide position of a sixth first level derivative of the reference nucleic acid molecule from the group of derivatives of the reference nucleic acid molecule consisting of n derivatives and wherein the sixth first level derivative is one the binding characteristic of which exceeds the predetermined threshold value and wherein the nucleotide of the sixth nucleotide position is identical to the nucleotide at the modified position of the sixth first level derivative of the reference nucleic acid molecule.

In a fifty-fifth embodiment of the first aspect which is also an embodiment of the fifty-fourth embodiment of the first aspect, the first first level derivative, the second first level derivative, the third first level derivative, the fourth first level derivative, the fifth first level derivative and the sixth first level derivative is any combination of six first level derivatives, wherein the binding characteristic of each of the six first level derivatives exceeds the predetermined threshold.

In a fifty-sixth embodiment of the first aspect which is also an embodiment of the fifty-fourth and the fifty-fifth embodiment of the first aspect, the first first level derivative, the second first level derivative, the third first level derivative, the fourth first level derivative, the fifth first level derivative and the sixth first level derivative are the six first level derivatives which have a binding characteristic superior to the rest of the first level derivatives of the group of first level derivatives of the reference nucleic acid molecule consisting of n nucleotides.

In a fifty-seventh embodiment of the first aspect which is also an embodiment of the fifty-fourth, the fifty-fifth and the fifty-sixth embodiment of the first aspect, the sixth level derivative of the reference nucleic acid molecule is capable of binding to the target molecule.

In a fifty-eighth embodiment of the first aspect which is also an embodiment of the fifty-fifth, the fifty-sixth and the fifty-seventh embodiment of the first aspect, the method comprises:
    determining the binding characteristic of the sixth level derivative of the reference nucleic acid molecule to the target molecule; and optionally
    identifying the/those sixth level derivative(s) of the reference nucleic acid molecule the binding characteristic of which exceed a predetermined threshold value.

In a fifty-ninth embodiment of the first aspect which is also an embodiment of the fifty-eighth embodiment of the first aspect, the binding characteristic is the binding affinity of the sixth level derivative(s) of the reference nucleic acid molecule to the target molecule.

In a sixtieth embodiment of the first aspect which is also an embodiment of the fifty-eighth and the fifty-ninth embodiment of the first aspect, the binding affinity is expressed as the $K_D$ value.

In a sixty-first embodiment of the first aspect which is also an embodiment of the fifty-eighth, the fifty-ninth and the sixtieth embodiment of the first aspect, the predetermined threshold value is Y with Y being the quotient of (binding affinity of the reference nucleic acid molecule)/(binding affinity of the sixth level derivative) and wherein $Y>1$, more preferably $Y \geq 2$ and most preferably $Y \geq 5$ or $Y \geq 10$ or $Y \geq 20$.

In a sixty-second embodiment of the first aspect which is also an embodiment of the fifty-eighth, the fifty-ninth, the sixtieth and the sixty-first embodiment of the first aspect, the predetermined threshold value is X with X being the quotient of (KD value of the reference nucleic acid molecule)/

(KD value of the sixth level derivative) and wherein X>1, more preferably X≥2 and most preferably X≥5 or X≥10 or X≥20.

In a sixty-third embodiment of the first aspect which is also an embodiment of the fifty-fourth, the fifty-fifth, the fifty-sixth, the fifty-seventh, the fifty-eighth, the fifty-ninth, the sixtieth, the sixty-first and the sixty-second embodiment of the first aspect, the sixth level derivative the binding characteristic of which exceeds the predetermined threshold value, is a or the nucleic acid molecule capable of binding to a or the target molecule.

In a sixty-fourth embodiment of the first aspect which is also an embodiment of the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth, the fifty-first, the fifty-second, the fifty-third, the fifty-fourth, the fifty-fifth, the fifty-sixth, the fifty-seventh, the fifty-eighth, the fifty-ninth, the sixtieth, the sixty-first, the sixty-second and the sixty-third embodiment of the first aspect, a seventh level derivative of the reference nucleic acid molecule is prepared, wherein the seventh level derivative differs from the reference nucleic acid molecule at at least a first nucleotide position, a second nucleotide position, a third nucleotide position, a fourth nucleotide position, a fifth nucleotide position, a sixth nucleotide position and a seventh nucleotide position, wherein the first nucleotide position is the modified nucleotide position of a first first level derivative of the reference nucleic acid molecule from the group of derivatives of the reference nucleic acid molecule consisting of n derivatives and wherein the first level derivative is one the binding characteristic of which exceeds the predetermined threshold value, and wherein the nucleotide of the first nucleotide position is identical to the nucleotide at the modified position of the first first level derivative of the reference nucleic acid molecule, wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule, wherein the third nucleotide position is the modified nucleotide position of a third first level derivative of the reference nucleic acid molecule from the group of derivatives of the reference nucleic acid molecule consisting of n derivatives and wherein the third first level derivative is one the binding characteristic of which exceeds the predetermined threshold value and wherein the nucleotide of the third nucleotide position is identical to the nucleotide at the modified position of the third level derivative of the reference nucleic acid molecule, wherein the fourth nucleotide position is the modified nucleotide position of a fourth first level derivative of the reference nucleic acid molecule from the group of derivatives of the reference nucleic acid molecule consisting of n derivatives and wherein the fourth first level derivative is one the binding characteristic of which exceeds the predetermined threshold value and wherein the nucleotide of the fourth nucleotide position is identical to the nucleotide at the modified position of the fourth first level derivative of the reference nucleic acid molecule, wherein the fifth nucleotide position is the modified nucleotide position of a fifth first level derivative of the reference nucleic acid molecule from the group of derivatives of the reference nucleic acid molecule consisting of n derivatives and wherein the fifth first level derivative is one the binding characteristic of which exceeds the predetermined threshold value and wherein the nucleotide of the fifth nucleotide position is identical to the nucleotide at the modified position of the fifth first level derivative of the reference nucleic acid molecule, wherein the sixth nucleotide position is the modified nucleotide position of a sixth first level derivative of the reference nucleic acid molecule from the group of derivatives of the reference nucleic acid molecule consisting of n derivatives and wherein the sixth first level derivative is one the binding characteristic of which exceeds the predetermined threshold value and wherein the nucleotide of the sixth nucleotide position is identical to the nucleotide at the modified position of the sixth first level derivative of the reference nucleic acid molecule, and wherein the seventh nucleotide position is the modified nucleotide position of a seventh first level derivative of the reference nucleic acid molecule from the group of derivatives of the reference nucleic acid molecule consisting of n derivatives and wherein the seventh first level derivative is one the binding characteristic of which exceeds the predetermined threshold value and wherein the nucleotide of the sixth nucleotide position is identical to the nucleotide at the modified position of the seventh first level derivative of the reference nucleic acid molecule.

In a sixty-fifth embodiment of the first aspect which is also an embodiment of the sixty-fourth embodiment of the first aspect, the first first level derivative, the second first level derivative, the third first level derivative, the fourth first level derivative, the fifth first level derivative, the sixth first level derivative and the seventh first level derivative is any combination of seven first level derivatives, wherein the binding characteristic of each of the seventh first level derivatives exceeds the predetermined threshold.

In a sixty-sixth embodiment of the first aspect which is also an embodiment of the sixty-fourth and the sixty-fifth embodiment of the first aspect, the first first level derivative, the second first level derivative, the third first level derivative, the fourth first level derivative, the fifth first level derivative, the sixth first level derivative and the seventh first level derivative are the seven first level derivatives which have a binding characteristic superior to the rest of the first level derivatives of the group of first level derivatives of the reference nucleic acid molecule consisting of n nucleotides.

In a sixty-seventh embodiment of the first aspect which is also an embodiment of the sixty-fourth, the sixty-fifth and the sixty-sixth embodiment of the first aspect, the seventh level derivative of the reference nucleic acid molecule is capable of binding to the target molecule.

In a sixty-eighth embodiment of the first aspect which is also an embodiment of the sixty-fifth, the sixty-sixth and the sixty-seventh embodiment of the first aspect, the method comprises:
- determining the binding characteristic of the seventh level derivative of the reference nucleic acid molecule to the target molecule; and optionally
- identifying the/those seventh level derivative(s) of the reference nucleic acid molecule the binding characteristic of which exceed a predetermined threshold value.

In a sixty-ninth embodiment of the first aspect which is also an embodiment of the sixty-eighth embodiment of the first aspect, the binding characteristic is the binding affinity of the seventh level derivative(s) of the reference nucleic acid molecule to the target molecule.

In a seventieth embodiment of the first aspect which is also an embodiment of the sixty-eighth and the sixty-ninth embodiment of the first aspect, the binding affinity is expressed as the $K_D$ value.

In a seventy-first embodiment of the first aspect which is also an embodiment of the sixty-eighth, the sixty-ninth and the seventieth embodiment of the first aspect, the predetermined threshold value is Y with Y being the quotient of (binding affinity of the reference nucleic acid molecule)/ (binding affinity of the seventh level derivative) and wherein Y>1, more preferably Y≥2 and most preferably Y≥5 or Y≥10 or Y≥20.

In a seventy-second embodiment of the first aspect which is also an embodiment of the sixty-eighth, the sixty-ninth, the seventieth and the seventy-first embodiment of the first aspect, the predetermined threshold value is X with X being the quotient of (KD value of the reference nucleic acid molecule)/(KD value of the seventh level derivative) and wherein X>1, more preferably X≥2 and most preferably X≥5 or X≥10 or X≥20.

In a seventy-third embodiment of the first aspect which is also an embodiment of the sixty-fourth, the sixty-fifth, the sixty-sixth, the sixty-seventh, the sixty-eighth, the sixty-ninth, the seventieth, the seventy-first and the seventy-second embodiment of the first aspect, the seventh level derivative the binding characteristic of which exceeds the predetermined threshold value, is a or the nucleic acid molecule capable of binding to a or the target molecule.

In a seventy-fourth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth, the fifty-first, the fifty-second, the fifty-third, the fifty-fourth, the fifty-fifth, the fifty-sixth, the fifty-seventh, the fifty-eighth, the fifty-ninth, the sixtieth, the sixty-first, the sixty-second, the sixty-third, the sixty-fourth, the sixty-fifth, the sixty-sixth, the sixty-seventh, the sixty-eighth, the sixty-ninth, the seventieth, the seventy-first, the seventy-second and the seventy-third embodiment of the first aspect, the nucleic acid capable of binding to a target molecule is an L-nucleic acid, the reference nucleic acid molecule is an L-nucleic acid and each and any of the derivatives of the reference nucleic acid molecule is an L-nucleic acid.

The problem underlying the present invention is solved in a second aspect which is also the first embodiment of the second aspect, by a nucleic acid molecule capable of binding to a target molecule obtainable by a method according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second, the twenty third, the twenty fourth, the twenty fifth, the twenty-sixth, the twenty seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth, the fifty-first, the fifty-second, the fifty-third, the fifty-fourth, the fifty-fifth, the fifty-sixth, the fifty-seventh, the fifty-eighth, the fifty-ninth, the sixtieth, the sixty-first, the sixty-second, the sixty-third, the sixty-fourth, the sixty-fifth, the sixty-sixth, the sixty-seventh, the sixty-eighth, the sixty-ninth, the seventieth, the seventy-first, the seventy-second, the seventy-third and the seventy-fourth embodiment of the first aspect.

In a second embodiment of the second aspect which is also an embodiment of the first embodiment of the second aspect, the nucleic acid molecule comprises at least one modification.

In a third embodiment of the second aspect which is also an embodiment of the first and the second embodiment of the second aspect, the nucleic acid molecule is for use in a method for the treatment and/or prevention of a disease.

In a fourth embodiment of the second aspect which is also an embodiment of the first and the second embodiment of the second aspect, the nucleic acid molecule is for use in a method for the diagnosis of a disease.

In a fifth embodiment of the second aspect which is also an embodiment of the third and the fourth embodiment of the second aspect, the disease is a disease which involves the target molecule.

The problem underlying the present invention is solved in a third aspect which is also the first embodiment of the third aspect, by use of a nucleic acid molecule according to any one of the first and the second embodiment of the second aspect for the manufacture of a medicament for the treatment of a disease.

The problem underlying the present invention is solved in a fourth aspect which is also the first embodiment of the fourth aspect, by use of a nucleic acid molecule according to any one of the first and the second embodiment of the second aspect for the manufacture of a diagnostic agent for the treatment of a disease.

In a second embodiment of the third aspect which is also the second embodiment of the fourth aspect and an embodiment of the first embodiment of the third aspect and an embodiment of the first embodiment of the fourth aspect, the disease is a disease which involves the target molecule.

The problem underlying the present invention is solved in a fifth aspect which is also the first embodiment of the fifth aspect, by a pharmaceutical composition comprising a nucleic acid molecule according to any one of the first and the second embodiment of the second aspect and a pharmaceutically acceptable carrier.

The problem underlying the present invention is solved in a sixth aspect which is also the first embodiment of the sixth aspect, by a nucleic acid molecule capable of binding to a target molecule,
wherein the nucleic acid molecule has a binding affinity to the target molecule,
wherein the binding affinity of the nucleic acid molecule to the target molecule is increased or the same compared to the binding affinity of a reference nucleic acid molecule to the target molecule,
wherein
a) the nucleic acid molecule comprises a sequence of nucleotides and the reference nucleic acid molecule comprises a sequence of nucleotides, or
b) the nucleic acid molecule comprises a sequence of nucleotides and at least one modification group and the reference nucleic acid molecule comprises a sequence of nucleotides and the at least one modification group,
wherein the sequence of nucleotides of the nucleic acid molecule and the sequence of nucleotides of the reference nucleic acid molecule are at least partially identical with respect to the nucleobase moiety of the nucleotides but differ with respect to the sugar moiety of the nucleotides,
wherein the sequence of nucleotides of the nucleic acid molecule consists of both ribonucleotides and 2'-deoxyribonucleotides and wherein the sequence of nucleotides of the reference nucleic acid molecule consists of either ribonucleotides or 2'-deoxyribonucleotides.

In a second embodiment of the sixth aspect which is also an embodiment of the first embodiment of the sixth aspect,
a) the nucleic acid molecule consists of a sequence of nucleotides and the reference nucleic acid molecule consists of a sequence of nucleotides, or
b) the nucleic acid molecule consists of a sequence of nucleotides and at least one modification group and the reference nucleic acid molecule consists of a sequence of nucleotides and the at least one modification group,
wherein the sequence of nucleotides of the nucleic acid molecule and the sequence of nucleotides of the reference nucleic acid molecule are identical with respect to the nucleobase moiety of the nucleotides but differ with respect to the sugar moiety of the nucleotides.

In a third embodiment of the sixth aspect which is also an embodiment of the second embodiment of the sixth aspect, the binding affinity of the nucleic acid molecule to the target molecule is increased compared to the binding affinity of a reference nucleic acid molecule to the target molecule.

In a fourth embodiment of the sixth aspect which is also the sixth embodiment of the second aspect and an embodiment of the first, the second, the third, the forth and the fifth embodiment of the second aspect, and an embodiment of first, the second and the third embodiment of the sixth aspect, the ribonucleotides are L-ribonucleotides and wherein the 2'-deoxyribonucleotides are L-2'-deoxyribonucleotides.

In a fifth embodiment of the sixth aspect which is also the seventh embodiment of the second aspect and an embodiment of the first, the second, the third, the forth, the fifth and the sixth embodiment of the second aspect, and an embodiment of first, the second, the third and the fourth embodiment of the sixth aspect, the nucleic acid molecule is an L-nucleic acid molecule, wherein the L-nucleic acid molecule consists of L-nucleotides, and the reference nucleic acid molecule is an L-reference nucleic acid molecule, wherein the L-reference nucleic acid molecule consists of L-nucleotides.

In a sixth embodiment of the sixth aspect which is also the eighth embodiment of the second aspect and an embodiment of the first, the second, the third, the forth, the fifth, the sixth and the seventh embodiment of the second aspect, and an embodiment of first, the second, the third, the fourth and the fifth embodiment of the sixth aspect, the nucleic acid molecule and/or the reference nucleic acid molecule are antagonists of an activity mediated by the target molecule.

In a seventh embodiment of the sixth aspect which is also the ninth embodiment of the second aspect and an embodiment of the first, the second, the third, the forth, the fifth, the sixth, the seventh and the eighth embodiment of the second aspect, and an embodiment of first, the second, the third, the fourth, the fifth and the sixth embodiment of the sixth aspect, excretion rate of the nucleic acid molecule comprising a sequence of nucleotides and at least one modification group from an organism is decreased compared to a nucleic acid molecule consisting of the sequence of nucleotides.

In an eighth embodiment of the sixth aspect which is also the tenth embodiment of the second aspect and an embodiment of the first, the second, the third, the forth, the fifth, the sixth, the seventh and the eighth embodiment of the second aspect, and an embodiment of first, the second, the third, the fourth, the fifth and the sixth embodiment of the sixth aspect, the nucleic acid molecule comprising a sequence of nucleotides and at least one modification has an increased retention time in an organism compared to a nucleic acid molecule consisting of the sequence of nucleotides.

In a ninth embodiment of the sixth aspect which is also the eleventh embodiment of the second aspect and an embodiment of the ninth and the tenth embodiment of the second aspect, and an embodiment of the seventh and the eighth embodiment of the sixth aspect, the modification group is selected from the group comprising biodegradable and non-biodegradable modifications, preferably the modification group is selected from the group comprising polyethylene glycol, linear polyethylene glycol, branched polyethylene glycol, hydroxyethyl starch, a peptide, a protein, a polysaccharide, a sterol, polyoxypropylene, polyoxyamidate and poly(2-hydroxyethyl)-L-glutamine.

In a tenth embodiment of the sixth aspect which is also the twelfth embodiment of the second aspect and an embodiment of the eleventh embodiment of the second aspect, and an embodiment of the ninth embodiment of the sixth aspect, the modification group is a polyethylene glycol, preferably consisting of a linear polyethylene glycol or branched polyethylene glycol, wherein the molecular weight of the polyethylene glycol is preferably from about 20,000 to about 120,000 Da, more preferably from about 30,000 to about 80,000 Da and most preferably about 40,000 Da.

In an eleventh embodiment of the sixth aspect which is also the thirteenth embodiment of the second aspect and an embodiment of the eleventh embodiment of the second aspect, and an embodiment of the ninth embodiment of the sixth aspect, the modification group is hydroxyethyl starch, wherein preferably the molecular weight of the hydroxyethyl starch is from about 50 to about 1000 kDa, more preferably from about 100 to about 700 kDa and most preferably from 200 to 500 kDa.

In a twelfth embodiment of the sixth aspect which is also the fourteenth embodiment of the second aspect and an embodiment of the ninth, the tenth, the eleventh, the twelfth and the thirteenth embodiment of the second aspect, and an embodiment of the seventh, the eighth, the ninth, the tenth, the eleventh and the twelfth embodiment of the sixth aspect, the organism is an animal or a human body, preferably a human body.

In a thirteenth embodiment of the sixth aspect which is also the fifteenth embodiment of the second aspect and an embodiment of the first, the second, the third, the fourth, the fifth, the sixth, the seventh, the eighth, the ninth, the tenth, the eleventh and the twelfth embodiment of the sixth aspect, and an embodiment of the sixth, the seventh, the eighth, the ninth, the tenth, the eleventh, the twelfth, the thirteenth and the fourteenth embodiment of the sixth aspect, the nucleic acid molecule is for use in a method for the treatment and/or prevention of a disease.

In a fourteenth embodiment of the sixth aspect which is also the sixteenth embodiment of the second aspect and an embodiment of the first, the second, the third, the fourth, the fifth, the sixth, the seventh, the eighth, the ninth, the tenth, the eleventh, the twelfth, the thirteenth, the fourteenth and the fifteenth embodiment of the second aspect, and an embodiment of the first, the second, the third, the fourth, the fifth, the sixth, the seventh, the eighth, the ninth, the tenth, the eleventh, the twelfth and the thirteenth embodiment of the sixth aspect, the nucleic acid molecule and the reference nucleic acid molecule are resistant to nuclease activity.

It will be understood by a person skilled in the art that the following embodiments and features may also be realized in connection with the features and embodiments described herein, in particular in connection with the aspects and embodiments as subject to the claims attached hereto.

The present inventors have also found that by following a rational approach starting from a reference nucleic acid molecule which is capable of binding to a target molecule a further nucleic acid molecule can be generated which binds to a target molecule, whereby it is preferred that the nucleic acid molecule which is capable of binding to a target molecule binds to the target molecule of the reference nucleic acid molecule. Such rational approach comprises a method comprising the following steps:

a) providing a reference nucleic acid molecule, wherein the reference nucleic acid molecule is capable of binding to the target molecule and wherein the reference nucleic acid molecule comprises a sequence of nucleotides, wherein the sequence of nucleotides comprises n nucleotides;

b) preparing a first level derivative of the reference nucleic acid molecule, wherein the first level derivative of the reference nucleic acid molecule differs from the reference nucleic acid molecule at one nucleotide position, wherein the first level derivative is prepared by replacing the ribonucleotide at the one nucleotide position by a deoxyribonucleotide in case the reference nucleic acid has a ribonucleotide at the nucleotide position and wherein the first level derivative is prepared by replacing the deoxyribonucleotide at the one nucleotide position by a ribonucleotide in case the reference nucleic acid has a deoxyribonucleotide at the nucleotide position and wherein the nucleotide position at which the replacement is made is the modified nucleotide position; and c) repeating step b) for each nucleotide position of the reference nucleic acid molecule, thus preparing a group of first level derivatives of the reference nucleic acid molecule, wherein the group of first level derivatives of the reference nucleic acid molecule consists of n first level derivatives, wherein each of the first level derivatives of the reference nucleic acid molecule differs from the reference nucleic acid molecule by a single nucleotide replacement and wherein each of the first level derivatives of the reference nucleic acid molecule has a single modified nucleotide position which is different from the single modified nucleotide of all of the single modified nucleotide positions of the other first level derivatives of the group of first level derivatives of the reference nucleic acid molecule.

In an embodiment the first level derivatives comprise a sequence of nucleotides, wherein the sequence of nucleotides comprises n nucleotides.

It is within the present invention that the terms first level derivative and first level derivative of the reference nucleic acid molecule are used in a synonymous manner if not indicated to the contrary.

It is also within the present invention that the terms group of first level derivatives and group of first level derivatives of the reference nucleic acid molecule are used in a synonymous manner if not indicated to the contrary.

It will be understood by a person skilled in the art that each first level derivative has only one nucleotide exchange relative to the reference nucleic acid molecule. It will also be understood that in an embodiment step b) is repeated (n−1)-times so that each and any of the n nucleotide positions of the reference nucleic acid molecule is subject to a nucleotide replacement. In such group of first level derivatives of the reference nucleic acid molecule, the group of first level derivatives, in its entirety, represents all derivatives which can be prepared starting from the reference nucleic acid molecule wherein each of the derivatives differs from the reference nucleic acid molecule at a single nucleotide position.

It is, however, also within the present invention that step b) is repeated less than (n−1)-times. It is also within the present invention that step b) is not repeated at all so that at only one nucleotide position a ribonucleotide is replaced by a deoxyribonucleotide and, respectively, a deoxyribonucleotide is replaced by a ribonucleotide. This latter embodiment will preferably be performed in case the single nucleotide replacement will result in a derivative, which is a first level derivative, if the derivative has an improved binding characteristic as defined herein compared to the reference nucleic acid molecule.

The embodiment of the method of the present invention will comprise less than (n−1) repetitions of step b), but preferably one or more than one repetition if upon repeating step b) one, two, three etc. but less than (n−1) first level derivatives are obtained which have an improved binding characteristic as defined herein compared to the reference nucleic acid molecule.

In a further embodiment of the method of the present invention the method comprises a step of determining the binding characteristic for each of the n first level derivatives of the reference nucleic acid. Preferably, the binding characteristic in terms of the binding of the first level derivatives to the target molecule is determined. In a further embodiment of the method of the present invention the binding characteristic is determined for less than the n first level derivatives, preferably the binding characteristic is determined for at least one of the n first level derivatives but not for all n first level derivatives. Also in these embodiments, the binding characteristic in terms of the binding of the first level derivatives to the target molecule is determined.

In a further embodiment of the method of the present invention the method comprises a step of identifying the/those first level derivative(s) of the reference nucleic acid molecule the binding characteristic of which exceed or reach a predetermined threshold value. In an embodiment thereof, either all of the first level derivatives which exceed or reach the predetermined threshold value are identified or only some of the first level derivatives which exceed or reach the predetermined threshold value are identified.

It is also within the present invention that the threshold value is the binding affinity of the reference nucleic acid molecule. In this embodiment the derivative of the reference nucleic acid of any level has the same or a similar binding affinity to the target molecule as the reference nucleic acid molecule. This embodiment is an embodiment of any level derivative as disclosed herein.

In accordance with the method of the present invention the nucleic acid to be generated is a first level derivative of the reference nucleic acid molecule or any level derivative of the reference nucleic acid which is capable of binding to the target molecule to which the reference nucleic acid molecule is capable of binding and which reaches a threshold value.

It is within the present invention that the reference nucleic acid molecule is an RNA molecule. In this embodiment the reference nucleic acid molecule consists of ribonucleotides.

It is within the present invention that the reference nucleic acid molecule is a DNA molecule. In this embodiment the reference nucleic acid molecule consists of deoxyribonucleotides.

It is also within the present invention that the reference nucleic acid molecule consists of both ribonucleotides and deoxyribonucleotides, whereby at each position of the sequence of nucleotides forming the reference nucleic acid sequence the nucleotide is either a deoxyribonucleotide or a ribonucleotide.

A further aspect of the present invention is a second level derivative of the reference nucleic acid molecule. Such second level derivative of the reference nucleic acid molecule can be obtained or is obtainable by the method of the present invention as disclosed herein and is described herein in connection with the method of the present invention. More specifically, the second level derivative differs from the reference nucleic acid molecule at at least a first nucleotide position and a second nucleotide position, wherein the first nucleotide position is the modified nucleotide position of a first first level derivative of the reference nucleic acid molecule from the group of derivatives of the reference nucleic acid molecule consisting of n derivatives and wherein the first first level derivative is one the binding characteristic of which exceeds the predetermined threshold value, and wherein the nucleotide of the first nucleotide position is identical to the nucleotide at the modified position of the first first level derivative of the reference nucleic acid molecule, and wherein the second nucleotide position is the modified nucleotide position of a second first level derivative of the reference nucleic acid molecule from the group of derivatives of the reference nucleic acid molecule consisting of n derivatives and wherein the second first level derivative is one the binding characteristic of which exceeds the predetermined threshold value and wherein the nucleotide of the second nucleotide position is identical to the nucleotide at the modified position of the second first level derivative of the reference nucleic acid molecule.

Further aspects of the present invention are related to a third level derivative of the reference nucleic acid molecule, a fourth level derivative of the reference nucleic acid molecule, a fifth level derivative of the reference nucleic acid molecule, a sixth level derivative of the reference nucleic acid molecule and a seventh level derivative of the reference nucleic acid molecule. Such third, fourth, fifth, sixth and seventh level derivative of the reference nucleic acid molecule can be obtained or is obtainable by the method of the present invention as disclosed herein and are described herein in connection with the method of the present invention.

It is to be acknowledged that in connection with the second, third, fourth, fifth, sixth and seventh level derivative of the reference nucleic acid molecule, all of which are a nucleic acid molecule according to the present invention, the number of replacements is not limited to two nucleotides in connection with the second level derivative of the reference nucleic acid molecule, is not limited to three nucleotides in connection with the third level derivative of the reference nucleic acid molecule, is not limited to four nucleotides in connection with the fourth level derivative of the reference nucleic acid molecule, is not limited to five nucleotides in connection with the fifth level derivative of the reference nucleic acid molecule, is not limited to six nucleotides in connection with the sixth level derivative of the reference nucleic acid molecule, and is not limited to seven nucleotides in connection with the seventh level derivative of the reference nucleic acid molecule; rather such derivatives may comprise further replacements at other positions.

Finally, higher order level derivatives of the reference nucleic acid molecule are encompassed, disclosed and thus encompassed by the present invention and are, accordingly, a nucleic acid molecule according to the present invention. Such higher order level derivatives are, for example, the eighth level derivatives, ninth order derivatives etc. The maximum order level derivative is the $n^{th}$ level derivative of the reference nucleic acid molecule in view of the fact that the reference nucleic acid molecule comprises n nucleotides. As the reference nucleic acid molecule comprises n nucleotides a maximum of n nucleotides of the reference nucleic acid molecule are replaced in accordance with the rules and guidance provided herein. In such nth level derivative of the reference nucleic acid molecule each and any nucleotide is thus replaced in accordance with the present invention. It is, however, also within the present invention that the higher order level derivatives are $(n-x)^{th}$ order level derivatives with x being any integer from 1 to n+2. In such $(n-x)^{th}$ order level derivatives with x being any integer from 1 to n+2, (n-x) nucleotides of such derivative are replaced relative to the reference nucleic acid molecule in accordance with the technical teaching provided herein, with x being any integer from 1 to n+2.

It is also an embodiment of the method of the present invention that when combining the nucleotide replacements of various first level derivatives of the reference nucleic acid molecule into higher order level derivatives that the various individual first level derivatives reach or exceed a or the predetermined threshold value. It is, however, also an embodiment of the method of the present invention that when combining the nucleotide replacements of various first level derivatives of the reference nucleic acid molecule into higher order level derivatives none of the various individual first level derivatives reaches or exceeds a or the predetermined threshold value. Finally it is an embodiment of the method of the present invention that when combining the nucleotide replacements of various first level derivatives of the reference nucleic acid molecule into higher order level derivatives some of the first level derivatives of the reference nucleic acid molecule reach or exceed a or the predetermined threshold value, whereas others of the first level derivatives of the reference nucleic acid molecule do not reach or nor not exceed a or the predetermined threshold.

The present invention is also based on the surprising finding that it is possible to increase the binding affinity of a nucleic acid molecule to a target compared to the binding affinity of a reference nucleic acid molecule, wherein the nucleic acid molecule comprise a sequence of nucleotides and the reference molecule comprise a sequence of nucleotides, wherein the sequence of nucleotides of the nucleic acid molecule and the sequence of nucleotides of the reference nucleic acid molecule are at least partially identical with respect to the nucleobase moiety of the nucleotides but differ with respect to the sugar moiety of the nucleotides, wherein the sequence of nucleotides of the nucleic acid molecule consists of both ribonucleotides and deoxyribonucleotides and wherein the sequence of nucleotides of the reference nucleic acid molecule consists of either ribonucleotides or deoxyribonucleotides.

As preferably used herein a reference nucleic acid molecule is a nucleic acid molecule which is used as a reference or benchmark for a certain characteristic which is to be assessed or determined for both a nucleic acid molecule and a nucleic acid molecule of the invention in particular on the one hand, and, on the other hand, for the nucleic acid molecule acting as or being used as (the) reference nucleic acid molecule. In an embodiment the characteristic is the binding affinity of the nucleic acid molecule, preferably the nucleic acid molecule of the present invention, and the binding affinity of the reference nucleic acid molecule for the target molecule of the nucleic acid molecule of the present invention and for the target molecule of the reference the nucleic acid molecule. In a preferred embodiment, the target molecule of the nucleic acid molecule of the present invention is the target molecule of the reference nucleic acid molecule, more preferably the target molecule of the nucleic acid molecule of the present invention is the same target molecule as the reference nucleic acid molecule.

As preferably used herein, a sequence of nucleotides of a nucleic acid molecule of the present invention is partially identical with or to a sequence of nucleotides of the reference nucleic acid molecule if at least one nucleobase of a nucleotide contained in the sequence of nucleotides of the nucleic acid molecule of the present invention is identical to at least one nucleobase of a nucleotide contained in the sequence of nucleotides of the reference nucleic acid molecule. In an embodiment, at least 75% preferably 85%, more preferably 90% and most preferably more than 95%, 96%, 97%, 98%, 99% or 100% of the nucleobases of the nucleotides of the nucleic acid molecule of the present invention are identical to the nucleobases of the nucleotides of the reference nucleic acid molecule. In an alternative embodiment, at least 75% preferably 85%, more preferably 90% and most preferably more than 95%, 96%, 97%, 98%, 99% or 100% of the nucleobases of the nucleotides of the reference nucleic acid molecule of the present invention are identical to the nucleobases of the nucleotides of the nucleic acid molecule of the present invention. In a further embodiment of the nucleic acid molecule of the present invention all of the nucleobases are identical to the nucleobases of the reference nucleic acid molecule with the exception that in case a 2'-deoxyribonucleotide is replaced by a ribonucleotide and the deoxyribonucleotide is 2'-deoxyadenosine-5-phosphate; 2'-deoxyguanosine-5'-phosphate; 2'-deoxycytidine-5'phosphate; thymidine-5'-phosphate, the ribonucleotide is adenosine-5'-phosphate, guanosine-5'-phosphate cytidine-5'-5-methyl-uridine-5'-phosphate phosphate or uridine-5'-phosphate and that in case a ribonucleotide is replaced by a deoxyribonucleotide and the ribonucleotide is adenosine-5'-phosphate, guanosine-5'-phosphate cytidine-5'phosphate, uridine-5'-phosphate, the deoxyribonucleotide is 2'-deoxyadenosine-5-phosphate; 2'-deoxyguanosine-5'-phosphate; 2'-deoxycytidine-5'phosphate; 2'-deoxyuridine-5'-phosphate or thymidine-5-phosphate.

In accordance with the present invention, the identity or partial identity of the sequence of nucleotides of the nucleic acid molecule of the present invention with or to the sequence of nucleotides of the reference nucleic acid molecule is determined based on or with respect to the nucleobase moiety of the nucleotides. In connection therewith and as preferably used herein a nucleobase or nucleobase moiety is the nitrogenous base of a nucleoside and a nucleotide, respectively. More preferably, a nucleobase is selected from the group comprising adenine, guanine, thymine, cytosine and uracil. Thus, the identity or partial identity of the sequence of nucleotides of the nucleic acid molecule of the present invention with or to the sequence of nucleotides of the reference nucleic acid molecule is determined by the chemistry of the nucleobase of the nucleotides. Accordingly, in connection with the present invention a 2'-deoxyadenosine-5'-(tri)phosphate is regarded as being identical to an adenosine-5'-(tri)phosphate, a 2'-deoxyguanosine-5'-(tri)phosphate is regarded as being identical to a guanosine-5'-(tri)phosphate, a thymidine-5'-(tri)phosphate is regarded as being identical to a 5-Methyluridine 5'-(tri)phosphate, a 2'-deoxycytidine 5'-(tri)phosphate is regarded as being identical to a cytidine 5'-(tri)phosphate and a deoxyuridine 5'-(tri)phosphate is regarded as being identical to an uridine 5'-(tri)phosphate.

Throughout this patent application commonly known acronyms are used to describe the composition of nucleic acids, whereby the letters A, G, C, U and T signify a ribonucleotide or a 2'-deoxyribonucleotide containing the nucleobase adenine, guanine, cytosine, uracil or thymine respectively. When positioned at the 5'-end of a synthetic oligonucleotide the nucleotide is a nucleoside, i.e. it carries no 5'-phosphate group. It is to be determined by the reader from the figure, the figure legend or the text of a given example whether the sequences shown are primarily ribonucleotide sequences (RNA) or 2'-deoxyribonucleotide sequences (also referred to as deoxyribonucleotide sequences or DNA). Generally there is one or several positions that are then exchanged from a ribonucleotide to a 2'-deoxyribonucleotide or vice versa. The incorporation of one or several 2'deoxyribonucleotides into a primarily ribonucleotide sequence is signified by a lowercase "d" before the capital letter that indicates the identity of the nucleobase (see above). Conversely, one or several 2'deoxyribonucleotide incorporations into a ribonucleotide sequence are signified by a lowercase "d" before the capital letter that indicates the identity of the nucleobase. A nucleotide is known to someone skilled in the art as being a ribose-5'-phosphate or a 2'-deoxyribose-5'-phosphate, with a nucleobase attached at the 1'-position. The linkage with the nucleobase occurs with the 9-position of the purine nucleobases (A, G) and with the 1-position of the pyrimidine nucleobases (C, T, U).

It is within the present invention that the nucleic acid according to the present invention is a nucleic acid molecule. Insofar the terms nucleic acid and nucleic acid molecule are used herein in a synonymous manner if not indicated to the contrary. Moreover, such nucleic acids are preferably also referred to herein as the nucleic acid molecules according to the present invention, the nucleic acids according to the present invention, the inventive nucleic acids or the inventive nucleic acid molecules.

The features of the nucleic acid according to the present invention as described herein can be realised in any aspect of the present invention where the nucleic acid is used, either alone or in any combination.

As preferably used herein the term glucagon refers to any glucagon including, but not limited to, mammalian glucagon. Preferably, the mammalian glucagon is selected from the group comprising human, rat, mouse, monkey, pig, rabbit, hamster, dog, sheep, chicken and bovine glucagon.

As preferably used herein the term S1P refers to any S1P including, but not limited to, mammalian S1P. Preferably, the mammalian S1P is selected from the group comprising human, rat, mouse, monkey, pig, rabbit, hamster, dog, sheep, chicken and bovine S1P.

As preferably used herein the term CGRP refers to any CGRP including, but not limited to, mammalian CGRP. Preferably, the mammalian CGRP is selected from the group comprising human, rat, mouse, monkey, pig, rabbit, hamster, dog, sheep, chicken and bovine CGRP.

As preferably used herein the term C5a refers to any C5a including, but not limited to, mammalian C5a. Preferably, the mammalian C5a is selected from the group comprising human, rat, mouse, monkey, pig, rabbit, hamster, dog, sheep, chicken and bovine C5a.

An antagonist to glucagon as preferably used herein is a molecule that binds to glucagon such as the nucleic acid molecule disclosed herein—and inhibits the function of glucagon, preferably in an in vitro assay or in an in vivo model as described, for example, in the Examples.

An antagonist to S1P as preferably used herein is a molecule that binds to S1P such as the nucleic acid molecule disclosed herein—and inhibits the function of S1P, preferably in an in vitro assay or in an in vivo model as described, for example, in the Examples.

An antagonist to C5a as preferably used herein is a molecule that binds to C5a such as the nucleic acid molecule disclosed herein—and inhibits the function of C5a, preferably in an in vitro assay or in an in vivo model as described, for example, in the Examples.

An antagonist to CGRP as preferably used herein is a molecule that binds to CGRP such as the nucleic acid molecule disclosed herein—and inhibits the function of CGRP, preferably in an in vitro assay or in an in vivo model as described, for example, in the Examples.

The nucleic acid molecule according to the present invention as well as the reference nucleic acid preferably comprises three different stretches of nucleotides: a first terminal stretch of nucleotides, a central stretch of nucleotides and a second terminal stretch of nucleotides. As in the field of nucleic acid molecules any sequence of nucleotides is indicated in a 5'→3'-direction, the first terminal stretch of nucleotides is arranged at the 5' end of the central stretch, and the second terminal stretch of nucleotides is arranged at the 3' end of the central stretch of nucleotides. Because of this, the first terminal stretch of nucleotides is also referred to herein as the 5'-terminal stretch of nucleotides, and the second terminal stretch of nucleotides is also referred to herein as the 3'-terminal stretch of nucleotides, and vice versa. However, it is also within the present invention that the first terminal stretch of nucleotides is referred to herein as the 3'-terminal stretch of nucleotides, and the second terminal stretch of nucleotides is referred to herein as the 5'-terminal stretch of nucleotides, and vice versa. This applies in particular in those embodiments where the first stretch of nucleotides and the second stretch of nucleotides are base complementary to each other.

In an embodiment of the nucleic acid molecule of the present invention, the first stretch of nucleotides and the second stretch of nucleotides are base complementary to each other. As preferably used herein two stretches of nucleotides are base complementary to each other if said two stretches, at least on paper or in silico, hybridize to each other, whereby upon hybridization a double-stranded structure is formed. The hybridization occurs or is made in accordance with known rules for base pairing such as and preferably Watson-Crick base pairing rules. However, and as will be acknowledged by the one skilled in the art other base pairing rules such as Hoogsten base pairing may occur or may be applied. It will also be acknowledged by a person skilled in the art that, also in connection with the nucleic acid molecule of the present invention, such hybridization results in a double-stranded structure. Such double-stranded structure may be part of a single nucleic acid molecule where two spatially separated stretches of a single strand of a nucleic acid molecule are hybridized. Alternatively, such double-stranded structure may be formed by two or more separate strands of two or more separate nucleic acid molecules. It will also be acknowledged by a person skilled in the art that any hybridization is not necessarily occurring or made over the entire length of the two stretches.

In a further embodiment two stretches of nucleotides are base complementary to each other if said two stretches may, in principle, hybridize under in vitro and/or in vitro conditions. The same considerations disclosed herein as to the first stretch of nucleotides and the second stretch of nucleotides being base complementary to each other and as to hybridization of the first stretch of nucleotides and the second stretch of nucleotides on paper or in silico equally apply to this embodiment. However, it has to be acknowledged that under such in vitro and/or in vivo conditions hybridization may or may not occur.

It is also to be acknowledged that in connection with the instant invention the feature that two stretches hybridize to each other preferably indicates that such hybridization is assumed to happen due to base complementarity of the two stretches but does not necessarily have to happen under any in vitro and/or in vivo conditions.

The three stretches of nucleotides of nucleic acid molecules—the first terminal stretch of nucleotides, the central stretch of nucleotides and second terminal stretch of nucleotides—are arranged to each other in 5'→3'-direction: the first terminal stretch of nucleotides the central stretch of nucleotides the second terminal stretch of nucleotides. However, alternatively, the second terminal stretch of nucleotides, the central stretch of nucleotides and the terminal first stretch of nucleotides are arranged to each other in 5'→3'-direction.

The differences in the sequences of the defined stretches between the different nucleic acid molecules such as the nucleic acid molecule of the present invention on the one hand and the reference nucleic acid molecule on the other hand, influence the binding affinity to the target molecule the nucleic acid molecule of the present invention is capable of binding to. In a preferred embodiment, based on binding analysis of the nucleic acid molecule of the present invention the central stretch of nucleotides of the nucleic acids according to the present invention and the nucleotides forming the same are individually and more preferably in their entirety essential for binding of the nucleic acid molecule of the present invention to the target molecule.

The terms 'stretch' and 'stretch of nucleotide' are used herein in a synonymous manner if not indicated to the contrary.

In a preferred embodiment the nucleic acid according to the present invention is a single nucleic acid molecule. In a further embodiment, the single nucleic acid molecule is present as a multitude of the single nucleic acid molecule or as a multitude of the single nucleic acid molecule species.

It will be acknowledged by the ones skilled in the art that the nucleic acid molecule of the present invention preferably consists of nucleotides which are covalently linked to each other, preferably through phosphodiester links or linkages.

In a preferred embodiment the term arrangement as used herein, means the order or sequence of structural or functional features or elements described herein in connection with the nucleic acids disclosed herein.

A nucleic acid molecule of the present invention shall also comprise a nucleic acid molecule which is essentially homologous to the nucleic acid molecule of the present invention and in particular to the particular sequence(s) disclosed herein. The term substantially homologous shall be understood such as the homology is at least 75%, preferably 85%, more preferably 90% and most preferably more that 95%, 96%, 97%, 98% or 99%.

The actual percentage of homologous nucleotides present in the nucleic acid molecule of the present invention will depend on the total number of nucleotides present in the nucleic acid molecule. The percent modification can be based upon the total number of nucleotides present in the nucleic acid molecule.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the homology reference sequence. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

A nucleic acid molecule of the present invention shall also comprise nucleic acid molecule which has a certain degree of identity relative to the nucleic acid molecule of the present invention and in particular to the particular nucleic acid molecules of the present invention disclosed herein and defined by their nucleotide sequence. More preferably, the instant invention also comprises those nucleic acid molecules which have an identity of at least 75%, preferably relative to the nucleic acid molecule of the present invention and in particular to the particular nucleic acid molecule of the present invention disclosed herein and defined by their nucleotide sequence or a part thereof.

The term inventive nucleic acid or nucleic acid according to or of the present invention shall also comprise those nucleic acid molecules comprising the nucleic acids sequences disclosed herein or part thereof, such as, e.g., a metabolite or derivative of the nucleic acid according to the present invention, preferably to the extent that the nucleic acids or said parts are involved in the or capable of binding to glucagon. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

It is also within the present invention that the nucleic acid molecule of the present invention is part of a longer nucleic acid molecule whereby this longer nucleic acid molecule comprises several parts whereby at least one such part is a nucleic acid molecule, or a part thereof, of the present invention. The other part(s) of such longer nucleic acid molecule can be either one or several D-nucleic acid(s) or L-nucleic acid(s). Any combination may be used in connection with the present invention. These other part(s) of the longer nucleic acid can exhibit a function which is different from binding. One possible function is to allow interaction with other molecules, whereby such other molecules such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acid molecules as used herein are nucleic acid molecules consisting of L-nucleotides, preferably consisting completely of L-nucleotides, more preferably the L-nucleotides are L-ribonucleotides or L-2'-deoxyribonucleotides. In a preferred embodiment the L-nucleic acid molecules consisting completely of L-ribonucleotides or L-2'-deoxyribonucleotides. In another preferred embodiment the L-nucleic acid molecules consisting L-ribonucleotides and L-2'-deoxyribonucleotides.

D-nucleic acid molecules as used herein are nucleic acid molecules consisting of D-nucleotides, preferably consisting completely of D-nucleotides, more preferably the D-nucleotides are D-ribonucleotides or D-2'-deoxyribonucleotides. In a preferred embodiment the D-nucleic acid molecules consisting completely of D-ribonucleotides or D-2'-deoxyribonucleotides. In another preferred embodiment the D-nucleic acid molecules consisting D-ribonucleotides and D-2'-deoxyribonucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

As preferably used herein any position of a nucleotide is determined or referred to relative to the 5' end of a sequence, a stretch or a substretch. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

Designing the nucleic acid molecule of the present invention as an L-nucleic acid molecule is advantageous for several reasons. L-nucleic acids are enantiomers of naturally occurring D-nucleic acids. D-nucleic acids, however, are not very stable in aqueous solutions and particularly in biological systems or biological samples due to the widespread presence of nucleases. Naturally occurring nucleases, particularly nucleases from animal cells, are not capable of degrading L-nucleic acids. Because of this the biological half-life of an L-nucleic acid is significantly increased in such a system, including the animal and human body. Due to the lacking degradability of L-nucleic acids no nuclease degradation products are generated and thus no side effects arising therefrom observed. This aspect delimits the L-nucleic acids from factually all other compounds which are used in the therapy of diseases and/or disorders involving the presence of a target molecule. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers. Aptamers and spiegelmers as such are known to a person skilled in the art and are, among others, described in 'The Aptamer Handbook' (eds. Klussmann, 2006).

It is also within the present invention that the nucleic acid molecule of the present invention, regardless whether it is present as a D-nucleic acid molecule, an L-nucleic acid molecule or a D,L-nucleic acid molecule, may be present as a single stranded or a double stranded nucleic acid molecule. Preferably, the nucleic acid molecule of the present invention is a single stranded nucleic acid molecule which exhibits defined secondary structures due to the primary sequence and may thus also form tertiary structures. The nucleic acid molecule of the present invention, however, may also be double stranded in the meaning that two strands which are complementary or partially complementary to each other are hybridised to each other.

The nucleic acid molecule of the present invention may be modified or may comprise at least one modification group. Such modifications may be related to the single nucleotide of the nucleic acid and are well known in the art. Examples for such modification are described by, among others, Venkatesan et al. (Venkatesan, Kim et al. 2003) and Kusser (Kusser 2000). Such modification can be a H atom, a F atom or O—CH₃ group or NH₂-group at the 2' position of the individual nucleotide of which the nucleic acid consists. Also, the nucleic acid of the present invention can comprise at least one LNA nucleotide. In an embodiment the nucleic acid according to the present invention consists of LNA nucleotides.

In an embodiment, the nucleic acid molecule of the present invention may be a multipartite nucleic acid. A multipartite nucleic acid as used herein is a nucleic acid which consists of at least two separate nucleic acid strands. These at least two nucleic acid strands form a functional unit whereby the functional unit is a ligand to a target molecule, preferable the target molecule, or is capable of binding to a target molecule, preferable the target molecule. The at least two nucleic acid strands may be derived from any nucleic acid molecule of the present invention by either cleaving the nucleic acid molecule to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally, it is also within the present invention that a fully closed, i.e. circular structure for the nucleic acids of the present invention is realized, i.e. that the nucleic acid molecule according to the present invention is closed in an embodiment, preferably through a covalent linkage, whereby more preferably such covalent linkage is made between the 5' end and the 3' end of the nucleic acid sequence(s) of the nucleic acid molecule of the present invention.

A possibility to determine the binding constants of the nucleic acid molecule of the present invention is the use of the methods as described in the examples which confirms the above finding that the nucleic acid molecule of the present invention exhibits a favourable $K_D$ value range. An appropriate measure in order to express the intensity of the binding between the individual nucleic acid molecule and the target molecule is the so-called $K_D$ value which as such as well the method for its determination are known to the one skilled in the art.

Preferably, the $K_D$ value shown by the nucleic acid molecule of the present invention is below 1 µM. $K_D$ value of about 1 µM is said to be characteristic for a non-specific binding of a nucleic acid molecule to a target molecule. As will be acknowledged by the ones skilled in the art, the $K_D$ value of a group of compounds such as the nucleic acid molecule of the present invention is within a certain range. The above-mentioned $K_D$ of about 1 µM is a preferred upper limit for the $K_D$ value. The lower limit for the $K_D$ of a target binding nucleic acid molecule can be as little as about 10 picomolar or can be higher. It is within the present invention that the $K_D$ values of individual nucleic acid molecule binding to the target molecule are preferably within this range. Preferred ranges can be defined by choosing any first number within this range and any second number within this range. Preferred upper $K_D$ values are 250 nM and 100 nM, preferred lower $K_D$ values are 50 nM, 10 nM, 1 nM, 100 pM and 10 pM. The more preferred upper $K_D$ value is 10 nM, the more preferred lower $K_D$ value is 100 pM.

In addition to the binding properties of the nucleic acid molecule of the present invention, the nucleic acid molecule of the present invention inhibits the function of the respective target molecule. The inhibition of the function of the target molecule—for instance the stimulation of a respective receptor of the target molecule as described previously—is achieved by binding of nucleic acid molecule of the present invention to the target molecule and forming a complex of a nucleic acid molecule of the present invention and the target molecule. Such complex of a nucleic acid molecule and the target molecule cannot stimulate the receptor(s) that normally are stimulated by the target molecule. Accordingly, the inhibition of receptor function by a nucleic acid molecule of the present invention is independent from the respective receptor that can be stimulated by the target molecule, but results from preventing the stimulation of the receptor by the target molecule by the nucleic acid molecule according to the present invention.

A possibility to determine the inhibitory constant of the nucleic acid molecule of the present invention is the use of the methods as described in the examples which confirms the above finding that the nucleic acid molecule of the present invention exhibits a favourable inhibitory constant which allows the use of such nucleic acid molecule in a therapeutic treatment scheme. An appropriate measure in order to express the intensity of the inhibitory effect of the individual nucleic acid molecule on the interaction with the target molecule, the target molecule and the respective receptor, is the so-called half maximal inhibitory concentration (abbr. $IC_{50}$) which as such as well the method for its determination are known to the one skilled in the art.

Preferably, the $IC_{50}$ value shown by the nucleic acid molecule of the present invention is below 1 µM. An $IC_{50}$ value of about 1 µM is said to be characteristic for a non-specific inhibition of target functions by a nucleic acid molecule. As will be acknowledged by the ones skilled in the art, the $IC_{50}$ value of a group of compounds such as the nucleic acid molecule of the present invention is within a certain range. The above-mentioned $IC_{50}$ of about 1 µM is a preferred upper limit for the $IC_{50}$ value. The lower limit for the $IC_{50}$ of target binding nucleic acid molecules such as the nucleic acid molecule of the present invention can be as little as about 10 picomolar or can be higher. It is within the present invention that the $IC_{50}$ values of a nucleic acid molecule of the present invention is preferably within this range. Preferred ranges can be defined by choosing any first number within this range and any second number within this range. Preferred upper $IC_{50}$ values are 250 nM and 100 nM, preferred lower $IC_{50}$ values are 50 nM, 10 nM, 1 nM, 100 pM and 10 pM. The more preferred upper $IC_{50}$ value is 5 nM, the more preferred lower $IC_{50}$ value is 1 nM.

The nucleic acid molecule of the present invention may have any length provided that they are still able to bind to or inhibit a function of the target molecule. It will be acknowledged in the art that there are preferred lengths of the nucleic acid molecule of the present inventions. Typically, the length is between 15 and 120 nucleotides. It will be acknowledged by the ones skilled in the art that any integer between 15 and 120 is a possible length for the nucleic acid molecule of the present invention. More preferred ranges for the length of the nucleic acids according to the present invention are lengths of about 20 to 100 nucleotides, about 20 to 80 nucleotides, about 20 to 60 nucleotides, about 20 to 54 nucleotides and about 39 to 44 nucleotides.

It is within the present invention that the nucleic acids disclosed herein comprise a modification group which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethyl starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

In the case of PEG being such high molecular weight moiety the molecular weight is preferably about 20,000 to about 120,000 Da, more preferably from about 30,000 to about 80,000 Da and most preferably about 40,000 Da. In the case of HES being such high molecular weight moiety the molecular weight is preferably from about 50 to about 1000 kDa, more preferably from about 100 to about 700 kDa and most preferably from 200 to 500 kDa. HES exhibits a molar substitution of 0.1 to 1.5, more preferably of 1 to 1.5 and exhibits a substitution sample expressed as the C2/C6 ratio of approximately 0.1 to 15, preferably of approximately 3 to 10. The process of HES modification is, e.g., described in German patent application DE 1 2004 006 249.8 the disclosure of which is herewith incorporated in its entirety by reference.

The modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or indirectly, preferably through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in patent applications WO2005/074993 and WO2003/035665.

In a preferred embodiment the linker is a biodegradable linker. The biodegradable linker allows to modify the characteristics of the nucleic acid according to the present invention in terms of, among other, residence time in an animal body, preferably in a human body, due to release of the modification from the nucleic acid according to the present invention. Usage of a biodegradable linker may allow a better control of the residence time of the nucleic acid according to the present invention. A preferred embodiment of such biodegradable linker is a biodegradable linker as described in, but not limited to, international patent applications WO2006/052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows to modify the characteristics of the nucleic acid according to the present invention in terms of, among other, residence time in an animal body, preferably in a human body, due to release or degradation of the modification from the nucleic acid according to the present invention. Usage of biodegradable modification may allow a better control of the residence time of the nucleic acid according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

Beside the modifications as described above, other modifications can be used to modify the characteristics of the nucleic acids according to the present invention, whereby such other modifications may be selected from the group of proteins, lipids such as cholesterol and sugar chains such as amylase, dextran etc.

Without wishing to be bound by any theory, it seems that by modifying the nucleic acids according to the present invention with high molecular weight moiety such as a polymer and more particularly one or several of the polymers disclosed herein, which are preferably physiologically acceptable, the excretion kinetic is changed. More particularly, it seems that due to the increased molecular weight of such modified inventive nucleic acids and due to the nucleic acids of the invention not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acids is significantly reduced compared to the nucleic acids not having this kind of high molecular weight modification which results in an increase in the residence time in the animal body. In connection therewith it is particularly noteworthy that, despite such high molecular weight modification the specificity of the nucleic acids according to the present invention is not affected in a detrimental manner. Insofar, the nucleic acids according to the present invention have among others, the surprising characteristic—which normally cannot be expected from pharmaceutically active compounds—such that a pharmaceutical formulation providing for a sustained release is not necessarily required to provide for a sustained release of the nucleic acids according to the present invention. Rather the nucleic acids according to the present invention in their modified form comprising a high molecular weight moiety, can as such already be used as a sustained release-formulation as they act, due to their modification, already as if they were released from a sustained-release formulation. Insofar, the modification(s) of the nucleic acid molecules according to the present invention as disclosed herein and the thus modified nucleic acid molecules according to the present invention and any composition comprising the same may provide for a distinct, preferably controlled pharmacokinetics and biodistribution thereof. This also includes residence time in circulation and distribution to tissues. Such modifications are further described in the patent application WO2003/035665.

However, it is also within the present invention that the nucleic acids according to the present invention do not comprise any modification and particularly no high molecular weight modification such as PEGylation or HESylation. Such embodiment is particularly preferred when the nucleic acid according to the present invention shows preferential distribution to any target organ or tissue in the body or when a fast clearance of the nucleic acid according to the present invention from the body after administration is desired. Nucleic acids according to the present invention as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids according to the present invention from the body after administration might be desired, among others, in case of in vivo imaging or specific therapeutic dosing requirements using the nucleic acids according to the present invention or medicaments comprising the same.

A further aspect of the present invention is related to the use of a nucleic acid molecule of the present invention and/or an antagonists of the present invention for the generation or manufacture of a medicament or a diagnostic agent. A still further aspect of the present invention is related to the use of a nucleic acid molecule of the present invention, and/or an antagonists of the present invention in a method of treating or preventing a disease.

A further aspect of the present invention is related to a pharmaceutical composition of the present invention contains at least a nucleic acid molecule of the present invention optionally together with further pharmaceutically active compounds, whereby the nucleic acid molecule of the present invention preferably acts as pharmaceutically active compound itself. Such pharmaceutical composition comprises in a preferred embodiment at least a pharmaceutically acceptable carrier. Such carrier may be, e.g., water, buffer, PBS, glucose solution, preferably a 5% glucose, salt balanced solution, citrate, starch, sugar, gelatine or any other acceptable carrier substance. Such carriers are generally known to the one skilled in the art. It will be acknowledged by the person skilled in the art that any embodiments, use and aspects of or related to the pharmaceutical composition of the present invention is also applicable to the medicament of the present invention, and vice versa.

It will be acknowledged by a person skilled in the art that the nucleic acid molecule of the present invention, the medicament and/or pharmaceutical composition containing the same can be used in particular for the treatment and/or prevention and/or diagnosis of any disease in which the target molecule to which the nucleic acid molecule of the invention is capable of binding is involved. More specifically, such disease is any disease where the binding of the nucleic acid molecule of the present invention to the target molecule, or where antagonizing the effect of the target molecule, preferably by means of the nucleic acid molecule of the present invention, is, in principle, suitable to treat the disease, to prevent the disease or to alleviate the symptoms of the disease.

In one embodiment of the medicament of the present invention, such medicament is for use in combination with other treatments for any of the diseases disclosed herein, particularly those for which the medicament of the present invention is to be used.

In one embodiment of the pharmaceutical composition of the present invention, such pharmaceutical composition is for use in combination with other treatments for any of the diseases disclosed herein, particularly those for which the medicament of the present invention is to be used.

"Combination therapy" (or "co-therapy") includes the administration of a medicament of the invention and at least a second or further agent as part of a specific treatment regimen intended to provide the beneficial effect from the co-action of these therapeutic agents, i. e. the medicament of the present invention and said second or further agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may be, but generally is not, intended to encompass the administration of two or more of these therapeutic agents as part of separate monotherapy regimens. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiency.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels.

Subjects that will respond favorably to the method of the invention include medical and veterinary subjects generally, including human beings and human patients. Among other subjects for whom the methods and means of the invention are useful are cats, dogs, large animals, avians such as chickens, and the like.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable binder. Such binder can be any binder used and/or known in the art. More particularly such binder is any binder as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

The medicament of the invention can also be administered in oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethyl-aspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and crosslinked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 200 µM, preferably from 1 nM to 20 µM, more preferably from 5 nM to 20 µM, most preferably 50 nM to 20 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes.

As preferably used herein a diagnostic or diagostic agent or diagnostic means is suitable to detect, either directly or indirectly the target—which is in the present case glucagon or S1P. The diagnostic is suitable for the detection and/or follow-up of any of the disorders and diseases related to the target—which is in the present case glucagon or S1P, respectively, described herein. Such detection is possible through the binding of the nucleic acids according to the present invention to target. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to target. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by a secondary antibody which is modified with radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin the label is detected by streptavidin or avidin which naturally bind to biotin. Such antibody, streptavidin or avidin in turn is preferably modified with a respective label, e.g. a radioactive, enzymatic or fluorescent label (like a secondary antibody).

In a further embodiment the nucleic acid molecules according to the invention are detected or analysed by a second detection means, wherein the said detection means is a molecular beacon. The methodology of molecular beacon is known to persons skilled in the art and reviewed by Mairal et al. (Mairal et al., 2008).

In connection with the detection of target a preferred method comprises the following steps:
(a) providing a sample which is to be tested for the presence of target, (b) providing a nucleic acid according to the present invention,
(c) reacting the sample with the nucleic acid, preferably in a reaction vessel
whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of target and the nucleic acid, whereby more preferably said complex is detected. It is within an embodiment that from the complex the target is detected.

A respective detection means which is in compliance with this requirement is, for example, any detection means which is specific for that/those part(s) of the target. A particularly preferred detection means is a detection means which is selected from the group comprising nucleic acids, polypeptides, proteins and antibodies, the generation of which is known to the ones skilled in the art.

The method for the detection of target also comprises that the sample is removed from the reaction vessel which has preferably been used to perform step c).

The method comprises in a further embodiment also the step of immobilising an interaction partner of target on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV-label, a radio-label, and a chelator molecule. Alternatively, the second detection means interacts with the detection label which is preferably contained by, comprised by or attached to the nucleic acid. Particularly preferred combinations are as follows:

the detection label is biotin and the second detection means is an antibody directed against biotin, or wherein the detection label is biotin and the second detection means is an avidin or an avidin carrying molecule, or wherein the detection label is biotin and the second detection means is a streptavidin or a streptavidin carrying molecule, or wherein the detection label is biotin and the second detection means is a neutravidin or a neutravidin carrying molecule, or wherein the detection label is a bromo-desoxyuridine and the second detection means is an antibody directed against bromo-desoxyuridine, or wherein the detection label is a digoxigenin and the second detection means is an antibody directed against digoxigenin, or wherein the detection label is a chelator and the second detection means is a radio-nuclide, whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of target being immobilised on a surface and the nucleic acid according to the present invention is preferably added to the complex formed between the interaction partner and the target, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and target and free target.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the target is detected using fluorescence.

In an embodiment of the method a signal is created in step (c) or step (d) and preferably the signal is correlated with the concentration of target in the sample.

In a preferred aspect, the assays may be performed in 96-well plates, where components are immobilized in the reaction vessels as described above and the wells acting as reaction vessels.

It has to be acknowledged that the nucleic acid molecules which are capable of binding to glucagon as described herein and more specifically in the example part are an embodiment of the nucleic acid molecule of the present invention.

It has to be acknowledged that the nucleic acid molecules which are capable of binding to S1P as described herein and more specifically in the example part are an embodiment of the nucleic acid molecule of the present invention.

It has to be acknowledged that the nucleic acid molecules which are capable of binding to CGRP as described herein and more specifically in the example part are an embodiment of the nucleic acid molecule of the present invention.

It has to be acknowledged that the nucleic acid molecules which are capable of binding to C5a as described herein and more specifically in the example part are an embodiment of the nucleic acid molecule of the present invention.

The various SEQ. ID. Nos., the chemical nature of the nucleic acid molecules according to the present invention and the target molecules as used herein, the actual sequence thereof and the internal reference number is summarized in the following table.

TABLE 1

| SEQ ID NO | RNA/Peptide | Internal Reference | Sequence 5'→3' |
|---|---|---|---|
| 1 | L-Peptide | CGRP | ACDTATCVTHRLAGLLSRSGGVVKNNFVPTNVGSKAF-NH$_2$ |
| 2 | L-Peptide | Human C5a | TLQKKIEEAAKYKHSVVKKCCYDAGACVNNDETCEQRAARISLGPRC IKAFTECCVVASQLRANISHKDMQLGR |
| 3 | L-Peptide | Biotin-Glucagon | HSQGTFTSDYSKYLDSRRAQDFVQWLMNT-Biotin |
| 4 | L-Peptide | Peptide Glucagon | HSQGTFTSDYSKYLDSRRAQDFVQWLMNT |
| 5 | L-RNA | L-S1P-215-F9-002 | GCGUGAAUAGCCGUUGAAACGCCUUUAGAGAAGCACUAGCACGC |
| 6 | L-DNA/L-RNA | L-S1P-215-F9-002-D01 | dGCGUGAAUAGCCGUUGAAACGCCUUUAGAGAAGCACUAGCACGC |
| 7 | L-DNA/L-RNA | L-S1P-215-F9-002-D02 | GdCGUGAAUAGCCGUUGAAACGCCUUUAGAGAAGCACUAGCACGC |
| 8 | L-DNA/L-RNA | L-S1P-215-F9-002-D03 | GCdGUGAAUAGCCGUUGAAACGCCUUUAGAGAAGCACUAGCACGC |
| 9 | L-DNA/L-RNA | L-S1P-215-F9-002-D04 | GCGdTGAAUAGCCGUUGAAACGCCUUUAGAGAAGCACUAGCACGC |
| 10 | L-DNA/L-RNA | L-S1P-215-F9-002-D05 | GCGUdGAAUAGCCGUUGAAACGCCUUUAGAGAAGCACUAGCACGC |
| 11 | L-DNA/L-RNA | L-S1P-215-F9-002-D06 | GCGUGdAAUAGCCGUUGAAACGCCUUUAGAGAAGCACUAGCACGC |
| 12 | L-DNA/L-RNA | L-S1P-215-F9-002-D07 | GCGUGAdAUAGCCGUUGAAACGCCUUUAGAGAAGCACUAGCACGC |
| 13 | L-DNA/L-RNA | L-S1P-215-F9-002-D08 | GCGUGAAdTAGCCGUUGAAACGCCUUUAGAGAAGCACUAGCACGC |
| 14 | L-DNA/L-RNA | L-S1P-215-F9-002-D09 | GCGUGAAUdAGCCGUUGAAACGCCUUUAGAGAAGCACUAGCACGC |
| 15 | L-DNA/L-RNA | L-S1P-215-F9-002-D10 | GCGUGAAUAdGCCGUUGAAACGCCUUUAGAGAAGCACUAGCACGC |
| 16 | L-DNA/L-RNA | L-S1P-215-F9-002-D11 | GCGUGAAUAGdCCGUUGAAACGCCUUUAGAGAAGCACUAGCACGC |
| 17 | L-DNA/L-RNA | L-S1P-215-F9-002-D12 | GCGUGAAUAGCdCGUUGAAACGCCUUUAGAGAAGCACUAGCACGC |
| 18 | L-DNA/L-RNA | L-S1P-215-F9-002-D13 | GCGUGAAUAGCCdGUUGAAACGCCUUUAGAGAAGCACUAGCACGC |

TABLE 1-continued

| SEQ ID NO | RNA/Peptide | Internal Reference | Sequence 5'→3' |
|---|---|---|---|
| 19 | L-DNA/L-RNA | L-S1P-215-F9-002-D14 | GCGUGAAUAGCCGdTUGAAACGCCUUUAGAGAAGCACUAGCACGC |
| 20 | L-DNA/L-RNA | L-S1P-215-F9-002-D15 | GCGUGAAUAGCCGUdTGAAACGCCUUUAGAGAAGCACUAGCACGC |
| 21 | L-DNA/L-RNA | L-S1P-215-F9-002-D16 | GCGUGAAUAGCCGUUdGAAACGCCUUUAGAGAAGCACUAGCACGC |
| 22 | L-DNA/L-RNA | L-S1P-215-F9-002-D17 | GCGUGAAUAGCCGUUGdAAACGCCUUUAGAGAAGCACUAGCACGC |
| 23 | L-DNA/L-RNA | L-S1P-215-F9-002-D18 | GCGUGAAUAGCCGUUGAdAACGCCUUUAGAGAAGCACUAGCACGC |
| 24 | L-DNA/L-RNA | L-S1P-215-F9-002-D19 | GCGUGAAUAGCCGUUGAAdACGCCUUUAGAGAAGCACUAGCACGC |
| 25 | L-DNA/L-RNA | L-S1P-215-F9-002-D20 | GCGUGAAUAGCCGUUGAAAdCGCCUUUAGAGAAGCACUAGCACGC |
| 26 | L-DNA/L-RNA | L-S1P-215-F9-002-D21 | GCGUGAAUAGCCGUUGAAACdGCCUUUAGAGAAGCACUAGCACGC |
| 27 | L-DNA/L-RNA | L-S1P-215-F9-002-D22 | GCGUGAAUAGCCGUUGAAACGdCCUUUAGAGAAGCACUAGCACGC |
| 28 | L-DNA/L-RNA | L-S1P-215-F9-002-D23 | GCGUGAAUAGCCGUUGAAACGCdCUUUAGAGAAGCACUAGCACGC |
| 29 | L-DNA/L-RNA | L-S1P-215-F9-002-D24 | GCGUGAAUAGCCGUUGAAACGCCdTUUAGAGAAGCACUAGCACGC |
| 30 | L-DNA/L-RNA | L-S1P-215-F9-002-D25 | GCGUGAAUAGCCGUUGAAACGCCUdTUAGAGAAGCACUAGCACGC |
| 31 | L-DNA/L-RNA | L-S1P-215-F9-002-D26 | GCGUGAAUAGCCGUUGAAACGCCUUdTAGAGAAGCACUAGCACGC |
| 32 | L-DNA/L-RNA | L-S1P-215-F9-002-D27 | GCGUGAAUAGCCGUUGAAACGCCUUUdAGAGAAGCACUAGCACGC |
| 33 | L-DNA/L-RNA | L-S1P-215-F9-002-D28 | GCGUGAAUAGCCGUUGAAACGCCUUUAdGAGAAGCACUAGCACGC |
| 34 | L-DNA/L-RNA | L-S1P-215-F9-002-D29 | GCGUGAAUAGCCGUUGAAACGCCUUUAGdAGAAGCACUAGCACGC |
| 35 | L-DNA/L-RNA | L-S1P-215-F9-002-D30 | GCGUGAAUAGCCGUUGAAACGCCUUUAGAdGAAGCACUAGCACGC |
| 36 | L-DNA/L-RNA | L-S1P-215-F9-002-D31 | GCGUGAAUAGCCGUUGAAACGCCUUUAGAGdAAGCACUAGCACGC |
| 37 | L-DNA/L-RNA | L-S1P-215-F9-002-D32 | GCGUGAAUAGCCGUUGAAACGCCUUUAGAGAdAGCACUAGCACGC |
| 38 | L-DNA/L-RNA | L-S1P-215-F9-002-D33 | GCGUGAAUAGCCGUUGAAACGCCUUUAGAGAAdGCACUAGCACGC |
| 39 | L-DNA/L-RNA | L-S1P-215-F9-002-D34 | GCGUGAAUAGCCGUUGAAACGCCUUUAGAGAAGdCACUAGCACGC |
| 40 | L-DNA/L-RNA | L-S1P-215-F9-002-D35 | GCGUGAAUAGCCGUUGAAACGCCUUUAGAGAAGCdACUAGCACGC |
| 41 | L-DNA/L-RNA | L-S1P-215-F9-002-D36 | GCGUGAAUAGCCGUUGAAACGCCUUUAGAGAAGCAdCUAGCACGC |
| 42 | L-DNA/L-RNA | L-S1P-215-F9-002-D37 | GCGUGAAUAGCCGUUGAAACGCCUUUAGAGAAGCACdTAGCACGC |
| 43 | L-DNA/L-RNA | L-S1P-215-F9-002-D38 | GCGUGAAUAGCCGUUGAAACGCCUUUAGAGAAGCACUdAGCACGC |
| 44 | L-DNA/L-RNA | L-S1P-215-F9-002-D39 | GCGUGAAUAGCCGUUGAAACGCCUUUAGAGAAGCACUAdGCACGC |

TABLE 1-continued

| SEQ ID NO | RNA/Peptide | Internal Reference | Sequence 5'→3' |
|---|---|---|---|
| 45 | L-DNA/L-RNA | L-S1P-215-F9-002-D40 | GCGUGAAUAGCCGUUGAAACGCCUUUAGAGAAGCACUAGdCACGC |
| 46 | L-DNA/L-RNA | L-S1P-215-F9-002-D41 | GCGUGAAUAGCCGUUGAAACGCCUUUAGAGAAGCACUAGCdACGC |
| 47 | L-DNA/L-RNA | L-S1P-215-F9-002-D42 | GCGUGAAUAGCCGUUGAAACGCCUUUAGAGAAGCACUAGCAdCGC |
| 48 | L-DNA/L-RNA | L-S1P-215-F9-002-D43 | GCGUGAAUAGCCGUUGAAACGCCUUUAGAGAAGCACUAGCACdGC |
| 49 | L-DNA/L-RNA | L-S1P-215-F9-002-D44 | GCGUGAAUAGCCGUUGAAACGCCUUUAGAGAAGCACUAGCACGdC |
| 50 | L-DNA/L-RNA | L-S1P-215-F9-002-D21-22 | GCGUGAAUAGCCGUUGAAACdGdCCUUUAGAGAAGCACUAGCACGC |
| 51 | L-DNA/L-RNA | L-S1P-215-F9-002-D21-19 | GCGUGAAUAGCCGUUGAAdACdGCCUUUAGAGAAGCACUAGCACGC |
| 52 | L-DNA/L-RNA | L-S1P-215-F9-002-D21-19-22 | GCGUGAAUAGCCGUUGAAdACdGdCCUUUAGAGAAGCACUAGCACGC |
| 53 | L-DNA/L-RNA | L-S1P-215-F9-002-D01-19-21-32 | dGCGUGAAUAGCCGUUGAAdACdGCCUUUAGAGAdAGCACUAGCACGC |
| 54 | L-DNA/L-RNA | L-S1P-215-F9-002-D01-11-19-21-32 | dGCGUGAAUAGdCCGUUGAAdACdGCCUUUAGAGAdAGCACUAGCACGC |
| 55 | L-DNA/L-RNA | 226-F2-001 | CCGUGCUGUCGGAGACUACUCGUCGAGUAGAAAUAGGUCCCCUCCCACGG |
| 56 | L-DNA/L-RNA | 226-F2-001-D01 | dCCGUGCUGUCGGAGACUACUCGUCGAGUAGAAAUAGGUCCCCUCCCACGG |
| 57 | L-DNA/L-RNA | 226-F2-001-D02 | CdCGUGCUGUCGGAGACUACUCGUCGAGUAGAAAUAGGUCCCCUCCCACGG |
| 58 | L-DNA/L-RNA | 226-F2-001-D03 | CCdGUGCUGUCGGAGACUACUCGUCGAGUAGAAAUAGGUCCCCUCCCACGG |
| 59 | L-DNA/L-RNA | 226-F2-001-D04 | CCGdTGCUGUCGGAGACUACUCGUCGAGUAGAAAUAGGUCCCCUCCCACGG |
| 60 | L-DNA/L-RNA | 226-F2-001-D05 | CCGUdGCUGUCGGAGACUACUCGUCGAGUAGAAAUAGGUCCCCUCCCACGG |
| 61 | L-DNA/L-RNA | 226-F2-001-D06 | CCGUGdCUGUCGGAGACUACUCGUCGAGUAGAAAUAGGUCCCCUCCCACGG |
| 62 | L-DNA/L-RNA | 226-F2-001-D07 | CCGUGCdTGUCGGAGACUACUCGUCGAGUAGAAAUAGGUCCCCUCCCACGG |
| 63 | L-DNA/L-RNA | 226-F2-001-D08 | CCGUGCUdGUCGGAGACUACUCGUCGAGUAGAAAUAGGUCCCCUCCCACGG |
| 64 | L-DNA/L-RNA | 226-F2-001-D09 | CCGUGCUGdTCGGAGACUACUCGUCGAGUAGAAAUAGGUCCCCUCCCACGG |
| 65 | L-DNA/L-RNA | 226-F2-001-D10 | CCGUGCUGUdCGGAGACUACUCGUCGAGUAGAAAUAGGUCCCCUCCCACGG |
| 66 | L-DNA/L-RNA | 226-F2-001-D11 | CCGUGCUGUCdGGAGACUACUCGUCGAGUAGAAAUAGGUCCCCUCCCACGG |
| 67 | L-DNA/L-RNA | 226-F2-001-D12 | CCGUGCUGUCGdGAGACUACUCGUCGAGUAGAAAUAGGUCCCCUCCCACGG |
| 68 | L-DNA/L-RNA | 226-F2-001-D13 | CCGUGCUGUCGGdAGACUACUCGUCGAGUAGAAAUAGGUCCCCUCCCACGG |
| 69 | L-DNA/L-RNA | 226-F2-001-D14 | CCGUGCUGUCGGAdGACUACUCGUCGAGUAGAAAUAGGUCCCCUCCCACGG |

TABLE 1-continued

| SEQ ID NO | RNA/Peptide | Internal Reference | Sequence 5'→3' |
|---|---|---|---|
| 70 | L-DNA/L-RNA | 226-F2-001-D15 | CCGUGCUGUCGGAGdACUACUCGUCGAGUAGAAAUAGGUCCCCUCCCACGG |
| 71 | L-DNA/L-RNA | 226-F2-001-D16 | CCGUGCUGUCGGAGAdCUACUCGUCGAGUAGAAAUAGGUCCCCUCCCACGG |
| 72 | L-DNA/L-RNA | 226-F2-001-D17 | CCGUGCUGUCGGAGACdTACUCGUCGAGUAGAAAUAGGUCCCCUCCCACGG |
| 73 | L-DNA/L-RNA | 226-F2-001-D18 | CCGUGCUGUCGGAGACUdACUCGUCGAGUAGAAAUAGGUCCCCUCCCACGG |
| 74 | L-DNA/L-RNA | 226-F2-001-D19 | CCGUGCUGUCGGAGACUAdCUCGUCGAGUAGAAAUAGGUCCCCUCCCACGG |
| 75 | L-DNA/L-RNA | 226-F2-001-D20 | CCGUGCUGUCGGAGACUACdTCGUCGAGUAGAAAUAGGUCCCCUCCCACGG |
| 76 | L-DNA/L-RNA | 226-F2-001-D21 | CCGUGCUGUCGGAGACUACUdCGUCGAGUAGAAAUAGGUCCCCUCCCACGG |
| 77 | L-DNA/L-RNA | 226-F2-001-D22 | CCGUGCUGUCGGAGACUACUCdGUCGAGUAGAAAUAGGUCCCCUCCCACGG |
| 78 | L-DNA/L-RNA | 226-F2-001-D23 | CCGUGCUGUCGGAGACUACUCGdTCGAGUAGAAAUAGGUCCCCUCCCACGG |
| 79 | L-DNA/L-RNA | 226-F2-001-D24 | CCGUGCUGUCGGAGACUACUCGUdCGAGUAGAAAUAGGUCCCCUCCCACGG |
| 80 | L-DNA/L-RNA | 226-F2-001-D25 | CCGUGCUGUCGGAGACUACUCGUCdGAGUAGAAAUAGGUCCCCUCCCACGG |
| 81 | L-DNA/L-RNA | 226-F2-001-D26 | CCGUGCUGUCGGAGACUACUCGUCGdAGUAGAAAUAGGUCCCCUCCCACGG |
| 82 | L-DNA/L-RNA | 226-F2-001-D27 | CCGUGCUGUCGGAGACUACUCGUCGAdGUAGAAAUAGGUCCCCUCCCACGG |
| 83 | L-DNA/L-RNA | 226-F2-001-D28 | CCGUGCUGUCGGAGACUACUCGUCGAGdTAGAAAUAGGUCCCCUCCCACGG |
| 84 | L-DNA/L-RNA | 226-F2-001-D29 | CCGUGCUGUCGGAGACUACUCGUCGAGUdAGAAAUAGGUCCCCUCCCACGG |
| 85 | L-DNA/L-RNA | 226-F2-001-D30 | CCGUGCUGUCGGAGACUACUCGUCGAGUAdGAAAUAGGUCCCCUCCCACGG |
| 86 | L-DNA/L-RNA | 226-F2-001-D31 | CCGUGCUGUCGGAGACUACUCGUCGAGUAGdAAAUAGGUCCCCUCCCACGG |
| 87 | L-DNA/L-RNA | 226-F2-001-D32 | CCGUGCUGUCGGAGACUACUCGUCGAGUAGAdAAUAGGUCCCCUCCCACGG |
| 88 | L-DNA/L-RNA | 226-F2-001-D33 | CCGUGCUGUCGGAGACUACUCGUCGAGUAGAAdAUAGGUCCCCUCCCACGG |
| 89 | L-DNA/L-RNA | 226-F2-001-D34 | CCGUGCUGUCGGAGACUACUCGUCGAGUAGAAAdTAGGUCCCCUCCCACGG |
| 90 | L-DNA/L-RNA | 226-F2-001-D35 | CCGUGCUGUCGGAGACUACUCGUCGAGUAGAAAUdAGGUCCCCUCCCACGG |
| 91 | L-DNA/L-RNA | 226-F2-001-D36 | CCGUGCUGUCGGAGACUACUCGUCGAGUAGAAAUAdGGUCCCCUCCCACGG |
| 92 | L-DNA/L-RNA | 226-F2-001-D37 | CCGUGCUGUCGGAGACUACUCGUCGAGUAGAAAUAGdGUCCCCUCCCACGG |
| 93 | L-DNA/L-RNA | 226-F2-001-D38 | CCGUGCUGUCGGAGACUACUCGUCGAGUAGAAAUAGGdTCCCCUCCCACGG |
| 94 | L-DNA/L-RNA | 226-F2-001-D39 | CCGUGCUGUCGGAGACUACUCGUCGAGUAGAAAUAGGUdCCCCUCCCACGG |

TABLE 1-continued

| SEQ ID NO | RNA/Peptide | Internal Reference | Sequence 5'→3' |
|---|---|---|---|
| 95 | L-DNA/L-RNA | 226-F2-001-D40 | CCGUGCUGUCGGAGACUACUCGUCGAGUAGAAAUAGGUCdCCCUCCCACGG |
| 96 | L-DNA/L-RNA | 226-F2-001-D41 | CCGUGCUGUCGGAGACUACUCGUCGAGUAGAAAUAGGUCCdCCUCCCACGG |
| 97 | L-DNA/L-RNA | 226-F2-001-D42 | CCGUGCUGUCGGAGACUACUCGUCGAGUAGAAAUAGGUCCCdCUCCCACGG |
| 98 | L-DNA/L-RNA | 226-F2-001-D43 | CCGUGCUGUCGGAGACUACUCGUCGAGUAGAAAUAGGUCCCCdTCCCACGG |
| 99 | L-DNA/L-RNA | 226-F2-001-D44 | CCGUGCUGUCGGAGACUACUCGUCGAGUAGAAAUAGGUCCCCUdCCCACGG |
| 100 | L-DNA/L-RNA | 226-F2-001-D45 | CCGUGCUGUCGGAGACUACUCGUCGAGUAGAAAUAGGUCCCCUCdCCACGG |
| 101 | L-DNA/L-RNA | 226-F2-001-D46 | CCGUGCUGUCGGAGACUACUCGUCGAGUAGAAAUAGGUCCCCUCCdCACGG |
| 102 | L-DNA/L-RNA | 226-F2-001-D47 | CCGUGCUGUCGGAGACUACUCGUCGAGUAGAAAUAGGUCCCCUCCCdACGG |
| 103 | L-DNA/L-RNA | 226-F2-001-D48 | CCGUGCUGUCGGAGACUACUCGUCGAGUAGAAAUAGGUCCCCUCCCAdCGG |
| 104 | L-DNA/L-RNA | 226-F2-001-D49 | CCGUGCUGUCGGAGACUACUCGUCGAGUAGAAAUAGGUCCCCUCCCACdGG |
| 105 | L-DNA/L-RNA | 226-F2-001-D50 | CCGUGCUGUCGGAGACUACUCGUCGAGUAGAAAUAGGUCCCCUCCCACGdG |
| 106 | L-DNA/L-RNA | 226-F2-001-D41/D44 | CCGUGCUGUCGGAGACUACUCGUCGAGUAGAAAUAGGUCCdCUdCCCACGG |
| 107 | L-DNA/L-RNA | NOX-D19001 | GCCUGAUGUGGUGGUGAAGGGUUGUUGGGUGUCGACGCACAGGC |
| 108 | L-DNA/L-RNA | NOX-D19001-D01 | dGCCUGAUGUGGUGGUGAAGGGUUGUUGGGUGUCGACGCACAGGC |
| 109 | L-DNA/L-RNA | NOX-D19001-D02 | GdCCUGAUGUGGUGGUGAAGGGUUGUUGGGUGUCGACGCACAGGC |
| 110 | L-DNA/L-RNA | NOX-D19001-D03 | GCdCUGAUGUGGUGGUGAAGGGUUGUUGGGUGUCGACGCACAGGC |
| 111 | L-DNA/L-RNA | NOX-D19001-D04 | GCCdUGAUGUGGUGGUGAAGGGUUGUUGGGUGUCGACGCACAGGC |
| 112 | L-DNA/L-RNA | NOX-D19001-D05 | GCCUdGAUGUGGUGGUGAAGGGUUGUUGGGUGUCGACGCACAGGC |
| 113 | L-DNA/L-RNA | NOX-D19001-D06 | GCCUGdAUGUGGUGGUGAAGGGUUGUUGGGUGUCGACGCACAGGC |
| 114 | L-DNA/L-RNA | NOX-D19001-D07 | GCCUGAdUGUGGUGGUGAAGGGUUGUUGGGUGUCGACGCACAGGC |
| 115 | L-DNA/L-RNA | NOX-D19001-D08 | GCCUGAUdGUGGUGGUGAAGGGUUGUUGGGUGUCGACGCACAGGC |
| 116 | L-DNA/L-RNA | NOX-D19001-D09 | GCCUGAUGdUGGUGGUGAAGGGUUGUUGGGUGUCGACGCACAGGC |
| 117 | L-DNA/L-RNA | NOX-D19001-D10 | GCCUGAUGUdGGUGGUGAAGGGUUGUUGGGUGUCGACGCACAGGC |
| 118 | L-DNA/L-RNA | NOX-D19001-D11 | GCCUGAUGUGdGGUGAAGGGUUGUUGGGUGUCGACGCACAGGC |
| 119 | L-DNA/L-RNA | NOX-D19001-D12 | GCCUGAUGUGGdUGGUGAAGGGUUGUUGGGUGUCGACGCACAGGC |

TABLE 1-continued

| SEQ ID NO | RNA/Peptide | Internal Reference | Sequence 5'→3' |
|---|---|---|---|
| 120 | L-DNA/L-RNA | NOX-D19001-D13 | GCCUGAUGUGGU<u>dG</u>GUGAAGGGUUGUUGGGUGUCGACGCACAGGC |
| 121 | L-DNA/L-RNA | NOX-D19001-D14 | GCCUGAUGUGGUG<u>dG</u>UGAAGGGUUGUUGGGUGUCGACGCACAGGC |
| 122 | L-DNA/L-RNA | NOX-D19001-D15 | GCCUGAUGUGGUGG<u>dU</u>GAAGGGUUGUUGGGUGUCGACGCACAGGC |
| 123 | L-DNA/L-RNA | NOX-D19001-D16 | GCCUGAUGUGGUGGU<u>dG</u>AAGGGUUGUUGGGUGUCGACGCACAGGC |
| 124 | L-DNA/L-RNA | NOX-D19001-D17 | GCCUGAUGUGGUGGUG<u>dA</u>AGGGUUGUUGGGUGUCGACGCACAGGC |
| 125 | L-DNA/L-RNA | NOX-D19001-D18 | GCCUGAUGUGGUGGUGA<u>dA</u>GGGUUGUUGGGUGUCGACGCACAGGC |
| 126 | L-DNA/L-RNA | NOX-D19001-D19 | GCCUGAUGUGGUGGUGAA<u>dG</u>GGUUGUUGGGUGUCGACGCACAGGC |
| 127 | L-DNA/L-RNA | NOX-D19001-D20 | GCCUGAUGUGGUGGUGAAG<u>dG</u>GUUGUUGGGUGUCGACGCACAGGC |
| 128 | L-DNA/L-RNA | NOX-D19001-D21 | GCCUGAUGUGGUGGUGAAGG<u>dG</u>UUGUUGGGUGUCGACGCACAGGC |
| 129 | L-DNA/L-RNA | NOX-D19001-D22 | GCCUGAUGUGGUGGUGAAGGG<u>dU</u>UGUUGGGUGUCGACGCACAGGC |
| 130 | L-DNA/L-RNA | NOX-D19001-D23 | GCCUGAUGUGGUGGUGAAGGGU<u>dU</u>GUUGGGUGUCGACGCACAGGC |
| 131 | L-DNA/L-RNA | NOX-D19001-D24 | GCCUGAUGUGGUGGUGAAGGGUU<u>dG</u>UUGGGUGUCGACGCACAGGC |
| 132 | L-DNA/L-RNA | NOX-D19001-D25 | GCCUGAUGUGGUGGUGAAGGGUUG<u>dU</u>UGGGUGUCGACGCACAGGC |
| 133 | L-DNA/L-RNA | NOX-D19001-D26 | GCCUGAUGUGGUGGUGAAGGGUUGU<u>dU</u>GGGUGUCGACGCACAGGC |
| 134 | L-DNA/L-RNA | NOX-D19001-D27 | GCCUGAUGUGGUGGUGAAGGGUUGUU<u>dG</u>GGUGUCGACGCACAGGC |
| 135 | L-DNA/L-RNA | NOX-D19001-D28 | GCCUGAUGUGGUGGUGAAGGGUUGUUG<u>dG</u>GUGUCGACGCACAGGC |
| 136 | L-DNA/L-RNA | NOX-D19001-D29 | GCCUGAUGUGGUGGUGAAGGGUUGUUGG<u>dG</u>UGUCGACGCACAGGC |
| 137 | L-DNA/L-RNA | NOX-D19001-D30 | GCCUGAUGUGGUGGUGAAGGGUUGUUGGG<u>dU</u>GUCGACGCACAGGC |
| 138 | L-DNA/L-RNA | NOX-D19001-D31 | GCCUGAUGUGGUGGUGAAGGGUUGUUGGGU<u>dG</u>UCGACGCACAGGC |
| 139 | L-DNA/L-RNA | NOX-D19001-D32 | GCCUGAUGUGGUGGUGAAGGGUUGUUGGGUG<u>dU</u>CGACGCACAGGC |
| 140 | L-DNA/L-RNA | NOX-D19001-D33 | GCCUGAUGUGGUGGUGAAGGGUUGUUGGGUGU<u>dC</u>GACGCACAGGC |
| 141 | L-DNA/L-RNA | NOX-D19001-D34 | GCCUGAUGUGGUGGUGAAGGGUUGUUGGGUGUC<u>dG</u>ACGCACAGGC |
| 142 | L-DNA/L-RNA | NOX-D19001-D35 | GCCUGAUGUGGUGGUGAAGGGUUGUUGGGUGUCG<u>dA</u>CGCACAGGC |
| 143 | L-DNA/L-RNA | NOX-D19001-D36 | GCCUGAUGUGGUGGUGAAGGGUUGUUGGGUGUCGA<u>dC</u>GCACAGGC |
| 144 | L-DNA/L-RNA | NOX-D19001-D37 | GCCUGAUGUGGUGGUGAAGGGUUGUUGGGUGUCGAC<u>dG</u>CACAGGC |

TABLE 1-continued

| SEQ ID NO | RNA/Peptide | Internal Reference | Sequence 5'→3' |
|---|---|---|---|
| 145 | L-DNA/L-RNA | NOX-D19001-D38 | GCCUGAUGUGGUGGUGAAGGGUUGUUGGGUGUCGACGdCACAGGC |
| 146 | L-DNA/L-RNA | NOX-D19001-D39 | GCCUGAUGUGGUGGUGAAGGGUUGUUGGGUGUCGACGCdACAGGC |
| 147 | L-DNA/L-RNA | NOX-D19001-D40 | GCCUGAUGUGGUGGUGAAGGGUUGUUGGGUGUCGACGCAdCAGGC |
| 148 | L-DNA/L-RNA | NOX-D19001-D41 | GCCUGAUGUGGUGGUGAAGGGUUGUUGGGUGUCGACGCACdAGGC |
| 149 | L-DNA/L-RNA | NOX-D19001-D42 | GCCUGAUGUGGUGGUGAAGGGUUGUUGGGUGUCGACGCACAdGGC |
| 150 | L-DNA/L-RNA | NOX-D19001-D43 | GCCUGAUGUGGUGGUGAAGGGUUGUUGGGUGUCGACGCACAGdGC |
| 151 | L-DNA/L-RNA | NOX-D19001-D44 | GCCUGAUGUGGUGGUGAAGGGUUGUUGGGUGUCGACGCACAGGdC |
| 152 | L-DNA/L-RNA | NOX-D19001-D09-30 | GCCUGAUGdUGGUGGUGAAGGGUUGUUGGGdUGUCGACGCACAGGC |
| 153 | L-DNA/L-RNA | NOX-D19001-D09-32 | GCCUGAUGdUGGUGGUGAAGGGUUGUUGGGUGdUCGACGCACAGGC |
| 154 | L-DNA/L-RNA | NOX-D19001-D09-40 | GCCUGAUGdUGGUGGUGAAGGGUUGUUGGGUGUCGACGCAdCAGGC |
| 155 | L-DNA/L-RNA | NOX-D19001-D30-32 | GCCUGAUGUGGUGGUGAAGGGUUGUUGGGdUGdUCGACGCACAGGC |
| 156 | L-DNA/L-RNA | NOX-D19001-D30-40 | GCCUGAUGUGGUGGUGAAGGGUUGUUGGGdUGUCGACGCAdCAGGC |
| 157 | L-DNA/L-RNA | NOX-D19001-D32-40 | GCCUGAUGUGGUGGUGAAGGGUUGUUGGGUGdUCGACGCAdCAGGC |
| 158 | L-DNA/L-RNA | NOX-D19001-D09-30-32 | GCCUGAUGdUGGUGGUGAAGGGUUGUUGGGdUGdUCGACGCACAGGC |
| 159 | L-DNA/L-RNA | NOX-D19001-D09-30-40 | GCCUGAUGdUGGUGGUGAAGGGUUGUUGGGdUGUCGACGCAdCAGGC |
| 160 | L-DNA/L-RNA | NOX-D19001-D09-32-40 | GCCUGAUGdUGGUGGUGAAGGGUUGUUGGGUGdUCGACGCAdCAGGC |
| 161 | L-DNA/L-RNA | NOX-D19001-D30-32-40 | GCCUGAUGUGGUGGUGAAGGGUUGUUGGGdUGdUCGACGCAdCAGGC |
| 162 | L-DNA/L-RNA | NOX-D19001-D09-30-32-40 | GCCUGAUGdUGGUGGUGAAGGGUUGUUGGGdUGdUCGACGCAdCAGGC |
| 163 | L-DNA/L-RNA | NOX-D19001-D09-16-30-32-40 | GCCUGAUGdUGGUGGUdGAAGGGUUGUUGGGdUGdUCGACGCAdCAGGC |
| 164 | L-DNA/L-RNA | NOX-D19001-D09-17-30-32-40 | GCCUGAUGdUGGUGGUGdAAGGGUUGUUGGGdUGdUCGACGCAdCAGGC |
| 165 | L-DNA/L-RNA | NOX-D19001-D09-16-17-30-32-40 (= NOX-D19001-6xDNA) | GCCUGAUGdUGGUGGUdGdAAGGGUUGUUGGGdUGdUCGACGCAdCAGGC |
| 166 | L-DNA/L-RNA | NOX-D19001-D07-30 | GCCUGAdUGUGGUGGUGAAGGGUUGUUGGGdUGUCGACGCACAGGC |
| 167 | L-DNA/L-RNA | NOX-D19001-D07-30-40 | GCCUGAdUGUGGUGGUGAAGGGUUGUUGGGdUGUCGACGCAdCAGGC |
| 168 | L-DNA/L-RNA | NOX-D19001-D07-30-32-40 | GCCUGAdUGUGGUGGUGAAGGGUUGUUGGGdUGdUCGACGCAdCAGGC |
| 169 | L-DNA/L-RNA | NOX-D19001-D07-16-30-32-40 | GCCUGAdUGUGGUGGUdGAAGGGUUGUUGGGdUGdUCGACGCAdCAGGC |

TABLE 1-continued

| SEQ ID NO | RNA/ L-DNA/ Peptide | Internal Reference | Sequence 5'→3' |
|---|---|---|---|
| 170 | L-DNA/ L-RNA | NOX-D19001-D07-17-30-32-40 | GCCUGAdUGUGGUGGUGdAAGGGUUGUUGGGdUGdUCGACGCAdCAGGC |
| 171 | L-DNA/ L-RNA | NOX-D19001-D07-16-17-30-32-40 | GCCUGAdUGUGGUGGUdGdAAGGGUUGUUGGGdUGdUCGACGCAdCAGGC |
| 172 | L-DNA/ L-RNA | NOX-G11stabi2 | CAGACGUGUGUGGGUAGAUGCACCUGCGAUUCGCUAAAAAGUGCCACACGUCUG |
| 173 | L-DNA/ L-RNA | NOX-G11-D01 | dCAGACGUGUGUGGGUAGAUGCACCUGCGAUUCGCUAAAAAGUGCCACACGUCUG |
| 174 | L-DNA/ L-RNA | NOX-G11-D02 | CdAGACGUGUGUGGGUAGAUGCACCUGCGAUUCGCUAAAAAGUGCCACACGUCUG |
| 175 | L-DNA/ L-RNA | NOX-G11-D03 | CAdGACGUGUGUGGGUAGAUGCACCUGCGAUUCGCUAAAAAGUGCCACACGUCUG |
| 176 | L-DNA/ L-RNA | NOX-G11-D04 | CAGdACGUGUGUGGGUAGAUGCACCUGCGAUUCGCUAAAAAGUGCCACACGUCUG |
| 177 | L-DNA/ L-RNA | NOX-G11-D05 | CAGAdCGUGUGUGGGUAGAUGCACCUGCGAUUCGCUAAAAAGUGCCACACGUCUG |
| 178 | L-DNA/ L-RNA | NOX-G11-D06 | CAGACdGUGUGUGGGUAGAUGCACCUGCGAUUCGCUAAAAAGUGCCACACGUCUG |
| 179 | L-DNA/ L-RNA | NOX-G11-D07 | CAGACGdTGUGUGGGUAGAUGCACCUGCGAUUCGCUAAAAAGUGCCACACGUCUG |
| 180 | L-DNA/ L-RNA | NOX-G11-D08 | CAGACGUdGUGUGGGUAGAUGCACCUGCGAUUCGCUAAAAAGUGCCACACGUCUG |
| 181 | L-DNA/ L-RNA | NOX-G11-D09 | CAGACGUGdTGUGGGUAGAUGCACCUGCGAUUCGCUAAAAAGUGCCACACGUCUG |
| 182 | L-DNA/ L-RNA | NOX-G11-D10 | CAGACGUGUdGUGGGUAGAUGCACCUGCGAUUCGCUAAAAAGUGCCACACGUCUG |
| 183 | L-DNA/ L-RNA | NOX-G11-D11 | CAGACGUGUGdTGGGUAGAUGCACCUGCGAUUCGCUAAAAAGUGCCACACGUCUG |
| 184 | L-DNA/ L-RNA | NOX-G11-D12 | CAGACGUGUGUdGGGUAGAUGCACCUGCGAUUCGCUAAAAAGUGCCACACGUCUG |
| 185 | L-DNA/ L-RNA | NOX-G11-D13 | CAGACGUGUGUGdGGUAGAUGCACCUGCGAUUCGCUAAAAAGUGCCACACGUCUG |
| 186 | L-DNA/ L-RNA | NOX-G11-D14 | CAGACGUGUGUGGdGUAGAUGCACCUGCGAUUCGCUAAAAAGUGCCACACGUCUG |
| 187 | L-DNA/ L-RNA | NOX-G11-D15 | CAGACGUGUGUGGGdTAGAUGCACCUGCGAUUCGCUAAAAAGUGCCACACGUCUG |
| 188 | L-DNA/ L-RNA | NOX-G11-D16 | CAGACGUGUGUGGGUdAGAUGCACCUGCGAUUCGCUAAAAAGUGCCACACGUCUG |
| 189 | L-DNA/ L-RNA | NOX-G11-D17 | CAGACGUGUGUGGGUAdGAUGCACCUGCGAUUCGCUAAAAAGUGCCACACGUCUG |
| 190 | L-DNA/ L-RNA | NOX-G11-D18 | CAGACGUGUGUGGGUAGdAUGCACCUGCGAUUCGCUAAAAAGUGCCACACGUCUG |
| 191 | L-DNA/ L-RNA | NOX-G11-D19 | CAGACGUGUGUGGGUAGAdTGCACCUGCGAUUCGCUAAAAAGUGCCACACGUCUG |
| 192 | L-DNA/ L-RNA | NOX-G11-D20 | CAGACGUGUGUGGGUAGAUdGCACCUGCGAUUCGCUAAAAAGUGCCACACGUCUG |
| 193 | L-DNA/ L-RNA | NOX-G11-D21 | CAGACGUGUGUGGGUAGAUGdCACCUGCGAUUCGCUAAAAAGUGCCACACGUCUG |
| 194 | L-DNA/ L-RNA | NOX-G11-D22 | CAGACGUGUGUGGGUAGAUGCdACCUGCGAUUCGCUAAAAAGUGCCACACGUCUG |
| 195 | L-DNA/ L-RNA | NOX-G11-D23 | CAGACGUGUGUGGGUAGAUGCAdCCUGCGAUUCGCUAAAAAGUGCCACACGUCUG |

TABLE 1-continued

| SEQ ID NO | RNA/Peptide | Internal Reference | Sequence 5'→3' |
|---|---|---|---|
| 196 | L-DNA/L-RNA | NOX-G11-D24 | CAGACGUGUGUGGGUAGAUGCACdCUGCGAUUCGCUAAAAAGUGCCACACGUCUG |
| 197 | L-DNA/L-RNA | NOX-G11-D25 | CAGACGUGUGUGGGUAGAUGCACCdTGCGAUUCGCUAAAAAGUGCCACACGUCUG |
| 198 | L-DNA/L-RNA | NOX-G11-D26 | CAGACGUGUGUGGGUAGAUGCACCUdGCGAUUCGCUAAAAAGUGCCACACGUCUG |
| 199 | L-DNA/L-RNA | NOX-G11-D27 | CAGACGUGUGUGGGUAGAUGCACCUGdCGAUUCGCUAAAAAGUGCCACACGUCUG |
| 200 | L-DNA/L-RNA | NOX-G11-D28 | CAGACGUGUGUGGGUAGAUGCACCUGCdGAUUCGCUAAAAAGUGCCACACGUCUG |
| 201 | L-DNA/L-RNA | NOX-G11-D29 | CAGACGUGUGUGGGUAGAUGCACCUGCGdAUUCGCUAAAAAGUGCCACACGUCUG |
| 202 | L-DNA/L-RNA | NOX-G11-D30 | CAGACGUGUGUGGGUAGAUGCACCUGCGAdTUCGCUAAAAAGUGCCACACGUCUG |
| 203 | L-DNA/L-RNA | NOX-G11-D31 | CAGACGUGUGUGGGUAGAUGCACCUGCGAUdTCGCUAAAAAGUGCCACACGUCUG |
| 204 | L-DNA/L-RNA | NOX-G11-D32 | CAGACGUGUGUGGGUAGAUGCACCUGCGAUUdCGCUAAAAAGUGCCACACGUCUG |
| 205 | L-DNA/L-RNA | NOX-G11-D33 | CAGACGUGUGUGGGUAGAUGCACCUGCGAUUCdGCUAAAAAGUGCCACACGUCUG |
| 206 | L-DNA/L-RNA | NOX-G11-D34 | CAGACGUGUGUGGGUAGAUGCACCUGCGAUUCGdCUAAAAAGUGCCACACGUCUG |
| 207 | L-DNA/L-RNA | NOX-G11-D35 | CAGACGUGUGUGGGUAGAUGCACCUGCGAUUCGCdTAAAAAGUGCCACACGUCUG |
| 208 | L-DNA/L-RNA | NOX-G11-D36 | CAGACGUGUGUGGGUAGAUGCACCUGCGAUUCGCUdAAAAAGUGCCACACGUCUG |
| 209 | L-DNA/L-RNA | NOX-G11-D37 | CAGACGUGUGUGGGUAGAUGCACCUGCGAUUCGCUAdAAAAGUGCCACACGUCUG |
| 210 | L-DNA/L-RNA | NOX-G11-D38 | CAGACGUGUGUGGGUAGAUGCACCUGCGAUUCGCUAAdAAAGUGCCACACGUCUG |
| 211 | L-DNA/L-RNA | NOX-G11-D39 | CAGACGUGUGUGGGUAGAUGCACCUGCGAUUCGCUAAAdAAGUGCCACACGUCUG |
| 212 | L-DNA/L-RNA | NOX-G11-D40 | CAGACGUGUGUGGGUAGAUGCACCUGCGAUUCGCUAAAAdAGUGCCACACGUCUG |
| 213 | L-DNA/L-RNA | NOX-G11-D41 | CAGACGUGUGUGGGUAGAUGCACCUGCGAUUCGCUAAAAAdGUGCCACACGUCUG |
| 214 | L-DNA/L-RNA | NOX-G11-D42 | CAGACGUGUGUGGGUAGAUGCACCUGCGAUUCGCUAAAAAGdTGCCACACGUCUG |
| 215 | L-DNA/L-RNA | NOX-G11-D43 | CAGACGUGUGUGGGUAGAUGCACCUGCGAUUCGCUAAAAAGUdGCCACACGUCUG |
| 216 | L-DNA/L-RNA | NOX-G11-D44 | CAGACGUGUGUGGGUAGAUGCACCUGCGAUUCGCUAAAAAGUGdCCACACGUCUG |
| 217 | L-DNA/L-RNA | NOX-G11-D45 | CAGACGUGUGUGGGUAGAUGCACCUGCGAUUCGCUAAAAAGUGCdCACACGUCUG |
| 218 | L-DNA/L-RNA | NOX-G11-D46 | CAGACGUGUGUGGGUAGAUGCACCUGCGAUUCGCUAAAAAGUGCCdACACGUCUG |
| 219 | L-DNA/L-RNA | NOX-G11-D47 | CAGACGUGUGUGGGUAGAUGCACCUGCGAUUCGCUAAAAAGUGCCAdCACGUCUG |
| 220 | L-DNA/L-RNA | NOX-G11-D48 | CAGACGUGUGUGGGUAGAUGCACCUGCGAUUCGCUAAAAAGUGCCACdACGUCUG |

TABLE 1-continued

| SEQ ID NO | RNA/Peptide | Internal Reference | Sequence 5'→3' |
|---|---|---|---|
| 221 | L-DNA/L-RNA | NOX-G11-D49 | CAGACGUGUGUGGGUAGAUGCACCUGCGAUUCGCUAAAAAGUGCCACAdCGUCUG |
| 222 | L-DNA/L-RNA | NOX-G11-D50 | CAGACGUGUGUGGGUAGAUGCACCUGCGAUUCGCUAAAAAGUGCCACACdGUCUG |
| 223 | L-DNA/L-RNA | NOX-G11-D51 | CAGACGUGUGUGGGUAGAUGCACCUGCGAUUCGCUAAAAAGUGCCACACGdTCUG |
| 224 | L-DNA/L-RNA | NOX-G11-D52 | CAGACGUGUGUGGGUAGAUGCACCUGCGAUUCGCUAAAAAGUGCCACACGUdCCUG |
| 225 | L-DNA/L-RNA | NOX-G11-D53 | CAGACGUGUGUGGGUAGAUGCACCUGCGAUUCGCUAAAAAGUGCCACACGUCdTG |
| 226 | L-DNA/L-RNA | NOX-G11-D54 | CAGACGUGUGUGGGUAGAUGCACCUGCGAUUCGCUAAAAAGUGCCACACGUCUdG |
| 227 | L-DNA/L-RNA | 257-E1-001 | GCAGTGGGGAAATGGGAGGGCTAGGTGGAAGGAATCTGAGCTACTGC |
| 228 | L-DNA/L-RNA | 257-E1-R1-001 | rGCAGTGGGGAAATGGGAGGGCTAGGTGGAAGGAATCTGAGCTACTGC |
| 229 | L-DNA/L-RNA | 257-E1-R2-001 | GrCAGTGGGGAAATGGGAGGGCTAGGTGGAAGGAATCTGAGCTACTGC |
| 230 | L-DNA/L-RNA | 257-E1-R3-001 | GCrAGTGGGGAAATGGGAGGGCTAGGTGGAAGGAATCTGAGCTACTGC |
| 231 | L-DNA/L-RNA | 257-E1-R4-001 | GCArGTGGGGAAATGGGAGGGCTAGGTGGAAGGAATCTGAGCTACTGC |
| 232 | L-DNA/L-RNA | 257-E1-R5-001 | GCAGrUGGGGAAATGGGAGGGCTAGGTGGAAGGAATCTGAGCTACTGC |
| 233 | L-DNA/L-RNA | 257-E1-R6-001 | GCAGTrGGGGAAATGGGAGGGCTAGGTGGAAGGAATCTGAGCTACTGC |
| 234 | L-DNA/L-RNA | 257-E1-R7-001 | GCAGTGrGGGAAATGGGAGGGCTAGGTGGAAGGAATCTGAGCTACTGC |
| 235 | L-DNA/L-RNA | 257-E1-R8-001 | GCAGTGGrGGAAATGGGAGGGCTAGGTGGAAGGAATCTGAGCTACTGC |
| 236 | L-DNA/L-RNA | 257-E1-R9-001 | GCAGTGGGrGAAATGGGAGGGCTAGGTGGAAGGAATCTGAGCTACTGC |
| 237 | L-DNA/L-RNA | 257-E1-R10-001 | GCAGTGGGGrAAATGGGAGGGCTAGGTGGAAGGAATCTGAGCTACTGC |
| 238 | L-DNA/L-RNA | 257-E1-R11-001 | GCAGTGGGGArAATGGGAGGGCTAGGTGGAAGGAATCTGAGCTACTGC |
| 239 | L-DNA/L-RNA | 257-E1-R12-001 | GCAGTGGGGAArATGGGAGGGCTAGGTGGAAGGAATCTGAGCTACTGC |
| 240 | L-DNA/L-RNA | 257-E1-R13-001 | GCAGTGGGGAAArUGGGAGGGCTAGGTGGAAGGAATCTGAGCTACTGC |
| 241 | L-DNA/L-RNA | 257-E1-R14-001 | GCAGTGGGGAAATrGGGAGGGCTAGGTGGAAGGAATCTGAGCTACTGC |
| 242 | L-DNA/L-RNA | 257-E1-R15-001 | GCAGTGGGGAAATGrGGAGGGCTAGGTGGAAGGAATCTGAGCTACTGC |
| 243 | L-DNA/L-RNA | 257-E1-R16-001 | GCAGTGGGGAAATGGrGAGGGCTAGGTGGAAGGAATCTGAGCTACTGC |
| 244 | L-DNA/L-RNA | 257-E1-R17-001 | GCAGTGGGGAAATGGGrAGGGCTAGGTGGAAGGAATCTGAGCTACTGC |
| 245 | L-DNA/L-RNA | 257-E1-R18-001 | GCAGTGGGGAAATGGGArGGGCTAGGTGGAAGGAATCTGAGCTACTGC |

TABLE 1-continued

| SEQ ID NO | RNA/Peptide | Internal Reference | Sequence 5'→3' |
|---|---|---|---|
| 246 | L-DNA/L-RNA | 257-E1-R19-001 | GCAGTGGGGAAATGGGAGrGGCTAGGTGGAAGGAATCTGAGCTACTGC |
| 247 | L-DNA/L-RNA | 257-E1-R20-001 | GCAGTGGGGAAATGGGAGGrGCTAGGTGGAAGGAATCTGAGCTACTGC |
| 248 | L-DNA/L-RNA | 257-E1-R21-001 | GCAGTGGGGAAATGGGAGGGrCTAGGTGGAAGGAATCTGAGCTACTGC |
| 249 | L-DNA/L-RNA | 257-E1-R22-001 | GCAGTGGGGAAATGGGAGGGCrUAGGTGGAAGGAATCTGAGCTACTGC |
| 250 | L-DNA/L-RNA | 257-E1-R23-001 | GCAGTGGGGAAATGGGAGGGCTrAGGTGGAAGGAATCTGAGCTACTGC |
| 251 | L-DNA/L-RNA | 257-E1-R24-001 | GCAGTGGGGAAATGGGAGGGCTArGGTGGAAGGAATCTGAGCTACTGC |
| 252 | L-DNA/L-RNA | 257-E1-R25-001 | GCAGTGGGGAAATGGGAGGGCTAGrGTGGAAGGAATCTGAGCTACTGC |
| 253 | L-DNA/L-RNA | 257-E1-R26-001 | GCAGTGGGGAAATGGGAGGGCTAGGrUGGAAGGAATCTGAGCTACTGC |
| 254 | L-DNA/L-RNA | 257-E1-R27-001 | GCAGTGGGGAAATGGGAGGGCTAGGTrGGAAGGAATCTGAGCTACTGC |
| 255 | L-DNA/L-RNA | 257-E1-R28-001 | GCAGTGGGGAAATGGGAGGGCTAGGTGrGAAGGAATCTGAGCTACTGC |
| 256 | L-DNA/L-RNA | 257-E1-R29-001 | GCAGTGGGGAAATGGGAGGGCTAGGTGGrAAGGAATCTGAGCTACTGC |
| 257 | L-DNA/L-RNA | 257-E1-R30-001 | GCAGTGGGGAAATGGGAGGGCTAGGTGGArAGGAATCTGAGCTACTGC |
| 258 | L-DNA/L-RNA | 257-E1-R31-001 | GCAGTGGGGAAATGGGAGGGCTAGGTGGAArGGAATCTGAGCTACTGC |
| 259 | L-DNA/L-RNA | 257-E1-R32-001 | GCAGTGGGGAAATGGGAGGGCTAGGTGGAAGrGAATCTGAGCTACTGC |
| 260 | L-DNA/L-RNA | 257-E1-R33-001 | GCAGTGGGGAAATGGGAGGGCTAGGTGGAAGGrAATCTGAGCTACTGC |
| 261 | L-DNA/L-RNA | 257-E1-R34-001 | GCAGTGGGGAAATGGGAGGGCTAGGTGGAAGGArATCTGAGCTACTGC |
| 262 | L-DNA/L-RNA | 257-E1-R35-001 | GCAGTGGGGAAATGGGAGGGCTAGGTGGAAGGAArUCTGAGCTACTGC |
| 263 | L-DNA/L-RNA | 257-E1-R36-001 | GCAGTGGGGAAATGGGAGGGCTAGGTGGAAGGAATrCTGAGCTACTGC |
| 264 | L-DNA/L-RNA | 257-E1-R37-001 | GCAGTGGGGAAATGGGAGGGCTAGGTGGAAGGAATCrUGAGCTACTGC |
| 265 | L-DNA/L-RNA | 257-E1-R38-001 | GCAGTGGGGAAATGGGAGGGCTAGGTGGAAGGAATCTrGAGCTACTGC |
| 266 | L-DNA/L-RNA | 257-E1-R39-001 | GCAGTGGGGAAATGGGAGGGCTAGGTGGAAGGAATCTGrAGCTACTGC |
| 267 | L-DNA/L-RNA | 257-E1-R40-001 | GCAGTGGGGAAATGGGAGGGCTAGGTGGAAGGAATCTGArGCTACTGC |
| 268 | L-DNA/L-RNA | 257-E1-R41-001 | GCAGTGGGGAAATGGGAGGGCTAGGTGGAAGGAATCTGAGrCTACTGC |
| 269 | L-DNA/L-RNA | 257-E1-R42-001 | GCAGTGGGGAAATGGGAGGGCTAGGTGGAAGGAATCTGAGCrUACTGC |
| 270 | L-DNA/L-RNA | 257-E1-R43-001 | GCAGTGGGGAAATGGGAGGGCTAGGTGGAAGGAATCTGAGCTrACTGC |

TABLE 1-continued

| SEQ ID NO | RNA/Peptide | Internal Reference | Sequence 5'→3' |
|---|---|---|---|
| 271 | L-DNA/L-RNA | 257-E1-R44-001 | GCAGTGGGGAAATGGGAGGGCTAGGTGGAAGGAATCTGAGCTArCTGC |
| 272 | L-DNA/L-RNA | 257-E1-R45-001 | GCAGTGGGGAAATGGGAGGGCTAGGTGGAAGGAATCTGAGCTACrUGC |
| 273 | L-DNA/L-RNA | 257-E1-R46-001 | GCAGTGGGGAAATGGGAGGGCTAGGTGGAAGGAATCTGAGCTACTrGC |
| 274 | L-DNA/L-RNA | 257-E1-R47-001 | GCAGTGGGGAAATGGGAGGGCTAGGTGGAAGGAATCTGAGCTACTGrC |
| 275 | L-DNA/L-RNA | 257-E1-R15/29-001 | GCAGTGGGGAAATGrGGAGGGCTAGGTGGrAAGGAATCTGAGCTACTGC |
| 276 | L-DNA/L-RNA | 257-E1-R29/30-001 | GCAGTGGGGAAATGGGAGGGCTAGGTGGrArAGGAATCTGAGCTACTGC |
| 277 | L-DNA/L-RNA | 257-E1-R15/29/30-001 | GCAGTGGGGAAATGrGGAGGGCTAGGTGGrArAGGAATCTGAGCTACTGC |
| 278 | L-DNA/L-RNA | 257-E1-R18/29/30-001 | GCAGTGGGGAAATGGGArGGGCTAGGTGGrArAGGAATCTGAGCTACTGC |
| 279 | L-DNA/L-RNA | 257-E1-R15/18/29/30-001 | GCAGTGGGGAAATGrGGArGGGCTAGGTGGrArAGGAATCTGAGCTACTGC |
| 280 | L-DNA/L-RNA | 257-E1-6xR-001 (= 257-E1-R9/15/18/19/29/30-001) | GCAGTGGGrGAAATGrGGArGrGGCTAGGTGGrArAGGAATCTGAGCTACTGC |
| 281 | L-DNA/L-RNA | NOX-D19 | 5'-40 kDa-PEG-GCCUGAUGUGGUGGUGAAGGGUUGUUGGGUGUCGACGCACAGGC |
| 282 | L-DNA/L-RNA | 257-E1-7xR-021 | GCGCGGrGAAArTGrGGArGrGGCTAGGTGGrArAGGAATCTGAGCCGCGC |
| 283 | L-DNA/L-RNA | 257-E1-7xR-022 | GCGCGGrGAAATGrGGArGrGGCrTAGGTGGrArAGGAATCTGAGCCGCGC |
| 284 | L-DNA/L-RNA | 257-E1-7xR-023 | GCGCGGrGAAATGrGGArGrGGCTAGGrTGGrArAGGAATCTGAGCCGCGC |
| 285 | L-DNA/L-RNA | 257-E1-7xR-024 | GCGCGGrGAAATGrGGArGrGGCTAGGTGGrArAGGAArTCTGAGCCGCGC |
| 286 | L-DNA/L-RNA | 257-E1-7xR-025 | GCGCGGrGAAATGrGGArGrGGCTAGGTGGrArAGGAATCrTGAGCCGCGC |
| 287 | L-DNA/L-RNA | 259-H6-002 | ACTCGAGAGGAAAGGTTGGTAAAGGTTCGGTTGGATTCACTCGAGT |
| 288 | L-DNA/L-RNA | 259-H6-002-R01 | rACTCGAGAGGAAAGGTTGGTAAAGGTTCGGTTGGATTCACTCGAGT |
| 289 | L-DNA/L-RNA | 259-H6-002-R02 | ArCTCGAGAGGAAAGGTTGGTAAAGGTTCGGTTGGATTCACTCGAGT |
| 290 | L-DNA/L-RNA | 259-H6-002-R03 | ACrUCGAGAGGAAAGGTTGGTAAAGGTTCGGTTGGATTCACTCGAGT |
| 291 | L-DNA/L-RNA | 259-H6-002-R04 | ACTrCGAGAGGAAAGGTTGGTAAAGGTTCGGTTGGATTCACTCGAGT |
| 292 | L-DNA/L-RNA | 259-H6-002-R05 | ACTCrGAGAGGAAAGGTTGGTAAAGGTTCGGTTGGATTCACTCGAGT |
| 293 | L-DNA/L-RNA | 259-H6-002-R06 | ACTCGrAGAGGAAAGGTTGGTAAAGGTTCGGTTGGATTCACTCGAGT |
| 294 | L-DNA/L-RNA | 259-H6-002-R07 | ACTCGArGAGGAAAGGTTGGTAAAGGTTCGGTTGGATTCACTCGAGT |
| 295 | L-DNA/L-RNA | 259-H6-002-R08 | ACTCGAGrAGGAAAGGTTGGTAAAGGTTCGGTTGGATTCACTCGAGT |

TABLE 1-continued

| SEQ ID NO | RNA/Peptide | Internal Reference | Sequence 5'→3' |
|---|---|---|---|
| 296 | L-DNA/L-RNA | 259-H6-002-R09 | ACTCGAGArGGAAAGGTTGGTAAAGGTTCGGTTGGATTCACTCGAGT |
| 297 | L-DNA/L-RNA | 259-H6-002-R10 | ACTCGAGAGrGAAAGGTTGGTAAAGGTTCGGTTGGATTCACTCGAGT |
| 298 | L-DNA/L-RNA | 259-H6-002-R11 | ACTCGAGAGGrAAAGGTTGGTAAAGGTTCGGTTGGATTCACTCGAGT |
| 299 | L-DNA/L-RNA | 259-H6-002-R12 | ACTCGAGAGGArAAGGTTGGTAAAGGTTCGGTTGGATTCACTCGAGT |
| 300 | L-DNA/L-RNA | 259-H6-002-R13 | ACTCGAGAGGAArAGGTTGGTAAAGGTTCGGTTGGATTCACTCGAGT |
| 301 | L-DNA/L-RNA | 259-H6-002-R14 | ACTCGAGAGGAAArGGTTGGTAAAGGTTCGGTTGGATTCACTCGAGT |
| 302 | L-DNA/L-RNA | 259-H6-002-R15 | ACTCGAGAGGAAAGrGTTGGTAAAGGTTCGGTTGGATTCACTCGAGT |
| 303 | L-DNA/L-RNA | 259-H6-002-R16 | ACTCGAGAGGAAAGGrUGGTAAAGGTTCGGTTGGATTCACTCGAGT |
| 304 | L-DNA/L-RNA | 259-H6-002-R17 | ACTCGAGAGGAAAGGTrUGGTAAAGGTTCGGTTGGATTCACTCGAGT |
| 305 | L-DNA/L-RNA | 259-H6-002-R18 | ACTCGAGAGGAAAGGTTrGGTAAAGGTTCGGTTGGATTCACTCGAGT |
| 306 | L-DNA/L-RNA | 259-H6-002-R19 | ACTCGAGAGGAAAGGTTGrGTAAAGGTTCGGTTGGATTCACTCGAGT |
| 307 | L-DNA/L-RNA | 259-H6-002-R20 | ACTCGAGAGGAAAGGTTGGrUAAAGGTTCGGTTGGATTCACTCGAGT |
| 308 | L-DNA/L-RNA | 259-H6-002-R21 | ACTCGAGAGGAAAGGTTGGTrAAAGGTTCGGTTGGATTCACTCGAGT |
| 309 | L-DNA/L-RNA | 259-H6-002-R22 | ACTCGAGAGGAAAGGTTGGTArAAGGTTCGGTTGGATTCACTCGAGT |
| 310 | L-DNA/L-RNA | 259-H6-002-R23 | ACTCGAGAGGAAAGGTTGGTAArAGGTTCGGTTGGATTCACTCGAGT |
| 311 | L-DNA/L-RNA | 259-H6-002-R24 | ACTCGAGAGGAAAGGTTGGTAAArGGTTCGGTTGGATTCACTCGAGT |
| 312 | L-DNA/L-RNA | 259-H6-002-R25 | ACTCGAGAGGAAAGGTTGGTAAAGrGTTCGGTTGGATTCACTCGAGT |
| 313 | L-DNA/L-RNA | 259-H6-002-R26 | ACTCGAGAGGAAAGGTTGGTAAAGGrUTCGGTTGGATTCACTCGAGT |
| 314 | L-DNA/L-RNA | 259-H6-002-R27 | ACTCGAGAGGAAAGGTTGGTAAAGGTrUCGGTTGGATTCACTCGAGT |
| 315 | L-DNA/L-RNA | 259-H6-002-R28 | ACTCGAGAGGAAAGGTTGGTAAAGGTTrCGGTTGGATTCACTCGAGT |
| 316 | L-DNA/L-RNA | 259-H6-002-R29 | ACTCGAGAGGAAAGGTTGGTAAAGGTTCrGGTTGGATTCACTCGAGT |
| 317 | L-DNA/L-RNA | 259-H6-002-R30 | ACTCGAGAGGAAAGGTTGGTAAAGGTTCGrGTTGGATTCACTCGAGT |
| 318 | L-DNA/L-RNA | 259-H6-002-R31 | ACTCGAGAGGAAAGGTTGGTAAAGGTTCGGrUTGGATTCACTCGAGT |
| 319 | L-DNA/L-RNA | 259-H6-002-R32 | ACTCGAGAGGAAAGGTTGGTAAAGGTTCGGTrUGGATTCACTCGAGT |
| 320 | L-DNA/L-RNA | 259-H6-002-R33 | ACTCGAGAGGAAAGGTTGGTAAAGGTTCGGTTrGGATTCACTCGAGT |
| 321 | L-DNA/L-RNA | 259-H6-002-R34 | ACTCGAGAGGAAAGGTTGGTAAAGGTTCGGTTGrGATTCACTCGAGT |

TABLE 1-continued

| SEQ ID NO | RNA/Peptide | Internal Reference | Sequence 5'→3' |
|---|---|---|---|
| 322 | L-DNA/L-RNA | 259-H6-002-R35 | ACTCGAGAGGAAAGGTTGGTAAAGGTTCGGTTGGrATTCACTCGAGT |
| 323 | L-DNA/L-RNA | 259-H6-002-R36 | ACTCGAGAGGAAAGGTTGGTAAAGGTTCGGTTGGArUTCACTCGAGT |
| 324 | L-DNA/L-RNA | 259-H6-002-R37 | ACTCGAGAGGAAAGGTTGGTAAAGGTTCGGTTGGATrUCACTCGAGT |
| 325 | L-DNA/L-RNA | 259-H6-002-R38 | ACTCGAGAGGAAAGGTTGGTAAAGGTTCGGTTGGATTrCACTCGAGT |
| 326 | L-DNA/L-RNA | 259-H6-002-R39 | ACTCGAGAGGAAAGGTTGGTAAAGGTTCGGTTGGATTCrACTCGAGT |
| 327 | L-DNA/L-RNA | 259-H6-002-R40 | ACTCGAGAGGAAAGGTTGGTAAAGGTTCGGTTGGATTCArCTCGAGT |
| 328 | L-DNA/L-RNA | 259-H6-002-R41 | ACTCGAGAGGAAAGGTTGGTAAAGGTTCGGTTGGATTCACrUCGAGT |
| 329 | L-DNA/L-RNA | 259-H6-002-R42 | ACTCGAGAGGAAAGGTTGGTAAAGGTTCGGTTGGATTCACTrCGAGT |
| 330 | L-DNA/L-RNA | 259-H6-002-R43 | ACTCGAGAGGAAAGGTTGGTAAAGGTTCGGTTGGATTCACTCrGAGT |
| 331 | L-DNA/L-RNA | 259-H6-002-R44 | ACTCGAGAGGAAAGGTTGGTAAAGGTTCGGTTGGATTCACTCGrAGT |
| 332 | L-DNA/L-RNA | 259-H6-002-R45 | ACTCGAGAGGAAAGGTTGGTAAAGGTTCGGTTGGATTCACTCGArGT |
| 333 | L-DNA/L-RNA | 259-H6-002-R46 | ACTCGAGAGGAAAGGTTGGTAAAGGTTCGGTTGGATTCACTCGAGrU |
| 334 | L-DNA/L-RNA | 259-H6-002-R13-R24 | ACTCGAGAGGAArAGGTTGGTAAArGGTTCGGTTGGATTCACTCGAGT |
| 335 | L-DNA/L-RNA | 259-H6-002-R13-R36 | ACTCGAGAGGAArAGGTTGGTAAAGGTTCGGTTGGArUTCACTCGAGT |
| 336 | L-DNA/L-RNA | 259-H6-002-R13-R24-R36 | ACTCGAGAGGAArAGGTTGGTAAArGGTTCGGTTGGArUTCACTCGAGT |
| 337 | L-DNA/L-RNA | 259-H6-002-R13-R24-R30-R36 | ACTCGAGAGGAArAGGTTGGTAAArGGTTCGrGTTGGArUTCACTCGAGT |
| 338 | L-DNA/L-RNA | 226-F2-001-5'-40kDa-PEG | 5'-40 kDa-PEG-CCGUGCUGUCGGAGACUACUCGUCGAGUAGAAAUAGGUCCCCUCCCACGG |
| 339 | L-DNA/L-RNA | 226-F2-001-D41-5'-40kDa-PEG, NOX-L41 | 5'-40 kDa-PEG-CCGUGCUGUCGGAGACUACUCGUCGAGUAGAAAUAGGUCCdCCUCCCACGG |
| 340 | L-DNA/L-RNA | 5'-40kDa-PEG-L-S1P-215-F9-002 | 5'-40 kDa-PEG-GCGUGAAUAGCCGUUGAAACGCCUUUAGAGAAGCACUAGCACGC |
| 341 | L-DNA/L-RNA | 5'-40kDa-PEG-L-S1P-215-F9-002-D01-19-21-32 | 5'-40 kDa-dGCGUGAAUAGCCGUUGAAdACdGCCUUUAGAGAdAGCACUAGCACGC |
| 342 | D-RNA/L-RNA | L-S1P-215-F9-002-5-diD-G | GG-GCGUGAAUAGCCGUUGAAACGCCUUUAGAGAAGCACUAGCACGC 5'-GG is D-RNA |

The present invention is further illustrated by the figures, examples and the sequence listing from which further features, embodiments and advantages may be taken, wherein The present invention is further illustrated by the figures, examples and the sequence listing from which further features, embodiments and advantages may be taken, wherein FIGS. 1A-C show nucleic acid molecule L-S1P-215-F9-002 consisting of ribonucleotides and derivatives nucleic acid molecule L-S1P-215-F9-002, whereby the derivatives comprise single or multiple ribonucleotide (A, U, G, C) to 2'-deoxyribonucleotide (dA, dT, dG, dC) substitutions;

FIG. 2 shows the results of the competitive spiegelmer pull-down assay of ribo- to 2'-deoxyribonucleotide substituted 215-F9-002 (also referred to as L-S1P-215-F9-002) derivatives: 0.3 nM radioactively labeled L-S1P-215-F9-002-5'diD-G binding to 8 nM biotinylated D-e-S1P at 37° C. competed by 50 nM unlabeled spiegelmer (triplicates) as indicated;

FIG. 3 shows the results of the competitive spiegelmer pull-down assay of ribo- to 2'-deoxyribonucleotide substituted 215-F9-002 (also referred to as L-S1P-215-F9-002) derivatives, whereby
(A) 0.3 nM radioactively labeled L-S1P-215-F9-002-5'diD-G binding to 8 nM biotinylated D-e-S-1-P for 3 h at 37° C. competed by 36 nM unlabeled Spiegelmer (triplicates) as indicated;
(B) 0.5 nM radioactively labeled L-S1P-215-F9-002-5'diD-G binding to 7 nM biotinylated D-e-S-1-P for 2.5 h at 37° C. competed by titrating concentrations of 5'-40 kDa-PEG-L-S1P-215-F9-002 (circles) and 5'-40 kDa-PEG-L-S1P-215-F9-002-D01-19-21-32 (squares);

FIG. 4 shows the results of the inhibition of (Mean values of triplicate cultures±SD are shown):
10 nM D-e-S1P-induced β-arrestin recruitment in a reporter cell line expressing EDG1 by:
(A) 5'-40 kDa-PEG-L-S1P-215-F9-002 and
(B) 5'-40 kDa-PEG-L-S1P-215-F9-002-D01-19-21-32 (also referred to as NOX-S93)

FIGS. 5A-E shows nucleic acid molecule 226-F2-002 consisting of ribonucleotides and derivatives of nucleic acid molecule 226-F2-002, whereby the derivatives comprise single ribonucleotide (A, U, G, C) to 2'-deoxyribonucleotide (dA, dT, dG, dC) substitutions;

FIG. 6 shows a plot of the determined changes in affinity in respect to the parental Spiegelmer 226-F2-001 as determined by Biacore measurement;

FIG. 7 shows nucleic acid molecule 226-F2-002 consisting of ribonucleotides and the derivatives 226-F2-002-41, 226-F2-002-44 and 226-F2-002-41/44 of nucleic acid molecule 226-F2-002, whereby the derivatives comprise ribonucleotides (A, U, G, C) and one or two 2'-deoxyribonucleotides (dC);

Figure 12:
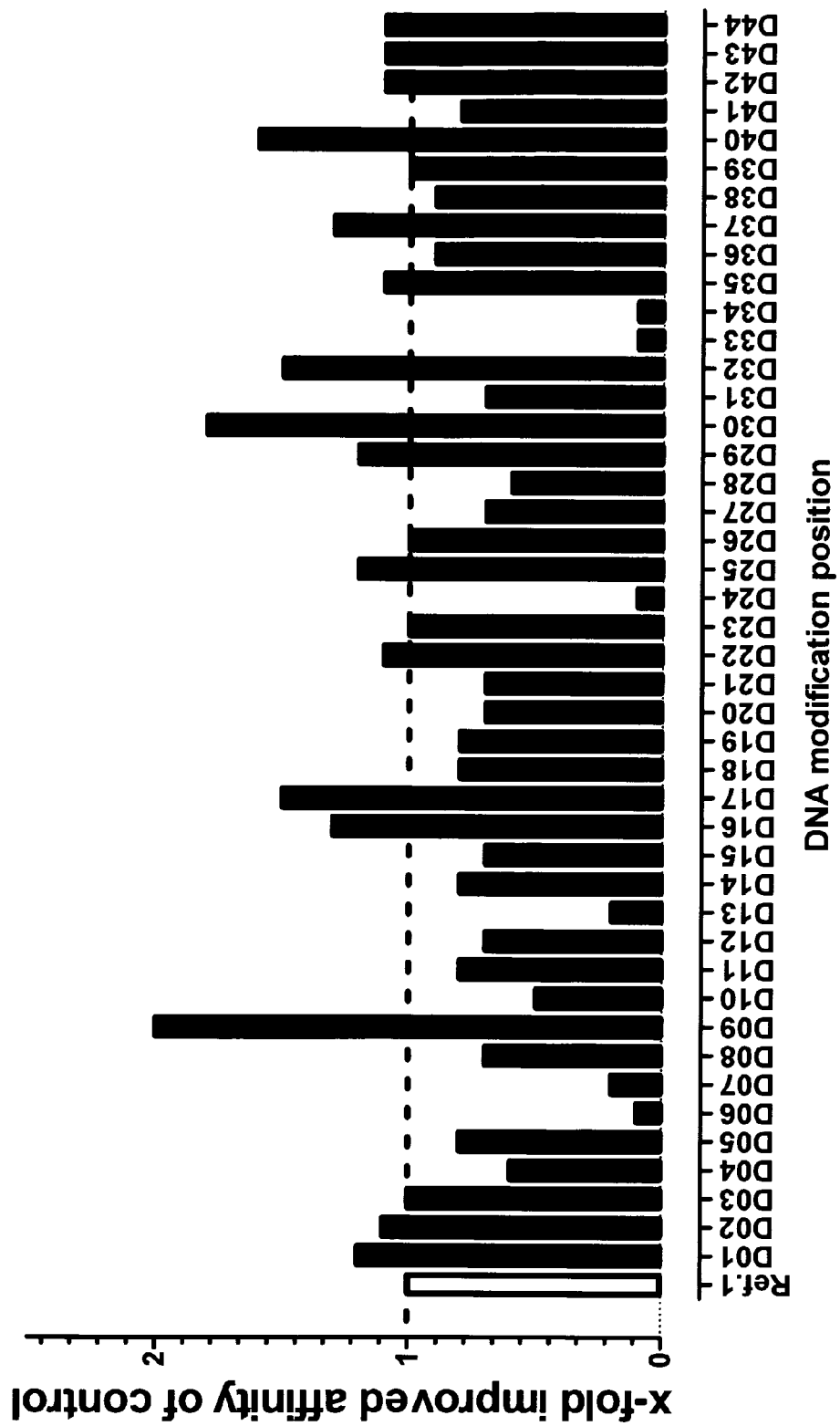
Figure 13:
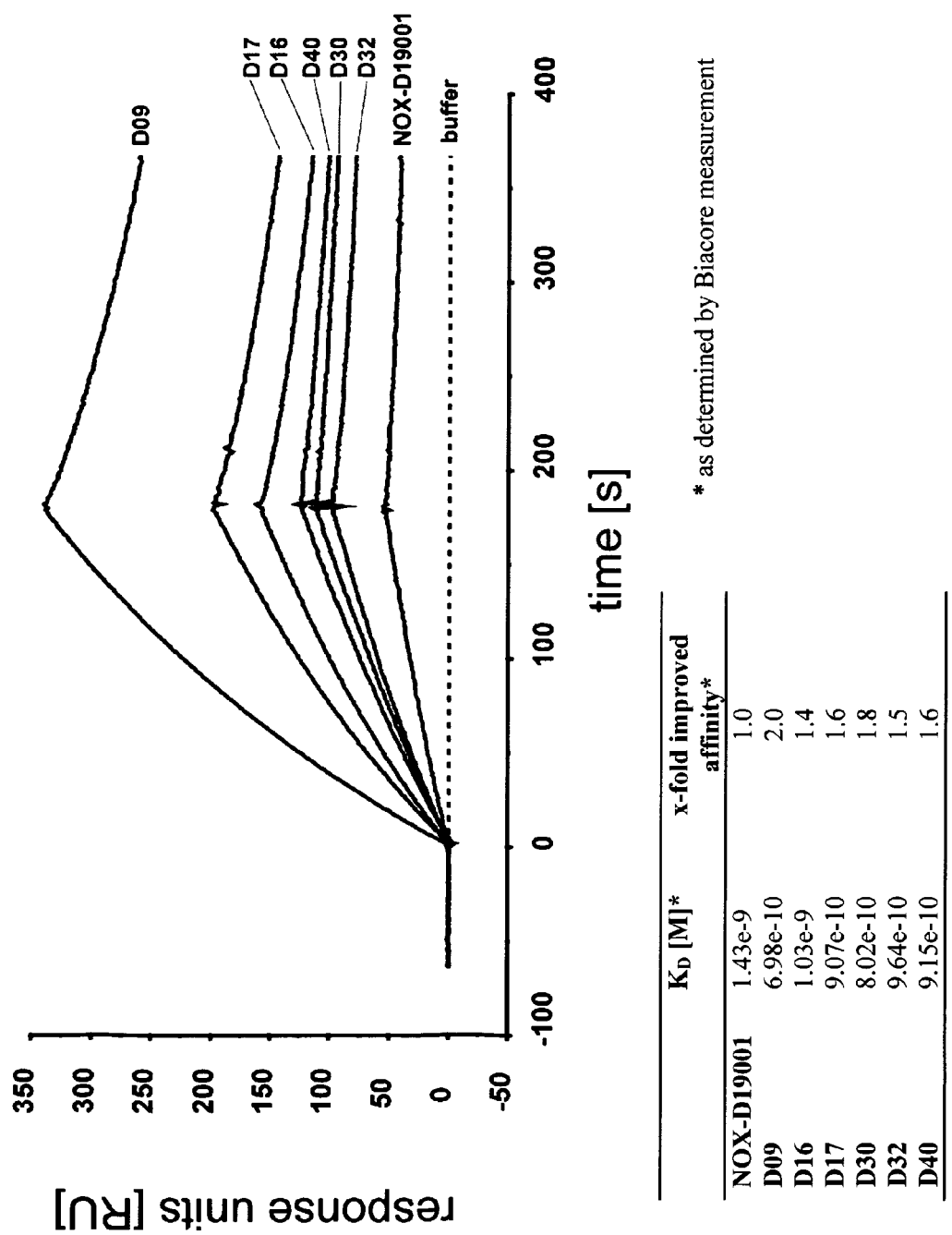
Figure 15:
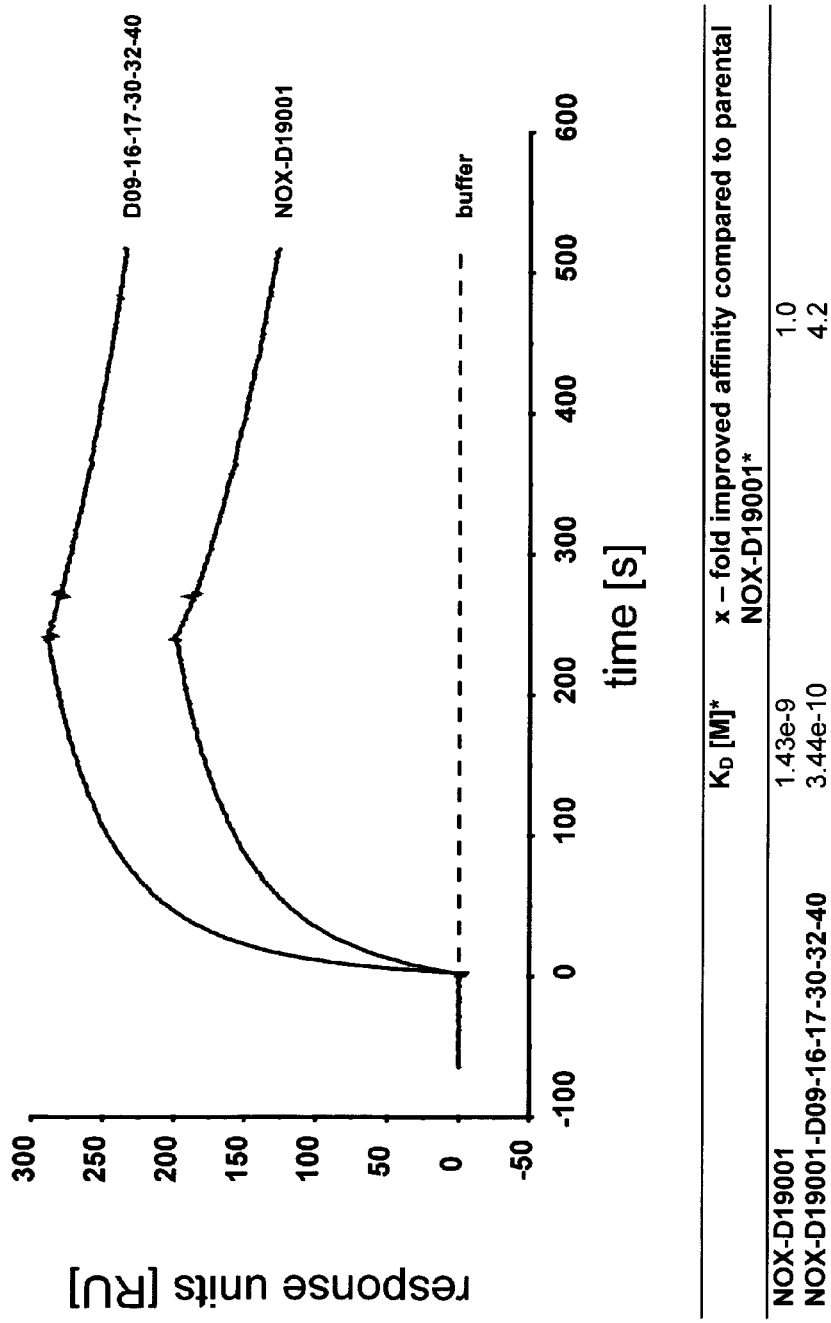
Figure 16:
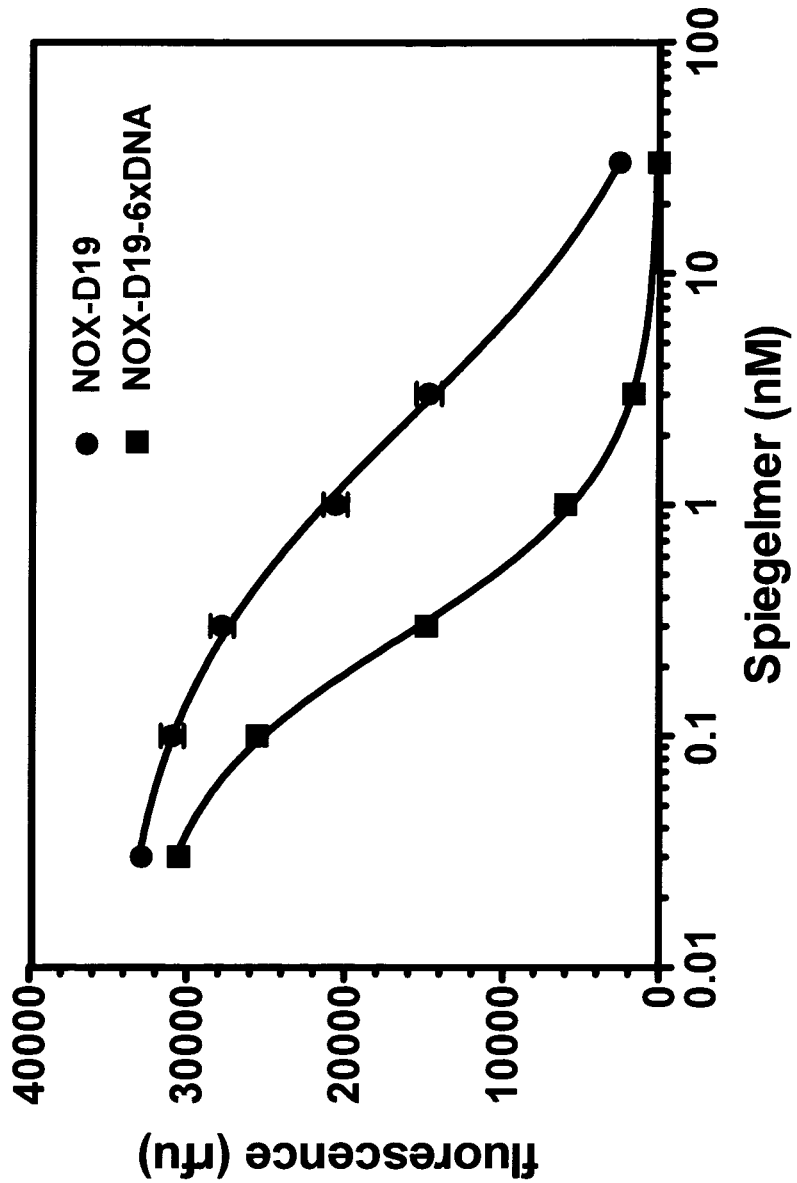
Figure 19:
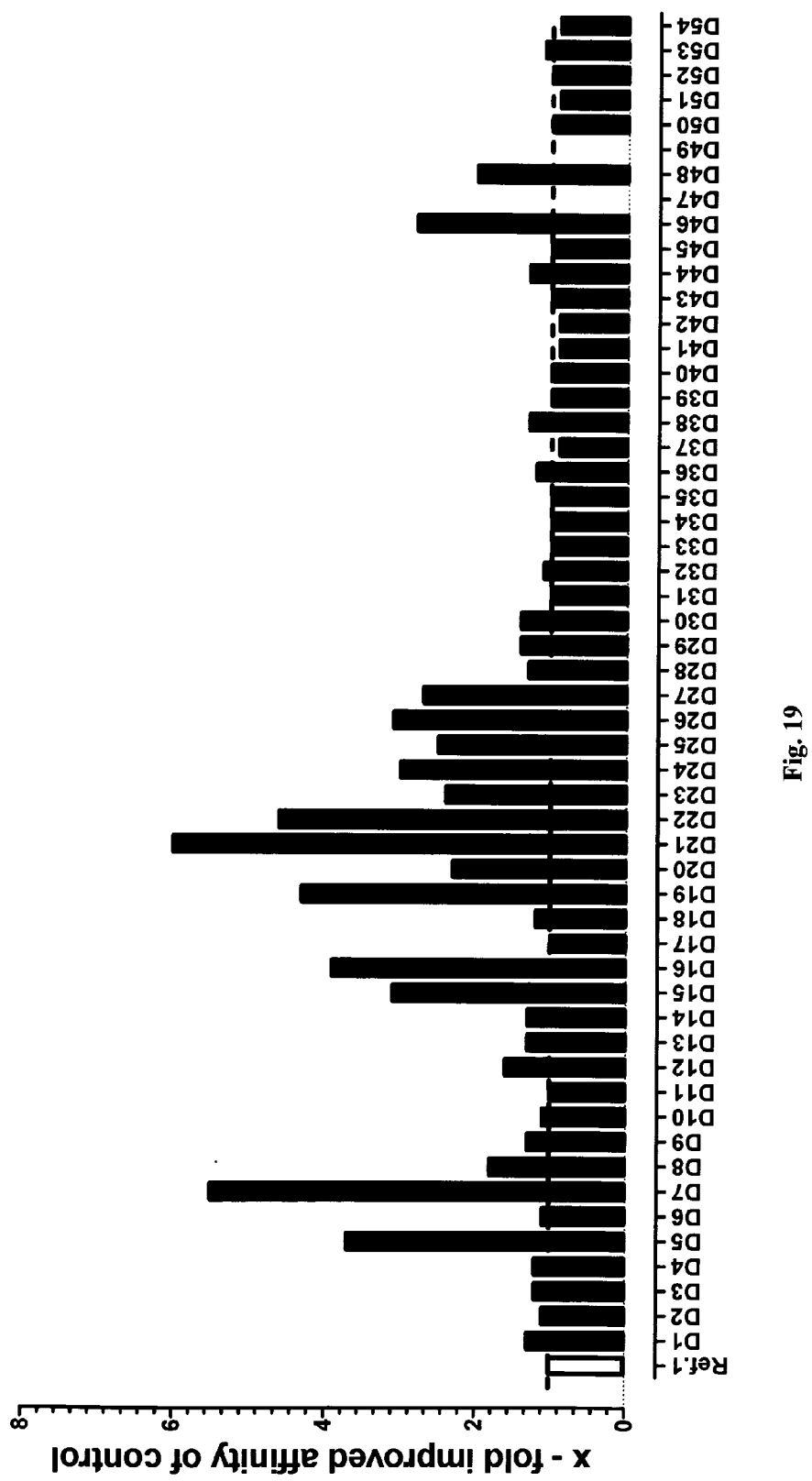
Figure 20:
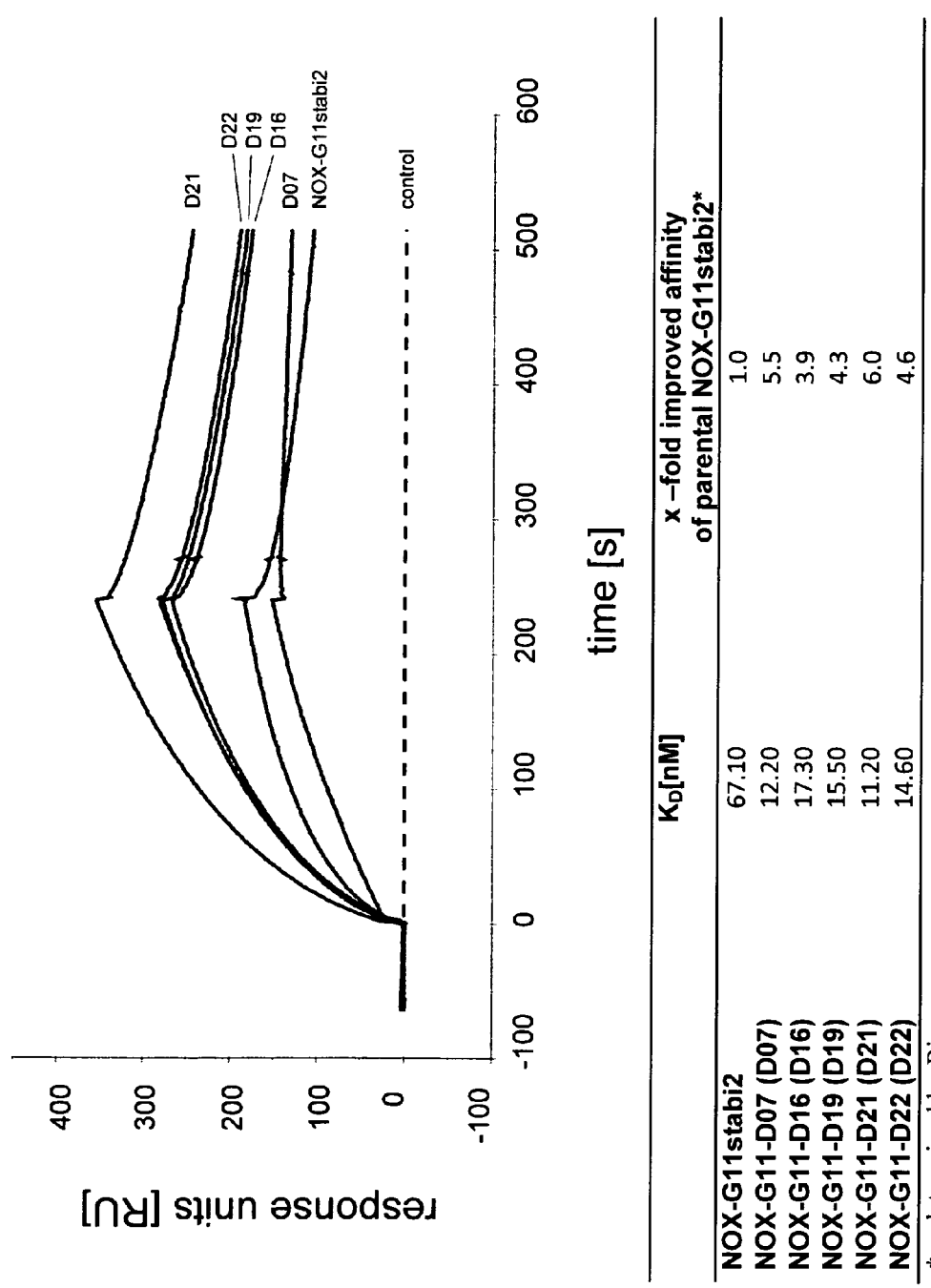
Figure 22:
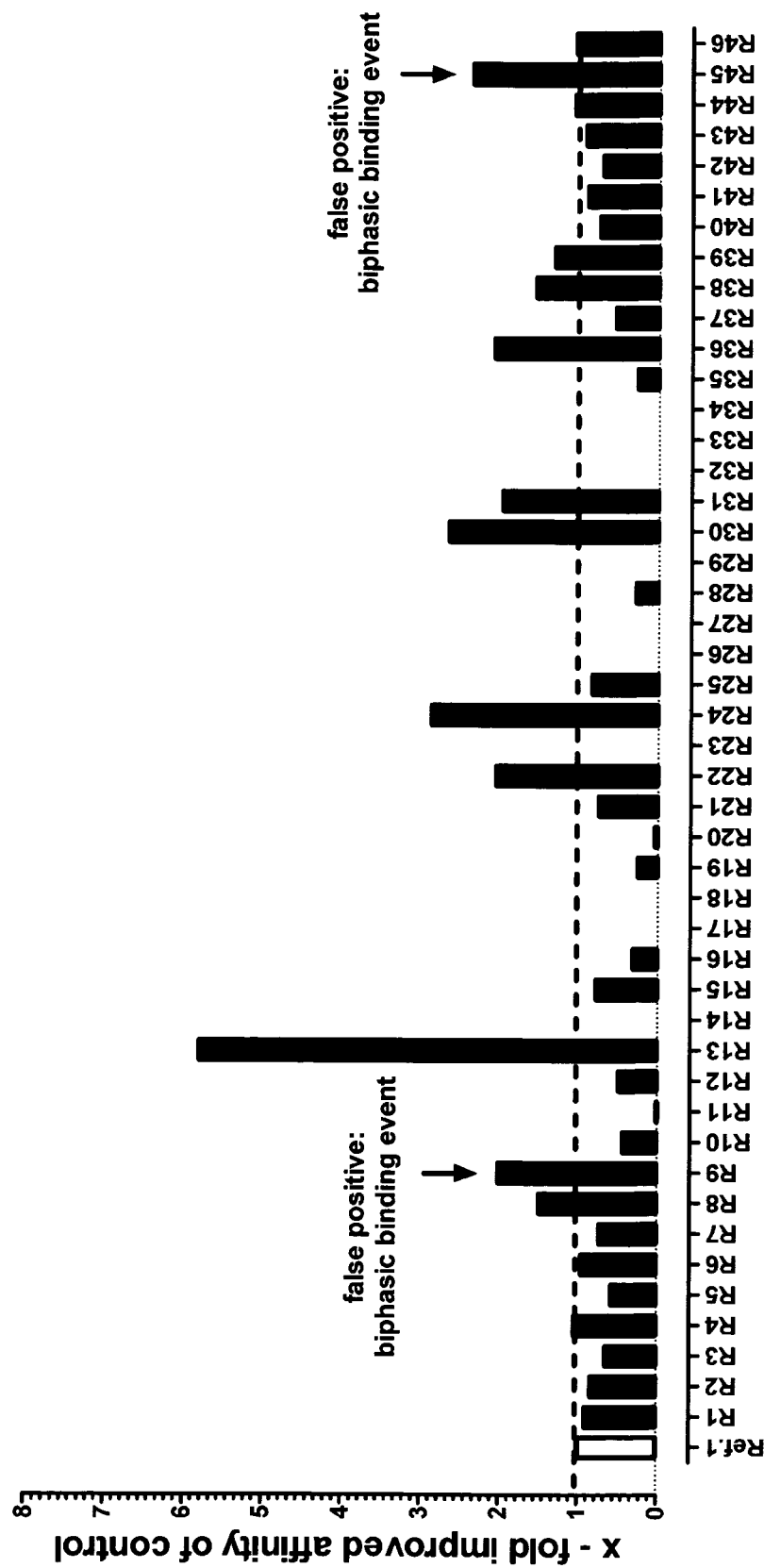
Figure 23:
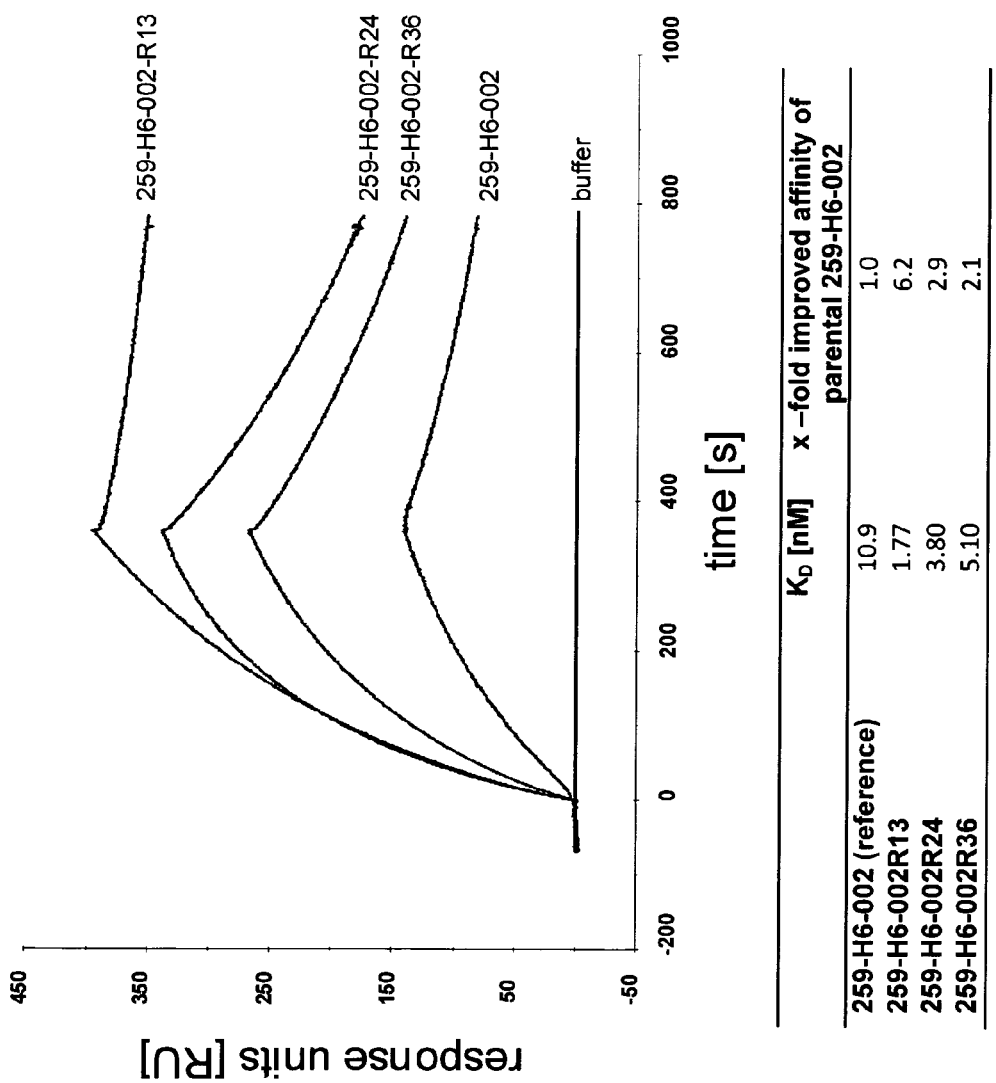
Figure 24:
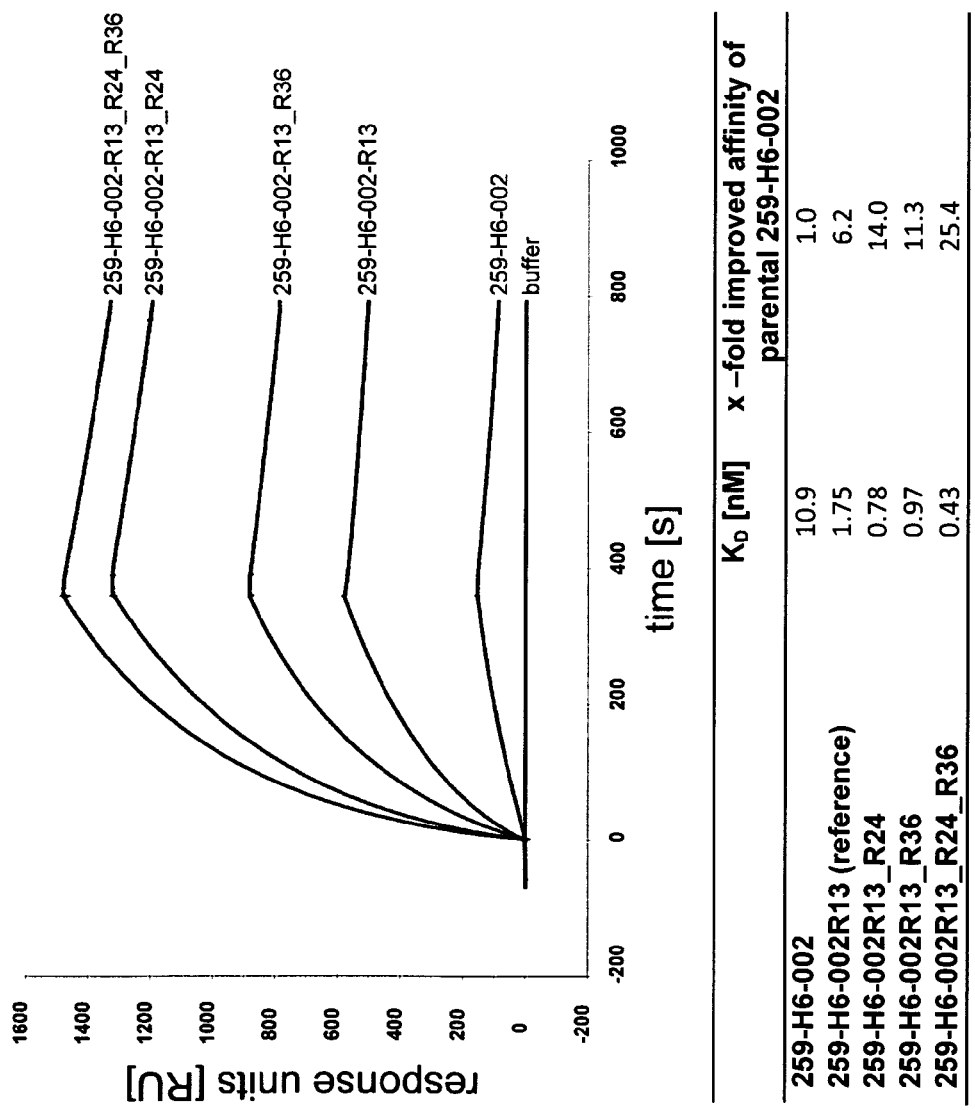
Figure 25:
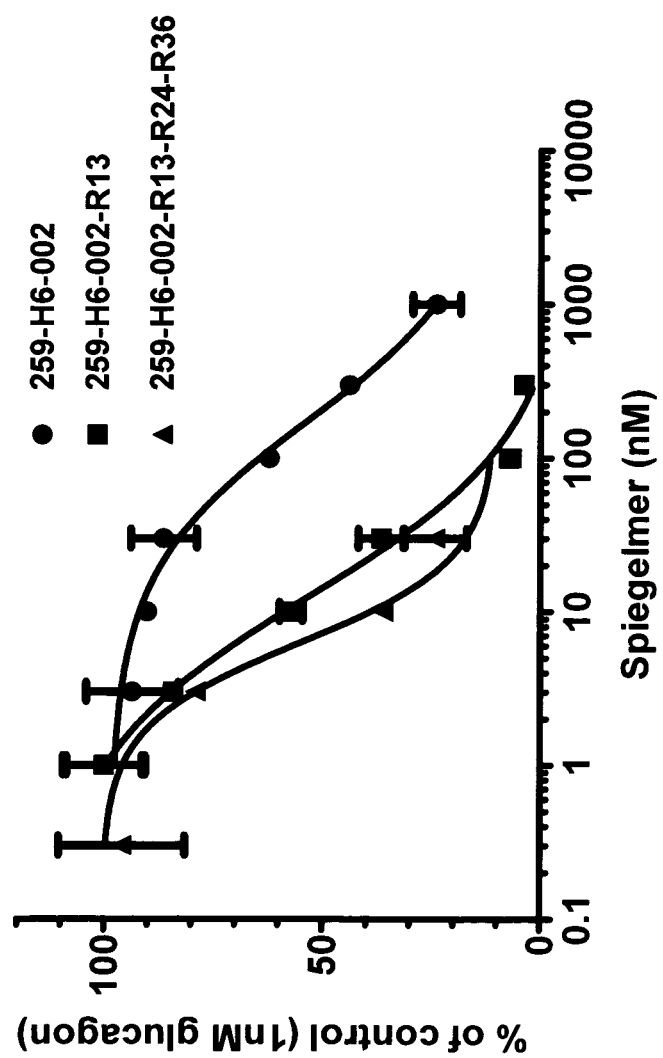

FIGS. 11A-E shows nucleic acid molecule NOX-D19001 consisting of ribonucleotides and derivatives of nucleic acid molecule NOX-D19001, whereby the derivatives comprise single ribonucleotide (A, U, G, C) to 2'-deoxyribonucleotide (dA, dU, dG, dC) substitutions;

FIG. 12 shows a plot of the determined changes in affinity in respect to the parental Spiegelmer NOX-D19001 as determined by Biacore measurement;

FIG. 13 shows the kinetic evaluation by Biacore measurement of Spiegelmers 226-F2-NOX-D19001 and derivatives NOX-D19001-D09, NOX-D19001-D16, NOX-D1900-D017, NOX-D19001-D30, NOX-D19001-D32 and NOX-D19001-D40 to human C5a;

FIG. 14 shows derivatives of nucleic acid molecule NOX-D19001, whereby the derivatives comprise multiple ribonucleotide (A, U, G, C) to 2'-deoxyribonucleotide (dA, dU, dG, dC) substitutions;

FIG. 15 shows the kinetic evaluation by Biacore measurement of Spiegelmers 226-F2-NOX-D19001 and NOX-D19001-D09-16-17-30-32-40 to human C5a;

FIG. 16 shows the efficacy of 5'-terminal 40 kDa PEGylated Spiegelmer NOX-D19001-5'PEG (also referred as NOX-D19) and Spiegelmer NOX-D19001-6xDNA in chemotaxis assays, wherein cells were allowed to migrate towards 0.1 nM huC5a preincubated at 37° C. with various amounts of Spiegelmers;

FIG. 17 shows derivatives of nucleic acid molecule NOX-D19001, whereby the derivatives comprise multiple ribonucleotide (A, U, G, C) to 2'-deoxyribonucleotide (dA, dU, dG, dC) substitutions;

FIGS. 18A-E shows nucleic acid molecule NOX-G11stabi2 consisting of ribonucleotides and derivatives of the nucleic acid molecule NOX-G11stabi2, whereby the derivatives comprise single or multiple ribonucleotide (A, C, G, U) to 2'-deoxyribonucleotide (dA, dC, dG, dT) substitutions;

FIG. 19 shows a plot of the determined changes in affinity in respect to the parental Spiegelmer NOX-G11stabi2 as determined by Biacore measurement;

FIG. 20 shows the kinetic evaluation by Biacore measurement of spiegelmers NOX-G11stabi2, NOX-G11-D07, NOX-G11-D16, NOX-G11-D19, NOX-G11-D21, NOX-G11-D22 to immobilized biotinylated human glucagon, FIGS. 21A-E show nucleic acid molecule 259-H6-002 consisting of ribonucleotides and derivatives of nucleic acid molecule 259-H6-002, whereby the derivatives comprise single or multiple deoxyribonucleotide (A, T, G, C) to ribonucleotide (rA, rU, rG, rC) to 2'-substitutions;

FIG. 22 shows a plot of the determined changes in affinity in respect to the parental Spiegelmer 259-H6-002 as determined by Biacore measurement;

FIG. 23 shows the kinetic evaluation by Biacore measurement of spiegelmers 259-H6-002, 259-H6-002R13, 259-H6-002R24 and 259-H6-002-R36 to immobilized biotinylated human glucagon, FIG. 24 shows the kinetic evaluation by Biacore measurement of spiegelmers 259-H6-002, 259-H6-002R13, 259-H6-002R13-R24, 259-H6-002R13-R36 and 259-H6-002R13-R24-R36 to immobilized biotinylated human glucagon, FIG. 25 shows inhibition of glucagon-induced production of cAMP by Spiegelmer 259-H6-002 and its derivatives 259-H6-002-R13 and 259-H6-002-R13-R24-R36 (also referred to as 259-H6-002-R13/24/36), whereby a) the generated amounts of cAMP per well were normalized to the largest value of each data set and depicted as percent activity against Spiegelmer concentration, b) the Spiegelmer concentrations at which cAMP production is inhibited by 50% ($IC_{50}$) were calculated using nonlinear regression (four parameter fit) with Prism5 software, c) the Spiegelmers used were 259-H6-002 (176 nM), 259-H6-002-R13 (12.5 nM) and 259-H6-002-R13-R24-R36 (6.2 nM) with the respective $IC_{50}$ values given in brackets.

Figure 26:
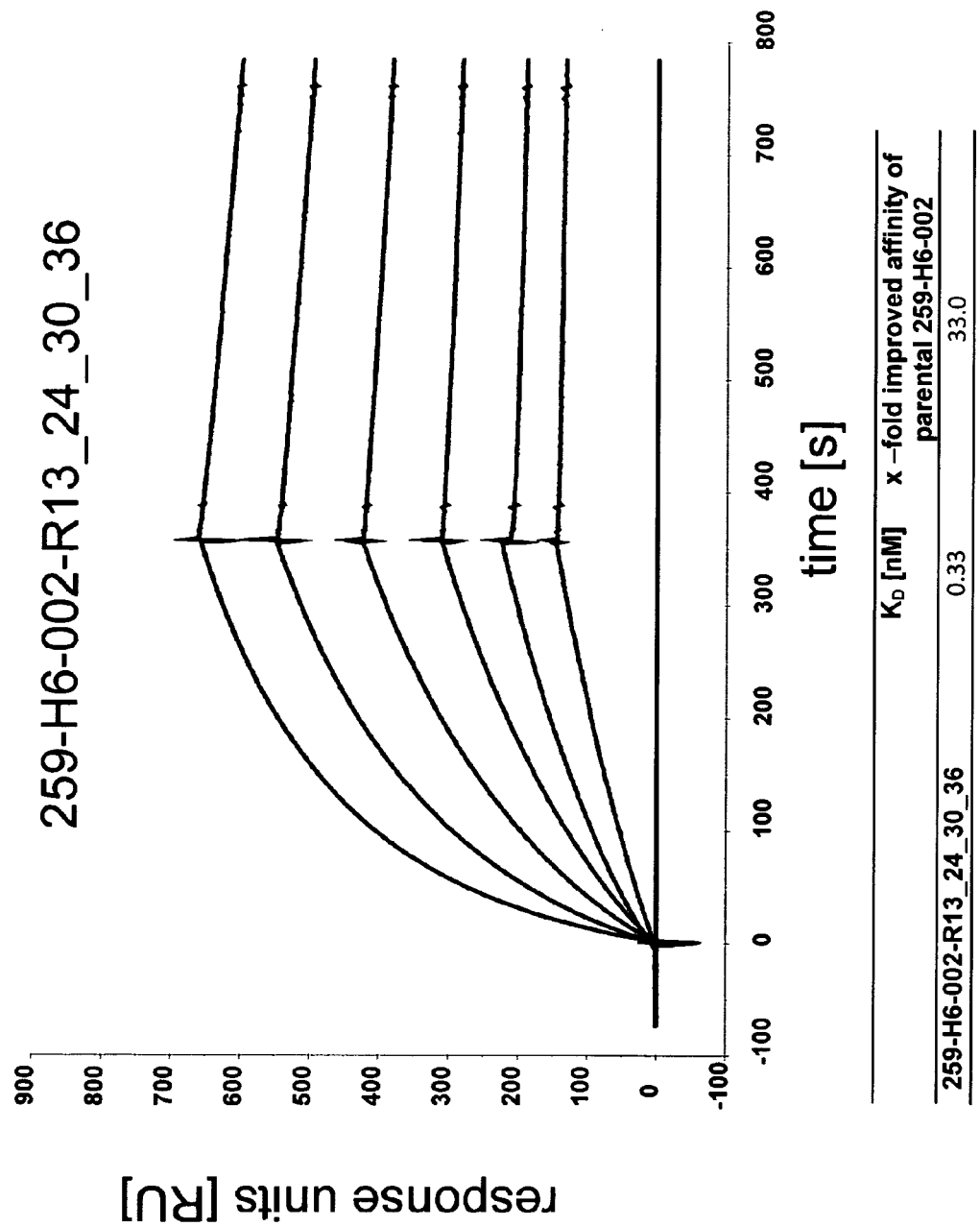
Figure 28:
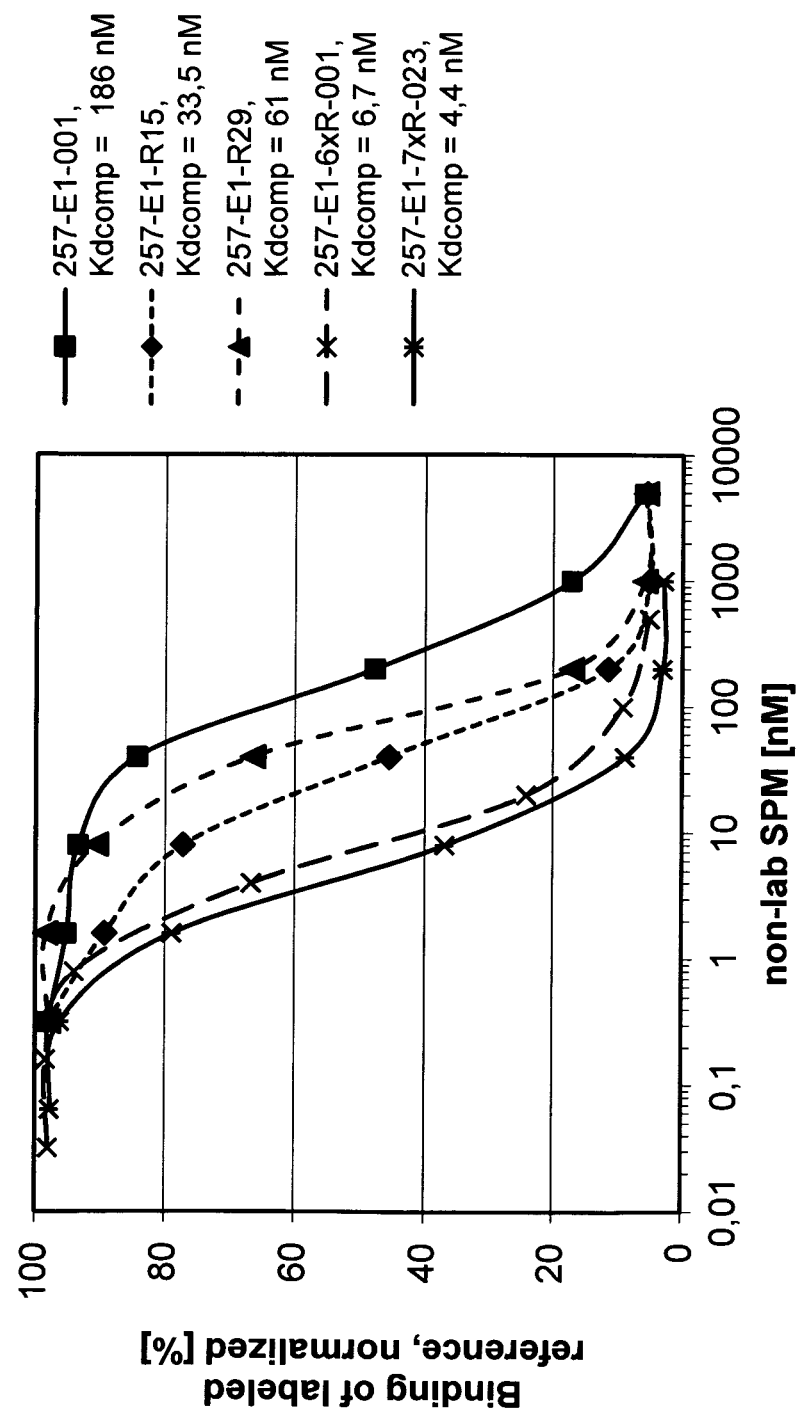

FIG. 26 shows the kinetic evaluation by Biacore measurement of spiegelmers 259-H6-002R13-R24-R30-R36 to immobilized biotinylated human glucagon, FIGS. 27A-E shows nucleic acid molecule 257-E1-001 consisting of 2'-deoxyribonucleotides and derivatives of the nucleic acid molecule 257-E1-001, whereby the derivatives comprise single or multiple 2'-deoxyribonucleotide (A, C, G, T) to ribonucleotide (rA, rC, rG, rU)) substitutions;

FIG. 27F shows derivatives of nucleic acid molecule 257-E1-6xR-001 consisting of 2'-deoxyribonucleotides and ribonucleotides;

FIG. 28 shows the results of competitive pull-down assays of nucleic acid molecule 257-E1-001 and its derivatives 257-E1-R15-001, 257-E1-R29-001, 257-E1-6xR-001 and 257-E1-7xR-03 to biotinylated glucagon.

EXAMPLE 1: NUCLEIC ACID MOLECULE HAVING INCREASED BINDING AFFINITY TO THE TARGET MOLECULE S1P

Starting from a nucleic acid molecule binding to S1P which was the result of a development process involving as a starting point the immediate screening product of the SELEX process, the method of the present invention was used in order to improve the binding affinity of the nucleic acid molecule to its target. In the instant case, the nucleic acid molecule binding to S1P was nucleic acid molecule L-S1P-215-F9-002.

Nucleic acid molecule L-S1P-215-F9-002 is a Spiegelmer, i.e. an L-nucleic acid molecule, which is capable of binding to S1P, has of a nucleotide sequence according to SEQ ID NO: 5 and consists of 44 ribonucleotides.

Figure 3:
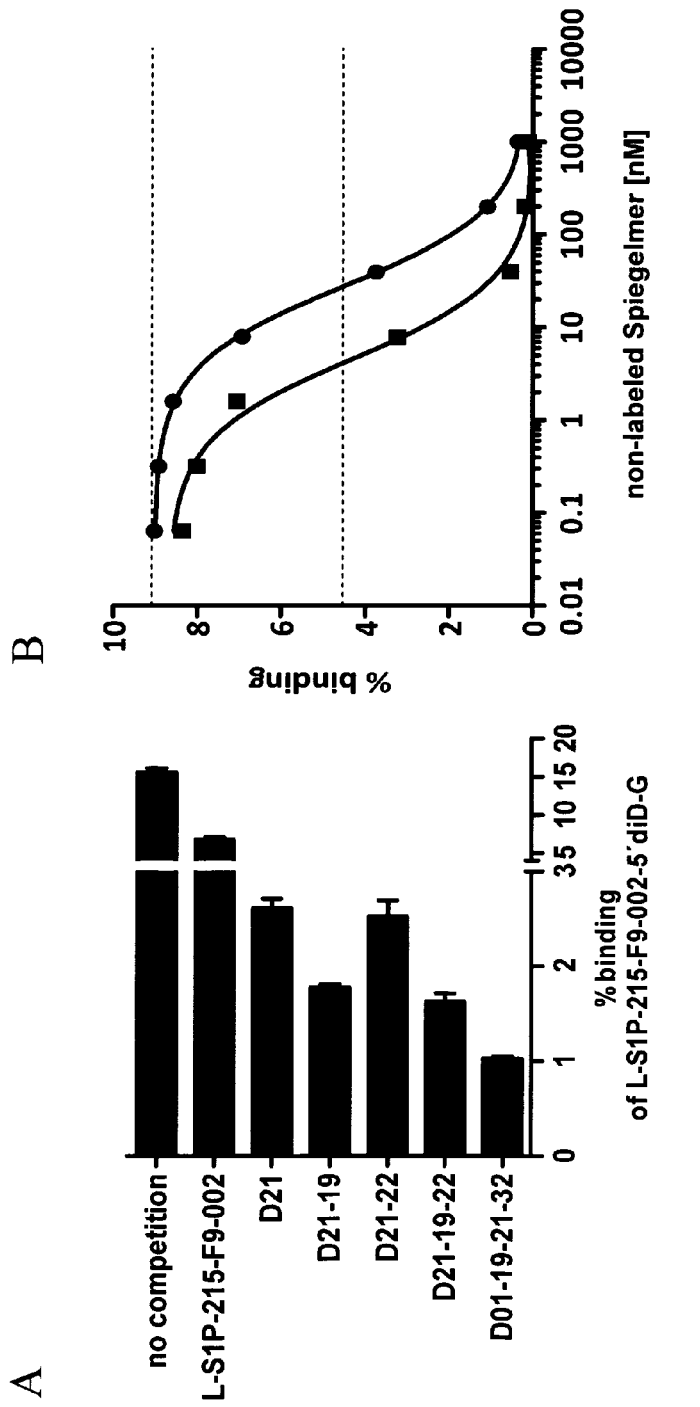

The binding characteristics of nucleic acid molecule L-S1P-215-F9-002 was determined by competitive Spiegelmer pull-down assay (as described in Example 9). Nucleic acid molecule L-S1P-215-F9-002 binds S1P with an affinity of 31.5 nM (FIG. 1 and FIG. 3B).

In order to improve the binding characteristics of nucleic acid molecule L-S1P-215-F9-002, derivatives of nucleic acid molecule L-S1P-215-F9-002 were synthesized. Said derivatives were L-nucleic acid molecules having the same sequence of nucleobases—guanine, cytosine, adenine, and uracil or thymine (in the case of a 2'deoxyribonucleotide)—as nucleic acid molecule L-S1P-215-F9-002, however, differed at a single position as to the sugar moiety of the nucleotide which was a 2'-deoxyribonucleotide rather than a ribonucleotide. In accordance therewith, derivative 1 had a 2'-deoxyribonucleoside at position 1 of the nucleotide sequence according to SEQ ID NO: 6, derivative 2 had a 2'-deoxyribonucleotide at position 2 of the nucleotide sequence according to SEQ ID NO: 7, etc. Because nucleic acid molecule L-S1P-215-F9-002 consists of 44 nucleotides a total of 44 derivatives was synthesized in order to provide a complete set of all possible derivatives of nucleic acid molecule L-S1P-215-F9-002 carrying a single ribonucleotide to 2'-deoxyribonucleotide substitution. Said complete set of derivatives is shown in FIGS. 1A-C. In the case of uracil in the sequence of molecule L-S1P-215-F9-002, uridine-5'-phosphate was replaced by thymidine-5'-phosphate.

The binding affinity to S1P of each derivative of said complete set of derivatives of nucleic acid molecule L-S1P-215-F9-002 was determined using the competitive pull-down assay described in Example 9, and compared to the binding affinity of nucleic acid molecule L-S1P-215-F9-002 (FIGS. 1 A-C).

As may be taken from FIGS. 1 A-C, depending on the position within the Spiegelmer L-S1P-215-F9-002 ribonucleotide to 2'-deoxyribonucleotide substitution may have different impact on binding affinity for the target. Surprisingly, a single substitution of a ribonucleotide by a 2' deoxyribonucleotide at some positions within nucleic acid molecule L-S1P-215-F9-002 resulted in an improved binding affinity to S1P, whereas substitution at other positions did not result in significant changes in binding affinity to S1P, or even decreased the binding affinity to S1P. The individual derivatives and relative changes of their binding affinities compared to the binding affinity of nucleic acid molecule 215-F9-002 to S1P are indicated in FIGS. 1 A-C.

Figure 2:
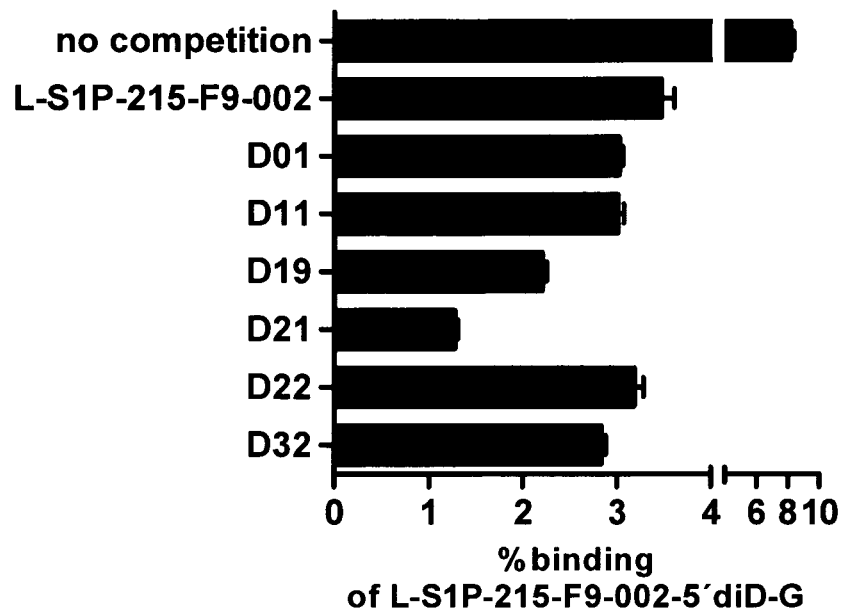

As may be taken from said figures, derivatives L-S1P-215-F9-002-D01, L-S1P-215-F9-002-D11, L-S1P-215-F9-002-D19, L-S1P-215-F9-002-D21, L-S1P-215-F9-002-D22, L-S1P-215-F9-002-D32 which have a 2'-deoxyribonucleotide at positions 1, 11, 19, 21, 22, and 32, respectively, belong to the first group of derivatives, i.e. derivatives of nucleic acid molecule L-S1P-215-F9-002 where substitution of a ribonucleotide by a 2'-deoxyribonucleotide results in an improved binding affinity for S1P (FIGS. 1 A-C and FIG. 2). The best binding affinity of said derivatives was shown for derivative L-S1P-215-F9-002-D19 and L-S1P-215-F9-002-D21 (FIGS. 1 A-C and FIG. 2). Accordingly, positions 1, 11, 19, 21, 22, and 32, preferably 19 and 21, are suitable to confer improved binding affinity for S1P to nucleic acid molecule L-S1P-215-F9-002. Adenosine-5'-phosphate to 2'-deoxyadenosine-5'-phosphate substitution at position 19 and guanosine-5'-phosphate to 2'-deoxyguanosine-5'-phosphate substitution at position 21 resulted in an improved binding affinity of 16 nM and 11.3 nM, respectively, compared to L-S1P-215-F9-002 ($K_D$ of 31.5 nM) (FIGS. 1 A-C).

Derivatives L-S1P-215-F9-002-D05, L-S1P-215-F9-002-D12, L-S1P-215-F9-002-D13, L-S1P-215-F9-002-D14, L-S1P-215-F9-002-D15, L-S1P-215-F9-002-D16, L-S1P-215-F9-002-D39, L-S1P-215-F9-002-D40, L-S1P-215-F9-002-D41, L-S1P-215-F9-002-D42 and L-S1P-215-F9-002-D43 which have a 2'-deoxyribonucleotide at positions 5, 12, 13 14, 15, 16, 39, 40, 41, 42 and 43, respectively, belong to the second group of derivatives, i.e. derivatives where substitution of a ribonucleotide by a 2'-deoxyribonucleotide does not affect the binding affinity for S1P. Accordingly, positions 5, 12, 13, 14, 15, 16, 39, 40, 41, 42 and 43 are not suitable to confer improved binding affinity nor do they have negative impact on binding affinity to S1P compared to nucleic acid molecule L-S1P-215-F9-002 (FIGS. 1 A-C).

Finally, derivatives were obtained which resulted in reduced binding affinity or a profound loss of binding. These derivatives, namely L-S1P-215-F9-002-D02, L-S1P-215-F9-002-D03, L-S1P-215-F9-002-D04, L-S1P-215-F9-002-D06, L-S1P-215-F9-002-D07, L-S1P-215-F9-002-D08, L-S1P-215-F9-002-D09, L-S1P-215-F9-002-D10, L-S1P-215-F9-002-D17, L-S1P-215-F9-002-D18, L-S1P-215-F9-002-D20, L-S1P-215-F9-002-D23, L-S1P-215-F9-002-D24, L-S1P-215-F9-002-D25, L-S1P-215-F9-002-D26, L-S1P-215-F9-002-D27, L-S1P-215-F9-002-D28, L-S1P-215-F9-002-D29, L-S1P-215-F9-002-D30, L-S1P-215-F9-002-D31, L-S1P-215-F9-002-D33, L-S1P-215-F9-002-D34, L-S1P-215-F9-002-D35, L-S1P-215-F9-002-D36, L-S1P-215-F9-002-D37, L-S1P-215-F9-002-D38 and L-S1P-215-F9-002-D44 which have a 2'-deoxyribonucleotide at position 2, 3, 4, 6, 7, 8, 9, 10, 17, 18, 20, 23, 24, 25, 26, 27, 28, 29, 30, 31, 33, 34, 35, 36, 37, 38 and 44, respectively, belong to the third group of derivatives, i.e. derivatives of nucleic acid molecule L-S1P-215-F9-002 where substitution of a ribonucleotide by a 2'-deoxyribonucleotide negatively affects the binding affinity to S1P (FIGS. 1 A-C).

In order to assess whether the binding affinity of the derivatives of nucleic acid molecule L-S1P-215-F9-002 can be further increased by introducing more than one substitution a group of further derivatives was generated (FIG. 1C). Said group of further derivatives started from the first group of derivatives where substitution of a ribonucleotide by a 2'-deoxyribonucleotide resulted in an improved binding affinity for S1P. Starting from nucleic acid molecule L-S1P-215-F9-002, the derivatives had at least two substitutions of ribonucleotides by 2'-deoxyribonucleotides at position 19, 21 and/or 22. Ribonucleotide to 2'-deoxyribonucleotide substitution at position 19 and 21 conferred the strongest improvements in binding affinity for S1P to nucleic acid molecule L-S1P-215-F9-002 while substitution at position 22 had only a weak effect (FIG. 2).

Competitive Spiegelmer pull-down assays of these derivatives showed that combining ribonucleotide to 2'-deoxyribonucleotide substitutions at multiple positions of the L-S1P-215-F9-002 Spiegelmer resulted in a further improvement of binding affinity for S1P. A Spiegelmer containing two substitutions, namely adenosine-5'-phosphate to 2'-deoxyadenosine-5'-phosphate at position 19 and guanosine-5'-phosphate to 2'-deoxyguanosine-5'-phosphate at position 21 (termed L-S1P-215-F9-002-D21-19) showed improved binding affinity compared to L-S1P-215-F9-002 and as well to L-S1P-215-F9-002-D21 containing a single substitution, namely guanosine-5'-phosphate to 2'-deoxyguanosine-5'-phosphate at position 21 (FIG. 3A). Additional substitution of cytidine-5'-phosphate to 2'-deoxycytidine-5'-phosphate at position 22 did not result in further improvement as L-S1P-215-F9-002-D21 and L-S1P-215-F9-002-D21-22 as well as L-S1P-215-F9-002-D21-19 and L-S1P-215-F9-002-D21-19-22 showed similar binding affinities for S1P, respectively (FIG. 1C and FIG. 3A). In contrast, a Spiegelmer containing four substitutions, namely guanosine to 2'-deoxyguanosine at position 01, guanosine-5'-phosphate to 2'-deoxyguanosine-5'-phosphate at position 21 and adenosine-5'-phosphate to 2'-deoxyadenosine-5'-phosphate at position 19 and 32 (termed L-S1P-215-F9-002-D01-19-21-32) showed significantly improved binding affinity in comparison to Spiegelmer L-S1P-215-F9-002-D21-19 which contains only two substitutions (FIG. 1C and FIG. 3A). In comparison to the parental molecule L-S1P-215-F9-002 ($K_D$ of 31.5 nM) substitution at four positions of ribonucleotides to 2'-deoxyribonucleotides in L-S1P-215-F9-002-D01-19-21-32 ($K_D$ of 5 nM) resulted in a 6.3-fold improvement of the binding affinity for S1P (FIG. 3B). An additional substitution of cytidine-5'-phosphate to 2'-deoxycytidine-5'-phosphate at position 11 of L-S1P-215-F9-002-D01-19-21-32 had no further positive effect on the binding affinity for S1P (FIG. 1C and FIG. 3A).

In order to prove and compare the functionality of Spiegelmers L-S1P-215-F9-002 and L-S1P-215-F9-002-D01-19-21-32 both nucleic acid molecules were synthesized comprising an amino-group at their 5'-ends. To the amino-modified Spiegelmers a 40 kDa PEG-moiety was coupled leading to Spiegelmers 5'-40 kDa-PEG-L-S1P-215-F9-002 and 5'-40 kDa-PEG-L-S1P-215-F9-002-D01-19-21-32 (also referred to as NOX-S93). Synthesis and PEGylation of the Spiegelmer is described in Example 7.

Figure 4:
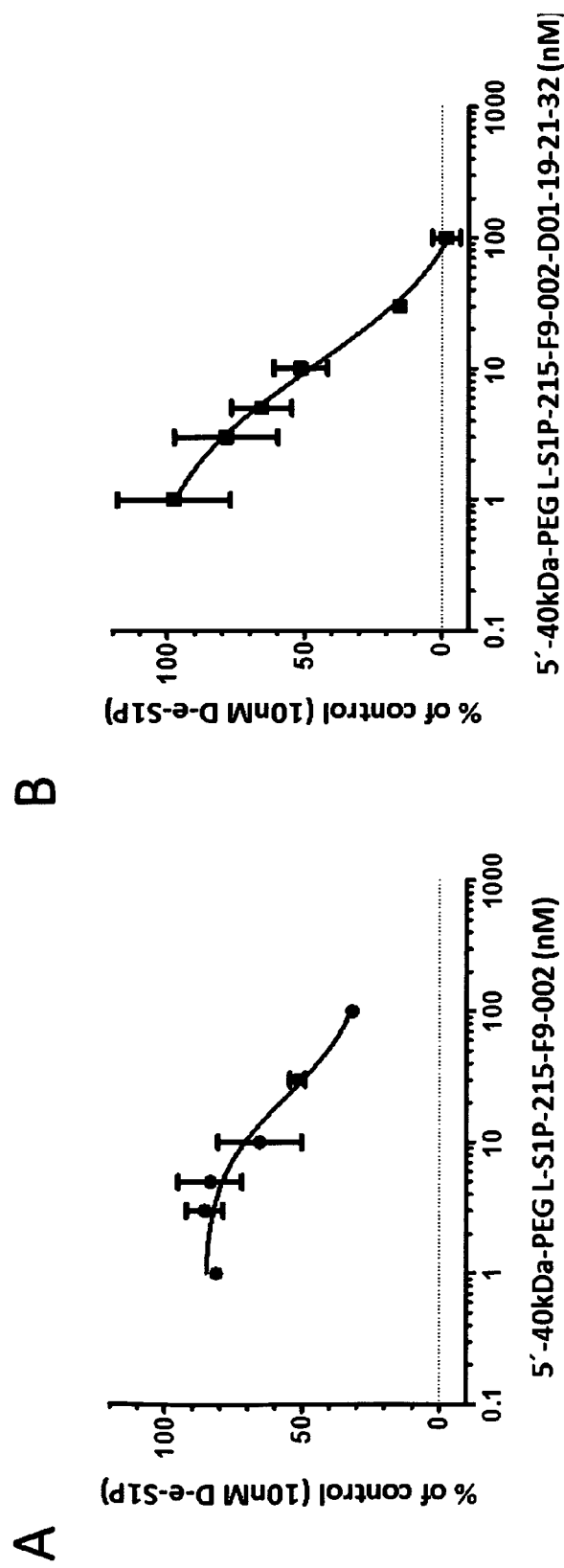

An in vitro cell-culture assay (protocol see Example 11) confirmed that improved affinity to S1P translates into an enhanced inhibition of S1P function. 5'-40 kDa-PEG-L-S1P-215-F9-002 and 5'-40 kDa-PEG-L-S1P-215-F9-002-D01-19-21-32 (also referred to as NOX-S93) inhibited S1P-induced arrestin recruitment in a reporter cell line expressing human S1P-receptor EDG1 with $IC_{50}$ values of 22.5 nM and 10.3 nM, respectively (FIGS. 4A, 4B). Thus, competitive Spiegelmer pull-down assays (Example 9, FIG. 3B) and in vitro cell culture experiments (Example 11, FIG. 4) unanimously showed that substitutions of ribonucleotides to 2'-deoxyribonucleotides significantly improved the binding affinity and the inhibitory activity of S1P-binding Spiegelmer 226-F2-001.

EXAMPLE 2: NUCLEIC ACID MOLECULE HAVING INCREASED BINDING AFFINITY TO THE TARGET MOLECULE HUMAN CGRP

Starting from a nucleic acid molecule binding to CGRP which was the result of a development process involving as a starting point the immediate screening product of the SELEX process, the method of the present invention was used in order to improve the binding affinity of the nucleic acid molecule to its target. In the instant case, the nucleic acid molecule binding to human CGRP was nucleic acid molecule 226-F2-001.

Nucleic acid molecule 226-F2-001 is a Spiegelmer, i.e. a L-nucleic acid molecule, which is capable of binding to human CGRP, has a nucleotide sequence according to SEQ ID NO: 55 and consists of 50 ribonucleotides.

Figure 8A:
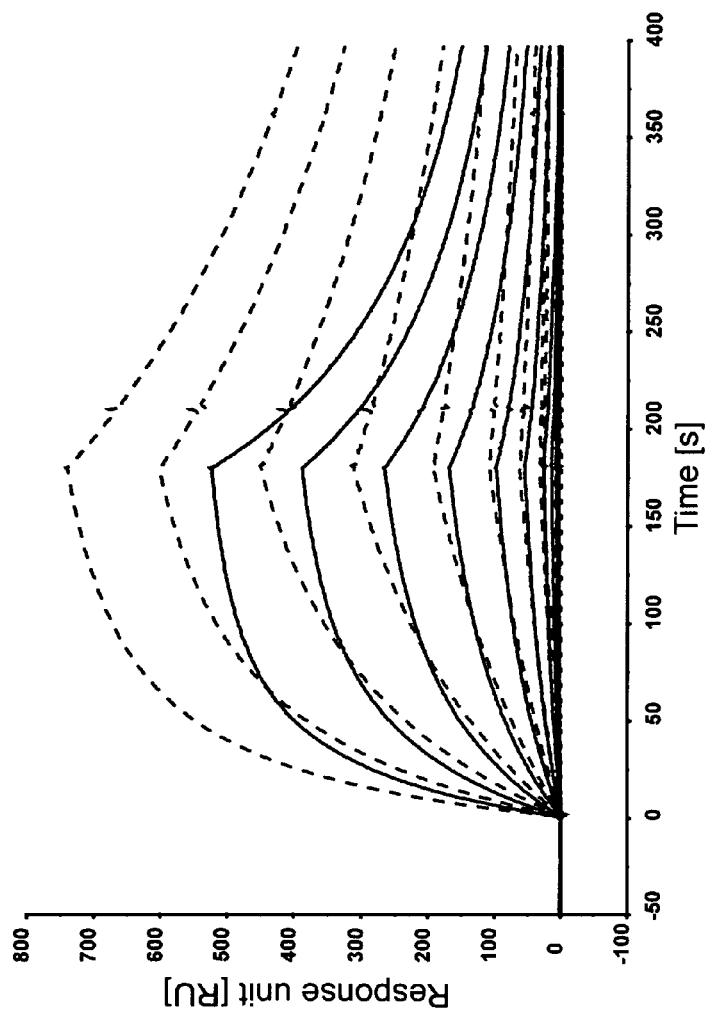
FIG. 8A shows the kinetic evaluation by Biacore measurement of CGRP binding Spiegelmers 226-F2-001 and 226-F2-001-D41 to human CGRP.
Figure 8B:
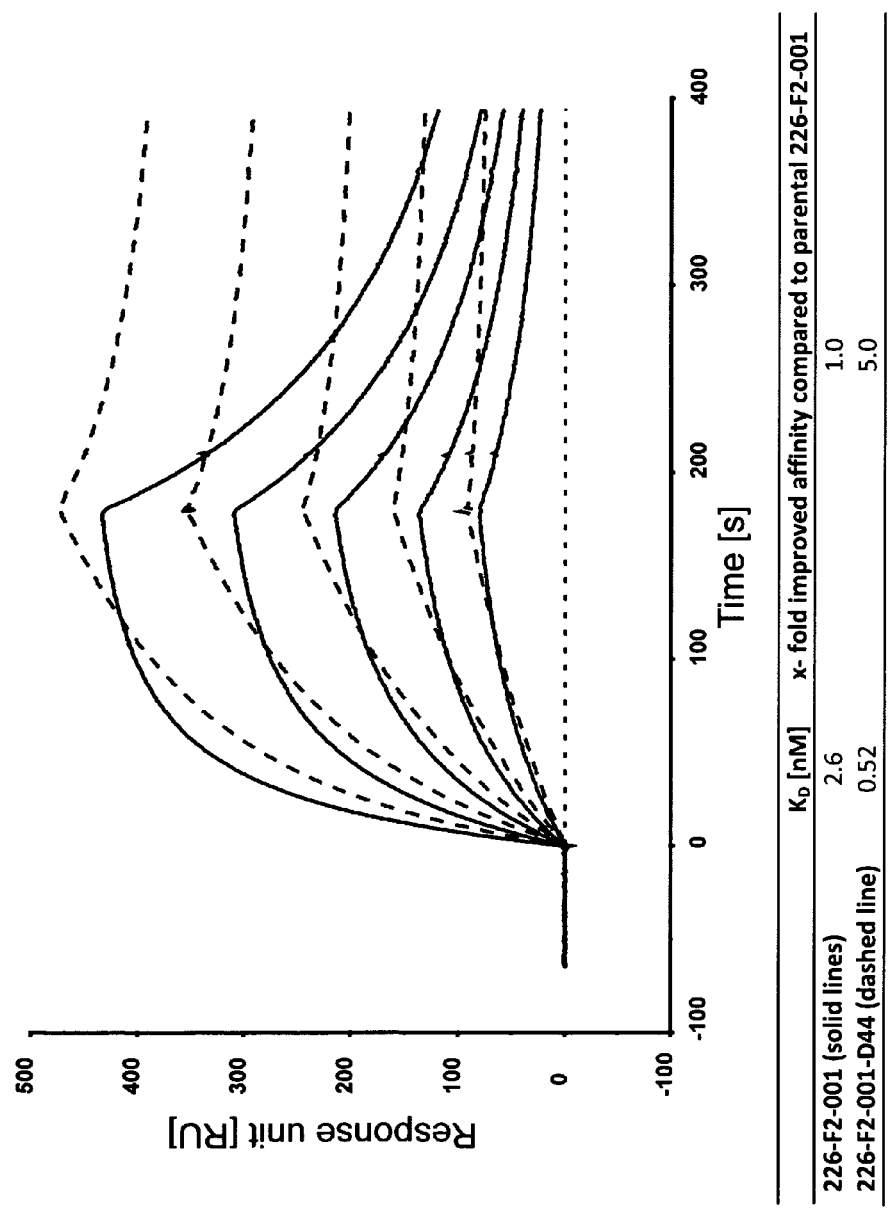
FIG. 8B shows the kinetic evaluation by Biacore measurement of CGRP binding Spiegelmers 226-F2-001 and 226-F2-001-D44 to human CGRP.

The binding characteristics of nucleic acid molecule 226-F2-001 were determined by surface plasmon resonance measurement (as described in Example 8). Nucleic acid molecule 226-F2-001 binds human CGRP with an affinity of 2.6 nM (FIG. 7, FIGS. 8A and 8B).

In order to improve the binding characteristics of nucleic acid molecule 226-F2-001, derivatives of nucleic acid molecule 226-F2-001 were synthesized. Said derivatives were L-nucleic acid molecules having the same sequence of nucleobases guanine, cytosine, adenine, and uracil or thymine (in the case of a 2'deoxyribonucleotide) as nucleic acid molecule 226-F2-001, however, differed at a single position as to the sugar moiety of the nucleotides which was a 2'-deoxyribonucleotide rather than a ribonucleotide. In accordance therewith, derivative 1 (termed 226-F2-001-D01) had a 2'-deoxyribonucleoside at position 1 of the nucleotide sequence according to SEQ ID NO: 56, derivative 2 (termed 226-F2-001-D02) had a 2'-deoxyribonucleotide at position 2 of the nucleotide sequence according to SEQ ID NO: 57, etc. Because nucleic acid molecule 226-F2-001 consisting of 50 nucleotides a total of 50 derivatives were synthesized in order to provide a complete set of all possible derivatives of nucleic acid molecule 226-F2-001 carrying a single ribonucleotide to 2'-deoxyribonucleotide substitution. Said complete set of derivatives is shown in FIGS. 5 A-E. In the case of uracil in the sequence of molecule 226-F2-001, the uridine-5'-phosphate was replaced by thymidine-5'-phosphate.

Figure 6:
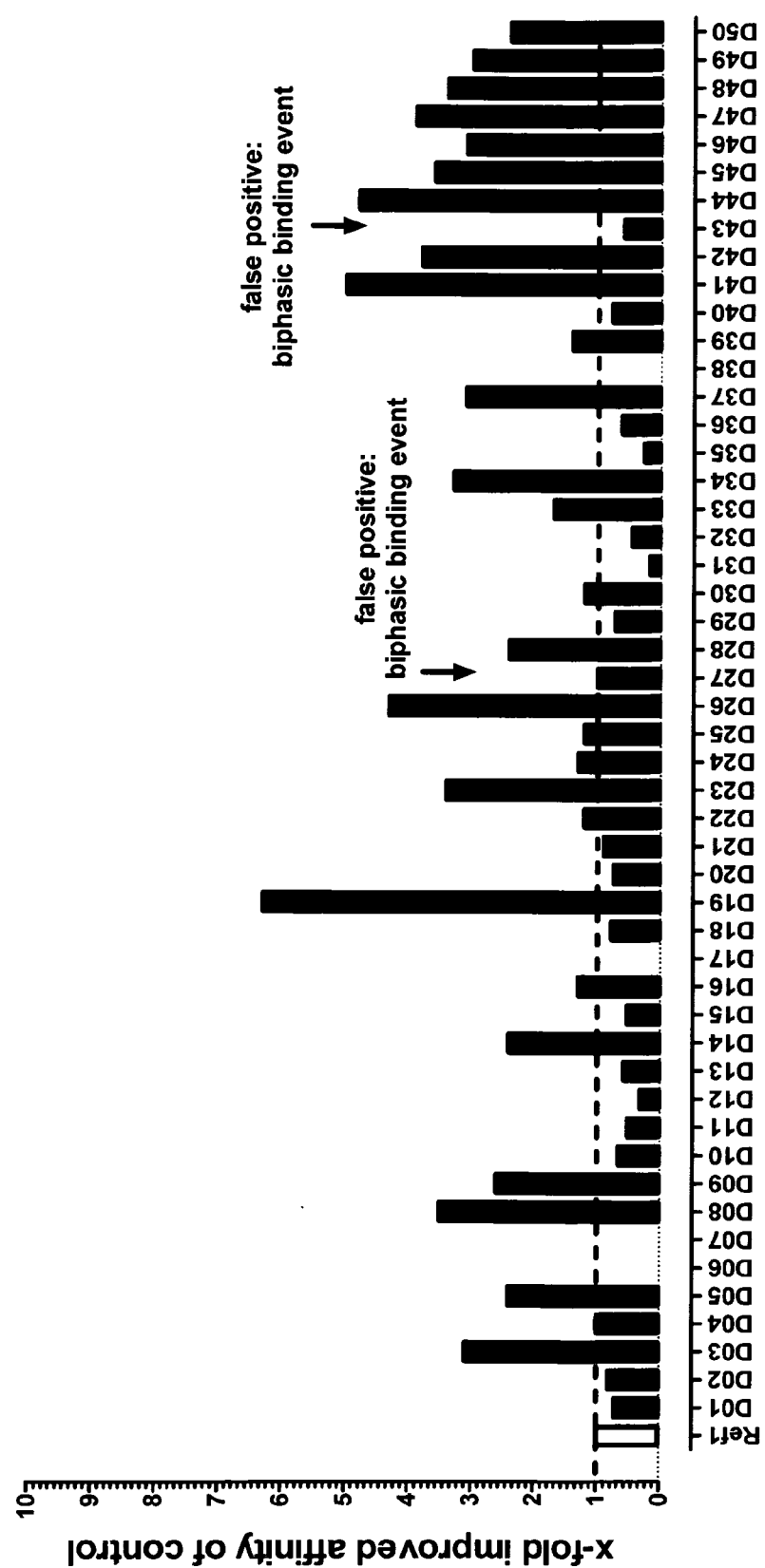

The binding affinity to human CGRP of each derivative of said complete set of derivatives of nucleic acid molecule 226-F2-001 was determined by surface plasmon resonance measurement described in Example 8, and compared to the binding affinity of nucleic acid molecule 226-F2-001. From a set of at least 5 individually determined $K_D$ values of 226-F2-001 the mean value was calculated (mean+/– standard error). $K_D$ values of individual derivatives were determined and changes in affinity are given as x-fold improvement compared to mean $K_D$ of 226-F2-001, wherein the value of x-fold improvement is the quotient of the $K_D$ of 226-F2-001 and the derivative of 226-F2-001. The determined standard error indicates a cutting point for positive hits. The data of the x-fold improved affinities is indicated in FIGS. 5 A-E and plotted in FIG. 6.

As may be taken from FIGS. 5A-E, depending on the position within the Spiegelmer ribonucleotide to 2'-deoxyribonucleotide substitutions may have different impact on binding affinity for the target. Surprisingly, at some positions within nucleic acid molecule 226-F2-001 a single ribonucleotide to 2'-deoxyribonucleotide substitution resulted in an improved binding affinity to human CGRP, whereas substitutions at other positions did not result in significant changes in binding affinity to human CGRP, or even decreased the binding affinity to human CGRP. The individual derivatives and the relative changes of their binding affinity to human CGRP compared to nucleic acid molecule 226-F2-001 are shown in FIGS. 5 A-E and FIG. 6.

As may be taken from said figures, derivatives 226-F2-001-D03, 226-F2-001-D05, 226-F2-001-D08, 226-F2-001-D09, 226-F2-001-D14, 226-F2-001-D16, 226-F2-001-D19, 226-F2-001-D22, 226-F2-001-D23, 226-F2-001-D24, 226-F2-001-D25, 226-F2-001-D26, 226-F2-001-D28, 226-F2-001-D30, 226-F2-001-D33, 226-F2-001-D34, 226-F2-001-D37, 226-F2-001-D39, 226-F2-001-D41, 226-F2-001-D42, 226-F2-001-D44, 226-F2-001-D45, 226-F2-001-D46, 226-F2-001-D47, 226-F2-001-D48, 226-F2-001-D49, 226-F2-001-D50 which have a 2'-deoxyribonucleotide at position 03, 05, 08, 09, 14, 16, 19, 22, 23, 24, 25, 26, 28, 30, 33, 34, 37, 39, 41, 42, 44, 45, 46, 47, 48, 49, 50, respectively, belong to the first group of derivatives, i.e. derivatives of nucleic acid molecule 226-F2-001 where substitution of a ribonucleotide by a 2'-deoxyribonucleotide results in an improved binding affinity for human CGRP (FIGS. 5A-E and FIG. 6). The best binding affinity of said derivatives was shown for 226-F2-001-D19, 226-F2-001-D41 and 226-F2-001-D44 (FIGS. 5A-E and FIG. 6). Accordingly, positions 19, 41 and 44, are suitable to confer to nucleic acid molecule 226-F2-001 an improved binding affinity to human CGRP. Only the nucleic acid molecules 226-F2-001-D41 and 226-F2-001-D44 were further characterized by surface plasmon resonance measurement. Single cytidine-5'-phosphate to 2'-deoxycytidine-5'-phosphate substitutions at position 41 and 44 resulted in an improved binding affinity with a $K_D$ of 0.55 nM and 0.52 nM, respectively, compared to a $K_D$ of 2.6 nM for 226-F2-001 (FIG. 7 and FIGS. 8A, B).

Derivatives 226-F2-001-D04 and 226-F2-001-D27 which have a 2'-deoxyribonucleotide at position 4 and 27, respectively, belong to the second group of derivatives, i.e. derivatives where the substitution of a ribonucleotide by a 2'-deoxyribonucleotide does not affect the binding affinity for human CGRP. Accordingly, positions 4 and 27 are not suitable to confer improved binding affinity nor do they have a negative impact on binding affinity to human CGRP compared to nucleic acid molecule 226-F2-001 (FIGS. 5A-E and FIG. 6).

Finally, derivatives were obtained which resulted in reduced binding affinity or a profound loss of binding. These derivatives, namely 226-F2-001-D01, 226-F2-001-D02, 226-F2-001-D06, 226-F2-001-D07, 226-F2-001-D10, 226-F2-001-D11, 226-F2-001-D12, 226-F2-001-D13, 226-F2-001-D15, 226-F2-001-D17, 226-F2-001-D18, 226-F2-001-D20, 226-F2-001-D21, 226-F2-001-D29, 226-F2-001-D31, 226-F2-001-D32, 226-F2-001-D35, 226-F2-001-D36, 226-F2-001-D38, 226-F2-001-D40 and 226-F2-001-D43, which have a 2'-deoxyribonucleotide at position 1, 2, 6, 7, 10, 11, 12, 13, 15, 17, 18, 20, 21, 29, 31, 32, 35, 36, 38, 40 and 43, respectively, belong to the third group of derivatives, i.e. derivatives of nucleic acid molecule 226-F2-001 where substitution of a ribonucleotide by a 2'-deoxyribonucleotide negatively affects the binding affinity to human CGRP (FIGS. 5A-E and FIG. 6).

In order to assess whether the binding affinity of the derivatives of nucleic acid molecule 226-F2-001 can be further increased by introducing more than one substitution another derivative was generated. Said derivative started from the first group of derivatives where substitution of a ribonucleotide by a 2'-deoxyribonucleotide resulted in an improved binding affinity for human CGRP. Starting from nucleic acid molecule 226-F2-001, the derivative had substitutions of ribonucleotides by 2'-deoxyribonucleotides at the two positions 41 and 44 (referred to as 226-F2-001-D41/D44), i.e. those positions that besides position 19 conferred the strongest improvement in binding affinity to nucleic acid molecule 226-F2-001.

Surface plasmon resonance measurement of 226-F2-001-D41/44 showed that combining ribonucleotide to 2'-deoxyribonucleotide substitutions at more than one position of 226-F2-001, namely cytidine-5'-phosphate to 2'-deoxycytidine-5'-phosphate at position 41 and 44, resulted in a further improvement of binding affinity to human CGRP compared to derivatives containing a single substitution, i.e. 226-F2-001-D41 or 226-F2-001-D44 (FIG. 7, FIGS. 8A, B and FIG. 9). Compared to the parental nucleic acid molecule 226-F2-001 ($K_D$=2.6 nM) substitution of two ribonucleotides by 2'-deoxyribonucleotides in 226-F2-001-D41/44 ($K_D$=0.2 nM) resulted in a 13-fold improvement of binding affinity to human CGRP as measured by surface plasmon resonance (FIG. 7 and FIG. 9).

In order to prove and compare the functionality of Spiegelmers 226-F2-001 and 226-F2-001-D41 both nucleic acid molecules were synthesized comprising an amino-group at their 5'-ends. To the amino-modified Spiegelmers a 40 kDa PEG-moiety was coupled leading to Spiegelmers 226-F2-001-5'40 kDa-PEG and 226-F2-001-D41-5'40 kDa-PEG (also referred to as NOX-L41). Synthesis and PEGylation of the Spiegelmer is described in Example 7.

An in vitro cell-culture assay (protocol see Example 12) confirmed functionality for both Spiegelmers by showing that they effectively inhibited human CGRP-induced cAMP production in a reporter cell line expressing human CGRP-receptor (FIG. 10). 226-F2-001-5'40 kDa-PEG and 226-F2-001-D41-5'-40 kDa-PEG (NOX-L41) inhibited the function of human CGRP-induced with $IC_{50}$ values of 3.8 nM and 0.39 nM, respectively. Thus, surface plasmon resonance measurement (Example 8, FIG. 8A) and in vitro cell culture experiments (Example 12, FIG. 10) unanimously showed that substitution of a single ribonucleotide by a 2'-deoxyribonucleotide was sufficient to significantly improve the binding affinity and the inhibitory activity of CGRP binding Spiegelmer 226-F2-001. The affinity can be further improved by ribonucleotide to 2'-deoxyribonucleotide substitutions at more than one position, as shown for 226-F2-001-D41/44 (FIG. 7 and FIG. 9).

EXAMPLE 3: NUCLEIC ACID MOLECULE HAVING INCREASED BINDING AFFINITY TO THE TARGET MOLECULE HUMAN C5A

Starting from a nucleic acid molecule binding to C5a which was the result of a development process involving as a starting point the immediate screening product of the SELEX process, the method of the present invention was used in order to improve the binding affinity of the nucleic acid molecule to its target. In the instant case, the nucleic acid molecule binding to human C5a was nucleic acid molecule NOX-D19001.

Nucleic acid molecule NOX-D19001 is Spiegelmer, i.e. an L-nucleic acid molecule, which is capable of binding to human C5a, has of a nucleotide sequence according to SEQ ID NO: 107 and consists of 44 ribonucleotides.

The binding characteristics of nucleic acid molecule NOX-D19001 was determined by surface plasmon resonance measurement (as described in Example 8). Nucleic acid molecule NOX-D19001 binds human C5a with an affinity of 1.4 nM as also shown in FIG. 13.

In order to improve the binding characteristics of nucleic acid molecule NOX-D19001, derivatives of nucleic acid molecule NOX-D19001 were synthesized. Said derivatives were L-nucleic acid molecules having the same sequence of nucleobases guanine, cytosine, adenine, and uracil—as nucleic acid molecule NOX-D19001, however, differed at a single position as to the sugar moiety of the nucleotides which was a 2'-deoxyribonucleotide rather than a ribonucleotide. In accordance therewith, derivative 1 (termed NOX-D19001-D01) had a 2'-deoxyribonucleoside at position 1 of the nucleotide sequence according to SEQ ID NO: 108 derivative 2 (termed NOX-D19001-D02) had a 2'-deoxyribonucleotide at position 2 of the nucleotide sequence according to SEQ ID NO: 109 etc. Because of nucleic acid molecule NOX-D19001 consisting of 44 nucleotides a total of 44 derivatives were synthesized in order to provide a complete set of all possible derivatives of nucleic acid molecule meeting the above requirement of a single substitution of a ribonucleotide by a 2'-deoxyribonucleotide. Said complete set of derivatives is shown in FIGS. 11 A-E. In the case of uracil in the sequence of molecule NOX-D19001, the uridine-5'-phosphate was replaced by 2'-deoxyuridine-5'-phosphate.

The binding affinity to human C5a of each derivative of said complete set of derivatives of nucleic acid molecule NOX-D19001 was determined by surface plasmon resonance measurement described in Example 8, and compared to the binding affinity of nucleic acid molecule NOX-D19001. From a set of at least 5 individual determined $K_D$ values of NOX-D19001 the mean value was calculated (mean±standard error). $K_D$ values of individual derivatives were determined and changes in affinity are given as x-fold improvement compared to mean NOX-D19001, wherein the value of the x-fold improvement is the quotient of the $K_D$ of NOX-D19001 and the derivative of NOX-D19001. The determined standard error indicates a cutting point for positive hits. The data of the x-fold improved affinity is indicated in FIGS. 11 A-E and plotted in FIG. 12.

As may be taken from FIGS. 11 A-E, depending on the position within the spiegelmer x-fold improved affinity ribo- to 2'-deoxyribonucleotide substitutions may have different impacts on binding affinity for the target. Surprisingly, a single substitution of a ribonucleotide by a 2'-deoxyribonucleotide at some positions within nucleic acid molecule NOX-D19001 resulted in an improved, i.e. lower binding affinity to human glucagon, whereas substitution at other positions of a ribonucleotide by a 2'-deoxyribonucleotide at some positions within nucleic acid molecule NOX-D19001 did not result in a significant change of the binding affinity to human C5a, or even decreased the binding affinity to human C5a. The individual derivatives, their binding affinity to human C5a and the relative change of their binding affinity compared to the binding affinity of nucleic acid molecule NOX-D19001 to human C5a is indicated in FIGS. 11 A-E.

As may be taken from said figures, derivatives NOX-D19001-D01, NOX-D19001-D02, NOX-D19001-D09, NOX-D19001-D16, NOX-D19001-D17, NOX-D19001-D22, NOX-D19001-D25, NOX-D19001-D29, NOX-D19001-D30, NOX-D19001-D32, NOX-D19001-D40, NOX-D19001-D42, and NOX-D19001-D43 which have a 2'-deoxyribonucleotide at positions 1, 2, 9, 16, 17, 22, 25, 29, 30, 32, 40, 42, and 43, respectively, belong to the first group of derivatives, i.e. derivatives where the substitution of a ribonucleotide by a 2'-deoxyribonucleotide results in an improved binding affinity for human C5a (FIGS. 11 A-E, FIG. 12). The best binding affinity of said derivatives was shown for derivative NOX-D19001-D09, NOX-D19001-D16, NOX-D19001-D17, NOX-D19001-D30, NOX-D19001-D32 and NOX-D19001-D40 (FIGS. 11 A-E, FIG. 12). Accordingly, positions 9, 16, 17, 30, 32 and 40 are suitable to confer to nucleic acid molecule NOX-D19001 an improved binding affinity to human C5a. The nucleic acid molecules NOX-D19001-D09, NOX-D19001-D16, NOX-D19001-D17, NOX-D19001-D30, NOX-D19001-D32 and NOX-D19001-D40 were further characterized by surface plasmon resonance measurement, whereby the binding affinities were determined (FIG. 13). Uridine-5'-phosphate to 2'-deoxy-uridine-5'-phosphate substitution at position 09 resulted in an improved of binding affinity by a factor of two (FIG. 13).

Derivatives NOX-D19001-D03, NOX-D19001-D23, NOX-D19001-D26, NOX-D19001-D35, NOX-D19001-D38, NOX-D19001-D39 and NOX-D19001-D44 which have a 2'-deoxyribonucleotide at positions 3, 23, 26, 35, 38, 39 and 44, respectively, belong to the second group of derivatives, i.e. derivatives where the substitution of a ribonucleotide by a 2'-deoxyribonucleotide does not change or affect the binding affinity for human C5a. The positions 35 and 44 result in an improved binding affinity of NOX-D19001 for human C5a. Accordingly, positions 3, 23, 38, and 39 are not suitable to confer to nucleic acid molecule NOX-D19001 an improved binding affinity to human C5a, however, do not have a negative impact on binding affinity of nucleic acid molecule NOX-D19001 to human C5a either.

Finally, derivatives were obtained which resulted in reduced binding affinity or a profound loss of binding affinity. These derivatives, namely NOX-D19001-D04, NOX-D19001-D05, NOX-D19001-D06, NOX-D19001-D07, NOX-D19001-D08, NOX-D19001-D10, NOX-D19001-D11, NOX-D19001-D12, NOX-D19001-D13, NOX-D19001-D14, NOX-D19001-D15, NOX-D19001-D18, NOX-D19001-D19, NOX-D19001-D20, NOX-D19001-D21, NOX-D19001-D24, NOX-D19001-D27, NOX-D19001-D28, NOX-D19001-D31, NOX-D19001-D33, NOX-D19001-D34, NOX-D19001-D36, NOX-D19001-D38 and NOX-D19001-D41, accordingly, belong to the third group of derivatives, i.e. those derivatives of nucleic acid molecule NOX-D19001 where the substitution of a ribonucleotide by a 2'-deoxyribonucleotide—negatively—affects the binding affinity for human C5a. Accordingly, positions 4, 5, 6, 7, 8, 10, 11, 12, 13, 14, 15, 18, 19, 20, 21, 24, 27, 28, 31, 33, 34, 36 and 41, have a negative impact on the binding affinity of nucleic acid molecule NOX-D19001 to human C5a.

In order to assess whether the binding affinity of the derivatives of nucleic acid molecule L-NOX-D19001 can be further increased by introducing more than one substitution a group of further derivatives was generated. Such group of further derivatives started from the above first group of derivatives comprising derivatives where the substitution of a ribonucleotide by a 2'-deoxyribonucleotide resulted in an improved binding affinity for human C5a. Starting from nucleic acid molecule NOX-D19001, the derivatives of the further group of derivatives had a substitution of a ribonucleotide by a 2'-deoxyribonucleotide at at least two of positions 9, 30, 32 and 40, i.e. those positions which have been proven to be suitable to confer to nucleic acid molecule NOX-D19001 an improved binding affinity to human C5a.

Figure 9:
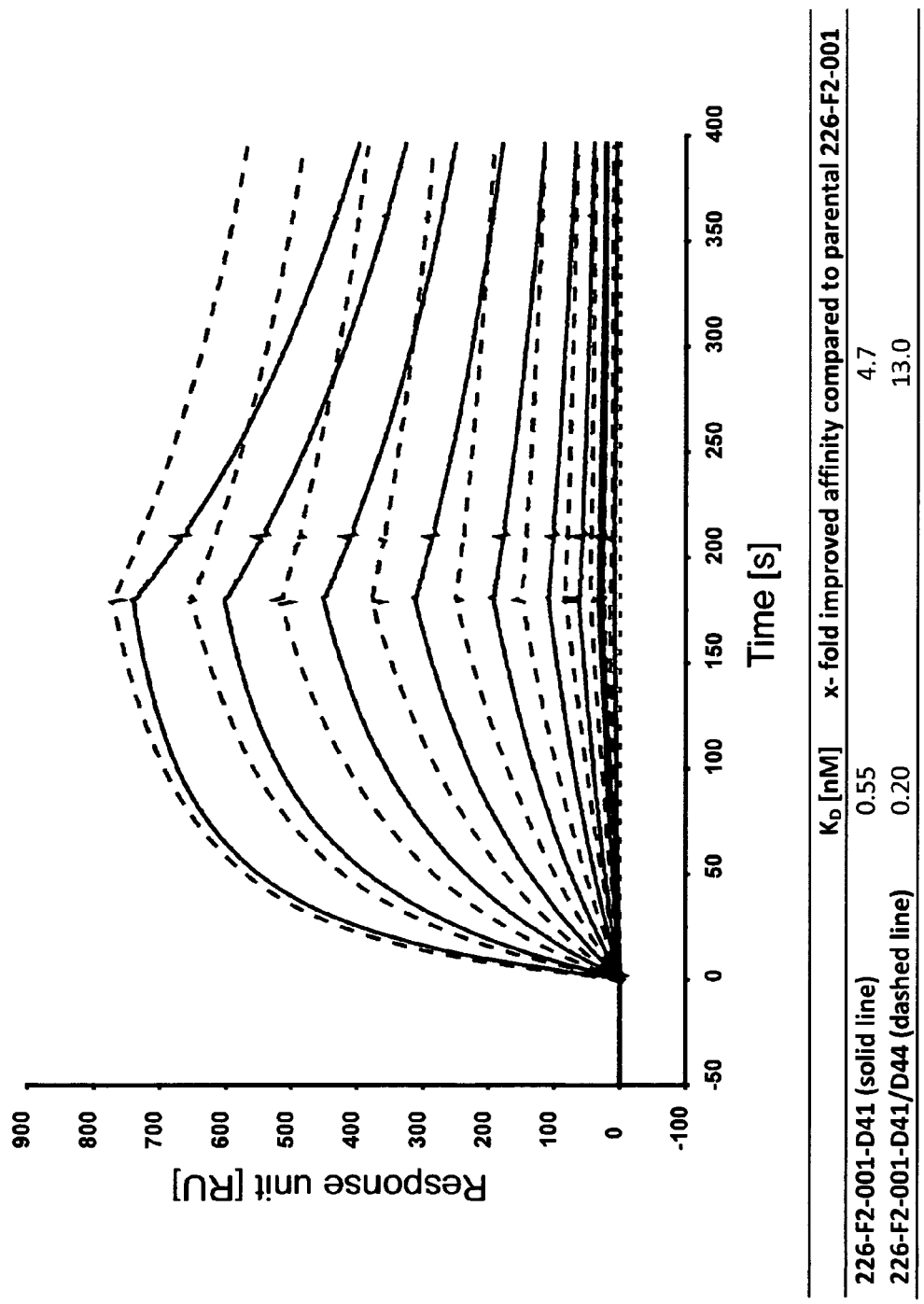
FIG. 9 shows the kinetic evaluation by Biacore measurement of CGRP binding Spiegelmers 226-F2-001-D41 and 226-F2-001-D41/44 to human CGRP.
Figure 10:
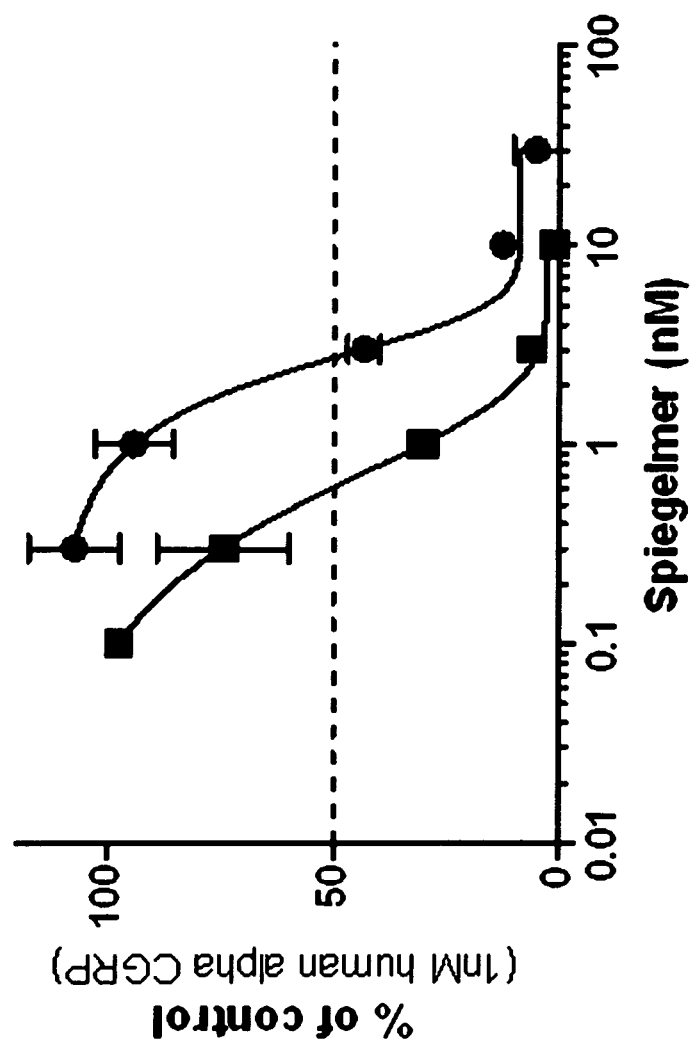
FIG. 10 shows inhibition of human CGRP-induced cAMP production by CGRP binding Spiegelmers 226-F2-001-5'40 kDa-PEG (black circles) and NOX-L41 (also referred to as 226-F2-001-D41-5'40 kDa-PEG, black squares), whereby the results are shown as relative amounts of cAMP produced in comparison to control (percent of control)

Surface plasmon resonance measurement of these representative example showed, as depicted in FIGS. 8 and 9, that combining ribonucleotide to 2'-deoxyribonucleotide substitutions at multiple positions of the spiegelmer NOX-D19001 resulted in an improvement of binding affinity.

Spiegelmers NOX-D19001-D09-30, NOX-D19001-D09-32, NOX-D19001-D09-40, NOX-D19001-D30-32, NOX-D19001-D30-40 and NOX-D19001-D32-40 all containing two substitutions, namely uridine-5'-phosphate to 2'-deoxy-uridine-5'-phosphate at position 9/30, 9/32, 9/40, 30/32, 30/40 and 32/40 showed better binding affinity as the molecules containing one substitution, namely uridine-5'-phosphate to 2'-deoxy-uridine-5'-phosphate at position 9, 30, 32 or 40 (FIG. 14).

Spiegelmers NOX-D19001-D09-30-32, NOX-D19001-D09-30-40, NOX-D19001-D09-32-40 and NOX-D19001-D30-32-40 were synthesized to test whether three substitutions in the nucleic acid molecule NOX-D19001, namely uridine-5'-phosphate to 2'-deoxy-uridine-5'-phosphate at position 9/30/32, 9/30/40, 9/32/40 and 30/32/40 led to further improved binding affinity in comparison to the NOX-D19001-D09-30, NOX-D19001-D09-32, NOX-D19001-D09-40, NOX-D19001-D30-32, NOX-D19001-D30-40 and NOX-D19001-D32-40 all containing two substitutions. Spiegelmers NOX-D19001-D09-30-40 and NOX-D19001-D09-32-40 all containing three substitutions, namely uridine-5'-phosphate to 2'-deoxy-uridine-5'-phosphate at position 9/30/40 and 9/32/40 showed better binding affinity as the molecules containing two substitution, namely uridine-5'-phosphate to 2'-deoxy-uridine-5'-phosphate at position 9, 30, 32 or 40 (FIG. 14).

Combining the four positions 9, 30, 32 or 40 (nucleic acid molecule NOX-D19001-D09-30-32-40) for substitution, namely uridine-5'-phosphate to 2'-deoxy-uridine-5'-phosphate at position 9/30/32/40 led to further improvement in comparison to the Spiegelmers NOX-D19001-D09-30-40 and NOX-D19001-D09-32-40 all containing three substitutions (FIG. 14).

Substitution of an additional ribonucleotide by 2'-deoxyribonucleotide at position 16 or 17 of NOX-D19001-D09-30-32-40 had a further positive effect on the binding affinity to human C5a (see NOX-D19001-D09-16-30-32-40 and see NOX-D19001-D09-17-30-32-40 FIG. 14). Substitution of two additional ribonucleotides by 2'-deoxyribonucleotides at position 16 or 17 of NOX-D19001-D09-30-32-40 had a no further positive effect on the binding affinity to human C5a (see NOX-D19001-D09-16-17-30-32-40, also referred to as NOX-D19001-6xDNA, FIGS. 14 and 15). In comparison to nucleic acid molecule NOX-D19001 nucleic acid molecule NOX-D19001-6xDNA shows an improvement of binding to human C5a by a factor of 4.2 (FIG. 15).

In order to prove and compare the functionality of spiegelmers NOX-D19001 and NOX-D19001-6xDNA both nucleic acid molecules were in an in vitro cell-culture assay (protocol see Example 14). As shown in FIG. 16, the in vitro cell-culture assay confirmed that improved affinity to human C5a translates into an enhanced inhibition of C5a function. The PEGylated Spiegelmers NOX-D19 and NOX-D19-6xDNA inhibited C5a-induced chemotaxis with 1050 values of 2.39 nM and 0.27 nM, respectively (FIG. 16).

As shown before, the substitution of multiple ribonucleotides by 2'-deoxyribonucleotides in the nucleic acid molecule NOX-D19-001 led to improved affinity to human C5a. However, such improvement can only be reached if the multiple substitutions are the result of single substitutions that already lead an improvement in binding to human C5a. The substitution of the ribonucleotide at position 7 by a 2'-deoxyribonucleotides led to reduced affinity (see FIG. 17). This reduced affinity can be 'healed' a little bit by additional substitutions at other positions, for example 16, 17, 30, 32 and 40 (see NOX-D19001-D07-16-17-30-32-40 in comparison to NOX-D19001-D07-30, FIG. 17).

EXAMPLE 4: DERIVATIVES OF NUCLEIC ACID MOLECULE NOX-G11STABI2 HAVING INCREASED BINDING AFFINITY TO THE TARGET MOLECULE GLUCAGON

Starting from a nucleic acid molecule binding to glucagon which was the result of a development process involving as a starting point the immediate screening product of the SELEX process, the method of the present invention was used in order to improve the binding affinity of the nucleic acid molecule to its target. In the instant case, the nucleic acid molecule binding to human glucagon was nucleic acid molecule NOX-G11stabi2.

Nucleic acid molecule NOX-G11stabi2 is a spiegelmer, i.e. an L-nucleic acid molecule, which is capable of binding to human glucagon, has of a nucleotide sequence according to SEQ ID NO: 172 and consists of 54 ribonucleotides.

The binding characteristics of nucleic acid molecule NOX-G11stabi2 was determined by surface plasmon resonance measurement (as described in Example 8). Nucleic acid molecule NOX-G11stabi2 binds human glucagon with an affinity of 67.1 nM as also shown in FIG. 20.

In order to improve the binding characteristics of nucleic acid molecule NOX-G11stabi2, derivatives of nucleic acid molecule NOX-G11stabi2 were synthesized. Said derivatives were L-nucleic acid molecules having the same sequence of nucleobases—guanine, cytosine, adenine, and uracil or alternatively thymine (in the case of a 2'deoxyribonucleotide)—as nucleic acid molecule NOX-G11stabi2, however, differed at a single position as to the sugar moiety of the nucleotides which was a 2'-deoxyribonucleotide rather than a ribonucleotide. In accordance therewith, derivative 1 (termed NOX-G11-D01) had a 2'-deoxyribonucleoside at position 1 of the nucleotide sequence according to SEQ ID NO: 172 derivative 2 (termed NOX-G11-D02) had a 2'-deoxyribonucleotide at position 2 of the nucleotide sequence according to SEQ ID NO: 173 etc. Because of nucleic acid molecule NOX-G11stabi2 consisting of 54 nucleotides a total of 54 derivatives were synthesized in order to provide a complete set of all possible derivatives of nucleic acid molecule meeting the above requirement of a single substitution of a 2'-ribonucleotide by a 2'-deoxyribonucleotide. Said complete set of derivatives is shown in FIGS. 18 A-E. In the case of uracil in the sequence of molecule NOX-G11stabi2, the uridine-5'-phosphate was replaced by thymidine-5'-phosphate.

The binding affinity to human Glucagon of each derivative of said complete set of derivatives of nucleic acid molecule NOX-G11stabi2 was determined by surface plasmon resonance measurement described in Example 8, and compared to the binding affinity of nucleic acid molecule NOX-G11stabi2. From a set of at least 5 individual determined $K_D$ values of NOX-G11stabi2 the mean value was calculated (mean±standard error). $K_D$ values of individual derivatives were determined and changes in affinity are given as x-fold improvement compared to mean NOX-G11stabi2, wherein the value of the x-fold improvement is the quotient of the $K_D$ of NOX-G11stabi2 and the derivative of NOX-G11stabi2. The determined standard error indicates a cutting point for positive hits. The data of the x-fold improved affinity is indicated in FIGS. 18 A-E.

As may be taken from FIGS. 18 A-E, depending on the position within the spiegelmer x-fold improved affinity ribo- to 2'-deoxyribonucleotide substitutions may have different impacts on binding affinity for the target. Surprisingly, a single substitution of a 2' ribonucleotide by a 2'deoxyribonucleotide at some positions within nucleic acid molecule NOX-G11stabi2 resulted in an improved, i.e. lower binding affinity to human glucagon, whereas substitution at other positions of a 2' ribonucleotides by a 2'deoxyribonucleotide at some positions within nucleic acid molecule NOX-G11stabi2 did not result in a significant change of the binding affinity to human Glucagon, or even decreased the binding affinity to human Glucagon. The individual derivatives, their binding affinity to human Glucagon and the relative change of their binding affinity compared to the binding affinity of nucleic acid molecule NOX-G11stabi2 to glucagon is indicated in FIGS. 18 A-E.

As may be taken from said figures, derivatives NOX-G11-D01, NOX-G11-D02, NOX-G11-D03, NOX-G11-D04, NOX-G11-D05, NOX-G11-D06, NOX-G11-D07, NOX-G11-D08, NOX-G11-D09, NOX-G11-D10, NOX-G11-D12, NOX-G11-D13, NOX-G11-D14, NOX-G11-D15, NOX-G11-D16, NOX-G11-D18, NOX-G11-D19, NOX-G11-D20, NOX-G11-D21, NOX-G11-D22, NOX-G11-D23, NOX-G11-D24, NOX-G11-D25, NOX-G11-D26, NOX-G11-D27, NOX-G11-D28, NOX-G11-D29, NOX-G11-D30, NOX-G11-D32, NOX-G11-D36, NOX-G11-D38, NOX-G11-D44, NOX-G11-D46, NOX-G11-D48 and NOX-G11-D53 which have a 2'-deoxyribonucleotide at positions 1, 2, 3, 4, 5, 6, 7, 8, 9, 10, 12, 13, 14, 15, 16, 18, 19, 20, 21, 22, 23, 24, 25, 26, 27, 28, 29, 30, 32, 36, 38, 44, 46, 48 and 53, respectively, belong to the first group of derivatives, i.e. derivatives where the substitution of a ribonucleotide by a 2'-deoxyribonucleotide results in an improved binding affinity for human glucagon (FIGS. 11 A-E, FIG. 19). The best binding affinity of said derivatives was shown for derivative NOX-G11-D07, NOX-G11-D16, NOX-G11-D19, NOX-G11-D19, NOX-G11-D21 and NOX-G11-D22 (FIGS. 11 A-E, FIG. 20). Accordingly, positions 7, 16, 19, 21 and 22 are suitable to confer to nucleic acid molecule NOX-G11stabi2 an improved binding affinity to human glucagon. The nucleic acid molecules NOX-G11-D07, NOX-G11-D16, NOX-G11-D19, NOX-G11-D19, NOX-G11-D21 and NOX-G11-D22 were further characterized by surface plasmon resonance measurement, whereby the binding affinities were determined (FIG. 20).

Derivatives NOX-G11-D11, NOX-G11-D17, NOX-G11-D31, NOX-G11-D33, NOX-G11-D34, NOX-G11-D35, NOX-G11-D39, NOX-G11-D40, NOX-G11-D43, NOX-G11-D45, NOX-G11-D50 and NOX-G11-D52, which have a 2'-deoxyribonucleotide at positions 11, 17, 31, 33, 34, 35, 39, 40, 43, 45, 50 and 52, respectively, belong to the second group of derivatives, i.e. derivatives where the substitution of a ribonucleotide by a 2'-deoxyribonucleotide does not change or affect the binding affinity for human glucagon. Accordingly, positions 11, 17, 31, 33, 34, 35, 39, 40, 43, 45, 50 and 52 are not suitable to confer to nucleic acid molecule NOX-G11stabi2 an improved binding affinity to human glucagon, however, do not have a negative impact on binding affinity of nucleic acid molecule NOX-G11stabi2 to human glucagon either.

Finally, derivatives were obtained which resulted in reduced binding affinity or a profound loss of binding affinity. These derivatives, namely NOX-G11-D37, NOX-G11-D41, NOX-G11-D42, NOX-G11-D47, NOX-G11-D49, NOX-G11-D51 and NOX-G11-D54, accordingly, belong to the third group of derivatives, i.e. those derivatives of nucleic acid molecule NOX-G11stabi2 where the substitution of a ribonucleotide by a 2'-deoxyribonucleotide—negatively—affects the binding affinity for human Glucagon. Accordingly, positions 37, 41, 42, 47, 49, 51 and 54, have a negative impact on the binding affinity of nucleic acid molecule NOX-G11stabi2 to human Glucagon.

EXAMPLE 5: DERIVATIVES OF NUCLEIC ACID MOLECULE 259-H6-002 HAVING INCREASED BINDING AFFINITY TO THE TARGET MOLECULE GLUCAGON

Starting from a nucleic acid molecule binding to glucagon which was the result of a development process involving as a starting point the immediate screening product of the SELEX process, the method of the present invention was used in order to improve the binding affinity of the nucleic acid molecule to its target. In the instant case, the nucleic acid molecule binding to human glucagon was nucleic acid molecule 259-H6-002.

Nucleic acid molecule 259-H6-002, a Spiegelmer, i.e. an L-nucleic acid molecule, which is capable of binding to human glucagon, has a nucleotide sequence according to SEQ ID NO: 287 and consists of 46 2'-deoxyribonucleotides.

The binding characteristics of nucleic acid molecule 259-H6-002 was determined by surface plasmon resonance measurement (as described in Example X). Nucleic acid molecule 259-H6-002 binds human glucagon with an affinity of 10.9 nM as also shown in FIG. 23.

In order to improve the binding characteristics of nucleic acid molecule 259-H6-002, derivatives of nucleic acid molecule 259-H6-002 were synthesized. Said derivatives were L-nucleic acid molecules having the same sequence of nucleobases guanine, cytosine, adenine, and uracil—as nucleic acid molecule 259-H6-002, however, differed at a single position as to the sugar moiety of the nucleotides which was a 2'-ribonucleotide rather than a deoxyribonucleotide. In accordance therewith, derivative 1 (termed 259-H6-002-R01) had a ribonucleoside at position 1 of the nucleotide sequence according to SEQ ID NO: 288 derivative 2 (termed 259-H6-002-R02) had a 2'-ribonucleotide at position 2 of the nucleotide sequence according to SEQ ID NO: 289 etc. Because of nucleic acid molecule 259-H6-002 consisting of 46 nucleotides a total of 46 derivatives were synthesized in order to provide a complete set of all possible derivatives of nucleic acid molecule meeting the above requirement of a single substitution of a 2'-deoxyribonucleotide by a ribonucleotide. Said complete set of derivatives is shown in FIGS. 21 A-E. In the case of thymidine in the sequence of molecule 259-H6-002, the thymidine-5'phosphate was replaced by uridine 5' phosphate.

The binding affinity to human glucagon of each derivative of said complete set of derivatives of nucleic acid molecule 259-H6-002 was determined by surface plasmon resonance measurement described in Example 8, and compared to the binding affinity of nucleic acid molecule 259-H6-002, whereby the binding affinity to human glucagon of each derivative of said complete set of derivatives of nucleic acid molecule 259-H6-002 was determined by surface plasmon resonance measurement described in Example 8, and compared to the binding affinity of nucleic acid molecule 259-H6-002. From a set of at least 5 individual determined $K_D$ values of 259-H6-002 the mean value was calculated (mean+/− standard error). $K_D$ values of individual derivatives were determined and changes in affinity are given as x-fold improvement compared to mean 259-H6-002, wherein the value of the x-fold improvement is the quotient of the $K_D$ of 259-H6-002 and the derivative of 259-H6-002. The determined standard error indicates a cutting point for positive hits. The data of the x-fold improved affinity is indicated in FIGS. 21 A-D and plotted in FIG. 22.

As may be taken from FIGS. 21 A-D, depending on the position within the spiegelmer 2'-deoxyribonucleotide to ribonucleotide substitutions may have different impacts on binding affinity for the target. Surprisingly, a single substitution of a 2'-deoxyribonucleotide by a ribonucleotide at some positions within nucleic acid molecule 259-H6-002 resulted in an improved, i.e. higher binding affinity to human glucagon, whereas substitution at other positions of a 2'-deoxyribonucleotide by a ribonucleotide within nucleic acid molecule 259-H6-002 did not result in a significant change of the binding affinity to human glucagon, or even decreased the binding affinity to human glucagon. The individual derivatives and the relative change of their binding affinity compared to the binding affinity of nucleic acid molecule 259-H6-002 to glucagon is indicated in FIGS. 21 A-D.

As may be taken from said figures, derivatives 259-H6-002-R8, 259-H6-002-R13, 259-H6-002-R22, 259-H6-002-R24, 259-H6-002-R30, 259-H6-002-R31, 259-H6-002-R36, 259-H6-002-R38, 259-H6-002-R39, and 259-H6-002-R44, which have a ribonucleotide at positions 8, 13, 22, 24, 30, 31, 36, 38, 39, and 44, respectively, belong to the first group of derivatives, i.e. derivatives where the substitution of a 2'-deoxyribonucleotide by a ribonucleotide results in an improved binding affinity for human glucagon (FIGS. 21 A-D, FIG. 22). The best binding affinity of said derivatives was shown for derivative 259-H6-002-R13, 259-H6-002-R24, 259-H6-002-R30 and 259-H6-002-R36 with improvement factors between 2.1 and 5.8 (FIG. 21 A-D, FIG. 22). Accordingly, positions 13, 24, 30 and 36 are suitable to confer to nucleic acid molecule 259-H6-002 an improved binding affinity to human glucagon. The nucleic acid molecules 259-H6-002-R13, 259-H6-002-R24, and 259-H6-002-R36 were further characterized by surface plasmon resonance measurement, whereby the binding affinities were determined (FIG. 23).

Derivatives 259-H6-002-R04, 259-H6-R06, and 259-H6-R46 ... which have a 2'-ribonucleotide at positions 4, 6, and 46 respectively, belong to the second group of derivatives, i.e. derivatives where the substitution of a 2'deoxyribonucleotide by a 2'-ribonucleotide does not significantly change or affect the binding affinity for human glucagon. Accordingly, positions 4, 6, and 46 are not suitable to confer to nucleic acid molecule 259-H6-002 an improved binding affinity to human glucagon, however, do not have a negative impact on binding affinity of nucleic acid molecule 259-H6-002 to human glucagon either.

Derivatives 259-H6-R09 and 259-H6-R45 show a biphasic binding behaviour on the Biacore. Therefore the improvement factor were judged to be artificial and positions 9 and 45 were not further considered for improvement of binding affinity.

Finally, 31 derivatives were obtained which resulted in reduced binding affinity or a profound loss of binding affinity. These derivatives, namely 259-H6-002-R01, 259-H6-002-R02, 259-H6-002-R03, 259-H6-002-R05, 259-H6-002-R07, 259-H6-002-R10, 259-H6-002-R11, 259-H6-002-R12, 259-H6-002-R14, 259-H6-002-R15, 259-H6-002-R16, 259-H6-002-R17, 259-H6-002-R18, 259-H6-002-R19, 259-H6-002-R20, 259-H6-002-R21, 259-H6-002-R23, 259-H6-002-R25, 259-H6-002-R26, 259-H6-002-R27, 259-H6-002-R28, 259-H6-002-R29, 259-H6-002-R32, 259-H6-002-R33, 259-H6-002-R34, 259-H6-002-R35, 259-H6-002-R37, 259-H6-002-R40, 259-H6-002-R41, 259-H6-002-R42, 259-H6-002-R43 accordingly, belong to the third group of derivatives, i.e. those derivatives of nucleic acid molecule 259-H6-002 where the substitution of a 2'-deoxyribonucleotide by a ribonucleotide—negatively—affects the binding affinity for human glucagon. Accordingly, positions 1, 2, 3, 5, 7, 10, 11, 12, 14, 15, 16, 17, 18, 19, 20, 21, 23, 25, 26, 27, 28, 29, 32, 33, 34, 35, 37, 40, 41, 42, and 43 have a negative impact on the binding affinity of nucleic acid molecule 259-H6-002 to human glucagon.

In order to assess whether the binding affinity of the derivatives of nucleic acid molecule L-259-H6-002 can be further increased by introducing more than one substitution a group of further derivatives was generated. Such group of further derivatives started from the above first group of derivatives comprising derivatives where the substitution of a 2'-deoxyribonucleotide by a ribonucleotide resulted in an improved binding affinity for human glucagon. Starting from nucleic acid molecule 259-H6-002, the derivatives of the further group of derivatives had a substitution of a 2'-deoxyribonucleotide by a ribonucleotide at at least two of positions 13, 24, 30 and 36, i.e. those positions which have been proven to be suitable to confer to nucleic acid molecule 259-H6-002 an improved binding affinity to human glucagon.

Surface plasmon resonance measurement of these representative example showed, as depicted in FIG. 24, that combining 2'-deoxyribonucleotide by a ribonucleotide substitutions at multiple positions of the spiegelmer 259-H6-002 resulted in an improvement of binding affinity.

Spiegelmers 259-H6-002-R13_R24 and 259-H6-002-R13_R36, all containing two substitutions, namely deoxyadenosine-5'-phosphate to adenosine-5'-phosphate at position 13, deoxyguanosine to guanosine-5'-phosphate at position 24 and/or thymidine-5'-phosphate to uridine-5'-phosphate at position 36, showed better binding affinity as the molecules containing one substitution (FIG. 24).

Spiegelmer 259-H6-002-R13_R24_R36 was synthesized to test whether three substitutions in the nucleic acid molecule 259-H6-002, namely deoxyadenosine-5-phosphate to adenosine-5'-phosphate at position 13, deoxyguanosine-5'-phosphate to guanosine-5'-phosphate at position 24 and thymidine-5'-phosphate to uridine-5'-phosphate at position 36, led to further improved binding affinity in comparison to the spiegelmers 259-H6-002-R13_R24 and 259-H6-002-R13_R36, all containing two substitutions (FIG. 24).

Combining the four positions 13, 24, 30 and 36 (nucleic acid molecule 259-H6-002-R13_R24_R30_R36) for substitution, namely deoxyadenosine-5'-phosphate to adenosine-5'-phosphate at position 13, deoxyguanosine-5-phosphate to guanosine-5'-phosphate at position 24 and 30 and thymidine-5'-phosphate to uridine-5'-phosphate at position 36, led to a slight improvement in comparison to the Spiegelmer 259-H6-002-R13_R24_R36 containing three substitutions (FIG. 26).

In order to prove and compare the functionality of Spiegelmers 259-H6-002, 259-H6-002-R13 and 259-H6-002-R13_R24_R36 all nucleic acid molecules were tested in an in vitro cell-culture assay (protocol see Example 14). As shown in FIG. 25, the in vitro cell-culture assay confirmed that improved affinity to human glucagon translates into an enhanced inhibition of human glucagon function. Spiegelmers 259-H6-002, 259-H6-002-R13 and 259-H6-002-R13_R24_R36 inhibited glucagon induced formation of intracellular cAMP with IC$_{50}$ values of 176 nM, 12.5 nM and 6.2 nM, respectively (FIG. 25).

EXAMPLE 6: DERIVATIVES OF NUCLEIC ACID MOLECULE 257-E1-001 HAVING INCREASED BINDING AFFINITY TO THE TARGET MOLECULE GLUCAGON

Starting from a nucleic acid molecule binding to glucagon which was the result of a development process involving as a starting point the immediate screening product of the SELEX process, the method of the present invention was used in order to improve the binding affinity of the nucleic acid molecule to its target. In the instant case, the nucleic acid molecule binding to human glucagon was nucleic acid molecule 257-E1-001.

Nucleic acid molecule 257-E1-001 is a Spiegelmer, i.e. a L-nucleic acid molecule, which is capable of binding to human glucagon, has a nucleotide sequence according to SEQ ID NO: 27 and consists of 47 2'-deoxyribonucleotides.

The binding characteristics of nucleic acid molecule 257-E1-001 were determined in the competitive pull-down assay format (as described in Example 10). Nucleic acid molecule 257-E1-001 binds human glucagon with an affinity of 186 nM as also shown in FIG. 28.

In order to improve the binding characteristics of nucleic acid molecule 257-E1-001, derivatives of nucleic acid molecule 257-E1-001 were synthesized (as described in Example 7). Said derivatives were L-nucleic acid molecules having the same sequence of nucleobases—guanine, cytosine, adenine, and uracil or alternatively thymine (in the case of a 2'deoxyribonucleotide)—as nucleic acid molecule 257-E1-001, however, differed at a single position as to the sugar moiety of the nucleotides which was a ribonucleotide rather than a 2'-deoxyribonucleotide. In accordance therewith, derivative 1 (termed 257-E1-R1-001) had a ribonucleoside at position 1 of the nucleotide sequence according to SEQ ID NO: 228, derivative 2 (termed 257-E1-R2-001) had a ribonucleotide at position 2 of the nucleotide sequence according to SEQ ID NO: 229 etc. Because of nucleic acid molecule 257-E1-001 consisting of 47 nucleotides a total of 47 derivatives was synthesized in order to provide a complete set of all possible derivatives of nucleic acid molecules meeting the above requirement of a single substitution of a 2'-deoxyribonucleotide by a ribonucleotide. Said complete set of derivatives is shown in FIGS. 27 A-D. In the case of a thymidine-5'-phosphate in the sequence of molecule 257-E1-001, the thymidine-5'-phosphate was replaced by the uridine-5'-phosphate.

The binding characteristics to human glucagon of each derivative of said complete set of derivatives of nucleic acid molecule 257-E1-001 was determined in competitive pull-down assays described in Example 10, and compared to the binding affinity of nucleic acid molecule 257-E1-001. As may be taken from FIGS. 27 A-D, depending on the position within the Spiegelmer 2'-deoxyribonucleotide to ribonucleotide substitutions may have different impacts on binding affinity for the target. Surprisingly, a single substitution of a 2'-deoxyribonucleotide by a ribonucleotide at some positions within nucleic acid molecule 257-E1-001 resulted in an improved, i.e. higher binding affinity to human glucagon, whereas the substitution of a 2'deoxyribonucleotide by a ribonucleotide at other positions within nucleic acid molecule 257-E1-001 did not result in a significant change of the binding affinity to human glucagon, or even decreased the binding affinity to human glucagon. The individual derivatives, and the relative change of their binding affinity compared to the binding affinity of nucleic acid molecule 257-E1-001 to glucagon is indicated in FIGS. 27 A-D.

As may be taken from said figures, derivatives 257-E1-R9-001, 257-E1-R15-001, 257-E1-R18-001, 257-E1-R19-001, 257-E1-R29-001, and 257-E1-R30-001 which have a ribonucleotide at position 9, 15, 18, 19, 29, or 30, respectively, belong to the first group of derivatives, i.e. derivatives where the substitution of a 2'-deoxyribonucleotide by a ribonucleotide results in an improved binding affinity for human glucagon (FIGS. 27 A-C, 28). The best binding affinity of said derivatives was shown for derivatives 257-E1-R15-001, 257-E1-R29-001, and 257-E1-R30-001 (FIGS. 27 B-C, 28). Accordingly, positions 15, 29, and 30 are suitable to confer to nucleic acid molecule 257-E1-001 an improved binding affinity to human glucagon. The nucleic acid molecules 257-E1-R15-001, and 257-E1-R29-001 were further characterized in competitive pull-down assays, whereby the binding affinities were determined (FIG. 28).

Derivatives 257-E1-R26-001 and 257-E1-R46-001, which have a ribonucleotide at positions 26 and 46, respectively, belong to the second group of derivatives, i.e. derivatives where the substitution of a 2'-deoxyribonucleotide by a ribonucleotide does not change or affect the binding affinity for human glucagon. Accordingly, positions 26 and 46 are not suitable to confer to nucleic acid molecule 257-E1-001 an improved binding affinity to human glucagon, however, do not have a negative impact on binding affinity of nucleic acid molecule 257-E1-001 to human glucagon either.

Finally, derivatives were obtained which resulted in reduced binding affinity or a profound loss of binding affinity. These derivatives, namely 257-E1-R1-001, 257-E1-R2-001, 257-E1-R3-001, 257-E4-R1-001, 257-E5-R1-001, 257-E1-R6-001, 257-E1-R7-001, 257-E1-R8-001, 257-E1-R10-001, 257-E1-R11-001, 257-E1-R12-001, 257-E1-R13-001, 257-E1-R14-001, 257-E1-R16-001, 257-E1-R17-001, 257-E1-R20-001, 257-E1-R21-001, 257-E1-R22-001, 257-E1-R23-001, 257-E1-R24-001, 257-E1-R25-001, 257-E1-R27-001, 257-E1-R28-001, 257-E1-R31-001, 257-E1-R32-001, 257-E1-R33-001, 257-E1-R34-001, 257-E1-R35-001, 257-E1-R36-001, 257-E1-R37-001, 257-E1-R38-001, 257-E1-R39-001, 257-E1-R40-001, 257-E1-R41-001, 257-E1-R42-001, 257-E1-R43-001, 257-E1-R44-001, 257-E1-R45-001, 257-E1-R47-001, accordingly, belong to the third group of derivatives, i.e. those derivatives of nucleic acid molecule 257-E1-001 where the substitution of a 2'-deoxyribonucleotide by a ribonucleotide—negatively—affects the binding affinity for human glucagon. Accordingly, positions 1, 2, 3, 4, 5, 6, 7, 8, 10, 11, 12, 13, 14, 16, 17, 20, 21, 22, 23, 24, 25, 27, 28, 31, 32, 33, 34, 35, 36, 37, 38, 39, 40, 41, 42, 43, 44, 45, 47, have a negative impact on the binding affinity of nucleic acid molecule 257-E1-001 to human glucagon.

In order to assess whether the binding affinity of the derivatives of nucleic acid molecule 257-E1-001 can be further increased by introducing more than one substitution a group of further derivatives was generated. Such group of further derivatives started from the above first group of derivatives comprising derivatives where the substitution of a 2'-deoxyribonucleotide by a ribonucleotide resulted in an improved binding affinity for human glucagon. Starting from nucleic acid molecule 257-E1-001, the derivatives of the further group of derivatives had a substitution of a 2'-deoxyribonucleotide by a ribonucleotide at least at two of positions 9, 15, 18, 19, 29, and 30, i.e. those positions which have been proven to be suitable to confer to nucleic acid molecule 257-E1-001 an improved binding affinity to human glucagon.

In competitive pull-down assays representative examples showed, as depicted in FIGS. 27E, F and 28, that combining 2'-deoxyribonucleotide by ribonucleotide substitutions at multiple positions of the Spiegelmer 257-E1-001 resulted in an improvement of binding affinity. The binding affinity to human glucagon of derivatives, containing combinations of at least two 2'-deoxyribonucleotide to ribonucleotide substitutions, was determined in competitive pull-down assays described in Example 10, and compared to the binding affinity of nucleic acid molecule 257-E1-001 or 257-E1-6xR-001, respectively. From a set of two or ten individual determined $K_D$ values of 257-E1-001 or 257-E1-6xR-001, respectively, the mean values were calculated (mean+/− standard error). $K_D$ values of Spiegelmers with combined substitutions were determined and changes in affinity are given as improvement factor of affinity compared to mean of 257-E1-001 or 257-E1-6xR-001, respectively, wherein the value of the x-fold improvement is the quotient of the $K_D$ of 257-E1-001 and the derivative of 257-E1-001. The determined standard error indicates a cutting point for improvement or decline. The improvement factors of affinity are indicated in FIGS. 27 E and F.

Spiegelmers 257-E1-R15/29-001 and 257-E1-R29/30-001, both containing two substitutions, namely 2'-deoxyguanosine-5'-phosphate to guanosine-5'-phosphate at position 15, 2'-deoxyadenosine-5'-phosphate to adenosine-5'-phosphate at position 29 and/or 2'-deoxyadenosine-5'-phosphate to adenosine-5'-phosphate at position 30, showed better binding affinity as the molecules containing one substitution (FIG. 27E).

Spiegelmers 257-E1-R15/29/30-001 and 257-E1-R18/29/30-001 were synthesized to test whether three substitutions in the nucleic acid molecule 257-E1-001 led to a further improved binding affinity compared to Spiegelmers 257-E1-R15/29-001 and 257-E1-R29/30-001, all containing two substitutions. Namely, the substitutions of 2'-deoxyguanosine-5'-phosphate to guanosine-5'-phosphate at position 15, 2'-deoxyadenosine-5'-phosphate to adenosine-5'-phosphate at position 29, and 2'-deoxyadenosine-5'-phosphate to adenosine-5'-phosphate at position 30 led to a further improved binding affinity compared to the Spiegelmer 257-E1-R29/30-001. However, the binding affinity of the three-fold substituted Spiegelmer 257-E1-R15/29/30-001 to glucagon is comparable to that of Spiegelmer 257-E1-R15/29-001, containing two substitutions. The substitution of 2'-deoxyguanosine-5'-phosphate to guanosine-5'-phosphate at position 18 instead of the 2'-deoxyguanosine-5'-phosphate to guanosine-5'-phosphate substitution at position 15 in Spiegelmer 257-E1-R18/29/30-001 led to an increased binding affinity compared to 257-E1-R29/30-001, but to a decreased affinity compared to 257-E1-R15/29/30 (FIG. 27E).

Combining the four positions 15, 18, 29 and 30 (nucleic acid molecule 257-E1-R15/18/29/30-001) for substitution, namely 2'-deoxyguanosine-5'-phosphate to guanosine-5'-phosphate at position 15, 2'-deoxyguanosine-5'-phosphate to guanosine-5'-phosphate at position 18, 2'-deoxyadenosine-5'-phosphate to adenosine-5'-phosphate at position 29, and 2'-deoxyadenosine-5'-phosphate to adenosine-5'-phosphate at position 30, did not lead to further improvement in comparison to the Spiegelmer 257-E1-R15/29/30-001 containing three substitutions (FIG. 27E).

Surprisingly, the combination of six 2'deoxyribonucleotide to ribonucleotide substitutions at positions 9, 15, 18, 19, 29, 30 (Spiegelmer 257-E1-R9/15/18/19/29/30-001=257-E1-6xR-001), namely 2'-deoxyguanosine-5'-phosphate to guanosine-5'-phosphate at position 9, 2'-deoxyguanosine-5'-phosphate to guanosine-5'-phosphate at position 15, 2'-deoxyguanosine-5'-phosphate to guanosine-5'-phosphate at position 18, 2'-deoxyguanosine-5'-phosphate to guanosine-5'-phosphate at position 19, 2'-deoxyadenosine-5'-phosphate to adenosine-5'-phosphate at position 29, and 2'-deoxyadenosine-5'-phosphate to adenosine-5'-phosphate at position 30, led to a further improved binding affinity to glucagon compared to the Spiegelmers 257-E1-R15/29-001 and 257-E1-R15/18/29/30-001, containing two and four substitutions, respectively (FIGS. 27E and 28).

In order to assess whether the binding affinity to glucagon of the Spiegelmer 257-E1-6xR-001, containing six 2'-deoxyribonucleotide to ribonucleotide substitutions, can be further increased by the exchange of thymidine-5'-phosphate with 5-methyl-uridine-5'-phosphate instead of with uridine-5'-phosphate, derivatives of nucleic acid molecule 257-E1-6xR-001 were synthesized. Said derivatives contain an additional, seventh substitution of thymidine-5'-phosphates to 5-methyl-uridine-5'-phosphate and are shown in FIG. 27 F. In fact, a single derivative nucleic acid molecule, containing seven substitutions (nucleic acid molecule 257-E1-7xR-023), namely four 2'-deoxyguanosine-5'-phosphate to guanosine-5'-phosphate substitutions at positions 9, 15, 18, and 19, one thymidine-5'-phosphate to 5-methyl-uridine-5'-phosphate substitution, and two 2'-deoxyadenosine-5'-phosphate to adenosine-5'-phosphate substitutions at positions 29 and 30, resulted in a slightly improved binding affinity compared to Spiegelmer 257-E1-6xR-001 (FIGS. 27F and 28).

Finally, the binding affinity of Spiegelmer 257-E1-7xR-023 to glucagon was improved by a factor of 43 in comparison to the SELEX derived, unmodified Spiegelmer 257-E1-001.

EXAMPLE 7: SYNTHESIS AND DERIVATIZATION OF SPIEGELMERS

Small Scale Synthesis

Spiegelmers (L-RNA nucleic acids or L-DNA modified L-RNA nucleic acids) were produced by solid-phase synthesis with an ABI 394 synthesizer (Applied Biosystems, Foster City, Calif., USA) using 2'TBDMS RNA and DNA phosphoramidite chemistry with standard exocyclic amine protecting groups (Damha and Ogilvie, 1993). For the RNA part of the oligonucleotide rA(N-Bz)-, rC(N-Ac)-, rG(N-ibu)-, and rU-phosphoramidites in the D- (if needed, see Ex 9/10) and L-configuration were used, while for the DNA part dA(N-Bz)-, dC(N-Ac)-, dG(N-ibu)-, and dT in the D- and L-configuration were applied. All phosphoramidites were purchased from ChemGenes, Wilmington, Mass. After synthesis and deprotection aptamers and spiegelmers were purified by gel electrophoresis.

Large Scale Synthesis Plus Modification

Spiegelmers were produced by solid-phase synthesis with an ÄktaPilot100 synthesizer (GE Healthcare, Freiburg) using 2'TBDMS RNA and DNA phosphoramidite chemistry with standard exocyclic amine protecting groups (Damha and Ogilvie, 1993). L-rA(N-Bz)-, L-rC(N-Ac)-, L-rG(N-ibu)-, L-rU-, L-dA(N-Bz)-, L-dC(N-Ac)-, L-dG(N-ibu)-, and L-dT-phosphoramidites were purchased from Chem-Genes, Wilmington, Mass. The 5'-amino-modifier was purchased from American International Chemicals Inc. (Framingham, Mass., USA). Synthesis of the unmodified or a 5'-Amino-modified spiegelmer was started on L-riboA, L-riboC, L-riboG, L-riboU, L-2'deoxyA, L-2'deoxyC, L-2'deoxyG, or L-2'deoxyT modified CPG pore size 1000 Å (Link Technology, Glasgow, UK. For coupling of the RNA and DNA phosphoramidites (15 min per cycle), 0.3 M benzylthiotetrazole (CMS-Chemicals, Abingdon, UK) in acetonitrile, and 2 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott et al., 1995) using Source15RPC medium (Amersham). The 5'DMT-group was removed with 80% acetic acid (30 min at RT). In case of 5'aminomodified Spiegelmers the 5'MMT-group was removed with 80% acetic acid (90 min at RT). Subsequently, aqueous 2 M NaOAc solution was added and the Spiegelmer was desalted by tangential-flow filtration using a 5 K regenerated cellulose membrane (Millipore, Bedford, Mass.).

Pegylation of Spiegelmers

In order to prolong the Spiegelmer's plasma residence time in vivo, a 40 kDa polyethylene glycol (PEG) moiety was covalently coupled at the 5'-end of the spiegelmers.

For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (Jenkem Technology, Allen, Tex., USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 8: BIACORE MEASUREMENT

Biacore Assay Setup

The Biacore 2000 instrument (Biacore AB, Sweden) was set to a constant temperature of 37° C. The instrument was cleaned using the DESORB method before the start of each experiment/immobilization of a new chip: After docking a maintenance chip, the instrument was consecutively primed with desorb solution 1 (0.5% sodium dodecyl sulphate, SDS), desorb solution 2 (50 mM glycine, pH 9.5) and HBS-EP pH 7.4 buffer. Finally, the system was primed with HBS-EP pH 7.4 buffer. All reagents were purchased from GE Healthcare unless otherwise indicated.

Target Immobilization

The target immobilization procedure was established individually for each target. Examples for the targets described herein are listed below:

Immobilization of Biotinylated Human L-Glucagon

The immobilization buffer was HBS-EP pH 7.4 buffer. Synthetic biotinylated human L-glucagon (glucagon1-29-AEEAc-AEEAc-biotin, custom synthesis by BACHEM, Switzerland) was immobilized on a carboxymethylated dextran-coated sensor chip (CM5, GE Healthcare) which had been prepared by covalent immobilization of soluble neutravidin (Sigma Aldrich, Germany) using a 1:1 mixture of 0.4 M EDC (1-ethyl-3-(3-dimethylaminopropyl) carbodiimide in $H_2O$) and 0.1 M NHS (N-hydroxysuccinimide in $H_2O$). The reference flow cell on the same sensor chip was blocked with biotin.

Immobilization of Human L-C5a

The immobilization buffer was HBS-EP pH 7.4 buffer. Recombinant human L-C5a (Sigma Aldrich) in 10 mM NaOAc pH 5.5 was immobilized by amine coupling on a carboxymethylated dextran-coated sensor chip (CM5, GE Healthcare) which had been activated using a 1:1 mixture of 0.4 M EDC (1-ethyl-3-(3-dimethylaminopropyl) carbodiimide in $H_2O$) and 0.1 M NHS (N-hydroxysuccinimide in $H_2O$).

Immobilization of Human L-Alpha-CGRP

The immobilization buffer was HBS-EP pH 7.4 buffer. Synthetic human L-αCGRP (Bachem) in 10 mM NaOAc pH 5.5 was immobilized by amine coupling on a carboxymethylated dextran-coated sensor chip (CM5, GE Healthcare) which had been activated using a 1:1 mixture of 0.4 M EDC (1-ethyl-3-(3-dimethylaminopropyl) carbodiimide in $H_2O$) and 0.1 M NHS (N-hydroxysuccinimide in $H_2O$).

Identification of Spiegelmer Derivatives with Improved Binding Affinity

Binding analysis and kinetic parameter assessment of the individual single-position modified spiegelmer derivatives was performed by injecting Spiegelmer at a concentration of 1 µM at a device temperature of 37°. Before and after the total injection series, as well as every tenth injection an injection of blank running buffer and of a Spiegelmer reference were injected to monitor sensor chip decay, due to the regeneration procedure or/and limited peptide stability on the sensor chip surface.

From at least 5 individually determined $K_d$ values of the parent (all-DNA or all-RNA) spiegelmer the mean value was calculated (mean±standard error). $K_d$ values of individual derivatives were determined and changes in affinity are given as x-fold improvement compared to the mean of the parent molecule, wherein the value of the x-fold improvement is the quotient of the $K_D$ of the parent molecule and the derivative of the parent molecule. The determined standard error indicates a cutting point for positive hits.

Data analysis and calculation of dissociation constants ($K_d$) was done with the BIAevaluation 3.1.1 software (BIACORE AB, Uppsala, Sweden) and Prism 5.0 (GraphPad) software for calculation of mean values and standard errors.

Derivatives of the parent molecule that showed improved binding properties in respect of the target recognition (association constant $k_a$) or/and Spiegelmer target complex stability (dissociation constant $k_d$) resulting in an overall improved affinity (dissociation constant $K_d$) were characterized by measuring detailed binding kinetics (injection of a concentration series of the respective Spiegelmer).

Detailed Kinetic Evaluation of Selected Derivatives of the Parent Molecule

Kinetic parameters and dissociation constants were evaluated by a series of Spiegelmer injections at concentrations of 2,000-1,000-500-200-125-62.5-31.3-15.6 (2×)-7.8-3.9-1.95-0.98-0.48-0.24-0.12-0 nM diluted in running buffer, starting with the lowest concentration. In all experiments, the analysis was performed at 37° C. using the Kinject command defining an association time of 240 to 360 seconds and a dissociation time of 240 to 360 seconds at a flow of 30 μl/min. The assay was double referenced, whereas Flow Cell 1 (FC1) served as (blocked) surface control (bulk contribution of each Spiegelmer concentration) and a series of buffer injections without analyte determined the bulk contribution of the buffer itself. At least one Spiegelmer concentration was injected twice to monitor the regeneration efficiency and chip integrity during the experiments. Data analysis and calculation of dissociation constants ($K_d$) was done with the BIAevaluation 3.1.1 software (BIACORE AB)

Combination of Identified Exchange Positions that Lead to Improved Binding

Finally two or more of the positive single positions for substitutions were combined and the resulting sequences were again studied with detailed binding kinetics.

The results of the Biacore measurements are described in Examples 2 to 5.

EXAMPLE 9: COMPETITIVE SPIEGELMER PULL-DOWN ASSAY OF S1P SPIEGELMERS

Affinity constants of S1P binding spiegelmers were determined by competitive pull-down assays. In order to allow for radioactive labeling of the spiegelmer by T4 polynucleotide kinase two guanosine residues in the D-configuration were added to the 5'-end of the L-S1P-215-F9-002 spiegelmer. Unlabeled spiegelmers were then tested for their ability to compete with 300-600 pM radiolabeled spiegelmer L-S1P-215-F9-002-5'diD-G for binding to a constant amount of biotinylated D-e-S1P, i.e. decreasing the binding signal according to the binding affinity of the non-labeled spiegelmer to D-e-S1P. D-e-S1P was used at a concentration of 8 nM resulting in a final binding of approximately 10% of radiolabeled spiegelmer L-S1P-215-F9-002-5'diD-G in the absence of competitor spiegelmers. Assays were performed in 250 μl selection buffer (20 mM Tris-HCl pH 7.4; 150 mM NaCl; 5 mM KCl; 1 mM $MgCl_2$; 1 mM $CaCl_2$; 0.1% [w/vol] Tween-20; 4 mg/ml bovine serum albumin; 10 μg/ml Yeast-RNA) for 3-4 hours at 37° C. Biotinylated D-e-S1P and complexes of spiegelmer and biotinylated S1P were immobilized on 5 μl Neutravidin Ultralink Plus beads (Pierce Biotechnology, Rockford, USA) which had been pre-equilibrated with selection buffer before addition to the binding reactions. Beads were kept in suspension for 30 min at 37° C. in a thermomixer. After removal of supernatants and appropriate washing, immobilized radioactivity was quantified in a scintillation counter. The percentage of binding or normalized percentage of bound radiolabeled spiegelmer L-S1P-215-F9-002-5'diD-G was plotted against the corresponding concentration of competitor spiegelmer. Dissociation constants were obtained using GraphPad Prism software. The same assay format was used for comparative ranking of a set of different spiegelmers. In this case competitor spiegelmers were used at a single concentration as indicated.

EXAMPLE 10: DETERMINATION OF BINDING AFFINITY TO GLUCAGON (PULL-DOWN ASSAY)

For binding analysis to glucagon the glucagon binding nucleic acid molecules were synthesized as spiegelmers consisting of L-nucleotides. The binding analysis of spieglmers was done with biotinylated human L-glucagon consisting of L-amino acids.

Direct Pull-Down Assay

Two additional adenosinresidues in the D-configuration at the Spiegelmer's 5'-end enabled 5'-phosphate labeling by T4 polynucleotide kinase (Invitrogen, Karlsruhe, Germany) using [γ-$^{32}$P]-labeled ATP (Hartmann Analytic, Braunschweig, Germany). The specific radioactivity of labeled nucleic acids was 200,000-800,000 cpm/pmol. After de- and renaturation (1' 94° C., ice/$H_2O$) labeled nucleic acids were incubated at 100-700 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20; 0.1% [w/vol] CHAPS) together with varying amounts of biotinylated human D- or L-glucagon, respectively, for 2-6 hours in order to reach equilibrium at low concentrations. Selection buffer was supplemented with 100 μg/ml human serum albumin (Sigma-Aldrich, Steinheim, Germany), and 10 μg/ml yeast RNA (Ambion, Austin, USA) in order to prevent unspecific adsorption of binding partners to surfaces of used plasticware or to the immobilization matrix. The concentration range of biotinylated L-glucagon for Spiegelmer binding was set from 0.32 nM to 5 μM; total reaction volume was 50 μl. Biotinylated glucagon and complexes of nucleic acids and biotinylated glucagon were immobilized on 4 μl High Capacity Neutravidin Agarose particles (Thermo Scientific, Rockford, USA) which had been preequilibrated with selection buffer. Particles were kept in suspension for 20 mM at the respective temperature in a thermomixer. Immobilized radioactivity was quantitated in a scintillation counter after removal the supernatant and appropriate washing. The percentage of binding was plotted against the concentration of biotinylated glucagon and dissociation constants were obtained by using software algorithms (GRAFIT; Erithacus Software; Surrey U.K.) assuming a 1:1 stoichiometry.

Competitive Pull-Down Assay for Ranking of Glucagon Binding Nucleic Acids

In order to compare the binding of different Spiegelmers to glucagon a competitive ranking assay was performed. For this purpose either the most affine spiegelmer available was radioactively labeled (see above) and served as reference for glucagon binding spiegelmers, respectively. After de- and renaturation the labeled nucleic acids were incubated at 37° C. with biotinylated glucagon in 50 or 100 μl selection buffer at conditions that resulted in around 5-10% binding to the biotinylated glucagon after immobilization on 1.5 μl High Capacity Neutravidin Agarose particles (Thermo Scientific, Rockford, USA) and washing without competition. An excess of de- and renatured non-labeled spiegelmer variants was added at different concentrations together with the labeled reference spiegelmer to parallel binding reactions. De- and renatured non-labeled Spiegelmer derivatives were applied at concentrations of 1, 10, and 100 nM together with the reference Spiegelmer in parallel binding reactions. The nucleic acids to be tested competed with the reference nucleic acid for target binding, thus decreasing the binding signal in dependence of their binding characteristics. The aptamer or Spiegelmer, respectively that was found most active in this assay could then serve as a new reference for comparative analysis of other glucagon binding nucleic acid molecules.

Competitive Pull-Down Assay for Determination of Affinity

In addition to comparative ranking experiments the competitive pull-down assay was also performed to determine the affinity constants of glucagon binding nucleic acids. For this purpose either a L-glucagon binding Spiegelmer was radioactively labeled and served as reference as described above. After de- and renaturation the labeled reference nucleic acid and a set of 5-fold dilutions ranging e.g. from 0.128 to 2000 nM of competitor molecules were incubated with a constant amount of biotinylated glucagon in 0.1 or 0.2 ml selection buffer at 37° C. for 2-4 hours. The chosen protein concentration should cause final binding of approximately 5-10% of the radiolabeled reference molecule at the lowest competitor concentration. In order to measure the binding constants of derivative nucleic acid sequences an excess of the appropriate de- and renatured non-labeled Spiegelmer variants served as competitors, whereas for Spiegelmers unmodified as well as PEGylated forms were tested. In another assay approach non-biotinylated glucagon at different concentrations competed against the biotinylated glucagon for Spiegelmer binding. After immobilization of biotinylated glucagon and the bound nucleic acids on 1.5 µl High Capacity Neutravidin Agarose matrix, washing and scintillation counting (see above), the normalized percentage of bound radiolabeled Spiegelmer was plotted against the corresponding concentration of competitor molecules. The resulting dissociation constant was calculated employing the GraFit Software.

EXAMPLE 11: INHIBITION OF β-ARRESTIN RECRUITMENT INDUCED BY S1P VIA EDG1 RECEPTOR BY S1P-BINDING SPIEGELMERS

PathHunter™ eXpress EDG-1 CHO-K1 β-arrestin GPCR cells (DiscoverX) were seeded at $1\times10^4$ cells per well in a white 96 well-plate with clear bottom (Greiner) and cultivated for 48 h at 37° C. and 5% $CO_2$ in 100 µl Culture Medium (DiscoverX). Stimulation solutions (D-e-S1P+various concentrations of Spiegelmer) are made up as 11× concentrated solutions in HBSS (Gibco) supplemented with 1 mg/ml BSA and 20 mM HEPES, mixed thoroughly and incubated at 37° C. for 30 min. 10 µl stimulation solution were added per well (triplicates) and cells were incubated for 90 min at 37° C. and 5% $CO_2$.

Upon receptor activation by D-e-S1P, the interaction of activated EDG1 with β-arrestin leads to β-galactosidase enzyme fragment complementation.

For quantification of β-galactosidase activity 55 µl Working Detection Reagent Solution (DiscoverX) were added and incubated for 90 min at room temperature. Luminescence was subsequently measured in a Fluostar Optima multidetection plate reader (BMG).

To show the efficacy of anti-S1P-spiegelmers, cells were stimulated with 10 nM D-e-S1P or D-e-S1P preincubated with various amounts of spiegelmers. The results show the percentage of luminescence signal normalized to the signal obtained without addition of spiegelmer. Mean values±SD from triplicate cultures are shown.

EXAMPLE 12: INHIBITION OF ALPHACGRP-INDUCED CAMP PRODUCTION IN HUMAN NEUROBLASTOMA CELLS

Biological efficacy of CGRP-binding Spiegelmers was analysed as follows.

SK-N-MC human neuroblastoma cells (DSMZ, Braunschweig) were seeded at 5×10e4 cells/well in a flat-bottomed 96-well plate (Greiner) and cultivated for 48 h at 37° C. and 5% $CO_2$ in 100 µl in DMEM (1000 mg/L glucose, Invitrogen) supplemented with 10% heat-inactivated fetal calf serum (FCS), 4 mM L-alanyl-L-glutamine (GLUTA-MAX), 50 units/ml Penicillin and 50 µg/ml Streptomycin.

Stimulation solutions (1 nM human or rat L-alphaCGRP (Bachem)+increasing concentrations of Spiegelmer) were prepared as triplicates in HBSS (Gibco) supplemented with 1 mg/ml BSA and 20 mM HEPES using v-bottomed 0.2 ml low profile 96-well plates and incubated at 37° C. for 60 min in total. Blank values (no L-alphaCGRP, no Spiegelmer) and control values (1 nM L-alphaCGRP, no Spiegelmer) were included as triplicates. 20 min prior to stimulation 1 mM phosphodiesterase inhibitor 3-Isobutyl-1-methylxanthine (IBMX, Sigma; 50 mM stock in DMSO diluted in HBSS/BSA/HEPES) was added to the cells and the stimulation solutions. For stimulation, cell culture medium was removed from the cells and substituted by 100 µl pre-incubated stimulation solution. Cell were stimulated for 30 min at 37° C., 5% $CO_2$. After removal of stimulation solutions cells were lysed by addition of 50 µl/well assay/lysis buffer (Applied Biosystems, Tropix cAMP-Screen™ System kit) for 30 min at 37° C.

The amount of cAMP produced per well was subsequently measured using the Tropix cAMP-Screen™ ELISA System kit (Applied Biosystems) according to manufacturer's instructions. Briefly, a standard curve is prepared in assay/lysis buffer ranging from 6 nmol to 0.6 pmol cAMP/well. Cell lysates diluted in assay/lysis buffer and standard curves are added to microplates precoated with goat anti-rabbit IgG. cAMP alkaline phosphatase conjugate and anti-cAMP antibody are added to the samples and incubated for 60 min at room temperature. Subsequently, plates are washed and chemiluminescent substrate is added. After 30 min chemiluminescence is measured in a FLUOstar OPTIMA plate reader unit (BMG Labtech). The cAMP-Screen™ ELISA system is a competitive immunoassay format. Thus, light signal intensity is inversely proportional to the cAMP level in the sample or standard preparation.

This assay system was used to test Spiegelmers within the scope of Examples 1 and 7 described herein. The result is illustrated in FIGS. 7 and 8. Quantities of cAMP produced are given as percentage of the control. The concentration of Spiegelmer required for 50% inhibition of cAMP production relative to control defines the inhibitory constant $IC_{50}$.

EXAMPLE 13: DETERMINATION OF INHIBITORY CONCENTRATION IN A CHEMOTAXIS ASSAY

Generation of a Cell Line Expressing the Human Receptor for C5a

A stably transfected cell line expressing the human receptor for C5a was generated by transfecting BA/F3 mouse pro B cells with a plasmid coding for the human C5a receptor (NCBI accession NM_001736 in pcDNA3.1+). Cells expressing C5aR were selected by treatment with geneticin and tested for expression with RT-PCR and for functionality with chemotaxis assay.

Chemotaxis Assay

The day before the experiment, cells are seeded in a new flask at $0.3\times10^6$/ml. For the experiment, cells were centrifuged, washed once in HBH (HBSS, containing 1 mg/ml bovine serum albumin and 20 mM HEPES) and resuspended at $1.33\times10^6$ cells/ml. 75 µl of this suspension were added to the upper compartments of a 96 well Corning Transwell plate with 5 µm pores (Costar Corning, #3388; NY, USA). In the lower compartments recombinant human C5a (SEQ. ID. 50) or mouse C5a (SEQ. ID. 54) was pre-incubated together with Spiegelmers in various concentrations in 235 µl HBH at 37° C. for 20 to 30 min prior to addition of cells. Cells were allowed to migrate at 37° C. for 3 hours.

Thereafter the insert plate (upper compartments) was removed and 30 μl of 440 μM resazurin (Sigma, Deisenhofen, Germany) in phosphate buffered saline was added to the lower compartments. After incubation at 37° C. for 2.5 hours, fluorescence was measured at an excitation wavelength of 544 nm and an emission wavelength of 590 nm.

Fluorescence values are corrected for background fluorescence (no C5a in well) and plotted against Spiegelmer concentration. The $IC_{50}$ values are determined with non-linear regression (4 parameter fit) using GraphPad Prism. Alternatively, the value for the sample without Spiegelmer (C5a only) is set 100% and the values for the samples with Spiegelmer are calculated as percent of this. The percent-values are plotted against Spiegelmer concentration and the $IC_{50}$-values are determined as described above.

Determination of the Half-Maximal Effective Concentration ($EC_{50}$) for Human and Mouse C5a After 3 hours migration of BA/F3/huC5aR cells towards various human C5a or mouse C5a concentrations, dose-response curves for human and mouse C5a were obtained, indicating half effective concentrations ($EC_H$) of 0.1 nM for huC5a and 0.3 nM for mC5a. For the experiments on inhibition of chemotaxis by Spiegelmers 0.1 nM human C5a and 0.3 nM mouse C5a were used.

EXAMPLE 14: INHIBITION OF GLUCAGON-INDUCED CAMP PRODUCTION BY GLUCAGON-BINDING SPIEGELMERS

A stably transfected cell line expressing the human receptor for glucagon was generated by cloning the sequence coding for the human glucagon receptor (NCBI accession NM_000160) into the pCR3.1 vector (Invitrogen). CHO cells adapted to growth in serum-free medium (UltraCHO, Lonza) were transfected with the glucagon receptor plasmid and stably transfected cells were selected by treatment with geneticin.

For an inhibition experiment CHO cells expressing the glucagon receptor were plated on a 96 well plate (cell culture treated, flat bottom) at a density of $4-6 \times 10^4$/well and cultivated overnight at 37° C. 5% $CO_2$ in UltraCHO medium containing 100 units/ml penicillin, 100 μg/ml streptomycin and 0.5 mg/ml geneticin. 20 min before stimulation a solution of 3-isobutyl-1-methylxanthine (IBMX) was added to a final concentration of 1 mM.

The stimulation solutions (glucagon+various concentrations of Spiegelmers) were made up in Hank's balanced salt solution (HBSS)+1 mg/ml BSA and were incubated for 30 min at 37° C. Shortly before addition to the cells, IBMX was added to a final concentration of 1 mM. For stimulation, the medium was removed from the cells and the stimulation solutions (glucagon+Spiegelmer) were added. After incubation for 30 min at 37° C. the solutions were removed and the cells were lysed in lysis-buffer which is a component of the cAMP-Screen™ System kit (Applied Biosystems). This kit was used for determination of the cAMP content following the supplier's instructions.

REFERENCES

The complete bibliographic data of the documents recited herein are, if not indicated to the contrary, as follows, whereby the disclosure of said references is incorporated herein by reference.

Altschul S. F., Gish W., et al. (1990) Basic local alignment search tool. J Mol Biol. 215(3):403-10.

Altschul S. F., Madden T. L., et al. (1997) Gapped BLAST and PSI-BLAST: a new generation of protein database search programs. Nucleic Acids Res. 25(17):3389-402.

Damha M J, Ogilvie K K. (1993) Oligoribonucleotide synthesis. The silyl-phosphoramidite method. Methods Mol Biol. 20:81-114

Klussmann S. (2006). The Aptamer Handbook—Functional Oligonucleotides and their Applications. Edited by S. Klussmann. WILEY-VCH, Weinheim, Germany, ISBN 3-527-31059-2

Kusser W. (2000) Chemically modified nucleic acid aptamers for in vitro selections: evolving evolution. J Biotechnol 74(1): 27-38.

Mairal T., Ozalp V. C., Lozano Sánchez P., et al. (2008) Aptamers: molecular tools for analytical applications. Anal Bioanal Chem. 390(4):989-1007

McGinnis S., Madden T. L. et al. (2004) BLAST: at the core of a powerful and diverse set of sequence analysis tools. Nucleic Acids Res. 32 (Web Server issue):W20-5.

Needleman and Wunsch (1970) A general method applicable to the search for similarities in the amino acid sequence of two proteins. J Mol Biol. 48(3):443-53.

Pearson and Lipman (1988) Improved tools for biological sequence comparison. Proc. Nat'l. Acad. Sci. USA 85: 2444

Smith and Waterman (1981), Adv. Appl. Math. 2: 482

Venkatesan N., Kim S. J., et al. (2003) Novel phosphoramidite building blocks in synthesis and applications toward modified oligonucleotides. Curr Med Chem 10(19): 1973-91

Wincott F, DiRenzo A, et al. (1995). Synthesis, deprotection, analysis and purification of RNA and ribozymes. Nucleic Acids Res.; 23(14):2677-84.

The features of the present invention disclosed in the specification, the claims and/or the drawings may both separately and in any combination thereof be material for realizing the invention in various forms thereof.

The invention claimed is:

1. A method for generating an L-nucleic acid molecule that binds a target molecule, by a mechanism other than base pairing comprising the following steps:
   a) providing a reference L-nucleic acid molecule, wherein the reference L-nucleic acid molecule binds the target molecule, and wherein the reference L-nucleic acid molecule comprises a sequence of L-nucleotides, wherein the sequence of L-nucleotides comprises n L-nucleotides;
   b) preparing a first level derivative of the reference L-nucleic acid molecule, wherein the first level derivative of the reference L-nucleic acid molecule differs from the reference L-nucleic acid molecule at one nucleotide position; wherein the first level derivative is prepared by replacing 2'-deoxyribonucleotide at the one nucleotide position by a ribonucleotide in case the reference L-nucleic acid molecule has a 2'-deoxyribonucleotide at the one nucleotide position; wherein the first level derivative is prepared by replacing ribonucleotide at the one nucleotide position by a 2'-deoxyribonucleotide in case the reference L-nucleic acid molecule has a ribonucleotide at the one nucleotide position; and wherein the nucleotide position at which the replacement is made is the modified nucleotide position;
   c) repeating step b) for each nucleotide position of the reference L-nucleic acid molecule, thereby preparing a group of first level derivatives of the reference L-nucleic acid molecule, wherein the group of first level derivatives of the reference L-nucleic acid molecule consists of n first level derivatives, wherein each of the first level derivatives of the reference L-nucleic acid molecule differs from the reference L-nucleic acid molecule by a single nucleotide replacement and wherein each of the first level derivatives of the reference L-nucleic acid molecule has a single modified nucleotide position which is different from the single modified nucleotide of all of the single modified nucleotide positions of the other first level derivatives of the group of first level derivatives of the reference L-nucleic acid molecule;

d) determining a binding characteristic of each of the n first level derivatives of the reference L-nucleic acid molecule that binds the target molecule, wherein the binding characteristic comprises binding affinity of the first level derivative(s) of the reference L-nucleic acid molecule that binds the target molecule, wherein the binding affinity is expressed as $K_D$ value; and e) identifying first level derivative(s) of the reference L-nucleic acid molecule that binds the target molecule, comprising binding affinity that exceeds binding affinity of the reference L-nucleic acid molecule that binds the target molecule, thereby obtaining L-nucleic acid molecules that bind(s) the target molecule by a mechanism other than base pairing.

2. The method according to claim 1, wherein first level derivative(s) of the reference L-nucleic acid molecule that binds the target molecule, identified in step e) comprise a binding affinity that exceeds a predetermined threshold value.

3. The method according to claim 2, wherein the predetermined threshold value is Y with Y being the quotient of (binding affinity of the reference L-nucleic acid molecule)/(binding affinity of a first level derivative) and wherein Y>1, Y≥2, Y≥5 or Y≥10.

4. The method according to claim 1, wherein a second level derivative of the reference nucleic acid molecule is prepared, wherein the second level derivative differs from the reference L-nucleic acid molecule at least at a first nucleotide position and a second nucleotide position, wherein the first nucleotide position is the modified nucleotide position of a first level derivative of the reference L-nucleic acid molecule from the group of derivatives of the reference L-nucleic acid molecule consisting of n derivatives, and wherein the first level derivative comprises binding affinity that exceeds binding affinity of the reference L-nucleic acid molecule that binds the target molecule, and wherein the nucleotide of the first nucleotide position is identical to the nucleotide at the modified position of the first level derivative of the reference L-nucleic acid molecule, wherein the second nucleotide position is the modified nucleotide position of a second first level derivative of the reference L-nucleic acid molecule from the group of derivatives of the reference L-nucleic acid molecule consisting of n derivatives, and wherein the second first level derivative comprises binding affinity that exceeds binding affinity of the reference L-nucleic acid that binds the target molecule, and wherein the nucleotide of the second nucleotide position is identical to the nucleotide at the modified position of the second first level derivative of the reference L-nucleic acid molecule, the method further comprising:

f) determining a binding characteristic of the second level derivative of the reference L-nucleic acid molecule that binds the target molecule, wherein the binding characteristic comprises binding affinity of the second level derivative(s) of the reference L-nucleic acid molecule that binds the target molecule, wherein the binding affinity is expressed as $K_D$ value; and (g) identifying second level derivative(s) of the reference L-nucleic acid molecule that binds the target molecule, comprising binding affinity that exceeds binding affinity of the reference L-nucleic acid molecule that binds the target molecule.

5. The method according to claim 4, wherein second level derivative(s) of the reference L-nucleic acid molecule that binds the target molecule, identified in step g) comprise a binding affinity that exceeds a predetermined threshold value.

6. The method according to claim 5, wherein the predetermined threshold value is Y, with Y being the quotient of (binding affinity of the reference L-nucleic acid molecule)/(binding affinity of a second level derivative) and wherein Y>1, Y≥2, Y≥5, Y≥10 or Y≥20.

* * * * *

SEQUENCE LISTING

```
<160> NUMBER OF SEQ ID NOS: 342

<210> SEQ ID NO 1
<211> LENGTH: 37
<212> TYPE: PRT
<213> ORGANISM: Homo sapiens
<220> FEATURE:
<221> NAME/KEY: misc_feature
<222> LOCATION: (1)..(37)
<223> OTHER INFORMATION: L-peptide
<220> FEATURE:
<221> NAME/KEY: misc_feature
<222> LOCATION: (37)..(37)
```

<223> OTHER INFORMATION: NH2-moiety attached to C-terminus

<400> SEQUENCE: 1

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 2
<211> LENGTH: 74
<212> TYPE: PRT
<213> ORGANISM: Homo sapiens
<220> FEATURE:
<221> NAME/KEY: misc_feature
<222> LOCATION: (1)..(74)
<223> OTHER INFORMATION: L-peptide

<400> SEQUENCE: 2

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 3
<211> LENGTH: 29
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-peptide
<220> FEATURE:
<221> NAME/KEY: misc_feature
<222> LOCATION: (29)..(29)
<223> OTHER INFORMATION: biotinylated at C-terminus

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 4
<211> LENGTH: 29
<212> TYPE: PRT
<213> ORGANISM: Homo sapiens
<220> FEATURE:
<221> NAME/KEY: misc_feature
<222> LOCATION: (1)..(29)
<223> OTHER INFORMATION: L-peptide

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 5
<211> LENGTH: 44
<212> TYPE: RNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-RNA

<400> SEQUENCE: 5
gcgugaauag ccguugaaac gccuuuagag aagcacuagc acgc                    44

<210> SEQ ID NO 6
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(44)
<223> OTHER INFORMATION: L-RNA

<400> SEQUENCE: 6
gcgugaauag ccguugaaac gccuuuagag aagcacuagc acgc                    44

<210> SEQ ID NO 7
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-RNA
<220> FEATURE:
<221> NAME/KEY: misc_feature
<222> LOCATION: (2)..(2)
<223> OTHER INFORMATION: L-DNA
<220> FEATURE:
<221> NAME/KEY: misc_feature
<222> LOCATION: (3)..(44)
<223> OTHER INFORMATION: L-RNA

<400> SEQUENCE: 7
gcgugaauag ccguugaaac gccuuuagag aagcacuagc acgc                    44

<210> SEQ ID NO 8
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: L-RNA
<220> FEATURE:
<221> NAME/KEY: misc_feature
<222> LOCATION: (3)..(3)
<223> OTHER INFORMATION: L-DNA
<220> FEATURE:

```
<221> NAME/KEY: misc_feature
<222> LOCATION: (4)..(44)
<223> OTHER INFORMATION: L-RNA

<400> SEQUENCE: 8
gcgugaauag ccguugaaac gccuuuagag aagcacuagc acgc                    44

<210> SEQ ID NO 9
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(3)
<223> OTHER INFORMATION: L-RNA
<220> FEATURE:
<221> NAME/KEY: misc_feature
<222> LOCATION: (4)..(4)
<223> OTHER INFORMATION: L-DNA
<220> FEATURE:
<221> NAME/KEY: misc_feature
<222> LOCATION: (5)..(44)
<223> OTHER INFORMATION: L-RNA

<400> SEQUENCE: 9
gcgtgaauag ccguugaaac gccuuuagag aagcacuagc acgc                    44

<210> SEQ ID NO 10
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(4)
<223> OTHER INFORMATION: L-RNA
<220> FEATURE:
<221> NAME/KEY: misc_feature
<222> LOCATION: (5)..(5)
<223> OTHER INFORMATION: L-DNA
<220> FEATURE:
<221> NAME/KEY: misc_feature
<222> LOCATION: (6)..(44)
<223> OTHER INFORMATION: L-RNA

<400> SEQUENCE: 10
gcgugaauag ccguugaaac gccuuuagag aagcacuagc acgc                    44

<210> SEQ ID NO 11
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (6)..(6)
<223> OTHER INFORMATION: L-DNA
<220> FEATURE:
<221> NAME/KEY: misc_feature
<222> LOCATION: (7)..(44)
<223> OTHER INFORMATION: L-RNA

<400> SEQUENCE: 11
gcgugaauag ccguugaaac gccuuuagag aagcacuagc acgc                    44
```

<210> SEQ ID NO 12
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(44)
<223> OTHER INFORMATION: L-RNA

<400> SEQUENCE: 12
gcgugaauag ccguugaaac gccuuuagag aagcacuagc acgc         44

<210> SEQ ID NO 13
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-RNA
<220> FEATURE:
<221> NAME/KEY: misc_feature
<222> LOCATION: (8)..(8)
<223> OTHER INFORMATION: L-DNA
<220> FEATURE:
<221> NAME/KEY: misc_feature
<222> LOCATION: (9)..(44)
<223> OTHER INFORMATION: L-RNA

<400> SEQUENCE: 13
gcgugaatag ccguugaaac gccuuuagag aagcacuagc acgc         44

<210> SEQ ID NO 14
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(44)
<223> OTHER INFORMATION: L-RNA

<400> SEQUENCE: 14
gcgugaauag ccguugaaac gccuuuagag aagcacuagc acgc         44

<210> SEQ ID NO 15
<211> LENGTH: 44
<212> TYPE: DNA
<213> ORGANISM: artificial
<220> FEATURE:

```
<223> OTHER INFORMATION: synthetic
<220> FEATURE:
<221> NAME/KEY: misc_feature
<222> LOCATION: (1)..(9)
<223> OTHER INFORMATION: L-RNA
<220> FEATURE:
<221> NAME/KEY: misc_feature
<222> LOCATION: (10)..(10)
<223> OTHER INFORMATION: L-DNA
<220> FEATURE:
<221> NAME/KEY: misc_feature
<222> LOCATION: (11)..(44)
<223> OTHER INFORMATION: L-RNA

<400> SEQUENCE: 15
gcgugaauag ccguugaaac gccuuuagag aagcacuagc acgc                44

<210> SEQ ID NO 16
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (11)..(11)
<223> OTHER INFORMATION: L-DNA
<220> FEATURE:
<221> NAME/KEY: misc_feature
<222> LOCATION: (12)..(44)
<223> OTHER INFORMATION: L-RNA

<400> SEQUENCE: 16
gcgugaauag ccguugaaac gccuuuagag aagcacuagc acgc                44

<210> SEQ ID NO 17
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-RNA
<220> FEATURE:
<221> NAME/KEY: misc_feature
<222> LOCATION: (12)..(12)
<223> OTHER INFORMATION: L-DNA
<220> FEATURE:
<221> NAME/KEY: misc_feature
<222> LOCATION: (13)..(44)
<223> OTHER INFORMATION: L-RNA

<400> SEQUENCE: 17
gcgugaauag ccguugaaac gccuuuagag aagcacuagc acgc                44

<210> SEQ ID NO 18
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-RNA
<220> FEATURE:
<221> NAME/KEY: misc_feature
```

-continued

```
<222> LOCATION: (13)..(13)
<223> OTHER INFORMATION: L-DNA
<220> FEATURE:
<221> NAME/KEY: misc_feature
<222> LOCATION: (14)..(44)
<223> OTHER INFORMATION: L-RNA

<400> SEQUENCE: 18
gcgugaauag ccguugaaac gccuuuagag aagcacuagc acgc            44

<210> SEQ ID NO 19
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(13)
<223> OTHER INFORMATION: L-RNA
<220> FEATURE:
<221> NAME/KEY: misc_feature
<222> LOCATION: (14)..(14)
<223> OTHER INFORMATION: L-DNA
<220> FEATURE:
<221> NAME/KEY: misc_feature
<222> LOCATION: (15)..(44)
<223> OTHER INFORMATION: L-RNA

<400> SEQUENCE: 19
gcgugaauag ccgtugaaac gccuuuagag aagcacuagc acgc            44

<210> SEQ ID NO 20
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-RNA
<220> FEATURE:
<221> NAME/KEY: misc_feature
<222> LOCATION: (15)..(15)
<223> OTHER INFORMATION: L-DNA
<220> FEATURE:
<221> NAME/KEY: misc_feature
<222> LOCATION: (16)..(44)
<223> OTHER INFORMATION: L-RNA

<400> SEQUENCE: 20
gcgugaauag ccgutgaaac gccuuuagag aagcacuagc acgc            44

<210> SEQ ID NO 21
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(15)
<223> OTHER INFORMATION: L-RNA
<220> FEATURE:
<221> NAME/KEY: misc_feature
<222> LOCATION: (16)..(16)
<223> OTHER INFORMATION: L-DNA
<220> FEATURE:
<221> NAME/KEY: misc_feature
<222> LOCATION: (17)..(44)
<223> OTHER INFORMATION: L-RNA
```

<400> SEQUENCE: 21
gcgugaauag ccguugaaac gccuuuagag aagcacuagc acgc        44

<210> SEQ ID NO 22
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: L-RNA
<220> FEATURE:
<221> NAME/KEY: misc_feature
<222> LOCATION: (17)..(17)
<223> OTHER INFORMATION: L-DNA
<220> FEATURE:
<221> NAME/KEY: misc_feature
<222> LOCATION: (18)..(44)
<223> OTHER INFORMATION: L-RNA

<400> SEQUENCE: 22
gcgugaauag ccguugaaac gccuuuagag aagcacuagc acgc        44

<210> SEQ ID NO 23
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-RNA
<220> FEATURE:
<221> NAME/KEY: misc_feature
<222> LOCATION: (18)..(18)
<223> OTHER INFORMATION: L-DNA
<220> FEATURE:
<221> NAME/KEY: misc_feature
<222> LOCATION: (19)..(44)
<223> OTHER INFORMATION: L-RNA

<400> SEQUENCE: 23
gcgugaauag ccguugaaac gccuuuagag aagcacuagc acgc        44

<210> SEQ ID NO 24
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(44)
<223> OTHER INFORMATION: L-RNA

<400> SEQUENCE: 24
gcgugaauag ccguugaaac gccuuuagag aagcacuagc acgc        44

<210> SEQ ID NO 25
<211> LENGTH: 44

```
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA
<220> FEATURE:
<221> NAME/KEY: misc_feature
<222> LOCATION: (20)..(20)
<223> OTHER INFORMATION: L-DNA
<220> FEATURE:
<221> NAME/KEY: misc_feature
<222> LOCATION: (21)..(44)
<223> OTHER INFORMATION: L-RNA

<400> SEQUENCE: 25
gcgugaauag ccguugaaac gccuuuagag aagcacuagc acgc            44

<210> SEQ ID NO 26
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(44)
<223> OTHER INFORMATION: L-RNA

<400> SEQUENCE: 26
gcgugaauag ccguugaaac gccuuuagag aagcacuagc acgc            44

<210> SEQ ID NO 27
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(21)
<223> OTHER INFORMATION: L-RNA
<220> FEATURE:
<221> NAME/KEY: misc_feature
<222> LOCATION: (22)..(22)
<223> OTHER INFORMATION: L-DNA
<220> FEATURE:
<221> NAME/KEY: misc_feature
<222> LOCATION: (23)..(44)
<223> OTHER INFORMATION: L-RNA

<400> SEQUENCE: 27
gcgugaauag ccguugaaac gccuuuagag aagcacuagc acgc            44

<210> SEQ ID NO 28
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(22)
```

```
<223> OTHER INFORMATION: L-RNA
<220> FEATURE:
<221> NAME/KEY: misc_feature
<222> LOCATION: (23)..(23)
<223> OTHER INFORMATION: L-DNA
<220> FEATURE:
<221> NAME/KEY: misc_feature
<222> LOCATION: (24)..(44)
<223> OTHER INFORMATION: L-RNA

<400> SEQUENCE: 28
gcgugaauag ccguugaaac gccuuuagag aagcacuagc acgc                44

<210> SEQ ID NO 29
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: L-RNA
<220> FEATURE:
<221> NAME/KEY: misc_feature
<222> LOCATION: (24)..(24)
<223> OTHER INFORMATION: L-DNA
<220> FEATURE:
<221> NAME/KEY: misc_feature
<222> LOCATION: (25)..(44)
<223> OTHER INFORMATION: L-RNA

<400> SEQUENCE: 29
gcgugaauag ccguugaaac gcctuuagag aagcacuagc acgc                44

<210> SEQ ID NO 30
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(24)
<223> OTHER INFORMATION: L-RNA
<220> FEATURE:
<221> NAME/KEY: misc_feature
<222> LOCATION: (25)..(25)
<223> OTHER INFORMATION: L-DNA
<220> FEATURE:
<221> NAME/KEY: misc_feature
<222> LOCATION: (26)..(44)
<223> OTHER INFORMATION: L-RNA

<400> SEQUENCE: 30
gcgugaauag ccguugaaac gccutuagag aagcacuagc acgc                44

<210> SEQ ID NO 31
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(25)
<223> OTHER INFORMATION: L-RNA
<220> FEATURE:
<221> NAME/KEY: misc_feature
<222> LOCATION: (26)..(26)
<223> OTHER INFORMATION: L-DNA
<220> FEATURE:
<221> NAME/KEY: misc_feature
```

```
<222> LOCATION: (27)..(44)
<223> OTHER INFORMATION: L-RNA

<400> SEQUENCE: 31
gcgugaauag ccguugaaac gccuutagag aagcacuagc acgc                    44

<210> SEQ ID NO 32
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-RNA
<220> FEATURE:
<221> NAME/KEY: misc_feature
<222> LOCATION: (27)..(27)
<223> OTHER INFORMATION: L-DNA
<220> FEATURE:
<221> NAME/KEY: misc_feature
<222> LOCATION: (28)..(44)
<223> OTHER INFORMATION: L-RNA

<400> SEQUENCE: 32
gcgugaauag ccguugaaac gccuuuagag aagcacuagc acgc                    44

<210> SEQ ID NO 33
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA
<220> FEATURE:
<221> NAME/KEY: misc_feature
<222> LOCATION: (28)..(28)
<223> OTHER INFORMATION: L-DNA
<220> FEATURE:
<221> NAME/KEY: misc_feature
<222> LOCATION: (29)..(44)
<223> OTHER INFORMATION: L-RNA

<400> SEQUENCE: 33
gcgugaauag ccguugaaac gccuuuagag aagcacuagc acgc                    44

<210> SEQ ID NO 34
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-RNA
<220> FEATURE:
<221> NAME/KEY: misc_feature
<222> LOCATION: (29)..(29)
<223> OTHER INFORMATION: L-DNA
<220> FEATURE:
<221> NAME/KEY: misc_feature
<222> LOCATION: (30)..(44)
<223> OTHER INFORMATION: L-RNA

<400> SEQUENCE: 34
gcgugaauag ccguugaaac gccuuuagag aagcacuagc acgc                    44
```

<210> SEQ ID NO 35
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(44)
<223> OTHER INFORMATION: L-RNA

<400> SEQUENCE: 35
gcgugaauag ccguugaaac gccuuuagag aagcacuagc acgc       44

<210> SEQ ID NO 36
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-RNA
<220> FEATURE:
<221> NAME/KEY: misc_feature
<222> LOCATION: (31)..(31)
<223> OTHER INFORMATION: L-DNA
<220> FEATURE:
<221> NAME/KEY: misc_feature
<222> LOCATION: (32)..(44)
<223> OTHER INFORMATION: L-RNA

<400> SEQUENCE: 36
gcgugaauag ccguugaaac gccuuuagag aagcacuagc acgc       44

<210> SEQ ID NO 37
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 37
gcgugaauag ccguugaaac gccuuuagag aagcacuagc acgc       44

<210> SEQ ID NO 38
<211> LENGTH: 44
<212> TYPE: DNA
<213> ORGANISM: artificial
<220> FEATURE:
<223> OTHER INFORMATION: synthetic

```
<220> FEATURE:
<221> NAME/KEY: misc_feature
<222> LOCATION: (1)..(32)
<223> OTHER INFORMATION: L-RNA
<220> FEATURE:
<221> NAME/KEY: misc_feature
<222> LOCATION: (33)..(33)
<223> OTHER INFORMATION: L-DNA
<220> FEATURE:
<221> NAME/KEY: misc_feature
<222> LOCATION: (34)..(44)
<223> OTHER INFORMATION: L-RNA

<400> SEQUENCE: 38
gcgugaauag ccguugaaac gccuuuagag aagcacuagc acgc                44

<210> SEQ ID NO 39
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-RNA
<220> FEATURE:
<221> NAME/KEY: misc_feature
<222> LOCATION: (34)..(34)
<223> OTHER INFORMATION: L-DNA
<220> FEATURE:
<221> NAME/KEY: misc_feature
<222> LOCATION: (35)..(44)
<223> OTHER INFORMATION: L-RNA

<400> SEQUENCE: 39
gcgugaauag ccguugaaac gccuuuagag aagcacuagc acgc                44

<210> SEQ ID NO 40
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA
<220> FEATURE:
<221> NAME/KEY: misc_feature
<222> LOCATION: (35)..(35)
<223> OTHER INFORMATION: L-DNA
<220> FEATURE:
<221> NAME/KEY: misc_feature
<222> LOCATION: (36)..(44)
<223> OTHER INFORMATION: L-RNA

<400> SEQUENCE: 40
gcgugaauag ccguugaaac gccuuuagag aagcacuagc acgc                44

<210> SEQ ID NO 41
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA
<220> FEATURE:
<221> NAME/KEY: misc_feature
<222> LOCATION: (36)..(36)
```

<223> OTHER INFORMATION: L-DNA
<220> FEATURE:
<221> NAME/KEY: misc_feature
<222> LOCATION: (37)..(44)
<223> OTHER INFORMATION: L-RNA

<400> SEQUENCE: 41
gcgugaauag ccguugaaac gccuuuagag aagcacuagc acgc                    44

<210> SEQ ID NO 42
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA
<220> FEATURE:
<221> NAME/KEY: misc_feature
<222> LOCATION: (37)..(37)
<223> OTHER INFORMATION: L-DNA
<220> FEATURE:
<221> NAME/KEY: misc_feature
<222> LOCATION: (38)..(44)
<223> OTHER INFORMATION: L-RNA

<400> SEQUENCE: 42
gcgugaauag ccguugaaac gccuuuagag aagcactagc acgc                    44

<210> SEQ ID NO 43
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(37)
<223> OTHER INFORMATION: L-RNA
<220> FEATURE:
<221> NAME/KEY: misc_feature
<222> LOCATION: (38)..(38)
<223> OTHER INFORMATION: L-DNA
<220> FEATURE:
<221> NAME/KEY: misc_feature
<222> LOCATION: (39)..(44)
<223> OTHER INFORMATION: L-RNA

<400> SEQUENCE: 43
gcgugaauag ccguugaaac gccuuuagag aagcacuagc acgc                    44

<210> SEQ ID NO 44
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (39)..(39)
<223> OTHER INFORMATION: L-DNA
<220> FEATURE:
<221> NAME/KEY: misc_feature
<222> LOCATION: (40)..(44)
<223> OTHER INFORMATION: L-RNA

<400> SEQUENCE: 44

-continued gcgugaauag ccguugaaac gccuuuagag aagcacuagc acgc                44

<210> SEQ ID NO 45
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 45
gcgugaauag ccguugaaac gccuuuagag aagcacuagc acgc                44

<210> SEQ ID NO 46
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
<222> LOCATION: (41)..(41)
<223> OTHER INFORMATION: L-DNA
<220> FEATURE:
<221> NAME/KEY: misc_feature
<222> LOCATION: (42)..(44)
<223> OTHER INFORMATION: L-RNA

<400> SEQUENCE: 46
gcgugaauag ccguugaaac gccuuuagag aagcacuagc acgc                44

<210> SEQ ID NO 47
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-RNA
<220> FEATURE:
<221> NAME/KEY: misc_feature
<222> LOCATION: (42)..(42)
<223> OTHER INFORMATION: L-DNA
<220> FEATURE:
<221> NAME/KEY: misc_feature
<222> LOCATION: (43)..(44)
<223> OTHER INFORMATION: L-RNA

<400> SEQUENCE: 47
gcgugaauag ccguugaaac gccuuuagag aagcacuagc acgc                44

<210> SEQ ID NO 48
<211> LENGTH: 44
<212> TYPE: DNA

```
<213> ORGANISM: artificial
<220> FEATURE:
<223> OTHER INFORMATION: synthetic
<220> FEATURE:
<221> NAME/KEY: misc_feature
<222> LOCATION: (1)..(42)
<223> OTHER INFORMATION: L-RNA
<220> FEATURE:
<221> NAME/KEY: misc_feature
<222> LOCATION: (43)..(43)
<223> OTHER INFORMATION: L-DNA
<220> FEATURE:
<221> NAME/KEY: misc_feature
<222> LOCATION: (44)..(44)
<223> OTHER INFORMATION: L-RNA

<400> SEQUENCE: 48
gcgugaauag ccguugaaac gccuuuagag aagcacuagc acgc         44

<210> SEQ ID NO 49
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA
<220> FEATURE:
<221> NAME/KEY: misc_feature
<222> LOCATION: (44)..(44)
<223> OTHER INFORMATION: L-DNA

<400> SEQUENCE: 49
gcgugaauag ccguugaaac gccuuuagag aagcacuagc acgc         44

<210> SEQ ID NO 50
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-RNA
<220> FEATURE:
<221> NAME/KEY: misc_feature
<222> LOCATION: (21)..(22)
<223> OTHER INFORMATION: L-DNA
<220> FEATURE:
<221> NAME/KEY: misc_feature
<222> LOCATION: (23)..(44)
<223> OTHER INFORMATION: L-RNA

<400> SEQUENCE: 50
gcgugaauag ccguugaaac gccuuuagag aagcacuagc acgc         44

<210> SEQ ID NO 51
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
```

```
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(44)
<223> OTHER INFORMATION: L-RNA

<400> SEQUENCE: 51
gcgugaauag ccguugaaac gccuuuagag aagcacuagc acgc                44

<210> SEQ ID NO 52
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(22)
<223> OTHER INFORMATION: L-DNA
<220> FEATURE:
<221> NAME/KEY: misc_feature
<222> LOCATION: (23)..(44)
<223> OTHER INFORMATION: L-RNA

<400> SEQUENCE: 52
gcgugaauag ccguugaaac gccuuuagag aagcacuagc acgc                44

<210> SEQ ID NO 53
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(31)
```

```
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 53
gcgugaauag ccguugaaac gccuuuagag aagcacuagc acgc             44

<210> SEQ ID NO 54
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(10)
<223> OTHER INFORMATION: L-RNA
<220> FEATURE:
<221> NAME/KEY: misc_feature
<222> LOCATION: (11)..(11)
<223> OTHER INFORMATION: L-DNA
<220> FEATURE:
<221> NAME/KEY: misc_feature
<222> LOCATION: (12)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 54
gcgugaauag ccguugaaac gccuuuagag aagcacuagc acgc             44

<210> SEQ ID NO 55
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(50)
<223> OTHER INFORMATION: L-RNA

<400> SEQUENCE: 55
```
ccgugcuguc ggagacuacu cgucgaguag aaauaggucc ccucccacgg        50

<210> SEQ ID NO 56
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(50)
<223> OTHER INFORMATION: L-RNA

<400> SEQUENCE: 56
ccgugcuguc ggagacuacu cgucgaguag aaauaggucc ccucccacgg        50

<210> SEQ ID NO 57
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-RNA
<220> FEATURE:
<221> NAME/KEY: misc_feature
<222> LOCATION: (2)..(2)
<223> OTHER INFORMATION: L-DNA
<220> FEATURE:
<221> NAME/KEY: misc_feature
<222> LOCATION: (3)..(50)
<223> OTHER INFORMATION: L-RNA

<400> SEQUENCE: 57
ccgugcuguc ggagacuacu cgucgaguag aaauaggucc ccucccacgg        50

<210> SEQ ID NO 58
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: L-RNA
<220> FEATURE:
<221> NAME/KEY: misc_feature
<222> LOCATION: (3)..(3)
<223> OTHER INFORMATION: L-DNA
<220> FEATURE:
<221> NAME/KEY: misc_feature
<222> LOCATION: (4)..(50)
<223> OTHER INFORMATION: L-RNA

<400> SEQUENCE: 58
ccgugcuguc ggagacuacu cgucgaguag aaauaggucc ccucccacgg        50

<210> SEQ ID NO 59
<211> LENGTH: 50
<212> TYPE: DNA
<213> ORGANISM: artificial
<220> FEATURE:
<223> OTHER INFORMATION: synthetic
<220> FEATURE:

```
<221> NAME/KEY: misc_feature
<222> LOCATION: (1)..(3)
<223> OTHER INFORMATION: L-RNA
<220> FEATURE:
<221> NAME/KEY: misc_feature
<222> LOCATION: (4)..(4)
<223> OTHER INFORMATION: L-DNA
<220> FEATURE:
<221> NAME/KEY: misc_feature
<222> LOCATION: (5)..(50)
<223> OTHER INFORMATION: L-RNA

<400> SEQUENCE: 59
ccgtgcuguc ggagacuacu cgucgaguag aaauaggucc ccucccacgg            50

<210> SEQ ID NO 60
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(4)
<223> OTHER INFORMATION: L-RNA
<220> FEATURE:
<221> NAME/KEY: misc_feature
<222> LOCATION: (5)..(5)
<223> OTHER INFORMATION: L-DNA
<220> FEATURE:
<221> NAME/KEY: misc_feature
<222> LOCATION: (6)..(50)
<223> OTHER INFORMATION: L-RNA

<400> SEQUENCE: 60
ccgugcuguc ggagacuacu cgucgaguag aaauaggucc ccucccacgg            50

<210> SEQ ID NO 61
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (6)..(6)
<223> OTHER INFORMATION: L-DNA
<220> FEATURE:
<221> NAME/KEY: misc_feature
<222> LOCATION: (7)..(50)
<223> OTHER INFORMATION: L-RNA

<400> SEQUENCE: 61
ccgugcuguc ggagacuacu cgucgaguag aaauaggucc ccucccacgg            50

<210> SEQ ID NO 62
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
```

<220> FEATURE:
<221> NAME/KEY: misc_feature
<222> LOCATION: (8)..(50)
<223> OTHER INFORMATION: L-RNA

<400> SEQUENCE: 62
ccgugctguc ggagacuacu cgucgaguag aaauaggucc ccucccacgg                50

<210> SEQ ID NO 63
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-RNA
<220> FEATURE:
<221> NAME/KEY: misc_feature
<222> LOCATION: (8)..(8)
<223> OTHER INFORMATION: L-DNA
<220> FEATURE:
<221> NAME/KEY: misc_feature
<222> LOCATION: (9)..(50)
<223> OTHER INFORMATION: L-RNA

<400> SEQUENCE: 63
ccgugcuguc ggagacuacu cgucgaguag aaauaggucc ccucccacgg                50

<210> SEQ ID NO 64
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(50)
<223> OTHER INFORMATION: L-RNA

<400> SEQUENCE: 64
ccgugcugtc ggagacuacu cgucgaguag aaauaggucc ccucccacgg                50

<210> SEQ ID NO 65
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(9)
<223> OTHER INFORMATION: L-RNA
<220> FEATURE:
<221> NAME/KEY: misc_feature
<222> LOCATION: (10)..(10)
<223> OTHER INFORMATION: L-DNA
<220> FEATURE:
<221> NAME/KEY: misc_feature
<222> LOCATION: (11)..(50)
<223> OTHER INFORMATION: L-RNA

<400> SEQUENCE: 65
ccgugcuguc ggagacuacu cgucgaguag aaauaggucc ccucccacgg            50

<210> SEQ ID NO 66
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (11)..(11)
<223> OTHER INFORMATION: L-DNA
<220> FEATURE:
<221> NAME/KEY: misc_feature
<222> LOCATION: (12)..(50)
<223> OTHER INFORMATION: L-RNA

<400> SEQUENCE: 66
ccgugcuguc ggagacuacu cgucgaguag aaauaggucc ccucccacgg            50

<210> SEQ ID NO 67
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-RNA
<220> FEATURE:
<221> NAME/KEY: misc_feature
<222> LOCATION: (12)..(12)
<223> OTHER INFORMATION: L-DNA
<220> FEATURE:
<221> NAME/KEY: misc_feature
<222> LOCATION: (13)..(50)
<223> OTHER INFORMATION: L-RNA

<400> SEQUENCE: 67
ccgugcuguc ggagacuacu cgucgaguag aaauaggucc ccucccacgg            50

<210> SEQ ID NO 68
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-RNA
<220> FEATURE:
<221> NAME/KEY: misc_feature
<222> LOCATION: (13)..(13)
<223> OTHER INFORMATION: L-DNA
<220> FEATURE:
<221> NAME/KEY: misc_feature
<222> LOCATION: (14)..(50)
<223> OTHER INFORMATION: L-RNA

<400> SEQUENCE: 68
ccgugcuguc ggagacuacu cgucgaguag aaauaggucc ccucccacgg            50

<210> SEQ ID NO 69
<211> LENGTH: 50
<212> TYPE: DNA
<213> ORGANISM: artificial

```
<220> FEATURE:
<223> OTHER INFORMATION: synthetic
<220> FEATURE:
<221> NAME/KEY: misc_feature
<222> LOCATION: (1)..(13)
<223> OTHER INFORMATION: L-RNA
<220> FEATURE:
<221> NAME/KEY: misc_feature
<222> LOCATION: (14)..(14)
<223> OTHER INFORMATION: L-DNA
<220> FEATURE:
<221> NAME/KEY: misc_feature
<222> LOCATION: (15)..(50)
<223> OTHER INFORMATION: L-RNA

<400> SEQUENCE: 69
ccgugcuguc ggagacuacu cgucgaguag aaauaggucc ccucccacgg            50

<210> SEQ ID NO 70
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-RNA
<220> FEATURE:
<221> NAME/KEY: misc_feature
<222> LOCATION: (15)..(15)
<223> OTHER INFORMATION: L-DNA
<220> FEATURE:
<221> NAME/KEY: misc_feature
<222> LOCATION: (16)..(50)
<223> OTHER INFORMATION: L-RNA

<400> SEQUENCE: 70
ccgugcuguc ggagacuacu cgucgaguag aaauaggucc ccucccacgg            50

<210> SEQ ID NO 71
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(15)
<223> OTHER INFORMATION: L-RNA
<220> FEATURE:
<221> NAME/KEY: misc_feature
<222> LOCATION: (16)..(16)
<223> OTHER INFORMATION: L-DNA
<220> FEATURE:
<221> NAME/KEY: misc_feature
<222> LOCATION: (17)..(50)
<223> OTHER INFORMATION: L-RNA

<400> SEQUENCE: 71
ccgugcuguc ggagacuacu cgucgaguag aaauaggucc ccucccacgg            50

<210> SEQ ID NO 72
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: L-RNA
<220> FEATURE:
```

```
<221> NAME/KEY: misc_feature
<222> LOCATION: (17)..(17)
<223> OTHER INFORMATION: L-DNA
<220> FEATURE:
<221> NAME/KEY: misc_feature
<222> LOCATION: (18)..(50)
<223> OTHER INFORMATION: L-RNA

<400> SEQUENCE: 72
ccgugcuguc ggagactacu cgucgaguag aaauaggucc ccucccacgg          50

<210> SEQ ID NO 73
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-RNA
<220> FEATURE:
<221> NAME/KEY: misc_feature
<222> LOCATION: (18)..(18)
<223> OTHER INFORMATION: L-DNA
<220> FEATURE:
<221> NAME/KEY: misc_feature
<222> LOCATION: (19)..(50)
<223> OTHER INFORMATION: L-RNA

<400> SEQUENCE: 73
ccgugcuguc ggagacuacu cgucgaguag aaauaggucc ccucccacgg          50

<210> SEQ ID NO 74
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(50)
<223> OTHER INFORMATION: L-RNA

<400> SEQUENCE: 74
ccgugcuguc ggagacuacu cgucgaguag aaauaggucc ccucccacgg          50

<210> SEQ ID NO 75
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA
<220> FEATURE:
<221> NAME/KEY: misc_feature
<222> LOCATION: (20)..(20)
<223> OTHER INFORMATION: L-DNA
<220> FEATURE:
<221> NAME/KEY: misc_feature
<222> LOCATION: (21)..(50)
<223> OTHER INFORMATION: L-RNA
```

```
<400> SEQUENCE: 75
ccgugcuguc ggagacuact cgucgaguag aaauaggucc ccucccacgg        50

<210> SEQ ID NO 76
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(50)
<223> OTHER INFORMATION: L-RNA

<400> SEQUENCE: 76
ccgugcuguc ggagacuacu cgucgaguag aaauaggucc ccucccacgg        50

<210> SEQ ID NO 77
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(21)
<223> OTHER INFORMATION: L-RNA
<220> FEATURE:
<221> NAME/KEY: misc_feature
<222> LOCATION: (22)..(22)
<223> OTHER INFORMATION: L-DNA
<220> FEATURE:
<221> NAME/KEY: misc_feature
<222> LOCATION: (23)..(50)
<223> OTHER INFORMATION: L-RNA

<400> SEQUENCE: 77
ccgugcuguc ggagacuacu cgucgaguag aaauaggucc ccucccacgg        50

<210> SEQ ID NO 78
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(22)
<223> OTHER INFORMATION: L-RNA
<220> FEATURE:
<221> NAME/KEY: misc_feature
<222> LOCATION: (23)..(23)
<223> OTHER INFORMATION: L-DNA
<220> FEATURE:
<221> NAME/KEY: misc_feature
<222> LOCATION: (24)..(50)
<223> OTHER INFORMATION: L-RNA

<400> SEQUENCE: 78
ccgugcuguc ggagacuacu cgtcgaguag aaauaggucc ccucccacgg        50

<210> SEQ ID NO 79
```

```
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: L-RNA
<220> FEATURE:
<221> NAME/KEY: misc_feature
<222> LOCATION: (24)..(24)
<223> OTHER INFORMATION: L-DNA
<220> FEATURE:
<221> NAME/KEY: misc_feature
<222> LOCATION: (25)..(50)
<223> OTHER INFORMATION: L-RNA

<400> SEQUENCE: 79
ccgugcuguc ggagacuacu cgucgaguag aaauaggucc ccucccacgg              50

<210> SEQ ID NO 80
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(24)
<223> OTHER INFORMATION: L-RNA
<220> FEATURE:
<221> NAME/KEY: misc_feature
<222> LOCATION: (25)..(25)
<223> OTHER INFORMATION: L-DNA
<220> FEATURE:
<221> NAME/KEY: misc_feature
<222> LOCATION: (26)..(50)
<223> OTHER INFORMATION: L-RNA

<400> SEQUENCE: 80
ccgugcuguc ggagacuacu cgucgaguag aaauaggucc ccucccacgg              50

<210> SEQ ID NO 81
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(25)
<223> OTHER INFORMATION: L-RNA
<220> FEATURE:
<221> NAME/KEY: misc_feature
<222> LOCATION: (26)..(26)
<223> OTHER INFORMATION: L-DNA
<220> FEATURE:
<221> NAME/KEY: misc_feature
<222> LOCATION: (27)..(50)
<223> OTHER INFORMATION: L-RNA

<400> SEQUENCE: 81
ccgugcuguc ggagacuacu cgucgaguag aaauaggucc ccucccacgg              50

<210> SEQ ID NO 82
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
```

<222> LOCATION: (1)..(26)
<223> OTHER INFORMATION: L-RNA
<220> FEATURE:
<221> NAME/KEY: misc_feature
<222> LOCATION: (27)..(27)
<223> OTHER INFORMATION: L-DNA
<220> FEATURE:
<221> NAME/KEY: misc_feature
<222> LOCATION: (28)..(50)
<223> OTHER INFORMATION: L-RNA

<400> SEQUENCE: 82
ccgugcuguc ggagacuacu cgucgaguag aaauaggucc ccucccacgg           50

<210> SEQ ID NO 83
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA
<220> FEATURE:
<221> NAME/KEY: misc_feature
<222> LOCATION: (28)..(28)
<223> OTHER INFORMATION: L-DNA
<220> FEATURE:
<221> NAME/KEY: misc_feature
<222> LOCATION: (29)..(50)
<223> OTHER INFORMATION: L-RNA

<400> SEQUENCE: 83
ccgugcuguc ggagacuacu cgucgagtag aaauaggucc ccucccacgg           50

<210> SEQ ID NO 84
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-RNA
<220> FEATURE:
<221> NAME/KEY: misc_feature
<222> LOCATION: (29)..(29)
<223> OTHER INFORMATION: L-DNA
<220> FEATURE:
<221> NAME/KEY: misc_feature
<222> LOCATION: (30)..(50)
<223> OTHER INFORMATION: L-RNA

<400> SEQUENCE: 84
ccgugcuguc ggagacuacu cgucgaguag aaauaggucc ccucccacgg           50

<210> SEQ ID NO 85
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:

```
<221> NAME/KEY: misc_feature
<222> LOCATION: (31)..(50)
<223> OTHER INFORMATION: L-RNA

<400> SEQUENCE: 85
ccgugcuguc ggagacuacu cgucgaguag aaauaggucc ccucccacgg         50

<210> SEQ ID NO 86
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-RNA
<220> FEATURE:
<221> NAME/KEY: misc_feature
<222> LOCATION: (31)..(31)
<223> OTHER INFORMATION: L-DNA
<220> FEATURE:
<221> NAME/KEY: misc_feature
<222> LOCATION: (32)..(50)
<223> OTHER INFORMATION: L-RNA

<400> SEQUENCE: 86
ccgugcuguc ggagacuacu cgucgaguag aaauaggucc ccucccacgg         50

<210> SEQ ID NO 87
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(50)
<223> OTHER INFORMATION: L-RNA

<400> SEQUENCE: 87
ccgugcuguc ggagacuacu cgucgaguag aaauaggucc ccucccacgg         50

<210> SEQ ID NO 88
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(32)
<223> OTHER INFORMATION: L-RNA
<220> FEATURE:
<221> NAME/KEY: misc_feature
<222> LOCATION: (33)..(33)
<223> OTHER INFORMATION: L-DNA
<220> FEATURE:
<221> NAME/KEY: misc_feature
<222> LOCATION: (34)..(50)
<223> OTHER INFORMATION: L-RNA

<400> SEQUENCE: 88
ccgugcuguc ggagacuacu cgucgaguag aaauaggucc ccucccacgg         50
```

<210> SEQ ID NO 89
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-RNA
<220> FEATURE:
<221> NAME/KEY: misc_feature
<222> LOCATION: (34)..(34)
<223> OTHER INFORMATION: L-DNA
<220> FEATURE:
<221> NAME/KEY: misc_feature
<222> LOCATION: (35)..(50)
<223> OTHER INFORMATION: L-RNA

<400> SEQUENCE: 89
ccgugcuguc ggagacuacu cgucgaguag aaataggucc ccucccacgg          50

<210> SEQ ID NO 90
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA
<220> FEATURE:
<221> NAME/KEY: misc_feature
<222> LOCATION: (35)..(35)
<223> OTHER INFORMATION: L-DNA
<220> FEATURE:
<221> NAME/KEY: misc_feature
<222> LOCATION: (36)..(50)
<223> OTHER INFORMATION: L-RNA

<400> SEQUENCE: 90
ccgugcuguc ggagacuacu cgucgaguag aaauaggucc ccucccacgg          50

<210> SEQ ID NO 91
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA
<220> FEATURE:
<221> NAME/KEY: misc_feature
<222> LOCATION: (36)..(36)
<223> OTHER INFORMATION: L-DNA
<220> FEATURE:
<221> NAME/KEY: misc_feature
<222> LOCATION: (37)..(50)
<223> OTHER INFORMATION: L-RNA

<400> SEQUENCE: 91
ccgugcuguc ggagacuacu cgucgaguag aaauaggucc ccucccacgg          50

<210> SEQ ID NO 92
<211> LENGTH: 50
<212> TYPE: DNA
<213> ORGANISM: artificial
<220> FEATURE:

<223> OTHER INFORMATION: synthetic
<220> FEATURE:
<221> NAME/KEY: misc_feature
<222> LOCATION: (1)..(36)
<223> OTHER INFORMATION: L-RNA
<220> FEATURE:
<221> NAME/KEY: misc_feature
<222> LOCATION: (37)..(37)
<223> OTHER INFORMATION: L-DNA
<220> FEATURE:
<221> NAME/KEY: misc_feature
<222> LOCATION: (38)..(50)
<223> OTHER INFORMATION: L-RNA

<400> SEQUENCE: 92
ccgugcuguc ggagacuacu cgucgaguag aaauaggucc ccucccacgg    50

<210> SEQ ID NO 93
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(37)
<223> OTHER INFORMATION: L-RNA
<220> FEATURE:
<221> NAME/KEY: misc_feature
<222> LOCATION: (38)..(38)
<223> OTHER INFORMATION: L-DNA
<220> FEATURE:
<221> NAME/KEY: misc_feature
<222> LOCATION: (39)..(50)
<223> OTHER INFORMATION: L-RNA

<400> SEQUENCE: 93
ccgugcuguc ggagacuacu cgucgaguag aaauaggtcc ccucccacgg    50

<210> SEQ ID NO 94
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (39)..(39)
<223> OTHER INFORMATION: L-DNA
<220> FEATURE:
<221> NAME/KEY: misc_feature
<222> LOCATION: (40)..(50)
<223> OTHER INFORMATION: L-RNA

<400> SEQUENCE: 94
ccgugcuguc ggagacuacu cgucgaguag aaauaggucc ccucccacgg    50

<210> SEQ ID NO 95
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA
<220> FEATURE:
<221> NAME/KEY: misc_feature

```
<222> LOCATION: (40)..(40)
<223> OTHER INFORMATION: L-DNA
<220> FEATURE:
<221> NAME/KEY: misc_feature
<222> LOCATION: (41)..(50)
<223> OTHER INFORMATION: L-RNA

<400> SEQUENCE: 95
ccgugcuguc ggagacuacu cgucgaguag aaauaggucc ccucccacgg        50

<210> SEQ ID NO 96
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
<222> LOCATION: (41)..(41)
<223> OTHER INFORMATION: L-DNA
<220> FEATURE:
<221> NAME/KEY: misc_feature
<222> LOCATION: (42)..(50)
<223> OTHER INFORMATION: L-RNA

<400> SEQUENCE: 96
ccgugcuguc ggagacuacu cgucgaguag aaauaggucc ccucccacgg        50

<210> SEQ ID NO 97
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-RNA
<220> FEATURE:
<221> NAME/KEY: misc_feature
<222> LOCATION: (42)..(42)
<223> OTHER INFORMATION: L-DNA
<220> FEATURE:
<221> NAME/KEY: misc_feature
<222> LOCATION: (43)..(50)
<223> OTHER INFORMATION: L-RNA

<400> SEQUENCE: 97
ccgugcuguc ggagacuacu cgucgaguag aaauaggucc ccucccacgg        50

<210> SEQ ID NO 98
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(42)
<223> OTHER INFORMATION: L-RNA
<220> FEATURE:
<221> NAME/KEY: misc_feature
<222> LOCATION: (43)..(43)
<223> OTHER INFORMATION: L-DNA
<220> FEATURE:
<221> NAME/KEY: misc_feature
<222> LOCATION: (44)..(50)
<223> OTHER INFORMATION: L-RNA
```

<400> SEQUENCE: 98
ccgugcuguc ggagacuacu cgucgaguag aaauaggucc cctcccacgg                50

<210> SEQ ID NO 99
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA
<220> FEATURE:
<221> NAME/KEY: misc_feature
<222> LOCATION: (44)..(44)
<223> OTHER INFORMATION: L-DNA
<220> FEATURE:
<221> NAME/KEY: misc_feature
<222> LOCATION: (45)..(50)
<223> OTHER INFORMATION: L-RNA

<400> SEQUENCE: 99
ccgugcuguc ggagacuacu cgucgaguag aaauaggucc ccucccacgg                50

<210> SEQ ID NO 100
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-RNA
<220> FEATURE:
<221> NAME/KEY: misc_feature
<222> LOCATION: (45)..(45)
<223> OTHER INFORMATION: L-DNA
<220> FEATURE:
<221> NAME/KEY: misc_feature
<222> LOCATION: (46)..(50)
<223> OTHER INFORMATION: L-RNA

<400> SEQUENCE: 100
ccgugcuguc ggagacuacu cgucgaguag aaauaggucc ccucccacgg                50

<210> SEQ ID NO 101
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA
<220> FEATURE:
<221> NAME/KEY: misc_feature
<222> LOCATION: (46)..(46)
<223> OTHER INFORMATION: L-DNA
<220> FEATURE:
<221> NAME/KEY: misc_feature
<222> LOCATION: (47)..(50)
<223> OTHER INFORMATION: L-RNA

<400> SEQUENCE: 101
ccgugcuguc ggagacuacu cgucgaguag aaauaggucc ccucccacgg                50

<210> SEQ ID NO 102
<211> LENGTH: 50

```
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(46)
<223> OTHER INFORMATION: L-RNA
<220> FEATURE:
<221> NAME/KEY: misc_feature
<222> LOCATION: (47)..(47)
<223> OTHER INFORMATION: L-DNA
<220> FEATURE:
<221> NAME/KEY: misc_feature
<222> LOCATION: (48)..(50)
<223> OTHER INFORMATION: L-RNA

<400> SEQUENCE: 102
ccgugcuguc ggagacuacu cgucgaguag aaauaggucc ccucccacgg            50

<210> SEQ ID NO 103
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(47)
<223> OTHER INFORMATION: L-RNA
<220> FEATURE:
<221> NAME/KEY: misc_feature
<222> LOCATION: (48)..(48)
<223> OTHER INFORMATION: L-DNA
<220> FEATURE:
<221> NAME/KEY: misc_feature
<222> LOCATION: (49)..(50)
<223> OTHER INFORMATION: L-RNA

<400> SEQUENCE: 103
ccgugcuguc ggagacuacu cgucgaguag aaauaggucc ccucccacgg            50

<210> SEQ ID NO 104
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(48)
<223> OTHER INFORMATION: L-RNA
<220> FEATURE:
<221> NAME/KEY: misc_feature
<222> LOCATION: (49)..(49)
<223> OTHER INFORMATION: L-DNA
<220> FEATURE:
<221> NAME/KEY: misc_feature
<222> LOCATION: (50)..(50)
<223> OTHER INFORMATION: L-RNA

<400> SEQUENCE: 104
ccgugcuguc ggagacuacu cgucgaguag aaauaggucc ccucccacgg            50

<210> SEQ ID NO 105
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(49)
```

```
<223> OTHER INFORMATION: L-RNA
<220> FEATURE:
<221> NAME/KEY: misc_feature
<222> LOCATION: (50)..(50)
<223> OTHER INFORMATION: L-DNA

<400> SEQUENCE: 105
ccgugcuguc ggagacuacu cgucgaguag aaauaggucc ccucccacgg            50

<210> SEQ ID NO 106
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
<222> LOCATION: (41)..(41)
<223> OTHER INFORMATION: L-DNA
<220> FEATURE:
<221> NAME/KEY: misc_feature
<222> LOCATION: (42)..(43)
<223> OTHER INFORMATION: L-RNA
<220> FEATURE:
<221> NAME/KEY: misc_feature
<222> LOCATION: (44)..(44)
<223> OTHER INFORMATION: L-DNA
<220> FEATURE:
<221> NAME/KEY: misc_feature
<222> LOCATION: (45)..(50)
<223> OTHER INFORMATION: L-RNA

<400> SEQUENCE: 106
ccgugcuguc ggagacuacu cgucgaguag aaauaggucc ccucccacgg            50

<210> SEQ ID NO 107
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-RNA

<400> SEQUENCE: 107
gccugaugug guggugaagg guuguugggu gucgacgcac aggc                  44

<210> SEQ ID NO 108
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(44)
<223> OTHER INFORMATION: L-RNA

<400> SEQUENCE: 108
gccugaugug guggugaagg guuguugggu gucgacgcac aggc                  44
```

```
<210> SEQ ID NO 109
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-RNA
<220> FEATURE:
<221> NAME/KEY: misc_feature
<222> LOCATION: (2)..(2)
<223> OTHER INFORMATION: L-DNA
<220> FEATURE:
<221> NAME/KEY: misc_feature
<222> LOCATION: (3)..(44)
<223> OTHER INFORMATION: L-RNA

<400> SEQUENCE: 109
gccugaugug guggugaagg guuguugggu gucgacgcac aggc        44

<210> SEQ ID NO 110
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: L-RNA
<220> FEATURE:
<221> NAME/KEY: misc_feature
<222> LOCATION: (3)..(3)
<223> OTHER INFORMATION: L-DNA
<220> FEATURE:
<221> NAME/KEY: misc_feature
<222> LOCATION: (4)..(44)
<223> OTHER INFORMATION: L-RNA

<400> SEQUENCE: 110
gccugaugug guggugaagg guuguugggu gucgacgcac aggc        44

<210> SEQ ID NO 111
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(3)
<223> OTHER INFORMATION: L-RNA
<220> FEATURE:
<221> NAME/KEY: misc_feature
<222> LOCATION: (4)..(4)
<223> OTHER INFORMATION: L-DNA
<220> FEATURE:
<221> NAME/KEY: misc_feature
<222> LOCATION: (5)..(44)
<223> OTHER INFORMATION: L-RNA

<400> SEQUENCE: 111
gccugaugug guggugaagg guuguugggu gucgacgcac aggc        44

<210> SEQ ID NO 112
<211> LENGTH: 44
<212> TYPE: DNA
<213> ORGANISM: artificial
<220> FEATURE:
<223> OTHER INFORMATION: synthetic
<220> FEATURE:
```

```
<221> NAME/KEY: misc_feature
<222> LOCATION: (1)..(4)
<223> OTHER INFORMATION: L-RNA
<220> FEATURE:
<221> NAME/KEY: misc_feature
<222> LOCATION: (5)..(5)
<223> OTHER INFORMATION: L-DNA
<220> FEATURE:
<221> NAME/KEY: misc_feature
<222> LOCATION: (6)..(44)
<223> OTHER INFORMATION: L-RNA

<400> SEQUENCE: 112
gccugaugug guggugaagg guuguugggu gucgacgcac aggc                44

<210> SEQ ID NO 113
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (6)..(6)
<223> OTHER INFORMATION: L-DNA
<220> FEATURE:
<221> NAME/KEY: misc_feature
<222> LOCATION: (7)..(44)
<223> OTHER INFORMATION: L-RNA

<400> SEQUENCE: 113
gccugaugug guggugaagg guuguugggu gucgacgcac aggc                44

<210> SEQ ID NO 114
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(44)
<223> OTHER INFORMATION: L-RNA

<400> SEQUENCE: 114
gccugaugug guggugaagg guuguugggu gucgacgcac aggc                44

<210> SEQ ID NO 115
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-RNA
<220> FEATURE:
<221> NAME/KEY: misc_feature
<222> LOCATION: (8)..(8)
<223> OTHER INFORMATION: L-DNA
```

```
<220> FEATURE:
<221> NAME/KEY: misc_feature
<222> LOCATION: (9)..(44)
<223> OTHER INFORMATION: L-RNA

<400> SEQUENCE: 115
gccugaugug guggugaagg guuguuggu gucgacgcac aggc                    44

<210> SEQ ID NO 116
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(44)
<223> OTHER INFORMATION: L-RNA

<400> SEQUENCE: 116
gccugaugug guggugaagg guuguugggu gucgacgcac aggc                   44

<210> SEQ ID NO 117
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(9)
<223> OTHER INFORMATION: L-RNA
<220> FEATURE:
<221> NAME/KEY: misc_feature
<222> LOCATION: (10)..(10)
<223> OTHER INFORMATION: L-DNA
<220> FEATURE:
<221> NAME/KEY: misc_feature
<222> LOCATION: (11)..(44)
<223> OTHER INFORMATION: L-RNA

<400> SEQUENCE: 117
gccugaugug guggugaagg guuguugggu gucgacgcac aggc                   44

<210> SEQ ID NO 118
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (11)..(11)
<223> OTHER INFORMATION: L-DNA
<220> FEATURE:
<221> NAME/KEY: misc_feature
<222> LOCATION: (12)..(44)
<223> OTHER INFORMATION: L-RNA

<400> SEQUENCE: 118
```
gccugaugug guggugaagg guuguugggu gucgacgcac aggc        44

<210> SEQ ID NO 119
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-RNA
<220> FEATURE:
<221> NAME/KEY: misc_feature
<222> LOCATION: (12)..(12)
<223> OTHER INFORMATION: L-DNA
<220> FEATURE:
<221> NAME/KEY: misc_feature
<222> LOCATION: (13)..(44)
<223> OTHER INFORMATION: L-RNA

<400> SEQUENCE: 119
gccugaugug guggugaagg guuguugggu gucgacgcac aggc        44

<210> SEQ ID NO 120
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-RNA
<220> FEATURE:
<221> NAME/KEY: misc_feature
<222> LOCATION: (13)..(13)
<223> OTHER INFORMATION: L-DNA
<220> FEATURE:
<221> NAME/KEY: misc_feature
<222> LOCATION: (14)..(44)
<223> OTHER INFORMATION: L-RNA

<400> SEQUENCE: 120
gccugaugug guggugaagg guuguugggu gucgacgcac aggc        44

<210> SEQ ID NO 121
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(13)
<223> OTHER INFORMATION: L-RNA
<220> FEATURE:
<221> NAME/KEY: misc_feature
<222> LOCATION: (14)..(14)
<223> OTHER INFORMATION: L-DNA
<220> FEATURE:
<221> NAME/KEY: misc_feature
<222> LOCATION: (15)..(44)
<223> OTHER INFORMATION: L-RNA

<400> SEQUENCE: 121
gccugaugug guggugaagg guuguugggu gucgacgcac aggc        44

<210> SEQ ID NO 122
<211> LENGTH: 44
<212> TYPE: DNA
<213> ORGANISM: artificial

```
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-RNA
<220> FEATURE:
<221> NAME/KEY: misc_feature
<222> LOCATION: (15)..(15)
<223> OTHER INFORMATION: L-DNA
<220> FEATURE:
<221> NAME/KEY: misc_feature
<222> LOCATION: (16)..(44)
<223> OTHER INFORMATION: L-RNA

<400> SEQUENCE: 122
gccugaugug guggugaagg guuguugggu gucgacgcac aggc                44

<210> SEQ ID NO 123
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(15)
<223> OTHER INFORMATION: L-RNA
<220> FEATURE:
<221> NAME/KEY: misc_feature
<222> LOCATION: (16)..(16)
<223> OTHER INFORMATION: L-DNA
<220> FEATURE:
<221> NAME/KEY: misc_feature
<222> LOCATION: (17)..(44)
<223> OTHER INFORMATION: L-RNA

<400> SEQUENCE: 123
gccugaugug guggugaagg guuguugggu gucgacgcac aggc                44

<210> SEQ ID NO 124
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: L-RNA
<220> FEATURE:
<221> NAME/KEY: misc_feature
<222> LOCATION: (17)..(17)
<223> OTHER INFORMATION: L-DNA
<220> FEATURE:
<221> NAME/KEY: misc_feature
<222> LOCATION: (18)..(44)
<223> OTHER INFORMATION: L-RNA

<400> SEQUENCE: 124
gccugaugug guggugaagg guuguugggu gucgacgcac aggc                44

<210> SEQ ID NO 125
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-RNA
<220> FEATURE:
```

```
<221> NAME/KEY: misc_feature
<222> LOCATION: (18)..(18)
<223> OTHER INFORMATION: L-DNA
<220> FEATURE:
<221> NAME/KEY: misc_feature
<222> LOCATION: (19)..(44)
<223> OTHER INFORMATION: L-RNA

<400> SEQUENCE: 125
gccugaugug guggugaagg guuguugggu gucgacgcac aggc        44

<210> SEQ ID NO 126
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(44)
<223> OTHER INFORMATION: L-RNA

<400> SEQUENCE: 126
gccugaugug guggugaagg guuguugggu gucgacgcac aggc        44

<210> SEQ ID NO 127
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA
<220> FEATURE:
<221> NAME/KEY: misc_feature
<222> LOCATION: (20)..(20)
<223> OTHER INFORMATION: L-DNA
<220> FEATURE:
<221> NAME/KEY: misc_feature
<222> LOCATION: (21)..(44)
<223> OTHER INFORMATION: L-RNA

<400> SEQUENCE: 127
gccugaugug guggugaagg guuguugggu gucgacgcac aggc        44

<210> SEQ ID NO 128
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(44)
<223> OTHER INFORMATION: L-RNA
```

<400> SEQUENCE: 128
gccugaugug guggugaagg guuguugggu gucgacgcac aggc            44

<210> SEQ ID NO 129
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(21)
<223> OTHER INFORMATION: L-RNA
<220> FEATURE:
<221> NAME/KEY: misc_feature
<222> LOCATION: (22)..(22)
<223> OTHER INFORMATION: L-DNA
<220> FEATURE:
<221> NAME/KEY: misc_feature
<222> LOCATION: (23)..(44)
<223> OTHER INFORMATION: L-RNA

<400> SEQUENCE: 129
gccugaugug guggugaagg guuguugggu gucgacgcac aggc            44

<210> SEQ ID NO 130
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(22)
<223> OTHER INFORMATION: L-RNA
<220> FEATURE:
<221> NAME/KEY: misc_feature
<222> LOCATION: (23)..(23)
<223> OTHER INFORMATION: L-DNA
<220> FEATURE:
<221> NAME/KEY: misc_feature
<222> LOCATION: (24)..(44)
<223> OTHER INFORMATION: L-RNA

<400> SEQUENCE: 130
gccugaugug guggugaagg guuguugggu gucgacgcac aggc            44

<210> SEQ ID NO 131
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: L-RNA
<220> FEATURE:
<221> NAME/KEY: misc_feature
<222> LOCATION: (24)..(24)
<223> OTHER INFORMATION: L-DNA
<220> FEATURE:
<221> NAME/KEY: misc_feature
<222> LOCATION: (25)..(44)
<223> OTHER INFORMATION: L-RNA

<400> SEQUENCE: 131
gccugaugug guggugaagg guuguugggu gucgacgcac aggc            44

<210> SEQ ID NO 132

```
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(24)
<223> OTHER INFORMATION: L-RNA
<220> FEATURE:
<221> NAME/KEY: misc_feature
<222> LOCATION: (25)..(25)
<223> OTHER INFORMATION: L-DNA
<220> FEATURE:
<221> NAME/KEY: misc_feature
<222> LOCATION: (26)..(44)
<223> OTHER INFORMATION: L-RNA

<400> SEQUENCE: 132
gccugaugug guggugaagg guuguugggu gucgacgcac aggc                    44

<210> SEQ ID NO 133
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(25)
<223> OTHER INFORMATION: L-RNA
<220> FEATURE:
<221> NAME/KEY: misc_feature
<222> LOCATION: (26)..(26)
<223> OTHER INFORMATION: L-DNA
<220> FEATURE:
<221> NAME/KEY: misc_feature
<222> LOCATION: (27)..(44)
<223> OTHER INFORMATION: L-RNA

<400> SEQUENCE: 133
gccugaugug guggugaagg guuguugggu gucgacgcac aggc                    44

<210> SEQ ID NO 134
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-RNA
<220> FEATURE:
<221> NAME/KEY: misc_feature
<222> LOCATION: (27)..(27)
<223> OTHER INFORMATION: L-DNA
<220> FEATURE:
<221> NAME/KEY: misc_feature
<222> LOCATION: (28)..(44)
<223> OTHER INFORMATION: L-RNA

<400> SEQUENCE: 134
gccugaugug guggugaagg guuguugggu gucgacgcac aggc                    44

<210> SEQ ID NO 135
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
```

```
<222> LOCATION: (1)..(27)
<223> OTHER INFORMATION: L-RNA
<220> FEATURE:
<221> NAME/KEY: misc_feature
<222> LOCATION: (28)..(28)
<223> OTHER INFORMATION: L-DNA
<220> FEATURE:
<221> NAME/KEY: misc_feature
<222> LOCATION: (29)..(44)
<223> OTHER INFORMATION: L-RNA

<400> SEQUENCE: 135
gccugaugug guggugaagg guuguugggu gucgacgcac aggc        44

<210> SEQ ID NO 136
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-RNA
<220> FEATURE:
<221> NAME/KEY: misc_feature
<222> LOCATION: (29)..(29)
<223> OTHER INFORMATION: L-DNA
<220> FEATURE:
<221> NAME/KEY: misc_feature
<222> LOCATION: (30)..(44)
<223> OTHER INFORMATION: L-RNA

<400> SEQUENCE: 136
gccugaugug guggugaagg guuguugggu gucgacgcac aggc        44

<210> SEQ ID NO 137
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(44)
<223> OTHER INFORMATION: L-RNA

<400> SEQUENCE: 137
gccugaugug guggugaagg guuguugggu gucgacgcac aggc        44

<210> SEQ ID NO 138
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-RNA
<220> FEATURE:
<221> NAME/KEY: misc_feature
<222> LOCATION: (31)..(31)
<223> OTHER INFORMATION: L-DNA
<220> FEATURE:
```

<221> NAME/KEY: misc_feature
<222> LOCATION: (32)..(44)
<223> OTHER INFORMATION: L-RNA

<400> SEQUENCE: 138
gccugaugug guggugaagg guuguugggu gucgacgcac aggc            44

<210> SEQ ID NO 139
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 139
gccugaugug guggugaagg guuguugggu gucgacgcac aggc            44

<210> SEQ ID NO 140
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(32)
<223> OTHER INFORMATION: L-RNA
<220> FEATURE:
<221> NAME/KEY: misc_feature
<222> LOCATION: (33)..(33)
<223> OTHER INFORMATION: L-DNA
<220> FEATURE:
<221> NAME/KEY: misc_feature
<222> LOCATION: (34)..(44)
<223> OTHER INFORMATION: L-RNA

<400> SEQUENCE: 140
gccugaugug guggugaagg guuguugggu gucgacgcac aggc            44

<210> SEQ ID NO 141
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-RNA
<220> FEATURE:
<221> NAME/KEY: misc_feature
<222> LOCATION: (34)..(34)
<223> OTHER INFORMATION: L-DNA
<220> FEATURE:
<221> NAME/KEY: misc_feature
<222> LOCATION: (35)..(44)
<223> OTHER INFORMATION: L-RNA

<400> SEQUENCE: 141
gccugaugug guggugaagg guuguugggu gucgacgcac aggc            44

<210> SEQ ID NO 142
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA
<220> FEATURE:
<221> NAME/KEY: misc_feature
<222> LOCATION: (35)..(35)
<223> OTHER INFORMATION: L-DNA
<220> FEATURE:
<221> NAME/KEY: misc_feature
<222> LOCATION: (36)..(44)
<223> OTHER INFORMATION: L-RNA

<400> SEQUENCE: 142
gccugaugug guggugaagg guuguugggu gucgacgcac aggc                44

<210> SEQ ID NO 143
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA
<220> FEATURE:
<221> NAME/KEY: misc_feature
<222> LOCATION: (36)..(36)
<223> OTHER INFORMATION: L-DNA
<220> FEATURE:
<221> NAME/KEY: misc_feature
<222> LOCATION: (37)..(44)
<223> OTHER INFORMATION: L-RNA

<400> SEQUENCE: 143
gccugaugug guggugaagg guuguugggu gucgacgcac aggc                44

<210> SEQ ID NO 144
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA
<220> FEATURE:
<221> NAME/KEY: misc_feature
<222> LOCATION: (37)..(37)
<223> OTHER INFORMATION: L-DNA
<220> FEATURE:
<221> NAME/KEY: misc_feature
<222> LOCATION: (38)..(44)
<223> OTHER INFORMATION: L-RNA

<400> SEQUENCE: 144
gccugaugug guggugaagg guuguugggu gucgacgcac aggc                44

<210> SEQ ID NO 145
<211> LENGTH: 44
<212> TYPE: DNA
<213> ORGANISM: artificial
<220> FEATURE:

```
<223> OTHER INFORMATION: synthetic
<220> FEATURE:
<221> NAME/KEY: misc_feature
<222> LOCATION: (1)..(37)
<223> OTHER INFORMATION: L-RNA
<220> FEATURE:
<221> NAME/KEY: misc_feature
<222> LOCATION: (38)..(38)
<223> OTHER INFORMATION: L-DNA
<220> FEATURE:
<221> NAME/KEY: misc_feature
<222> LOCATION: (39)..(44)
<223> OTHER INFORMATION: L-RNA

<400> SEQUENCE: 145
gccugaugug guggugaagg guuguugggu gucgacgcac aggc                     44

<210> SEQ ID NO 146
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (39)..(39)
<223> OTHER INFORMATION: L-DNA
<220> FEATURE:
<221> NAME/KEY: misc_feature
<222> LOCATION: (40)..(44)
<223> OTHER INFORMATION: L-RNA

<400> SEQUENCE: 146
gccugaugug guggugaagg guuguugggu gucgacgcac aggc                     44

<210> SEQ ID NO 147
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 147
gccugaugug guggugaagg guuguugggu gucgacgcac aggc                     44

<210> SEQ ID NO 148
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
```

```
<222> LOCATION: (41)..(41)
<223> OTHER INFORMATION: L-DNA
<220> FEATURE:
<221> NAME/KEY: misc_feature
<222> LOCATION: (42)..(44)
<223> OTHER INFORMATION: L-RNA

<400> SEQUENCE: 148
gccugaugug guggugaagg guuguugggu gucgacgcac aggc            44

<210> SEQ ID NO 149
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-RNA
<220> FEATURE:
<221> NAME/KEY: misc_feature
<222> LOCATION: (42)..(42)
<223> OTHER INFORMATION: L-DNA
<220> FEATURE:
<221> NAME/KEY: misc_feature
<222> LOCATION: (43)..(44)
<223> OTHER INFORMATION: L-RNA

<400> SEQUENCE: 149
gccugaugug guggugaagg guuguugggu gucgacgcac aggc            44

<210> SEQ ID NO 150
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(42)
<223> OTHER INFORMATION: L-RNA
<220> FEATURE:
<221> NAME/KEY: misc_feature
<222> LOCATION: (43)..(43)
<223> OTHER INFORMATION: L-DNA
<220> FEATURE:
<221> NAME/KEY: misc_feature
<222> LOCATION: (44)..(44)
<223> OTHER INFORMATION: L-RNA

<400> SEQUENCE: 150
gccugaugug guggugaagg guuguugggu gucgacgcac aggc            44

<210> SEQ ID NO 151
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA
<220> FEATURE:
<221> NAME/KEY: misc_feature
<222> LOCATION: (44)..(44)
<223> OTHER INFORMATION: L-DNA

<400> SEQUENCE: 151
gccugaugug guggugaagg guuguugggu gucgacgcac aggc            44
```

<210> SEQ ID NO 152
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(44)
<223> OTHER INFORMATION: L-RNA

<400> SEQUENCE: 152
gccugaugug guggugaagg guuguugggu gucgacgcac aggc            44

<210> SEQ ID NO 153
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 153
gccugaugug guggugaagg guuguugggu gucgacgcac aggc            44

<210> SEQ ID NO 154
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA

```
<220> FEATURE:
<221> NAME/KEY: misc_feature
<222> LOCATION: (10)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 154
gccugaugug guggugaagg guuguugggu gucgacgcac aggc            44

<210> SEQ ID NO 155
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 155
gccugaugug guggugaagg guuguugggu gucgacgcac aggc            44

<210> SEQ ID NO 156
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 156
```
gccugaugug guggugaagg guuguugggu gucgacgcac aggc 44

<210> SEQ ID NO 157
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 157
gccugaugug guggugaagg guuguugggu gucgacgcac aggc 44

<210> SEQ ID NO 158
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 158
gccugaugug guggugaagg guuguugggu gucgacgcac aggc 44

<210> SEQ ID NO 159
<211> LENGTH: 44
<212> TYPE: DNA
<213> ORGANISM: artificial

```
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 159
gccugaugug guggugaagg guuguugggu gucgacgcac aggc            44

<210> SEQ ID NO 160
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 160
gccugaugug guggugaagg guuguugggu gucgacgcac aggc            44

<210> SEQ ID NO 161
<211> LENGTH: 44
<212> TYPE: DNA
```

```
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 161
gccugaugug guggugaagg guuguuggu gucgacgcac aggc                    44

<210> SEQ ID NO 162
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA
```

<400> SEQUENCE: 162
gccugaugug guggugaagg guuguugggu gucgacgcac aggc                                44

<210> SEQ ID NO 163
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(15)
<223> OTHER INFORMATION: L-RNA
<220> FEATURE:
<221> NAME/KEY: misc_feature
<222> LOCATION: (16)..(16)
<223> OTHER INFORMATION: L-DNA
<220> FEATURE:
<221> NAME/KEY: misc_feature
<222> LOCATION: (17)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 163
gccugaugug guggugaagg guuguugggu gucgacgcac aggc                                44

<210> SEQ ID NO 164
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(16)

```
<223> OTHER INFORMATION: L-RNA
<220> FEATURE:
<221> NAME/KEY: misc_feature
<222> LOCATION: (17)..(17)
<223> OTHER INFORMATION: L-DNA
<220> FEATURE:
<221> NAME/KEY: misc_feature
<222> LOCATION: (18)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 164
gccugaugug guggugaagg guuguugggu gucgacgcac aggc                    44

<210> SEQ ID NO 165
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(15)
<223> OTHER INFORMATION: L-RNA
<220> FEATURE:
<221> NAME/KEY: misc_feature
<222> LOCATION: (16)..(17)
<223> OTHER INFORMATION: L-DNA
<220> FEATURE:
<221> NAME/KEY: misc_feature
<222> LOCATION: (18)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
```

```
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 165
gccugaugug guggugaagg guuguuggguu gucgacgcac aggc          44

<210> SEQ ID NO 166
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(44)
<223> OTHER INFORMATION: L-RNA

<400> SEQUENCE: 166
gccugaugug guggugaagg guuguugggu gucgacgcac aggc           44

<210> SEQ ID NO 167
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
```

```
<221> NAME/KEY: misc_feature
<222> LOCATION: (41)..(44)
<223> OTHER INFORMATION: L-RNA

<400> SEQUENCE: 167
gccugaugug guggugaagg guuguuggu gucgacgcac aggc                    44

<210> SEQ ID NO 168
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 168
gccugaugug guggugaagg guuguuggu gucgacgcac aggc                    44

<210> SEQ ID NO 169
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(15)
<223> OTHER INFORMATION: L-RNA
<220> FEATURE:
<221> NAME/KEY: misc_feature
<222> LOCATION: (16)..(16)
<223> OTHER INFORMATION: L-DNA
```

```
<220> FEATURE:
<221> NAME/KEY: misc_feature
<222> LOCATION: (17)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 169
gccugaugug guggugaagg guuguugggu gucgacgcac aggc            44

<210> SEQ ID NO 170
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(16)
<223> OTHER INFORMATION: L-RNA
<220> FEATURE:
<221> NAME/KEY: misc_feature
<222> LOCATION: (17)..(17)
<223> OTHER INFORMATION: L-DNA
<220> FEATURE:
<221> NAME/KEY: misc_feature
<222> LOCATION: (18)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
```

<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 170
gccugaugug guggugaagg guuguugggu gucgacgcac aggc            44

<210> SEQ ID NO 171
<211> LENGTH: 44
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
<220> FEATURE:
<221> NAME/KEY: misc_feature
<222> LOCATION: (8)..(15)
<223> OTHER INFORMATION: L-RNA
<220> FEATURE:
<221> NAME/KEY: misc_feature
<222> LOCATION: (16)..(17)
<223> OTHER INFORMATION: L-DNA
<220> FEATURE:
<221> NAME/KEY: misc_feature
<222> LOCATION: (18)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(39)
<223> OTHER INFORMATION: L-RNA
<220> FEATURE:
<221> NAME/KEY: misc_feature
<222> LOCATION: (40)..(40)
<223> OTHER INFORMATION: L-DNA
<220> FEATURE:
<221> NAME/KEY: misc_feature
<222> LOCATION: (41)..(44)
<223> OTHER INFORMATION: L-RNA

<400> SEQUENCE: 171
gccugaugug guggugaagg guuguugggu gucgacgcac aggc            44

<210> SEQ ID NO 172
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(54)
<223> OTHER INFORMATION: L-RNA

<400> SEQUENCE: 172
cagacgugug uggguagaug caccugcgau ucgcuaaaaa gugccacacg ucug                54

<210> SEQ ID NO 173
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(54)
<223> OTHER INFORMATION: L-RNA

<400> SEQUENCE: 173
cagacgugug uggguagaug caccugcgau ucgcuaaaaa gugccacacg ucug                54

<210> SEQ ID NO 174
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-RNA
<220> FEATURE:
<221> NAME/KEY: misc_feature
<222> LOCATION: (2)..(2)
<223> OTHER INFORMATION: L-DNA
<220> FEATURE:
<221> NAME/KEY: misc_feature
<222> LOCATION: (3)..(54)
<223> OTHER INFORMATION: L-RNA

<400> SEQUENCE: 174
cagacgugug uggguagaug caccugcgau ucgcuaaaaa gugccacacg ucug                54

<210> SEQ ID NO 175
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: L-RNA
<220> FEATURE:
<221> NAME/KEY: misc_feature
<222> LOCATION: (3)..(3)
<223> OTHER INFORMATION: L-DNA
<220> FEATURE:
<221> NAME/KEY: misc_feature
<222> LOCATION: (4)..(54)
<223> OTHER INFORMATION: L-RNA

<400> SEQUENCE: 175
cagacgugug uggguagaug caccugcgau ucgcuaaaaa gugccacacg ucug                54

<210> SEQ ID NO 176
<211> LENGTH: 54
<212> TYPE: DNA
<213> ORGANISM: artificial
<220> FEATURE:
<223> OTHER INFORMATION: synthetic
<220> FEATURE:

```
<221> NAME/KEY: misc_feature
<222> LOCATION: (1)..(3)
<223> OTHER INFORMATION: L-RNA
<220> FEATURE:
<221> NAME/KEY: misc_feature
<222> LOCATION: (4)..(4)
<223> OTHER INFORMATION: L-DNA
<220> FEATURE:
<221> NAME/KEY: misc_feature
<222> LOCATION: (5)..(54)
<223> OTHER INFORMATION: L-RNA

<400> SEQUENCE: 176
cagacgugug uggguagaug caccugcgau ucgcuaaaaa gugccacacg ucug        54

<210> SEQ ID NO 177
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(4)
<223> OTHER INFORMATION: L-RNA
<220> FEATURE:
<221> NAME/KEY: misc_feature
<222> LOCATION: (5)..(5)
<223> OTHER INFORMATION: L-DNA
<220> FEATURE:
<221> NAME/KEY: misc_feature
<222> LOCATION: (6)..(54)
<223> OTHER INFORMATION: L-RNA

<400> SEQUENCE: 177
cagacgugug uggguagaug caccugcgau ucgcuaaaaa gugccacacg ucug        54

<210> SEQ ID NO 178
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (6)..(6)
<223> OTHER INFORMATION: L-DNA
<220> FEATURE:
<221> NAME/KEY: misc_feature
<222> LOCATION: (7)..(54)
<223> OTHER INFORMATION: L-RNA

<400> SEQUENCE: 178
cagacgugug uggguagaug caccugcgau ucgcuaaaaa gugccacacg ucug        54

<210> SEQ ID NO 179
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (7)..(7)
<223> OTHER INFORMATION: L-DNA
```

-continued

```
<220> FEATURE:
<221> NAME/KEY: misc_feature
<222> LOCATION: (8)..(54)
<223> OTHER INFORMATION: L-RNA

<400> SEQUENCE: 179
cagacgtgug uggguagaug caccugcgau ucgcuaaaaa gugccacacg ucug        54

<210> SEQ ID NO 180
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-RNA
<220> FEATURE:
<221> NAME/KEY: misc_feature
<222> LOCATION: (8)..(8)
<223> OTHER INFORMATION: L-DNA
<220> FEATURE:
<221> NAME/KEY: misc_feature
<222> LOCATION: (9)..(54)
<223> OTHER INFORMATION: L-RNA

<400> SEQUENCE: 180
cagacgugug uggguagaug caccugcgau ucgcuaaaaa gugccacacg ucug        54

<210> SEQ ID NO 181
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-RNA
<220> FEATURE:
<221> NAME/KEY: misc_feature
<222> LOCATION: (9)..(9)
<223> OTHER INFORMATION: L-DNA
<220> FEATURE:
<221> NAME/KEY: misc_feature
<222> LOCATION: (10)..(54)
<223> OTHER INFORMATION: L-RNA

<400> SEQUENCE: 181
cagacgugtg uggguagaug caccugcgau ucgcuaaaaa gugccacacg ucug        54

<210> SEQ ID NO 182
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(9)
<223> OTHER INFORMATION: L-RNA
<220> FEATURE:
<221> NAME/KEY: misc_feature
<222> LOCATION: (10)..(10)
<223> OTHER INFORMATION: L-DNA
<220> FEATURE:
<221> NAME/KEY: misc_feature
<222> LOCATION: (11)..(54)
<223> OTHER INFORMATION: L-RNA

<400> SEQUENCE: 182
```
cagacgugug ugggulagaug caccugcgau ucgcuaaaaa gugccacacg ucug       54

<210> SEQ ID NO 183
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (11)..(11)
<223> OTHER INFORMATION: L-DNA
<220> FEATURE:
<221> NAME/KEY: misc_feature
<222> LOCATION: (12)..(54)
<223> OTHER INFORMATION: L-RNA

<400> SEQUENCE: 183
cagacgugug tggguagaug caccugcgau ucgcuaaaaa gugccacacg ucug       54

<210> SEQ ID NO 184
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-RNA
<220> FEATURE:
<221> NAME/KEY: misc_feature
<222> LOCATION: (12)..(12)
<223> OTHER INFORMATION: L-DNA
<220> FEATURE:
<221> NAME/KEY: misc_feature
<222> LOCATION: (13)..(54)
<223> OTHER INFORMATION: L-RNA

<400> SEQUENCE: 184
cagacgugug uggguagaug caccugcgau ucgcuaaaaa gugccacacg ucug       54

<210> SEQ ID NO 185
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-RNA
<220> FEATURE:
<221> NAME/KEY: misc_feature
<222> LOCATION: (13)..(13)
<223> OTHER INFORMATION: L-DNA
<220> FEATURE:
<221> NAME/KEY: misc_feature
<222> LOCATION: (14)..(54)
<223> OTHER INFORMATION: L-RNA

<400> SEQUENCE: 185
cagacgugug uggguagaug caccugcgau ucgcuaaaaa gugccacacg ucug       54

<210> SEQ ID NO 186
<211> LENGTH: 54
<212> TYPE: DNA
<213> ORGANISM: artificial

<220> FEATURE:
<223> OTHER INFORMATION: synthetic
<220> FEATURE:
<221> NAME/KEY: misc_feature
<222> LOCATION: (1)..(13)
<223> OTHER INFORMATION: L-RNA
<220> FEATURE:
<221> NAME/KEY: misc_feature
<222> LOCATION: (14)..(14)
<223> OTHER INFORMATION: L-DNA
<220> FEATURE:
<221> NAME/KEY: misc_feature
<222> LOCATION: (15)..(54)
<223> OTHER INFORMATION: L-RNA

<400> SEQUENCE: 186
cagacgugug uggguagaug caccugcgau ucgcuaaaaa gugccacacg ucug            54

<210> SEQ ID NO 187
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-RNA
<220> FEATURE:
<221> NAME/KEY: misc_feature
<222> LOCATION: (15)..(15)
<223> OTHER INFORMATION: L-DNA
<220> FEATURE:
<221> NAME/KEY: misc_feature
<222> LOCATION: (16)..(54)
<223> OTHER INFORMATION: L-RNA

<400> SEQUENCE: 187
cagacgugug ugggtagaug caccugcgau ucgcuaaaaa gugccacacg ucug            54

<210> SEQ ID NO 188
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(15)
<223> OTHER INFORMATION: L-RNA
<220> FEATURE:
<221> NAME/KEY: misc_feature
<222> LOCATION: (16)..(16)
<223> OTHER INFORMATION: L-DNA
<220> FEATURE:
<221> NAME/KEY: misc_feature
<222> LOCATION: (17)..(54)
<223> OTHER INFORMATION: L-RNA

<400> SEQUENCE: 188
cagacgugug uggguagaug caccugcgau ucgcuaaaaa gugccacacg ucug            54

<210> SEQ ID NO 189
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: L-RNA
<220> FEATURE:

```
<221> NAME/KEY: misc_feature
<222> LOCATION: (17)..(17)
<223> OTHER INFORMATION: L-DNA
<220> FEATURE:
<221> NAME/KEY: misc_feature
<222> LOCATION: (18)..(54)
<223> OTHER INFORMATION: L-RNA

<400> SEQUENCE: 189
cagacgugug uggguagaug caccugcgau ucgcuaaaaa gugccacacg ucug          54

<210> SEQ ID NO 190
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-RNA
<220> FEATURE:
<221> NAME/KEY: misc_feature
<222> LOCATION: (18)..(18)
<223> OTHER INFORMATION: L-DNA
<220> FEATURE:
<221> NAME/KEY: misc_feature
<222> LOCATION: (19)..(54)
<223> OTHER INFORMATION: L-RNA

<400> SEQUENCE: 190
cagacgugug uggguagaug caccugcgau ucgcuaaaaa gugccacacg ucug          54

<210> SEQ ID NO 191
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(54)
<223> OTHER INFORMATION: L-RNA

<400> SEQUENCE: 191
cagacgugug uggguagatg caccugcgau ucgcuaaaaa gugccacacg ucug          54

<210> SEQ ID NO 192
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA
<220> FEATURE:
<221> NAME/KEY: misc_feature
<222> LOCATION: (20)..(20)
<223> OTHER INFORMATION: L-DNA
<220> FEATURE:
<221> NAME/KEY: misc_feature
<222> LOCATION: (21)..(54)
<223> OTHER INFORMATION: L-RNA
```

<400> SEQUENCE: 192
cagacgugug uggguagaug caccugcgau ucgcuaaaaa gugccacacg ucug          54

<210> SEQ ID NO 193
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(54)
<223> OTHER INFORMATION: L-RNA

<400> SEQUENCE: 193
cagacgugug uggguagaug caccugcgau ucgcuaaaaa gugccacacg ucug          54

<210> SEQ ID NO 194
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(21)
<223> OTHER INFORMATION: L-RNA
<220> FEATURE:
<221> NAME/KEY: misc_feature
<222> LOCATION: (22)..(22)
<223> OTHER INFORMATION: L-DNA
<220> FEATURE:
<221> NAME/KEY: misc_feature
<222> LOCATION: (23)..(54)
<223> OTHER INFORMATION: L-RNA

<400> SEQUENCE: 194
cagacgugug uggguagaug caccugcgau ucgcuaaaaa gugccacacg ucug          54

<210> SEQ ID NO 195
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(22)
<223> OTHER INFORMATION: L-RNA
<220> FEATURE:
<221> NAME/KEY: misc_feature
<222> LOCATION: (23)..(23)
<223> OTHER INFORMATION: L-DNA
<220> FEATURE:
<221> NAME/KEY: misc_feature
<222> LOCATION: (24)..(54)
<223> OTHER INFORMATION: L-RNA

<400> SEQUENCE: 195
cagacgugug uggguagaug caccugcgau ucgcuaaaaa gugccacacg ucug          54

<210> SEQ ID NO 196

```
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: L-RNA
<220> FEATURE:
<221> NAME/KEY: misc_feature
<222> LOCATION: (24)..(24)
<223> OTHER INFORMATION: L-DNA
<220> FEATURE:
<221> NAME/KEY: misc_feature
<222> LOCATION: (25)..(54)
<223> OTHER INFORMATION: L-RNA

<400> SEQUENCE: 196
cagacgugug uggguagaug caccugcgau ucgcuaaaaa gugccacacg ucug            54

<210> SEQ ID NO 197
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(24)
<223> OTHER INFORMATION: L-RNA
<220> FEATURE:
<221> NAME/KEY: misc_feature
<222> LOCATION: (25)..(25)
<223> OTHER INFORMATION: L-DNA
<220> FEATURE:
<221> NAME/KEY: misc_feature
<222> LOCATION: (26)..(54)
<223> OTHER INFORMATION: L-RNA

<400> SEQUENCE: 197
cagacgugug uggguagaug cacctgcgau ucgcuaaaaa gugccacacg ucug            54

<210> SEQ ID NO 198
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(25)
<223> OTHER INFORMATION: L-RNA
<220> FEATURE:
<221> NAME/KEY: misc_feature
<222> LOCATION: (26)..(26)
<223> OTHER INFORMATION: L-DNA
<220> FEATURE:
<221> NAME/KEY: misc_feature
<222> LOCATION: (27)..(54)
<223> OTHER INFORMATION: L-RNA

<400> SEQUENCE: 198
cagacgugug uggguagaug caccugcgau ucgcuaaaaa gugccacacg ucug            54

<210> SEQ ID NO 199
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
```

```
<222> LOCATION: (1)..(26)
<223> OTHER INFORMATION: L-RNA
<220> FEATURE:
<221> NAME/KEY: misc_feature
<222> LOCATION: (27)..(27)
<223> OTHER INFORMATION: L-DNA
<220> FEATURE:
<221> NAME/KEY: misc_feature
<222> LOCATION: (28)..(54)
<223> OTHER INFORMATION: L-RNA

<400> SEQUENCE: 199
cagacgugug uggguagaug caccugcgau ucgcuaaaaa gugccacacg ucug        54

<210> SEQ ID NO 200
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA
<220> FEATURE:
<221> NAME/KEY: misc_feature
<222> LOCATION: (28)..(28)
<223> OTHER INFORMATION: L-DNA
<220> FEATURE:
<221> NAME/KEY: misc_feature
<222> LOCATION: (29)..(54)
<223> OTHER INFORMATION: L-RNA

<400> SEQUENCE: 200
cagacgugug uggguagaug caccugcgau ucgcuaaaaa gugccacacg ucug        54

<210> SEQ ID NO 201
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-RNA
<220> FEATURE:
<221> NAME/KEY: misc_feature
<222> LOCATION: (29)..(29)
<223> OTHER INFORMATION: L-DNA
<220> FEATURE:
<221> NAME/KEY: misc_feature
<222> LOCATION: (30)..(54)
<223> OTHER INFORMATION: L-RNA

<400> SEQUENCE: 201
cagacgugug uggguagaug caccugcgau ucgcuaaaaa gugccacacg ucug        54

<210> SEQ ID NO 202
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA
<220> FEATURE:
<221> NAME/KEY: misc_feature
<222> LOCATION: (30)..(30)
<223> OTHER INFORMATION: L-DNA
<220> FEATURE:
```

```
<221> NAME/KEY: misc_feature
<222> LOCATION: (31)..(54)
<223> OTHER INFORMATION: L-RNA

<400> SEQUENCE: 202
cagacgugug uggguagaug caccugcgat ucgcuaaaaa gugccacacg ucug        54

<210> SEQ ID NO 203
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-RNA
<220> FEATURE:
<221> NAME/KEY: misc_feature
<222> LOCATION: (31)..(31)
<223> OTHER INFORMATION: L-DNA
<220> FEATURE:
<221> NAME/KEY: misc_feature
<222> LOCATION: (32)..(54)
<223> OTHER INFORMATION: L-RNA

<400> SEQUENCE: 203
cagacgugug uggguagaug caccugcgau tcgcuaaaaa gugccacacg ucug        54

<210> SEQ ID NO 204
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(54)
<223> OTHER INFORMATION: L-RNA

<400> SEQUENCE: 204
cagacgugug uggguagaug caccugcgau ucgcuaaaaa gugccacacg ucug        54

<210> SEQ ID NO 205
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(32)
<223> OTHER INFORMATION: L-RNA
<220> FEATURE:
<221> NAME/KEY: misc_feature
<222> LOCATION: (33)..(33)
<223> OTHER INFORMATION: L-DNA
<220> FEATURE:
<221> NAME/KEY: misc_feature
<222> LOCATION: (34)..(54)
<223> OTHER INFORMATION: L-RNA

<400> SEQUENCE: 205
cagacgugug uggguagaug caccugcgau ucgcuaaaaa gugccacacg ucug        54
```

```
<210> SEQ ID NO 206
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-RNA
<220> FEATURE:
<221> NAME/KEY: misc_feature
<222> LOCATION: (34)..(34)
<223> OTHER INFORMATION: L-DNA
<220> FEATURE:
<221> NAME/KEY: misc_feature
<222> LOCATION: (35)..(54)
<223> OTHER INFORMATION: L-RNA

<400> SEQUENCE: 206
cagacgugug uggguagaug caccugcgau ucgcuaaaaa gugccacacg ucug            54

<210> SEQ ID NO 207
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA
<220> FEATURE:
<221> NAME/KEY: misc_feature
<222> LOCATION: (35)..(35)
<223> OTHER INFORMATION: L-DNA
<220> FEATURE:
<221> NAME/KEY: misc_feature
<222> LOCATION: (36)..(54)
<223> OTHER INFORMATION: L-RNA

<400> SEQUENCE: 207
cagacgugug uggguagaug caccugcgau ucgctaaaaa gugccacacg ucug            54

<210> SEQ ID NO 208
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA
<220> FEATURE:
<221> NAME/KEY: misc_feature
<222> LOCATION: (36)..(36)
<223> OTHER INFORMATION: L-DNA
<220> FEATURE:
<221> NAME/KEY: misc_feature
<222> LOCATION: (37)..(54)
<223> OTHER INFORMATION: L-RNA

<400> SEQUENCE: 208
cagacgugug uggguagaug caccugcgau ucgcuaaaaa gugccacacg ucug            54

<210> SEQ ID NO 209
<211> LENGTH: 54
<212> TYPE: DNA
<213> ORGANISM: artificial
<220> FEATURE:
```

```
<223> OTHER INFORMATION: synthetic
<220> FEATURE:
<221> NAME/KEY: misc_feature
<222> LOCATION: (1)..(36)
<223> OTHER INFORMATION: L-RNA
<220> FEATURE:
<221> NAME/KEY: misc_feature
<222> LOCATION: (37)..(37)
<223> OTHER INFORMATION: L-DNA
<220> FEATURE:
<221> NAME/KEY: misc_feature
<222> LOCATION: (38)..(54)
<223> OTHER INFORMATION: L-RNA

<400> SEQUENCE: 209
cagacgugug uggguagaug caccugcgau ucgcuaaaaa gugccacacg ucug          54

<210> SEQ ID NO 210
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(37)
<223> OTHER INFORMATION: L-RNA
<220> FEATURE:
<221> NAME/KEY: misc_feature
<222> LOCATION: (38)..(38)
<223> OTHER INFORMATION: L-DNA
<220> FEATURE:
<221> NAME/KEY: misc_feature
<222> LOCATION: (39)..(54)
<223> OTHER INFORMATION: L-RNA

<400> SEQUENCE: 210
cagacgugug uggguagaug caccugcgau ucgcuaaaaa gugccacacg ucug          54

<210> SEQ ID NO 211
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (39)..(39)
<223> OTHER INFORMATION: L-DNA
<220> FEATURE:
<221> NAME/KEY: misc_feature
<222> LOCATION: (40)..(54)
<223> OTHER INFORMATION: L-RNA

<400> SEQUENCE: 211
cagacgugug uggguagaug caccugcgau ucgcuaaaaa gugccacacg ucug          54

<210> SEQ ID NO 212
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA
<220> FEATURE:
<221> NAME/KEY: misc_feature
```

```
<222> LOCATION: (40)..(40)
<223> OTHER INFORMATION: L-DNA
<220> FEATURE:
<221> NAME/KEY: misc_feature
<222> LOCATION: (41)..(54)
<223> OTHER INFORMATION: L-RNA

<400> SEQUENCE: 212
cagacgugug uggguagaug caccugcgau ucgcuaaaaa gugccacacg ucug        54

<210> SEQ ID NO 213
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
<222> LOCATION: (41)..(41)
<223> OTHER INFORMATION: L-DNA
<220> FEATURE:
<221> NAME/KEY: misc_feature
<222> LOCATION: (42)..(54)
<223> OTHER INFORMATION: L-RNA

<400> SEQUENCE: 213
cagacgugug uggguagaug caccugcgau ucgcuaaaaa gugccacacg ucug        54

<210> SEQ ID NO 214
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-RNA
<220> FEATURE:
<221> NAME/KEY: misc_feature
<222> LOCATION: (42)..(42)
<223> OTHER INFORMATION: L-DNA
<220> FEATURE:
<221> NAME/KEY: misc_feature
<222> LOCATION: (43)..(54)
<223> OTHER INFORMATION: L-RNA

<400> SEQUENCE: 214
cagacgugug uggguagaug caccugcgau ucgcuaaaaa gtgccacacg ucug        54

<210> SEQ ID NO 215
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(42)
<223> OTHER INFORMATION: L-RNA
<220> FEATURE:
<221> NAME/KEY: misc_feature
<222> LOCATION: (43)..(43)
<223> OTHER INFORMATION: L-DNA
<220> FEATURE:
<221> NAME/KEY: misc_feature
<222> LOCATION: (44)..(54)
<223> OTHER INFORMATION: L-RNA
```

<400> SEQUENCE: 215
cagacgugug uggguagaug caccugcgau ucgcuaaaaa gugccacacg ucug            54

<210> SEQ ID NO 216
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA
<220> FEATURE:
<221> NAME/KEY: misc_feature
<222> LOCATION: (44)..(44)
<223> OTHER INFORMATION: L-DNA
<220> FEATURE:
<221> NAME/KEY: misc_feature
<222> LOCATION: (45)..(54)
<223> OTHER INFORMATION: L-RNA

<400> SEQUENCE: 216
cagacgugug uggguagaug caccugcgau ucgcuaaaaa gugccacacg ucug            54

<210> SEQ ID NO 217
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-RNA
<220> FEATURE:
<221> NAME/KEY: misc_feature
<222> LOCATION: (45)..(45)
<223> OTHER INFORMATION: L-DNA
<220> FEATURE:
<221> NAME/KEY: misc_feature
<222> LOCATION: (46)..(54)
<223> OTHER INFORMATION: L-RNA

<400> SEQUENCE: 217
cagacgugug uggguagaug caccugcgau ucgcuaaaaa gugccacacg ucug            54

<210> SEQ ID NO 218
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA
<220> FEATURE:
<221> NAME/KEY: misc_feature
<222> LOCATION: (46)..(46)
<223> OTHER INFORMATION: L-DNA
<220> FEATURE:
<221> NAME/KEY: misc_feature
<222> LOCATION: (47)..(54)
<223> OTHER INFORMATION: L-RNA

<400> SEQUENCE: 218
cagacgugug uggguagaug caccugcgau ucgcuaaaaa gugccacacg ucug            54

<210> SEQ ID NO 219
<211> LENGTH: 54

```
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(46)
<223> OTHER INFORMATION: L-RNA
<220> FEATURE:
<221> NAME/KEY: misc_feature
<222> LOCATION: (47)..(47)
<223> OTHER INFORMATION: L-DNA
<220> FEATURE:
<221> NAME/KEY: misc_feature
<222> LOCATION: (48)..(54)
<223> OTHER INFORMATION: L-RNA

<400> SEQUENCE: 219
cagacgugug uggguagaug caccugcgau ucgcuaaaaa gugccacacg ucug           54

<210> SEQ ID NO 220
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(47)
<223> OTHER INFORMATION: L-RNA
<220> FEATURE:
<221> NAME/KEY: misc_feature
<222> LOCATION: (48)..(48)
<223> OTHER INFORMATION: L-DNA
<220> FEATURE:
<221> NAME/KEY: misc_feature
<222> LOCATION: (49)..(54)
<223> OTHER INFORMATION: L-RNA

<400> SEQUENCE: 220
cagacgugug uggguagaug caccugcgau ucgcuaaaaa gugccacacg ucug           54

<210> SEQ ID NO 221
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(48)
<223> OTHER INFORMATION: L-RNA
<220> FEATURE:
<221> NAME/KEY: misc_feature
<222> LOCATION: (49)..(49)
<223> OTHER INFORMATION: L-DNA
<220> FEATURE:
<221> NAME/KEY: misc_feature
<222> LOCATION: (50)..(54)
<223> OTHER INFORMATION: L-RNA

<400> SEQUENCE: 221
cagacgugug uggguagaug caccugcgau ucgcuaaaaa gugccacacg ucug           54

<210> SEQ ID NO 222
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(49)
```

<223> OTHER INFORMATION: L-RNA
<220> FEATURE:
<221> NAME/KEY: misc_feature
<222> LOCATION: (50)..(50)
<223> OTHER INFORMATION: L-DNA
<220> FEATURE:
<221> NAME/KEY: misc_feature
<222> LOCATION: (51)..(54)
<223> OTHER INFORMATION: L-RNA

<400> SEQUENCE: 222
cagacgugug uggguagaug caccugcgau ucgcuaaaaa gugccacacg ucug        54

<210> SEQ ID NO 223
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(50)
<223> OTHER INFORMATION: L-RNA
<220> FEATURE:
<221> NAME/KEY: misc_feature
<222> LOCATION: (51)..(51)
<223> OTHER INFORMATION: L-DNA
<220> FEATURE:
<221> NAME/KEY: misc_feature
<222> LOCATION: (52)..(54)
<223> OTHER INFORMATION: L-RNA

<400> SEQUENCE: 223
cagacgugug uggguagaug caccugcgau ucgcuaaaaa gugccacacg tcug        54

<210> SEQ ID NO 224
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(51)
<223> OTHER INFORMATION: L-RNA
<220> FEATURE:
<221> NAME/KEY: misc_feature
<222> LOCATION: (52)..(52)
<223> OTHER INFORMATION: L-DNA
<220> FEATURE:
<221> NAME/KEY: misc_feature
<222> LOCATION: (53)..(54)
<223> OTHER INFORMATION: L-RNA

<400> SEQUENCE: 224
cagacgugug uggguagaug caccugcgau ucgcuaaaaa gugccacacg ucug        54

<210> SEQ ID NO 225
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(52)
<223> OTHER INFORMATION: L-RNA
<220> FEATURE:
<221> NAME/KEY: misc_feature
<222> LOCATION: (53)..(53)
<223> OTHER INFORMATION: L-DNA
<220> FEATURE:
<221> NAME/KEY: misc_feature

```
<222> LOCATION: (54)..(54)
<223> OTHER INFORMATION: L-RNA

<400> SEQUENCE: 225
cagacgugug uggguagaug caccugcgau ucgcuaaaaa gugccacacg uctg       54

<210> SEQ ID NO 226
<211> LENGTH: 54
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(53)
<223> OTHER INFORMATION: L-RNA
<220> FEATURE:
<221> NAME/KEY: misc_feature
<222> LOCATION: (54)..(54)
<223> OTHER INFORMATION: L-DNA

<400> SEQUENCE: 226
cagacgugug uggguagaug caccugcgau ucgcuaaaaa gugccacacg ucug       54

<210> SEQ ID NO 227
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(47)
<223> OTHER INFORMATION: L-DNA

<400> SEQUENCE: 227
gcagtgggga aatgggaggg ctaggtggaa ggaatctgag ctactgc              47

<210> SEQ ID NO 228
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-RNA
<220> FEATURE:
<221> NAME/KEY: misc_feature
<222> LOCATION: (2)..(47)
<223> OTHER INFORMATION: L-DNA

<400> SEQUENCE: 228
gcagtgggga aatgggaggg ctaggtggaa ggaatctgag ctactgc              47

<210> SEQ ID NO 229
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(2)
<223> OTHER INFORMATION: L-RNA
<220> FEATURE:
```

```
<221> NAME/KEY: misc_feature
<222> LOCATION: (3)..(47)
<223> OTHER INFORMATION: L-DNA

<400> SEQUENCE: 229
gcagtgggga aatgggaggg ctaggtggaa ggaatctgag ctactgc         47

<210> SEQ ID NO 230
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: L-DNA
<220> FEATURE:
<221> NAME/KEY: misc_feature
<222> LOCATION: (3)..(3)
<223> OTHER INFORMATION: L-RNA
<220> FEATURE:
<221> NAME/KEY: misc_feature
<222> LOCATION: (4)..(47)
<223> OTHER INFORMATION: L-DNA

<400> SEQUENCE: 230
gcagtgggga aatgggaggg ctaggtggaa ggaatctgag ctactgc         47

<210> SEQ ID NO 231
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(3)
<223> OTHER INFORMATION: L-DNA
<220> FEATURE:
<221> NAME/KEY: misc_feature
<222> LOCATION: (4)..(4)
<223> OTHER INFORMATION: L-RNA
<220> FEATURE:
<221> NAME/KEY: misc_feature
<222> LOCATION: (5)..(47)
<223> OTHER INFORMATION: L-DNA

<400> SEQUENCE: 231
gcagtgggga aatgggaggg ctaggtggaa ggaatctgag ctactgc         47

<210> SEQ ID NO 232
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(4)
<223> OTHER INFORMATION: L-DNA
<220> FEATURE:
<221> NAME/KEY: misc_feature
<222> LOCATION: (5)..(5)
<223> OTHER INFORMATION: L-RNA
<220> FEATURE:
<221> NAME/KEY: misc_feature
<222> LOCATION: (6)..(47)
<223> OTHER INFORMATION: L-DNA

<400> SEQUENCE: 232 gcaguggga aatgggaggg ctaggtggaa ggaatctgag ctactgc         47
```

<210> SEQ ID NO 233
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-DNA
<220> FEATURE:
<221> NAME/KEY: misc_feature
<222> LOCATION: (6)..(6)
<223> OTHER INFORMATION: L-RNA
<220> FEATURE:
<221> NAME/KEY: misc_feature
<222> LOCATION: (7)..(47)
<223> OTHER INFORMATION: L-DNA

<400> SEQUENCE: 233
gcagtgggga aatgggaggg ctaggtggaa ggaatctgag ctactgc                    47

<210> SEQ ID NO 234
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-DNA
<220> FEATURE:
<221> NAME/KEY: misc_feature
<222> LOCATION: (7)..(7)
<223> OTHER INFORMATION: L-RNA
<220> FEATURE:
<221> NAME/KEY: misc_feature
<222> LOCATION: (8)..(47)
<223> OTHER INFORMATION: L-DNA

<400> SEQUENCE: 234
gcagtgggga aatgggaggg ctaggtggaa ggaatctgag ctactgc                    47

<210> SEQ ID NO 235
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(47)
<223> OTHER INFORMATION: L-DNA

<400> SEQUENCE: 235
gcagtgggga aatgggaggg ctaggtggaa ggaatctgag ctactgc                    47

<210> SEQ ID NO 236
<211> LENGTH: 47
<212> TYPE: DNA
<213> ORGANISM: artificial
<220> FEATURE:

```
<223> OTHER INFORMATION: synthetic
<220> FEATURE:
<221> NAME/KEY: misc_feature
<222> LOCATION: (1)..(8)
<223> OTHER INFORMATION: L-DNA
<220> FEATURE:
<221> NAME/KEY: misc_feature
<222> LOCATION: (9)..(9)
<223> OTHER INFORMATION: L-RNA
<220> FEATURE:
<221> NAME/KEY: misc_feature
<222> LOCATION: (10)..(47)
<223> OTHER INFORMATION: L-DNA

<400> SEQUENCE: 236
gcagtgggga aatgggaggg ctaggtggaa ggaatctgag ctactgc                    47

<210> SEQ ID NO 237
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(9)
<223> OTHER INFORMATION: L-DNA
<220> FEATURE:
<221> NAME/KEY: misc_feature
<222> LOCATION: (10)..(10)
<223> OTHER INFORMATION: L-RNA
<220> FEATURE:
<221> NAME/KEY: misc_feature
<222> LOCATION: (11)..(47)
<223> OTHER INFORMATION: L-DNA

<400> SEQUENCE: 237
gcagtgggga aatgggaggg ctaggtggaa ggaatctgag ctactgc                    47

<210> SEQ ID NO 238
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-DNA
<220> FEATURE:
<221> NAME/KEY: misc_feature
<222> LOCATION: (11)..(11)
<223> OTHER INFORMATION: L-RNA
<220> FEATURE:
<221> NAME/KEY: misc_feature
<222> LOCATION: (12)..(47)
<223> OTHER INFORMATION: L-DNA

<400> SEQUENCE: 238
gcagtgggga aatgggaggg ctaggtggaa ggaatctgag ctactgc                    47

<210> SEQ ID NO 239
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-DNA
<220> FEATURE:
<221> NAME/KEY: misc_feature
```

```
<222> LOCATION: (12)..(12)
<223> OTHER INFORMATION: L-RNA
<220> FEATURE:
<221> NAME/KEY: misc_feature
<222> LOCATION: (13)..(47)
<223> OTHER INFORMATION: L-DNA

<400> SEQUENCE: 239
gcagtgggga aatgggaggg ctaggtggaa ggaatctgag ctactgc         47

<210> SEQ ID NO 240
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-DNA
<220> FEATURE:
<221> NAME/KEY: misc_feature
<222> LOCATION: (13)..(13)
<223> OTHER INFORMATION: L-RNA
<220> FEATURE:
<221> NAME/KEY: misc_feature
<222> LOCATION: (14)..(47)
<223> OTHER INFORMATION: L-DNA

<400> SEQUENCE: 240
gcagtgggga auugggaggg ctaggtggaa ggaatctgag ctactgc         47

<210> SEQ ID NO 241
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
<220> FEATURE:
<221> NAME/KEY: misc_feature
<222> LOCATION: (15)..(47)
<223> OTHER INFORMATION: L-DNA

<400> SEQUENCE: 241
gcagtgggga aatgggaggg ctaggtggaa ggaatctgag ctactgc         47

<210> SEQ ID NO 242
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-DNA
<220> FEATURE:
<221> NAME/KEY: misc_feature
<222> LOCATION: (15)..(15)
<223> OTHER INFORMATION: L-RNA
<220> FEATURE:
<221> NAME/KEY: misc_feature
<222> LOCATION: (16)..(47)
<223> OTHER INFORMATION: L-DNA
```

<400> SEQUENCE: 242
gcagtgggga aatgggaggg ctaggtggaa ggaatctgag ctactgc      47

<210> SEQ ID NO 243
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(15)
<223> OTHER INFORMATION: L-DNA
<220> FEATURE:
<221> NAME/KEY: misc_feature
<222> LOCATION: (16)..(16)
<223> OTHER INFORMATION: L-RNA
<220> FEATURE:
<221> NAME/KEY: misc_feature
<222> LOCATION: (17)..(47)
<223> OTHER INFORMATION: L-DNA

<400> SEQUENCE: 243
gcagtgggga aatgggaggg ctaggtggaa ggaatctgag ctactgc      47

<210> SEQ ID NO 244
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: L-DNA
<220> FEATURE:
<221> NAME/KEY: misc_feature
<222> LOCATION: (17)..(17)
<223> OTHER INFORMATION: L-RNA
<220> FEATURE:
<221> NAME/KEY: misc_feature
<222> LOCATION: (18)..(47)
<223> OTHER INFORMATION: L-DNA

<400> SEQUENCE: 244
gcagtgggga aatgggaggg ctaggtggaa ggaatctgag ctactgc      47

<210> SEQ ID NO 245
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-DNA
<220> FEATURE:
<221> NAME/KEY: misc_feature
<222> LOCATION: (18)..(18)
<223> OTHER INFORMATION: L-RNA
<220> FEATURE:
<221> NAME/KEY: misc_feature
<222> LOCATION: (19)..(47)
<223> OTHER INFORMATION: L-DNA

<400> SEQUENCE: 245
gcagtgggga aatgggaggg ctaggtggaa ggaatctgag ctactgc      47

<210> SEQ ID NO 246
<211> LENGTH: 47

```
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-DNA
<220> FEATURE:
<221> NAME/KEY: misc_feature
<222> LOCATION: (19)..(19)
<223> OTHER INFORMATION: L-RNA
<220> FEATURE:
<221> NAME/KEY: misc_feature
<222> LOCATION: (20)..(47)
<223> OTHER INFORMATION: L-DNA

<400> SEQUENCE: 246
gcagtgggga aatgggaggg ctaggtggaa ggaatctgag ctactgc                47

<210> SEQ ID NO 247
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-DNA
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(47)
<223> OTHER INFORMATION: L-DNA

<400> SEQUENCE: 247
gcagtgggga aatgggaggg ctaggtggaa ggaatctgag ctactgc                47

<210> SEQ ID NO 248
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-DNA
<220> FEATURE:
<221> NAME/KEY: misc_feature
<222> LOCATION: (21)..(21)
<223> OTHER INFORMATION: L-RNA
<220> FEATURE:
<221> NAME/KEY: misc_feature
<222> LOCATION: (22)..(47)
<223> OTHER INFORMATION: L-DNA

<400> SEQUENCE: 248
gcagtgggga aatgggaggg ctaggtggaa ggaatctgag ctactgc                47

<210> SEQ ID NO 249
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(21)
```

```
<223> OTHER INFORMATION: L-DNA
<220> FEATURE:
<221> NAME/KEY: misc_feature
<222> LOCATION: (22)..(22)
<223> OTHER INFORMATION: L-RNA
<220> FEATURE:
<221> NAME/KEY: misc_feature
<222> LOCATION: (23)..(47)
<223> OTHER INFORMATION: L-DNA

<400> SEQUENCE: 249
gcagtgggga aatgggaggg cuaggtggaa ggaatctgag ctactgc          47

<210> SEQ ID NO 250
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(22)
<223> OTHER INFORMATION: L-DNA
<220> FEATURE:
<221> NAME/KEY: misc_feature
<222> LOCATION: (23)..(23)
<223> OTHER INFORMATION: L-RNA
<220> FEATURE:
<221> NAME/KEY: misc_feature
<222> LOCATION: (24)..(47)
<223> OTHER INFORMATION: L-DNA

<400> SEQUENCE: 250
gcagtgggga aatgggaggg ctaggtggaa ggaatctgag ctactgc          47

<210> SEQ ID NO 251
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: L-DNA
<220> FEATURE:
<221> NAME/KEY: misc_feature
<222> LOCATION: (24)..(24)
<223> OTHER INFORMATION: L-RNA
<220> FEATURE:
<221> NAME/KEY: misc_feature
<222> LOCATION: (25)..(47)
<223> OTHER INFORMATION: L-DNA

<400> SEQUENCE: 251
gcagtgggga aatgggaggg ctaggtggaa ggaatctgag ctactgc          47

<210> SEQ ID NO 252
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(24)
<223> OTHER INFORMATION: L-DNA
<220> FEATURE:
<221> NAME/KEY: misc_feature
<222> LOCATION: (25)..(25)
<223> OTHER INFORMATION: L-RNA
<220> FEATURE:
<221> NAME/KEY: misc_feature
```

```
<222> LOCATION: (26)..(47)
<223> OTHER INFORMATION: L-DNA

<400> SEQUENCE: 252
gcagtgggga aatgggaggg ctaggtggaa ggaatctgag ctactgc        47

<210> SEQ ID NO 253
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(25)
<223> OTHER INFORMATION: L-DNA
<220> FEATURE:
<221> NAME/KEY: misc_feature
<222> LOCATION: (26)..(26)
<223> OTHER INFORMATION: L-RNA
<220> FEATURE:
<221> NAME/KEY: misc_feature
<222> LOCATION: (27)..(47)
<223> OTHER INFORMATION: L-DNA

<400> SEQUENCE: 253
gcagtgggga aatgggaggg ctagguggaa ggaatctgag ctactgc        47

<210> SEQ ID NO 254
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-DNA
<220> FEATURE:
<221> NAME/KEY: misc_feature
<222> LOCATION: (27)..(27)
<223> OTHER INFORMATION: L-RNA
<220> FEATURE:
<221> NAME/KEY: misc_feature
<222> LOCATION: (28)..(47)
<223> OTHER INFORMATION: L-DNA

<400> SEQUENCE: 254
gcagtgggga aatgggaggg ctaggtggaa ggaatctgag ctactgc        47

<210> SEQ ID NO 255
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-DNA
<220> FEATURE:
<221> NAME/KEY: misc_feature
<222> LOCATION: (28)..(28)
<223> OTHER INFORMATION: L-RNA
<220> FEATURE:
<221> NAME/KEY: misc_feature
<222> LOCATION: (29)..(47)
<223> OTHER INFORMATION: L-DNA

<400> SEQUENCE: 255
gcagtgggga aatgggaggg ctaggtggaa ggaatctgag ctactgc        47
```

```
<210> SEQ ID NO 256
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-DNA
<220> FEATURE:
<221> NAME/KEY: misc_feature
<222> LOCATION: (29)..(29)
<223> OTHER INFORMATION: L-RNA
<220> FEATURE:
<221> NAME/KEY: misc_feature
<222> LOCATION: (30)..(47)
<223> OTHER INFORMATION: L-DNA

<400> SEQUENCE: 256
gcagtgggga aatgggaggg ctaggtggaa ggaatctgag ctactgc          47

<210> SEQ ID NO 257
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-DNA
<220> FEATURE:
<221> NAME/KEY: misc_feature
<222> LOCATION: (30)..(30)
<223> OTHER INFORMATION: L-RNA
<220> FEATURE:
<221> NAME/KEY: misc_feature
<222> LOCATION: (31)..(47)
<223> OTHER INFORMATION: L-DNA

<400> SEQUENCE: 257
gcagtgggga aatgggaggg ctaggtggaa ggaatctgag ctactgc          47

<210> SEQ ID NO 258
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(47)
<223> OTHER INFORMATION: L-DNA

<400> SEQUENCE: 258
gcagtgggga aatgggaggg ctaggtggaa ggaatctgag ctactgc          47

<210> SEQ ID NO 259
<211> LENGTH: 47
<212> TYPE: DNA
<213> ORGANISM: artificial
<220> FEATURE:
<223> OTHER INFORMATION: synthetic
```

```
<220> FEATURE:
<221> NAME/KEY: misc_feature
<222> LOCATION: (1)..(31)
<223> OTHER INFORMATION: L-DNA
<220> FEATURE:
<221> NAME/KEY: misc_feature
<222> LOCATION: (32)..(32)
<223> OTHER INFORMATION: L-RNA
<220> FEATURE:
<221> NAME/KEY: misc_feature
<222> LOCATION: (33)..(47)
<223> OTHER INFORMATION: L-DNA

<400> SEQUENCE: 259
gcagtgggga aatgggaggg ctaggtggaa ggaatctgag ctactgc                47

<210> SEQ ID NO 260
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(32)
<223> OTHER INFORMATION: L-DNA
<220> FEATURE:
<221> NAME/KEY: misc_feature
<222> LOCATION: (33)..(33)
<223> OTHER INFORMATION: L-RNA
<220> FEATURE:
<221> NAME/KEY: misc_feature
<222> LOCATION: (34)..(47)
<223> OTHER INFORMATION: L-DNA

<400> SEQUENCE: 260
gcagtgggga aatgggaggg ctaggtggaa ggaatctgag ctactgc                47

<210> SEQ ID NO 261
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-DNA
<220> FEATURE:
<221> NAME/KEY: misc_feature
<222> LOCATION: (34)..(34)
<223> OTHER INFORMATION: L-RNA
<220> FEATURE:
<221> NAME/KEY: misc_feature
<222> LOCATION: (35)..(47)
<223> OTHER INFORMATION: L-DNA

<400> SEQUENCE: 261
gcagtgggga aatgggaggg ctaggtggaa ggaatctgag ctactgc                47

<210> SEQ ID NO 262
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-DNA
<220> FEATURE:
<221> NAME/KEY: misc_feature
<222> LOCATION: (35)..(35)
```

```
<223> OTHER INFORMATION: L-RNA
<220> FEATURE:
<221> NAME/KEY: misc_feature
<222> LOCATION: (36)..(47)
<223> OTHER INFORMATION: L-DNA

<400> SEQUENCE: 262
gcagtgggga aatgggaggg ctaggtggaa ggaauctgag ctactgc                    47

<210> SEQ ID NO 263
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-DNA
<220> FEATURE:
<221> NAME/KEY: misc_feature
<222> LOCATION: (36)..(36)
<223> OTHER INFORMATION: L-RNA
<220> FEATURE:
<221> NAME/KEY: misc_feature
<222> LOCATION: (37)..(47)
<223> OTHER INFORMATION: L-DNA

<400> SEQUENCE: 263
gcagtgggga aatgggaggg ctaggtggaa ggaatctgag ctactgc                    47

<210> SEQ ID NO 264
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-DNA
<220> FEATURE:
<221> NAME/KEY: misc_feature
<222> LOCATION: (37)..(37)
<223> OTHER INFORMATION: L-RNA
<220> FEATURE:
<221> NAME/KEY: misc_feature
<222> LOCATION: (38)..(47)
<223> OTHER INFORMATION: L-DNA

<400> SEQUENCE: 264
gcagtgggga aatgggaggg ctaggtggaa ggaatcugag ctactgc                    47

<210> SEQ ID NO 265
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(37)
<223> OTHER INFORMATION: L-DNA
<220> FEATURE:
<221> NAME/KEY: misc_feature
<222> LOCATION: (38)..(38)
<223> OTHER INFORMATION: L-RNA
<220> FEATURE:
<221> NAME/KEY: misc_feature
<222> LOCATION: (39)..(47)
<223> OTHER INFORMATION: L-DNA

<400> SEQUENCE: 265
```

-continued gcagtgggga aatgggaggg ctaggtggaa ggaatctgag ctactgc        47

<210> SEQ ID NO 266
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-DNA
<220> FEATURE:
<221> NAME/KEY: misc_feature
<222> LOCATION: (39)..(39)
<223> OTHER INFORMATION: L-RNA
<220> FEATURE:
<221> NAME/KEY: misc_feature
<222> LOCATION: (40)..(47)
<223> OTHER INFORMATION: L-DNA

<400> SEQUENCE: 266
gcagtgggga aatgggaggg ctaggtggaa ggaatctgag ctactgc        47

<210> SEQ ID NO 267
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-DNA
<220> FEATURE:
<221> NAME/KEY: misc_feature
<222> LOCATION: (40)..(40)
<223> OTHER INFORMATION: L-RNA
<220> FEATURE:
<221> NAME/KEY: misc_feature
<222> LOCATION: (41)..(47)
<223> OTHER INFORMATION: L-DNA

<400> SEQUENCE: 267
gcagtgggga aatgggaggg ctaggtggaa ggaatctgag ctactgc        47

<210> SEQ ID NO 268
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-DNA
<220> FEATURE:
<221> NAME/KEY: misc_feature
<222> LOCATION: (41)..(41)
<223> OTHER INFORMATION: L-RNA
<220> FEATURE:
<221> NAME/KEY: misc_feature
<222> LOCATION: (42)..(47)
<223> OTHER INFORMATION: L-DNA

<400> SEQUENCE: 268
gcagtgggga aatgggaggg ctaggtggaa ggaatctgag ctactgc        47

<210> SEQ ID NO 269
<211> LENGTH: 47
<212> TYPE: DNA

```
<213> ORGANISM: artificial
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-DNA
<220> FEATURE:
<221> NAME/KEY: misc_feature
<222> LOCATION: (42)..(42)
<223> OTHER INFORMATION: L-RNA
<220> FEATURE:
<221> NAME/KEY: misc_feature
<222> LOCATION: (43)..(47)
<223> OTHER INFORMATION: L-DNA

<400> SEQUENCE: 269
gcagtgggga aatgggaggg ctaggtggaa ggaatctgag cuactgc                47

<210> SEQ ID NO 270
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(42)
<223> OTHER INFORMATION: L-DNA
<220> FEATURE:
<221> NAME/KEY: misc_feature
<222> LOCATION: (43)..(43)
<223> OTHER INFORMATION: L-RNA
<220> FEATURE:
<221> NAME/KEY: misc_feature
<222> LOCATION: (44)..(47)
<223> OTHER INFORMATION: L-DNA

<400> SEQUENCE: 270
gcagtgggga aatgggaggg ctaggtggaa ggaatctgag ctactgc                47

<210> SEQ ID NO 271
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-DNA
<220> FEATURE:
<221> NAME/KEY: misc_feature
<222> LOCATION: (44)..(44)
<223> OTHER INFORMATION: L-RNA
<220> FEATURE:
<221> NAME/KEY: misc_feature
<222> LOCATION: (45)..(47)
<223> OTHER INFORMATION: L-DNA

<400> SEQUENCE: 271
gcagtgggga aatgggaggg ctaggtggaa ggaatctgag ctactgc                47

<210> SEQ ID NO 272
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-DNA
```

<220> FEATURE:
<221> NAME/KEY: misc_feature
<222> LOCATION: (45)..(45)
<223> OTHER INFORMATION: L-RNA
<220> FEATURE:
<221> NAME/KEY: misc_feature
<222> LOCATION: (46)..(47)
<223> OTHER INFORMATION: L-DNA

<400> SEQUENCE: 272
gcagtgggga aatgggaggg ctaggtggaa ggaatctgag ctacugc        47

<210> SEQ ID NO 273
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-DNA
<220> FEATURE:
<221> NAME/KEY: misc_feature
<222> LOCATION: (46)..(46)
<223> OTHER INFORMATION: L-RNA
<220> FEATURE:
<221> NAME/KEY: misc_feature
<222> LOCATION: (47)..(47)
<223> OTHER INFORMATION: L-DNA

<400> SEQUENCE: 273
gcagtgggga aatgggaggg ctaggtggaa ggaatctgag ctactgc        47

<210> SEQ ID NO 274
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(46)
<223> OTHER INFORMATION: L-DNA
<220> FEATURE:
<221> NAME/KEY: misc_feature
<222> LOCATION: (47)..(47)
<223> OTHER INFORMATION: L-RNA

<400> SEQUENCE: 274
gcagtgggga aatgggaggg ctaggtggaa ggaatctgag ctactgc        47

<210> SEQ ID NO 275
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-DNA
<220> FEATURE:
<221> NAME/KEY: misc_feature
<222> LOCATION: (15)..(15)
<223> OTHER INFORMATION: L-RNA
<220> FEATURE:
<221> NAME/KEY: misc_feature
<222> LOCATION: (16)..(28)
<223> OTHER INFORMATION: L-DNA
<220> FEATURE:
<221> NAME/KEY: misc_feature
<222> LOCATION: (29)..(29)

<223> OTHER INFORMATION: L-RNA
<220> FEATURE:
<221> NAME/KEY: misc_feature
<222> LOCATION: (30)..(47)
<223> OTHER INFORMATION: L-DNA

<400> SEQUENCE: 275
gcagtgggga aatgggaggg ctaggtggaa ggaatctgag ctactgc                47

<210> SEQ ID NO 276
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-DNA
<220> FEATURE:
<221> NAME/KEY: misc_feature
<222> LOCATION: (29)..(30)
<223> OTHER INFORMATION: L-RNA
<220> FEATURE:
<221> NAME/KEY: misc_feature
<222> LOCATION: (31)..(47)
<223> OTHER INFORMATION: L-DNA

<400> SEQUENCE: 276
gcagtgggga aatgggaggg ctaggtggaa ggaatctgag ctactgc                47

<210> SEQ ID NO 277
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-DNA
<220> FEATURE:
<221> NAME/KEY: misc_feature
<222> LOCATION: (15)..(15)
<223> OTHER INFORMATION: L-RNA
<220> FEATURE:
<221> NAME/KEY: misc_feature
<222> LOCATION: (16)..(28)
<223> OTHER INFORMATION: L-DNA
<220> FEATURE:
<221> NAME/KEY: misc_feature
<222> LOCATION: (29)..(30)
<223> OTHER INFORMATION: L-RNA
<220> FEATURE:
<221> NAME/KEY: misc_feature
<222> LOCATION: (31)..(47)
<223> OTHER INFORMATION: L-DNA

<400> SEQUENCE: 277
gcagtgggga aatgggaggg ctaggtggaa ggaatctgag ctactgc                47

<210> SEQ ID NO 278
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-DNA
<220> FEATURE:
<221> NAME/KEY: misc_feature -continued
<222> LOCATION: (18)..(18)
<223> OTHER INFORMATION: L-RNA
<220> FEATURE:
<221> NAME/KEY: misc_feature
<222> LOCATION: (19)..(28)
<223> OTHER INFORMATION: L-DNA
<220> FEATURE:
<221> NAME/KEY: misc_feature
<222> LOCATION: (29)..(30)
<223> OTHER INFORMATION: L-RNA
<220> FEATURE:
<221> NAME/KEY: misc_feature
<222> LOCATION: (31)..(47)
<223> OTHER INFORMATION: L-DNA

<400> SEQUENCE: 278
gcagtgggga aatgggaggg ctaggtggaa ggaatctgag ctactgc         47

<210> SEQ ID NO 279
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-DNA
<220> FEATURE:
<221> NAME/KEY: misc_feature
<222> LOCATION: (15)..(15)
<223> OTHER INFORMATION: L-RNA
<220> FEATURE:
<221> NAME/KEY: misc_feature
<222> LOCATION: (16)..(17)
<223> OTHER INFORMATION: L-DNA
<220> FEATURE:
<221> NAME/KEY: misc_feature
<222> LOCATION: (18)..(18)
<223> OTHER INFORMATION: L-RNA
<220> FEATURE:
<221> NAME/KEY: misc_feature
<222> LOCATION: (19)..(28)
<223> OTHER INFORMATION: L-DNA
<220> FEATURE:
<221> NAME/KEY: misc_feature
<222> LOCATION: (29)..(30)
<223> OTHER INFORMATION: L-RNA
<220> FEATURE:
<221> NAME/KEY: misc_feature
<222> LOCATION: (31)..(47)
<223> OTHER INFORMATION: L-DNA

<400> SEQUENCE: 279
gcagtgggga aatgggaggg ctaggtggaa ggaatctgag ctactgc         47

<210> SEQ ID NO 280
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-DNA
<220> FEATURE:
<221> NAME/KEY: misc_feature
<222> LOCATION: (9)..(9)
<223> OTHER INFORMATION: L-RNA
<220> FEATURE:
<221> NAME/KEY: misc_feature
<222> LOCATION: (10)..(14)
<223> OTHER INFORMATION: L-DNA
<220> FEATURE:

```
<221> NAME/KEY: misc_feature
<222> LOCATION: (15)..(15)
<223> OTHER INFORMATION: L-RNA
<220> FEATURE:
<221> NAME/KEY: misc_feature
<222> LOCATION: (16)..(17)
<223> OTHER INFORMATION: L-DNA
<220> FEATURE:
<221> NAME/KEY: misc_feature
<222> LOCATION: (18)..(19)
<223> OTHER INFORMATION: L-RNA
<220> FEATURE:
<221> NAME/KEY: misc_feature
<222> LOCATION: (20)..(28)
<223> OTHER INFORMATION: L-DNA
<220> FEATURE:
<221> NAME/KEY: misc_feature
<222> LOCATION: (29)..(30)
<223> OTHER INFORMATION: L-RNA
<220> FEATURE:
<221> NAME/KEY: misc_feature
<222> LOCATION: (31)..(47)
<223> OTHER INFORMATION: L-DNA

<400> SEQUENCE: 280
gcagtgggga aatgggaggg ctaggtggaa ggaatctgag ctactgc         47

<210> SEQ ID NO 281
<211> LENGTH: 44
<212> TYPE: RNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-RNA
<220> FEATURE:
<221> NAME/KEY: misc_feature
<222> LOCATION: (1)..(1)
<223> OTHER INFORMATION: 40kDa-PEG-moiety attached to 5'-end

<400> SEQUENCE: 281
gccugaugug guggugaagg guuguugggu gucgacgcac aggc            44

<210> SEQ ID NO 282
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(11)
<223> OTHER INFORMATION: L-DNA
<220> FEATURE:
<221> NAME/KEY: misc_feature
<222> LOCATION: (12)..(12)
<223> OTHER INFORMATION: L-RNA
<220> FEATURE:
<221> NAME/KEY: misc_feature
<222> LOCATION: (13)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
```

```
<220> FEATURE:
<221> NAME/KEY: misc_feature
<222> LOCATION: (15)..(16)
<223> OTHER INFORMATION: L-DNA
<220> FEATURE:
<221> NAME/KEY: misc_feature
<222> LOCATION: (17)..(18)
<223> OTHER INFORMATION: L-RNA
<220> FEATURE:
<221> NAME/KEY: misc_feature
<222> LOCATION: (19)..(27)
<223> OTHER INFORMATION: L-DNA
<220> FEATURE:
<221> NAME/KEY: misc_feature
<222> LOCATION: (28)..(29)
<223> OTHER INFORMATION: L-RNA
<220> FEATURE:
<221> NAME/KEY: misc_feature
<222> LOCATION: (30)..(45)
<223> OTHER INFORMATION: L-DNA

<400> SEQUENCE: 282
gcgcggggaa atgggagggc taggtggaag gaatctgagc cgcgc            45

<210> SEQ ID NO 283
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
<220> FEATURE:
<221> NAME/KEY: misc_feature
<222> LOCATION: (15)..(16)
<223> OTHER INFORMATION: L-DNA
<220> FEATURE:
<221> NAME/KEY: misc_feature
<222> LOCATION: (17)..(18)
<223> OTHER INFORMATION: L-RNA
<220> FEATURE:
<221> NAME/KEY: misc_feature
<222> LOCATION: (19)..(27)
<223> OTHER INFORMATION: L-DNA
<220> FEATURE:
<221> NAME/KEY: misc_feature
<222> LOCATION: (28)..(29)
<223> OTHER INFORMATION: L-RNA
<220> FEATURE:
<221> NAME/KEY: misc_feature
<222> LOCATION: (30)..(45)
<223> OTHER INFORMATION: L-DNA

<400> SEQUENCE: 283
gcgcggggaa atgggagggc taggtggaag gaatctgagc cgcgc            45

<210> SEQ ID NO 284
<211> LENGTH: 45
<212> TYPE: DNA
<213> ORGANISM: artificial
<220> FEATURE:
```

```
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
<220> FEATURE:
<221> NAME/KEY: misc_feature
<222> LOCATION: (15)..(16)
<223> OTHER INFORMATION: L-DNA
<220> FEATURE:
<221> NAME/KEY: misc_feature
<222> LOCATION: (17)..(18)
<223> OTHER INFORMATION: L-RNA
<220> FEATURE:
<221> NAME/KEY: misc_feature
<222> LOCATION: (19)..(24)
<223> OTHER INFORMATION: L-DNA
<220> FEATURE:
<221> NAME/KEY: misc_feature
<222> LOCATION: (25)..(25)
<223> OTHER INFORMATION: L-RNA
<220> FEATURE:
<221> NAME/KEY: misc_feature
<222> LOCATION: (26)..(27)
<223> OTHER INFORMATION: L-DNA
<220> FEATURE:
<221> NAME/KEY: misc_feature
<222> LOCATION: (28)..(29)
<223> OTHER INFORMATION: L-RNA
<220> FEATURE:
<221> NAME/KEY: misc_feature
<222> LOCATION: (30)..(45)
<223> OTHER INFORMATION: L-DNA

<400> SEQUENCE: 284
gcgcggggaa atgggagggc taggtggaag gaatctgagc cgcgc            45

<210> SEQ ID NO 285
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
<220> FEATURE:
<221> NAME/KEY: misc_feature
<222> LOCATION: (15)..(16)
<223> OTHER INFORMATION: L-DNA
<220> FEATURE:
<221> NAME/KEY: misc_feature
```

-continued

```
<222> LOCATION: (17)..(18)
<223> OTHER INFORMATION: L-RNA
<220> FEATURE:
<221> NAME/KEY: misc_feature
<222> LOCATION: (19)..(27)
<223> OTHER INFORMATION: L-DNA
<220> FEATURE:
<221> NAME/KEY: misc_feature
<222> LOCATION: (28)..(29)
<223> OTHER INFORMATION: L-RNA
<220> FEATURE:
<221> NAME/KEY: misc_feature
<222> LOCATION: (30)..(33)
<223> OTHER INFORMATION: L-DNA
<220> FEATURE:
<221> NAME/KEY: misc_feature
<222> LOCATION: (34)..(34)
<223> OTHER INFORMATION: L-RNA
<220> FEATURE:
<221> NAME/KEY: misc_feature
<222> LOCATION: (35)..(45)
<223> OTHER INFORMATION: L-DNA

<400> SEQUENCE: 285
gcgcggggaa atgggagggc taggtggaag gaatctgagc cgcgc            45

<210> SEQ ID NO 286
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
<220> FEATURE:
<221> NAME/KEY: misc_feature
<222> LOCATION: (15)..(16)
<223> OTHER INFORMATION: L-DNA
<220> FEATURE:
<221> NAME/KEY: misc_feature
<222> LOCATION: (16)..(27)
<223> OTHER INFORMATION: L-DNA
<220> FEATURE:
<221> NAME/KEY: misc_feature
<222> LOCATION: (17)..(18)
<223> OTHER INFORMATION: L-RNA
<220> FEATURE:
<221> NAME/KEY: misc_feature
<222> LOCATION: (28)..(29)
<223> OTHER INFORMATION: L-RNA
<220> FEATURE:
<221> NAME/KEY: misc_feature
<222> LOCATION: (30)..(35)
<223> OTHER INFORMATION: L-DNA
<220> FEATURE:
<221> NAME/KEY: misc_feature
<222> LOCATION: (36)..(36)
<223> OTHER INFORMATION: L-RNA
<220> FEATURE:
<221> NAME/KEY: misc_feature
<222> LOCATION: (37)..(45)
<223> OTHER INFORMATION: L-DNA
```

<400> SEQUENCE: 286
gcgcggggaa atgggagggc taggtggaag gaatctgagc cgcgc    45

<210> SEQ ID NO 287
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(46)
<223> OTHER INFORMATION: L-DNA

<400> SEQUENCE: 287
actcgagagg aaaggttggt aaaggttcgg ttggattcac tcgagt    46

<210> SEQ ID NO 288
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-RNA
<220> FEATURE:
<221> NAME/KEY: misc_feature
<222> LOCATION: (2)..(46)
<223> OTHER INFORMATION: L-DNA

<400> SEQUENCE: 288
actcgagagg aaaggttggt aaaggttcgg ttggattcac tcgagt    46

<210> SEQ ID NO 289
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (2)..(2)
<223> OTHER INFORMATION: L-RNA
<220> FEATURE:
<221> NAME/KEY: misc_feature
<222> LOCATION: (3)..(46)
<223> OTHER INFORMATION: L-DNA

<400> SEQUENCE: 289
actcgagagg aaaggttggt aaaggttcgg ttggattcac tcgagt    46

<210> SEQ ID NO 290
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: L-DNA
<220> FEATURE:
<221> NAME/KEY: misc_feature
<222> LOCATION: (3)..(3)
<223> OTHER INFORMATION: L-RNA

```
<220> FEATURE:
<221> NAME/KEY: misc_feature
<222> LOCATION: (4)..(46)
<223> OTHER INFORMATION: L-DNA

<400> SEQUENCE: 290
acucgagagg aaaggttggt aaaggttcgg ttggattcac tcgagt            46

<210> SEQ ID NO 291
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(3)
<223> OTHER INFORMATION: L-DNA
<220> FEATURE:
<221> NAME/KEY: misc_feature
<222> LOCATION: (4)..(4)
<223> OTHER INFORMATION: L-RNA
<220> FEATURE:
<221> NAME/KEY: misc_feature
<222> LOCATION: (5)..(46)
<223> OTHER INFORMATION: L-DNA

<400> SEQUENCE: 291
actcgagagg aaaggttggt aaaggttcgg ttggattcac tcgagt            46

<210> SEQ ID NO 292
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(4)
<223> OTHER INFORMATION: L-DNA
<220> FEATURE:
<221> NAME/KEY: misc_feature
<222> LOCATION: (5)..(5)
<223> OTHER INFORMATION: L-RNA
<220> FEATURE:
<221> NAME/KEY: misc_feature
<222> LOCATION: (6)..(46)
<223> OTHER INFORMATION: L-DNA

<400> SEQUENCE: 292
actcgagagg aaaggttggt aaaggttcgg ttggattcac tcgagt            46

<210> SEQ ID NO 293
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-DNA
<220> FEATURE:
<221> NAME/KEY: misc_feature
<222> LOCATION: (6)..(6)
<223> OTHER INFORMATION: L-RNA
<220> FEATURE:
<221> NAME/KEY: misc_feature
<222> LOCATION: (7)..(46)
<223> OTHER INFORMATION: L-DNA

<400> SEQUENCE: 293
```
actcgagagg aaaggttggt aaaggttcgg ttggattcac tcgagt      46

<210> SEQ ID NO 294
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-DNA
<220> FEATURE:
<221> NAME/KEY: misc_feature
<222> LOCATION: (7)..(7)
<223> OTHER INFORMATION: L-RNA
<220> FEATURE:
<221> NAME/KEY: misc_feature
<222> LOCATION: (8)..(46)
<223> OTHER INFORMATION: L-DNA

<400> SEQUENCE: 294
actcgagagg aaaggttggt aaaggttcgg ttggattcac tcgagt      46

<210> SEQ ID NO 295
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(7)
<223> OTHER INFORMATION: L-DNA
<220> FEATURE:
<221> NAME/KEY: misc_feature
<222> LOCATION: (8)..(8)
<223> OTHER INFORMATION: L-RNA
<220> FEATURE:
<221> NAME/KEY: misc_feature
<222> LOCATION: (9)..(46)
<223> OTHER INFORMATION: L-DNA

<400> SEQUENCE: 295
actcgagagg aaaggttggt aaaggttcgg ttggattcac tcgagt      46

<210> SEQ ID NO 296
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(8)
<223> OTHER INFORMATION: L-DNA
<220> FEATURE:
<221> NAME/KEY: misc_feature
<222> LOCATION: (9)..(9)
<223> OTHER INFORMATION: L-RNA
<220> FEATURE:
<221> NAME/KEY: misc_feature
<222> LOCATION: (10)..(46)
<223> OTHER INFORMATION: L-DNA

<400> SEQUENCE: 296
actcgagagg aaaggttggt aaaggttcgg ttggattcac tcgagt      46

<210> SEQ ID NO 297
<211> LENGTH: 46
<212> TYPE: DNA
<213> ORGANISM: artificial

```
<220> FEATURE:
<223> OTHER INFORMATION: synthetic
<220> FEATURE:
<221> NAME/KEY: misc_feature
<222> LOCATION: (1)..(9)
<223> OTHER INFORMATION: L-DNA
<220> FEATURE:
<221> NAME/KEY: misc_feature
<222> LOCATION: (10)..(10)
<223> OTHER INFORMATION: L-RNA
<220> FEATURE:
<221> NAME/KEY: misc_feature
<222> LOCATION: (11)..(46)
<223> OTHER INFORMATION: L-DNA

<400> SEQUENCE: 297
actcgagagg aaaggttggt aaaggttcgg ttggattcac tcgagt         46

<210> SEQ ID NO 298
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-DNA
<220> FEATURE:
<221> NAME/KEY: misc_feature
<222> LOCATION: (11)..(11)
<223> OTHER INFORMATION: L-RNA
<220> FEATURE:
<221> NAME/KEY: misc_feature
<222> LOCATION: (12)..(46)
<223> OTHER INFORMATION: L-DNA

<400> SEQUENCE: 298
actcgagagg aaaggttggt aaaggttcgg ttggattcac tcgagt         46

<210> SEQ ID NO 299
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-DNA
<220> FEATURE:
<221> NAME/KEY: misc_feature
<222> LOCATION: (12)..(12)
<223> OTHER INFORMATION: L-RNA
<220> FEATURE:
<221> NAME/KEY: misc_feature
<222> LOCATION: (13)..(46)
<223> OTHER INFORMATION: L-DNA

<400> SEQUENCE: 299
actcgagagg aaaggttggt aaaggttcgg ttggattcac tcgagt         46

<210> SEQ ID NO 300
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-DNA
<220> FEATURE:
```

<221> NAME/KEY: misc_feature
<222> LOCATION: (13)..(13)
<223> OTHER INFORMATION: L-RNA
<220> FEATURE:
<221> NAME/KEY: misc_feature
<222> LOCATION: (14)..(46)
<223> OTHER INFORMATION: L-DNA

<400> SEQUENCE: 300
actcgagagg aaaggttggt aaaggttcgg ttggattcac tcgagt        46

<210> SEQ ID NO 301
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(13)
<223> OTHER INFORMATION: L-DNA
<220> FEATURE:
<221> NAME/KEY: misc_feature
<222> LOCATION: (14)..(14)
<223> OTHER INFORMATION: L-RNA
<220> FEATURE:
<221> NAME/KEY: misc_feature
<222> LOCATION: (15)..(46)
<223> OTHER INFORMATION: L-DNA

<400> SEQUENCE: 301
actcgagagg aaaggttggt aaaggttcgg ttggattcac tcgagt        46

<210> SEQ ID NO 302
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: L-DNA
<220> FEATURE:
<221> NAME/KEY: misc_feature
<222> LOCATION: (15)..(15)
<223> OTHER INFORMATION: L-RNA
<220> FEATURE:
<221> NAME/KEY: misc_feature
<222> LOCATION: (16)..(46)
<223> OTHER INFORMATION: L-DNA

<400> SEQUENCE: 302
actcgagagg aaaggttggt aaaggttcgg ttggattcac tcgagt        46

<210> SEQ ID NO 303
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(15)
<223> OTHER INFORMATION: L-DNA
<220> FEATURE:
<221> NAME/KEY: misc_feature
<222> LOCATION: (16)..(16)
<223> OTHER INFORMATION: L-RNA
<220> FEATURE:
<221> NAME/KEY: misc_feature
<222> LOCATION: (17)..(46)
<223> OTHER INFORMATION: L-DNA

<400> SEQUENCE: 303
actcgagagg aaaggutggt aaaggttcgg ttggattcac tcgagt                46

<210> SEQ ID NO 304
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: L-DNA
<220> FEATURE:
<221> NAME/KEY: misc_feature
<222> LOCATION: (17)..(17)
<223> OTHER INFORMATION: L-RNA
<220> FEATURE:
<221> NAME/KEY: misc_feature
<222> LOCATION: (18)..(46)
<223> OTHER INFORMATION: L-DNA

<400> SEQUENCE: 304
actcgagagg aaaggtuggt aaaggttcgg ttggattcac tcgagt                46

<210> SEQ ID NO 305
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(17)
<223> OTHER INFORMATION: L-DNA
<220> FEATURE:
<221> NAME/KEY: misc_feature
<222> LOCATION: (18)..(18)
<223> OTHER INFORMATION: L-RNA
<220> FEATURE:
<221> NAME/KEY: misc_feature
<222> LOCATION: (19)..(46)
<223> OTHER INFORMATION: L-DNA

<400> SEQUENCE: 305
actcgagagg aaaggttggt aaaggttcgg ttggattcac tcgagt                46

<210> SEQ ID NO 306
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: L-DNA
<220> FEATURE:
<221> NAME/KEY: misc_feature
<222> LOCATION: (19)..(19)
<223> OTHER INFORMATION: L-RNA
<220> FEATURE:
<221> NAME/KEY: misc_feature
<222> LOCATION: (20)..(46)
<223> OTHER INFORMATION: L-DNA

<400> SEQUENCE: 306
actcgagagg aaaggttggt aaaggttcgg ttggattcac tcgagt                46

<210> SEQ ID NO 307

```
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-DNA
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(46)
<223> OTHER INFORMATION: L-DNA

<400> SEQUENCE: 307
actcgagagg aaaggttggu aaaggttcgg ttggattcac tcgagt          46

<210> SEQ ID NO 308
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(20)
<223> OTHER INFORMATION: L-DNA
<220> FEATURE:
<221> NAME/KEY: misc_feature
<222> LOCATION: (21)..(21)
<223> OTHER INFORMATION: L-RNA
<220> FEATURE:
<221> NAME/KEY: misc_feature
<222> LOCATION: (22)..(46)
<223> OTHER INFORMATION: L-DNA

<400> SEQUENCE: 308
actcgagagg aaaggttggt aaaggttcgg ttggattcac tcgagt          46

<210> SEQ ID NO 309
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(21)
<223> OTHER INFORMATION: L-DNA
<220> FEATURE:
<221> NAME/KEY: misc_feature
<222> LOCATION: (22)..(22)
<223> OTHER INFORMATION: L-RNA
<220> FEATURE:
<221> NAME/KEY: misc_feature
<222> LOCATION: (23)..(46)
<223> OTHER INFORMATION: L-DNA

<400> SEQUENCE: 309
actcgagagg aaaggttggt aaaggttcgg ttggattcac tcgagt          46

<210> SEQ ID NO 310
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
```

```
<222> LOCATION: (1)..(22)
<223> OTHER INFORMATION: L-DNA
<220> FEATURE:
<221> NAME/KEY: misc_feature
<222> LOCATION: (23)..(23)
<223> OTHER INFORMATION: L-RNA
<220> FEATURE:
<221> NAME/KEY: misc_feature
<222> LOCATION: (24)..(46)
<223> OTHER INFORMATION: L-DNA

<400> SEQUENCE: 310
actcgagagg aaaggttggt aaaggttcgg ttggattcac tcgagt         46

<210> SEQ ID NO 311
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: L-DNA
<220> FEATURE:
<221> NAME/KEY: misc_feature
<222> LOCATION: (24)..(24)
<223> OTHER INFORMATION: L-RNA
<220> FEATURE:
<221> NAME/KEY: misc_feature
<222> LOCATION: (25)..(46)
<223> OTHER INFORMATION: L-DNA

<400> SEQUENCE: 311
actcgagagg aaaggttggt aaaggttcgg ttggattcac tcgagt         46

<210> SEQ ID NO 312
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(24)
<223> OTHER INFORMATION: L-DNA
<220> FEATURE:
<221> NAME/KEY: misc_feature
<222> LOCATION: (25)..(25)
<223> OTHER INFORMATION: L-RNA
<220> FEATURE:
<221> NAME/KEY: misc_feature
<222> LOCATION: (26)..(46)
<223> OTHER INFORMATION: L-DNA

<400> SEQUENCE: 312
actcgagagg aaaggttggt aaaggttcgg ttggattcac tcgagt         46

<210> SEQ ID NO 313
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(25)
<223> OTHER INFORMATION: L-DNA
<220> FEATURE:
<221> NAME/KEY: misc_feature
<222> LOCATION: (26)..(26)
<223> OTHER INFORMATION: L-RNA
<220> FEATURE:
```

```
<221> NAME/KEY: misc_feature
<222> LOCATION: (27)..(46)
<223> OTHER INFORMATION: L-DNA

<400> SEQUENCE: 313
actcgagagg aaaggttggt aaaggutcgg ttggattcac tcgagt          46

<210> SEQ ID NO 314
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-DNA
<220> FEATURE:
<221> NAME/KEY: misc_feature
<222> LOCATION: (27)..(27)
<223> OTHER INFORMATION: L-RNA
<220> FEATURE:
<221> NAME/KEY: misc_feature
<222> LOCATION: (28)..(46)
<223> OTHER INFORMATION: L-DNA

<400> SEQUENCE: 314
actcgagagg aaaggttggt aaaggtucgg ttggattcac tcgagt          46

<210> SEQ ID NO 315
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-DNA
<220> FEATURE:
<221> NAME/KEY: misc_feature
<222> LOCATION: (28)..(28)
<223> OTHER INFORMATION: L-RNA
<220> FEATURE:
<221> NAME/KEY: misc_feature
<222> LOCATION: (29)..(46)
<223> OTHER INFORMATION: L-DNA

<400> SEQUENCE: 315
actcgagagg aaaggttggt aaaggttcgg ttggattcac tcgagt          46

<210> SEQ ID NO 316
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(28)
<223> OTHER INFORMATION: L-DNA
<220> FEATURE:
<221> NAME/KEY: misc_feature
<222> LOCATION: (29)..(29)
<223> OTHER INFORMATION: L-RNA
<220> FEATURE:
<221> NAME/KEY: misc_feature
<222> LOCATION: (30)..(46)
<223> OTHER INFORMATION: L-DNA

<400> SEQUENCE: 316
actcgagagg aaaggttggt aaaggttcgg ttggattcac tcgagt          46
```

<210> SEQ ID NO 317
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-DNA
<220> FEATURE:
<221> NAME/KEY: misc_feature
<222> LOCATION: (30)..(30)
<223> OTHER INFORMATION: L-RNA
<220> FEATURE:
<221> NAME/KEY: misc_feature
<222> LOCATION: (31)..(46)
<223> OTHER INFORMATION: L-DNA

<400> SEQUENCE: 317
actcgagagg aaaggttggt aaaggttcgg ttggattcac tcgagt        46

<210> SEQ ID NO 318
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-DNA
<220> FEATURE:
<221> NAME/KEY: misc_feature
<222> LOCATION: (31)..(31)
<223> OTHER INFORMATION: L-RNA
<220> FEATURE:
<221> NAME/KEY: misc_feature
<222> LOCATION: (32)..(46)
<223> OTHER INFORMATION: L-DNA

<400> SEQUENCE: 318
actcgagagg aaaggttggt aaaggttcgg utggattcac tcgagt        46

<210> SEQ ID NO 319
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-DNA
<220> FEATURE:
<221> NAME/KEY: misc_feature
<222> LOCATION: (32)..(32)
<223> OTHER INFORMATION: L-RNA
<220> FEATURE:
<221> NAME/KEY: misc_feature
<222> LOCATION: (32)..(46)
<223> OTHER INFORMATION: L-DNA

<400> SEQUENCE: 319
actcgagagg aaaggttggt aaaggttcgg tuggattcac tcgagt        46

<210> SEQ ID NO 320
<211> LENGTH: 46
<212> TYPE: DNA
<213> ORGANISM: artificial
<220> FEATURE:

```
<223> OTHER INFORMATION: synthetic
<220> FEATURE:
<221> NAME/KEY: misc_feature
<222> LOCATION: (1)..(32)
<223> OTHER INFORMATION: L-DNA
<220> FEATURE:
<221> NAME/KEY: misc_feature
<222> LOCATION: (33)..(33)
<223> OTHER INFORMATION: L-RNA
<220> FEATURE:
<221> NAME/KEY: misc_feature
<222> LOCATION: (34)..(46)
<223> OTHER INFORMATION: L-DNA

<400> SEQUENCE: 320
actcgagagg aaaggttggt aaaggttcgg ttggattcac tcgagt          46

<210> SEQ ID NO 321
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-DNA
<220> FEATURE:
<221> NAME/KEY: misc_feature
<222> LOCATION: (34)..(34)
<223> OTHER INFORMATION: L-RNA
<220> FEATURE:
<221> NAME/KEY: misc_feature
<222> LOCATION: (35)..(46)
<223> OTHER INFORMATION: L-DNA

<400> SEQUENCE: 321
actcgagagg aaaggttggt aaaggttcgg ttggattcac tcgagt          46

<210> SEQ ID NO 322
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-DNA
<220> FEATURE:
<221> NAME/KEY: misc_feature
<222> LOCATION: (35)..(35)
<223> OTHER INFORMATION: L-RNA
<220> FEATURE:
<221> NAME/KEY: misc_feature
<222> LOCATION: (36)..(46)
<223> OTHER INFORMATION: L-DNA

<400> SEQUENCE: 322
actcgagagg aaaggttggt aaaggttcgg ttggattcac tcgagt          46

<210> SEQ ID NO 323
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-DNA
<220> FEATURE:
<221> NAME/KEY: misc_feature
```

```
<222> LOCATION: (36)..(36)
<223> OTHER INFORMATION: L-RNA
<220> FEATURE:
<221> NAME/KEY: misc_feature
<222> LOCATION: (37)..(46)
<223> OTHER INFORMATION: L-DNA

<400> SEQUENCE: 323
actcgagagg aaaggttggt aaaggttcgg ttggautcac tcgagt            46

<210> SEQ ID NO 324
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-DNA
<220> FEATURE:
<221> NAME/KEY: misc_feature
<222> LOCATION: (37)..(37)
<223> OTHER INFORMATION: L-RNA
<220> FEATURE:
<221> NAME/KEY: misc_feature
<222> LOCATION: (38)..(46)
<223> OTHER INFORMATION: L-DNA

<400> SEQUENCE: 324
actcgagagg aaaggttggt aaaggttcgg ttggatucac tcgagt            46

<210> SEQ ID NO 325
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(37)
<223> OTHER INFORMATION: L-DNA
<220> FEATURE:
<221> NAME/KEY: misc_feature
<222> LOCATION: (38)..(38)
<223> OTHER INFORMATION: L-RNA
<220> FEATURE:
<221> NAME/KEY: misc_feature
<222> LOCATION: (39)..(46)
<223> OTHER INFORMATION: L-DNA

<400> SEQUENCE: 325
actcgagagg aaaggttggt aaaggttcgg ttggattcac tcgagt            46

<210> SEQ ID NO 326
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-DNA
<220> FEATURE:
<221> NAME/KEY: misc_feature
<222> LOCATION: (39)..(39)
<223> OTHER INFORMATION: L-RNA
<220> FEATURE:
<221> NAME/KEY: misc_feature
<222> LOCATION: (40)..(46)
<223> OTHER INFORMATION: L-DNA
```

<400> SEQUENCE: 326
actcgagagg aaaggttggt aaaggttcgg ttggattcac tcgagt            46

<210> SEQ ID NO 327
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-DNA
<220> FEATURE:
<221> NAME/KEY: misc_feature
<222> LOCATION: (40)..(40)
<223> OTHER INFORMATION: L-RNA
<220> FEATURE:
<221> NAME/KEY: misc_feature
<222> LOCATION: (41)..(46)
<223> OTHER INFORMATION: L-DNA

<400> SEQUENCE: 327
actcgagagg aaaggttggt aaaggttcgg ttggattcac tcgagt            46

<210> SEQ ID NO 328
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-DNA
<220> FEATURE:
<221> NAME/KEY: misc_feature
<222> LOCATION: (41)..(41)
<223> OTHER INFORMATION: L-RNA
<220> FEATURE:
<221> NAME/KEY: misc_feature
<222> LOCATION: (42)..(46)
<223> OTHER INFORMATION: L-DNA

<400> SEQUENCE: 328
actcgagagg aaaggttggt aaaggttcgg ttggattcac ucgagt            46

<210> SEQ ID NO 329
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-DNA
<220> FEATURE:
<221> NAME/KEY: misc_feature
<222> LOCATION: (42)..(42)
<223> OTHER INFORMATION: L-RNA
<220> FEATURE:
<221> NAME/KEY: misc_feature
<222> LOCATION: (43)..(46)
<223> OTHER INFORMATION: L-DNA

<400> SEQUENCE: 329
actcgagagg aaaggttggt aaaggttcgg ttggattcac tcgagt            46

<210> SEQ ID NO 330
<211> LENGTH: 46

```
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(42)
<223> OTHER INFORMATION: L-DNA
<220> FEATURE:
<221> NAME/KEY: misc_feature
<222> LOCATION: (43)..(43)
<223> OTHER INFORMATION: L-RNA
<220> FEATURE:
<221> NAME/KEY: misc_feature
<222> LOCATION: (44)..(46)
<223> OTHER INFORMATION: L-DNA

<400> SEQUENCE: 330
actcgagagg aaaggttggt aaaggttcgg ttggattcac tcgagt       46

<210> SEQ ID NO 331
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-DNA
<220> FEATURE:
<221> NAME/KEY: misc_feature
<222> LOCATION: (44)..(44)
<223> OTHER INFORMATION: L-RNA
<220> FEATURE:
<221> NAME/KEY: misc_feature
<222> LOCATION: (45)..(46)
<223> OTHER INFORMATION: L-DNA

<400> SEQUENCE: 331
actcgagagg aaaggttggt aaaggttcgg ttggattcac tcgagt       46

<210> SEQ ID NO 332
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-DNA
<220> FEATURE:
<221> NAME/KEY: misc_feature
<222> LOCATION: (45)..(45)
<223> OTHER INFORMATION: L-RNA
<220> FEATURE:
<221> NAME/KEY: misc_feature
<222> LOCATION: (46)..(46)
<223> OTHER INFORMATION: L-DNA

<400> SEQUENCE: 332
actcgagagg aaaggttggt aaaggttcgg ttggattcac tcgagt       46

<210> SEQ ID NO 333
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(45)
```

```
<223> OTHER INFORMATION: L-DNA
<220> FEATURE:
<221> NAME/KEY: misc_feature
<222> LOCATION: (46)..(46)
<223> OTHER INFORMATION: L-RNA

<400> SEQUENCE: 333
actcgagagg aaaggttggt aaaggttcgg ttggattcac tcgagu          46

<210> SEQ ID NO 334
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-DNA
<220> FEATURE:
<221> NAME/KEY: misc_feature
<222> LOCATION: (13)..(13)
<223> OTHER INFORMATION: L-RNA
<220> FEATURE:
<221> NAME/KEY: misc_feature
<222> LOCATION: (14)..(23)
<223> OTHER INFORMATION: L-DNA
<220> FEATURE:
<221> NAME/KEY: misc_feature
<222> LOCATION: (24)..(24)
<223> OTHER INFORMATION: L-RNA
<220> FEATURE:
<221> NAME/KEY: misc_feature
<222> LOCATION: (25)..(46)
<223> OTHER INFORMATION: L-DNA

<400> SEQUENCE: 334
actcgagagg aaaggttggt aaaggttcgg ttggattcac tcgagt          46

<210> SEQ ID NO 335
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-DNA
<220> FEATURE:
<221> NAME/KEY: misc_feature
<222> LOCATION: (13)..(13)
<223> OTHER INFORMATION: L-RNA
<220> FEATURE:
<221> NAME/KEY: misc_feature
<222> LOCATION: (14)..(35)
<223> OTHER INFORMATION: L-DNA
<220> FEATURE:
<221> NAME/KEY: misc_feature
<222> LOCATION: (36)..(36)
<223> OTHER INFORMATION: L-RNA
<220> FEATURE:
<221> NAME/KEY: misc_feature
<222> LOCATION: (37)..(46)
<223> OTHER INFORMATION: L-DNA

<400> SEQUENCE: 335
actcgagagg aaaggttggt aaaggttcgg ttggautcac tcgagt          46

<210> SEQ ID NO 336
<211> LENGTH: 46
<212> TYPE: DNA
<213> ORGANISM: artificial
```

```
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-DNA
<220> FEATURE:
<221> NAME/KEY: misc_feature
<222> LOCATION: (13)..(13)
<223> OTHER INFORMATION: L-RNA
<220> FEATURE:
<221> NAME/KEY: misc_feature
<222> LOCATION: (14)..(23)
<223> OTHER INFORMATION: L-DNA
<220> FEATURE:
<221> NAME/KEY: misc_feature
<222> LOCATION: (24)..(24)
<223> OTHER INFORMATION: L-RNA
<220> FEATURE:
<221> NAME/KEY: misc_feature
<222> LOCATION: (25)..(35)
<223> OTHER INFORMATION: L-DNA
<220> FEATURE:
<221> NAME/KEY: misc_feature
<222> LOCATION: (36)..(36)
<223> OTHER INFORMATION: L-RNA
<220> FEATURE:
<221> NAME/KEY: misc_feature
<222> LOCATION: (37)..(46)
<223> OTHER INFORMATION: L-DNA

<400> SEQUENCE: 336
actcgagagg aaaggttggt aaaggttcgg ttggautcac tcgagt                    46

<210> SEQ ID NO 337
<211> LENGTH: 46
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: L-DNA
<220> FEATURE:
<221> NAME/KEY: misc_feature
<222> LOCATION: (13)..(13)
<223> OTHER INFORMATION: L-RNA
<220> FEATURE:
<221> NAME/KEY: misc_feature
<222> LOCATION: (14)..(23)
<223> OTHER INFORMATION: L-DNA
<220> FEATURE:
<221> NAME/KEY: misc_feature
<222> LOCATION: (24)..(24)
<223> OTHER INFORMATION: L-RNA
<220> FEATURE:
<221> NAME/KEY: misc_feature
<222> LOCATION: (25)..(29)
<223> OTHER INFORMATION: L-DNA
<220> FEATURE:
<221> NAME/KEY: misc_feature
<222> LOCATION: (30)..(30)
<223> OTHER INFORMATION: L-RNA
<220> FEATURE:
<221> NAME/KEY: misc_feature
<222> LOCATION: (31)..(35)
<223> OTHER INFORMATION: L-DNA
<220> FEATURE:
<221> NAME/KEY: misc_feature
<222> LOCATION: (36)..(36)
<223> OTHER INFORMATION: L-RNA
<220> FEATURE:
<221> NAME/KEY: misc_feature
<222> LOCATION: (37)..(46)
<223> OTHER INFORMATION: L-DNA
```

<400> SEQUENCE: 337
actcgagagg aaaggttggt aaaggttcgg ttggautcac tcgagt          46

<210> SEQ ID NO 338
<211> LENGTH: 50
<212> TYPE: RNA
<213> ORGANISM: artificial
<220> FEATURE:
<223> OTHER INFORMATION: synthetic
<220> FEATURE:
<221> NAME/KEY: misc_feature
<222> LOCATION: (1)..(50)
<223> OTHER INFORMATION: L-RNA
<220> FEATURE:
<221> NAME/KEY: misc_feature
<222> LOCATION: (1)..(1)
<223> OTHER INFORMATION: 40kDa-PEG-moiety attached to 5'-end

<400> SEQUENCE: 338
ccgugcuguc ggagacuacu cgucgaguag aaauaggucc ccucccacgg          50

<210> SEQ ID NO 339
<211> LENGTH: 50
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
<222> LOCATION: (1)..(1)
<223> OTHER INFORMATION: 40kDa-PEG-moiety attached to 5'-end
<220> FEATURE:
<221> NAME/KEY: misc_feature
<222> LOCATION: (41)..(41)
<223> OTHER INFORMATION: L-DNA
<220> FEATURE:
<221> NAME/KEY: misc_feature
<222> LOCATION: (42)..(50)
<223> OTHER INFORMATION: L-RNA

<400> SEQUENCE: 339
ccgugcuguc ggagacuacu cgucgaguag aaauaggucc ccucccacgg          50

<210> SEQ ID NO 340
<211> LENGTH: 44
<212> TYPE: RNA
<213> ORGANISM: artificial
<220> FEATURE:
<223> OTHER INFORMATION: synthetic
<220> FEATURE:
<221> NAME/KEY: misc_feature
<222> LOCATION: (1)..(44)
<223> OTHER INFORMATION: L-RNA
<220> FEATURE:
<221> NAME/KEY: misc_feature
<222> LOCATION: (1)..(1)
<223> OTHER INFORMATION: 40kDa-PEG-moiety attached to 5'-end

<400> SEQUENCE: 340
gcgugaauag ccguugaaac gccuuuagag aagcacuagc acgc          44

<210> SEQ ID NO 341
<211> LENGTH: 44
<212> TYPE: DNA
<213> ORGANISM: artificial
<220> FEATURE:
<223> OTHER INFORMATION: synthetic

```
<220> FEATURE:
<221> NAME/KEY: misc_feature
<222> LOCATION: (1)..(1)
<223> OTHER INFORMATION: L-DNA
<220> FEATURE:
<221> NAME/KEY: misc_feature
<222> LOCATION: (1)..(1)
<223> OTHER INFORMATION: 40kDa-PEG-moiety attached to 5'-end
<220> FEATURE:
<221> NAME/KEY: misc_feature
<222> LOCATION: (2)..(18)
<223> OTHER INFORMATION: L-RNA
<220> FEATURE:
<221> NAME/KEY: misc_feature
<222> LOCATION: (19)..(19)
<223> OTHER INFORMATION: L-DNA
<220> FEATURE:
<221> NAME/KEY: misc_feature
<222> LOCATION: (20)..(20)
<223> OTHER INFORMATION: L-RNA
<220> FEATURE:
<221> NAME/KEY: misc_feature
<222> LOCATION: (21)..(21)
<223> OTHER INFORMATION: L-DNA
<220> FEATURE:
<221> NAME/KEY: misc_feature
<222> LOCATION: (22)..(31)
<223> OTHER INFORMATION: L-RNA
<220> FEATURE:
<221> NAME/KEY: misc_feature
<222> LOCATION: (32)..(32)
<223> OTHER INFORMATION: L-DNA
<220> FEATURE:
<221> NAME/KEY: misc_feature
<222> LOCATION: (33)..(44)
<223> OTHER INFORMATION: L-RNA

<400> SEQUENCE: 341
gcgugaauag ccguugaaac gccuuuagag aagcacuagc acgc         44

<210> SEQ ID NO 342
<211> LENGTH: 46
<212> TYPE: RNA
<213> ORGANISM: artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: D-RNA
<220> FEATURE:
<221> NAME/KEY: misc_feature
<222> LOCATION: (3)..(46)
<223> OTHER INFORMATION: L-RNA

<400> SEQUENCE: 342
gggcgugaau agccguugaa acgccuuuag agaagcacua gcacgc       46
```